US008618265B2

(12) United States Patent
Kosmeder et al.

(10) Patent No.: US 8,618,265 B2
(45) Date of Patent: Dec. 31, 2013

(54) HAPTENS, HAPTEN CONJUGATES, COMPOSITIONS THEREOF AND METHOD FOR THEIR PREPARATION AND USE

(75) Inventors: Jerome W. Kosmeder, Tucson, AZ (US); Mark Lefever, Tucson, AZ (US); Donald Johnson, Tucson, AZ (US); Michael Farrell, Tucson, AZ (US); Zhanna Zhilina, Oro Valley, AZ (US); Christopher Bieniarz, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 660 days.

(21) Appl. No.: 12/660,744

(22) Filed: Mar. 2, 2010

(65) Prior Publication Data

US 2010/0297725 A1     Nov. 25, 2010

Related U.S. Application Data

(62) Division of application No. 11/982,627, filed on Nov. 1, 2007, now Pat. No. 7,695,929.

(60) Provisional application No. 60/856,133, filed on Nov. 1, 2006.

(51) Int. Cl.
*C07K 16/00* (2006.01)
*C07K 1/13* (2006.01)
*C07K 1/04* (2006.01)

(52) U.S. Cl.
USPC ..... 530/389.8; 530/402; 530/403; 530/391.3; 530/391.5

(58) Field of Classification Search
None
See application file for complete search history.

(56) References Cited

U.S. PATENT DOCUMENTS

| | | |
|---|---|---|
| 3,892,530 A | 7/1975 | Felix et al. |
| 4,230,683 A | 10/1980 | Decker et al. |
| 4,425,427 A | 1/1984 | Luderer |
| 4,469,797 A | 9/1984 | Albarella |
| 4,490,473 A | 12/1984 | Brunhouse et al. |
| 4,495,296 A | 1/1985 | Neurath et al. |
| 4,879,224 A | 11/1989 | Wallner et al. |
| 5,198,537 A | 3/1993 | Huber et al. |
| 5,225,325 A | 7/1993 | Miller et al. |
| 5,322,771 A | 6/1994 | Rybski et al. |
| 5,350,686 A | 9/1994 | Jhingan |
| 5,393,891 A * | 2/1995 | Batt et al. ............ 546/170 |
| 5,403,747 A | 4/1995 | Akins et al. |
| 5,418,138 A | 5/1995 | Miller et al. |
| 5,447,841 A | 9/1995 | Gray et al. |
| 5,487,975 A | 1/1996 | Miller et al. |
| 5,643,761 A | 7/1997 | Fisher et al. |
| 5,648,211 A | 7/1997 | Fraiser et al. |
| 5,648,245 A | 7/1997 | Fire et al. |
| 5,650,327 A | 7/1997 | Copeland et al. |
| 5,654,200 A | 8/1997 | Copeland et al. |
| 5,661,040 A | 8/1997 | Huff et al. |
| 5,679,582 A | 10/1997 | Bowie et al. |
| 5,684,142 A | 11/1997 | Mishra et al. |
| 5,707,844 A | 1/1998 | Batt et al. |
| 5,731,171 A | 3/1998 | Bohlander |
| 5,756,696 A | 5/1998 | Gray et al. |
| 5,759,808 A | 6/1998 | Casterman et al. |
| 5,800,988 A | 9/1998 | Casterman et al. |
| 5,840,526 A | 11/1998 | Casterman et al. |
| 5,874,541 A | 2/1999 | Casterman et al. |
| 5,883,081 A | 3/1999 | Kraus et al. |
| 5,994,071 A | 11/1999 | Ross et al. |
| 6,005,079 A | 12/1999 | Casterman et al. |
| 6,015,695 A | 1/2000 | Casterman et al. |
| 6,057,099 A | 5/2000 | Nathan et al. |
| 6,100,099 A | 8/2000 | Gordon et al. |
| 6,124,120 A | 9/2000 | Lizardi |
| 6,180,349 B1 | 1/2001 | Ginzinger et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,152 B1 | 4/2001 | Auerbach |
| 6,218,371 B1 | 4/2001 | Krieg et al. |

(Continued)

FOREIGN PATENT DOCUMENTS

| | | |
|---|---|---|
| EP | 0 336 192 | 10/1989 |
| EP | 0 354 847 | 2/1990 |

(Continued)

OTHER PUBLICATIONS

Zeng et al. Development of an enzyme-linked immunosorbent assay for quantitative determinaiton of Quizalofor-p-ethyl. J. Agric. Food Chem. 2006, vol. 54, pp. 8682-8687.*
Foces-Foces et al., "Structure of 3-Nitropyrazole in Solution and in Solid State," *Journal of Physical Organic Chemistry* 10:637-645, 1997.
Maier et al., "Synthesis and Quality Control of Thiol Tagged Compound Libraries for Chemical Microarrays," *QSAR & Combinational Science* 11:1047-1054, 2006.
"Fluorescent Labels for Antibodies and Molecular Probes," http://hmds.org.uk/fluorochrome.html, HMDS, 8 pages, Nov. 11, 2003.
"Note 7.1—Product Highlight: Guide to Labeling Antibodies with Alexa Fluor Dyes," http://probes.invitrogen.com/handbook/boxes/2020.html, Invitrogen, pp. 6-9, Apr. 2, 2006.

(Continued)

*Primary Examiner* — Shafiqul Haq
(74) *Attorney, Agent, or Firm* — Klarquist Sparkman, LLP

(57) ABSTRACT

A method for performing a multiplexed diagnostic assay, such as for two or more different targets in a sample, is described. One embodiment comprised contacting the sample with two or more specific binding moieties that bind specifically to two or more different targets. The two or more specific binding moieties are conjugated to different haptens, and at least one of the haptens is an oxazole, a pyrazole, a thiazole, a nitroaryl compound other than dinitrophenyl, a benzofurazan, a triterpene, a urea, a thiourea, a rotenoid, a coumarin, a cyclolignan, a heterobiaryl, an azo aryl, or a benzodiazepine. The sample is contacted with two or more different anti-hapten antibodies that can be detected separately. The two or more different anti-hapten antibodies may be conjugated to different detectable labels.

5 Claims, 29 Drawing Sheets

(56) References Cited

U.S. PATENT DOCUMENTS

| | | |
|---|---|---|
| 6,235,480 B1 | 5/2001 | Shultz et al. |
| 6,239,116 B1 | 5/2001 | Krieg et al. |
| 6,280,929 B1 | 8/2001 | Gray et al. |
| 6,280,949 B1 | 8/2001 | Lizardi |
| 6,291,187 B1 | 9/2001 | Kingsmore et al. |
| 6,296,809 B1 | 10/2001 | Richards et al. |
| 6,322,901 B1 | 11/2001 | Bawendi et al. |
| 6,323,009 B1 | 11/2001 | Lasken et al. |
| 6,339,068 B1 | 1/2002 | Krieg et al. |
| 6,344,337 B1 | 2/2002 | Mansfield et al. |
| 6,352,861 B1 | 3/2002 | Copeland et al. |
| 6,358,682 B1 | 3/2002 | Jaffee et al. |
| 6,406,705 B1 | 6/2002 | Davis et al. |
| 6,414,133 B1 | 7/2002 | Dietz-Band et al. |
| 6,429,199 B1 | 8/2002 | Krieg et al. |
| 6,432,320 B1 | 8/2002 | Bonsignore et al. |
| 6,447,692 B1 | 9/2002 | Momoda et al. |
| 6,495,324 B1 | 12/2002 | Mirkin et al. |
| 6,506,564 B1 | 1/2003 | Mirkin et al. |
| 6,544,798 B1 | 4/2003 | Christensen et al. |
| 6,569,621 B1 | 5/2003 | Cremer et al. |
| 6,576,291 B2 | 6/2003 | Bawendi et al. |
| 6,582,921 B2 | 6/2003 | Mirkin et al. |
| 6,592,844 B2 | 7/2003 | Coombes et al. |
| 6,607,877 B1 | 8/2003 | Gray et al. |
| 6,617,137 B2 | 9/2003 | Dean et al. |
| 6,649,138 B2 | 11/2003 | Adams et al. |
| 6,656,685 B2 | 12/2003 | Utermohlen et al. |
| 6,673,214 B1 | 1/2004 | Marchitto et al. |
| 6,682,596 B2 | 1/2004 | Zehnder et al. |
| 6,695,974 B2 | 2/2004 | Withers et al. |
| 6,696,304 B1 | 2/2004 | Davies |
| 6,699,973 B1 | 3/2004 | O'Mahony et al. |
| 6,750,016 B2 | 6/2004 | Mirkin et al. |
| 6,767,702 B2 | 7/2004 | Mirkin et al. |
| 6,797,474 B2 | 9/2004 | Lizardi |
| 6,815,064 B2 | 11/2004 | Treadway et al. |
| 6,827,901 B2 | 12/2004 | Copeland et al. |
| 6,828,097 B1 | 12/2004 | Knoll et al. |
| 6,855,552 B2 | 2/2005 | Towne et al. |
| 6,921,496 B2 | 7/2005 | Anderson et al. |
| 6,933,117 B2 | 8/2005 | Wolf et al. |
| 6,942,970 B2 | 9/2005 | Isola et al. |
| 6,943,029 B2 | 9/2005 | Copeland et al. |
| 6,944,333 B2 | 9/2005 | Douglass |
| 6,962,789 B2 | 11/2005 | Bacus |
| 6,977,148 B2 | 12/2005 | Dean et al. |
| 7,014,997 B2 | 3/2006 | Knoll et al. |
| 7,045,504 B2 | 5/2006 | Wilhelm et al. |
| 7,056,471 B1 | 6/2006 | Han et al. |
| 7,067,325 B2 | 6/2006 | Christensen et al. |
| 7,087,379 B2 * | 8/2006 | Light ............................ 435/6.14 |
| 7,104,313 B2 | 9/2006 | Pokharna et al. |
| 7,200,252 B2 | 4/2007 | Douglass |
| 7,250,254 B2 | 7/2007 | Dietz-Band et al. |
| 7,285,289 B2 | 10/2007 | Nagy et al. |
| 7,292,718 B2 | 11/2007 | Douglass |
| 7,300,748 B2 | 11/2007 | Fischer et al. |
| 7,358,041 B2 | 4/2008 | Short et al. |
| 7,541,455 B2 | 6/2009 | Bieniarz et al. |
| 7,682,789 B2 | 3/2010 | Chen et al. |
| 7,695,929 B2 | 4/2010 | Kosmeder et al. |
| 7,985,557 B2 | 7/2011 | Kosmeder et al. |
| 2001/0051342 A1 | 12/2001 | Farrell |
| 2002/0019001 A1 | 2/2002 | Light |
| 2002/0117659 A1 | 8/2002 | Lieber et al. |
| 2003/0003537 A1 | 1/2003 | Fischer et al. |
| 2003/0008414 A1 | 1/2003 | Nie et al. |
| 2003/0022166 A1 | 1/2003 | Collins et al. |
| 2003/0022243 A1 | 1/2003 | Kondejewski et al. |
| 2003/0059790 A1 | 3/2003 | Jaffee et al. |
| 2003/0066998 A1 | 4/2003 | Lee |
| 2003/0122630 A1 | 7/2003 | Fallisgaard et al. |
| 2003/0165485 A1 | 9/2003 | Bertilsson et al. |
| 2004/0052685 A1 | 3/2004 | Richards |
| 2004/0057958 A1 | 3/2004 | Waggoner et al. |
| 2004/0877844 | 4/2004 | Jacobson et al. |
| 2004/0101822 A1 | 5/2004 | Wiesner et al. |
| 2004/0115727 A1 | 6/2004 | Steward et al. |
| 2004/0157231 A1 | 8/2004 | Meltola et al. |
| 2004/0161742 A1 | 8/2004 | Dean et al. |
| 2004/0209303 A1 | 10/2004 | Martin et al. |
| 2004/0214245 A1 | 10/2004 | Schmitt et al. |
| 2004/0229300 A1 | 11/2004 | Frederickson |
| 2004/0248151 A1 | 12/2004 | Bacus et al. |
| 2004/0253603 A1 | 12/2004 | Utermohlen et al. |
| 2004/0265897 A1 | 12/2004 | Lizardi |
| 2004/0265922 A1 | 12/2004 | Bieniarz et al. |
| 2005/0012182 A1 | 1/2005 | Jang et al. |
| 2005/0014133 A1 | 1/2005 | Light et al. |
| 2005/0019901 A1 | 1/2005 | Matveeva et al. |
| 2005/0048498 A1 | 3/2005 | Woudenberg et al. |
| 2005/0054578 A1 | 3/2005 | Sandberg et al. |
| 2005/0064488 A1 | 3/2005 | Huh et al. |
| 2005/0074890 A1 | 4/2005 | Lemme et al. |
| 2005/0106639 A1 | 5/2005 | Bacus et al. |
| 2005/0112636 A1 | 5/2005 | Hurt et al. |
| 2005/0118725 A1 | 6/2005 | Towne et al. |
| 2005/0158770 A1 | 7/2005 | Bieniarz et al. |
| 2005/0159432 A1 | 7/2005 | Shepard et al. |
| 2005/0164213 A1 | 7/2005 | Tabor et al. |
| 2005/0181394 A1 | 8/2005 | Steemers et al. |
| 2005/0272032 A1 | 12/2005 | Ji |
| 2006/0110744 A1 | 5/2006 | Sampas et al. |
| 2006/0148124 A1 | 7/2006 | Wilson |
| 2006/0160116 A1 | 7/2006 | Christian et al. |
| 2006/0182751 A1 | 8/2006 | Gazzard et al. |
| 2006/0192283 A1 | 8/2006 | Benson |
| 2006/0246524 A1 | 11/2006 | Bauer et al. |
| 2006/0275784 A1 | 12/2006 | Light et al. |
| 2007/0057263 A1 | 3/2007 | Kahen |
| 2007/0099283 A1 | 5/2007 | Mueller et al. |
| 2007/0117153 A1 | 5/2007 | Bieniarz |
| 2007/0274996 A1 | 11/2007 | Carter et al. |
| 2008/0057513 A1 | 3/2008 | Farrell |
| 2010/0151489 A1 | 6/2010 | Chen et al. |

FOREIGN PATENT DOCUMENTS

| | | |
|---|---|---|
| JP | 9-500874 | 1/1997 |
| JP | 11051935 | 2/1999 |
| JP | 11 240879 | 9/1999 |
| JP | 2001089484 | 4/2001 |
| JP | 2006-506447 | 2/2006 |
| WO | WO 93/20094 | 10/1993 |
| WO | WO 9320094 A1 * | 10/1993 |
| WO | WO 95/03296 | 2/1995 |
| WO | WO 01/88089 | 11/2001 |
| WO | WO 0188089 | 11/2001 |
| WO | WO 03/031419 | 4/2003 |
| WO | WO 2004/046730 | 6/2004 |
| WO | WO 2005/001889 | 1/2005 |
| WO | WO 2005/064018 | 7/2005 |
| WO | WO 2007/079128 | 7/2007 |
| WO | WO 2008/028156 | 3/2008 |

OTHER PUBLICATIONS

Baglin et al., "A Review of Natural and Modified Betulinic, Ursolic and Echinocystic Acid Derivatives as Potential Antineoplastic Agents," *Mini Review in Medicinal Chemistry*, 3:540-556, 2003.

Baltina, "Chemical Modification of Glycyrrhizic Acid as a Route to New Bioactive Compounds for Medicine," *Current Medicinal Chemistry*, 10:155-171, 2003.

Connolly and Hill, "Triterpenoids," *Nat. Prod. Rep.*, 19:494-513, 2002.

Crombie and Whiting, "Biosynthesis in Rotenoids Group of Natural Products: Application of Isotope Methodology," *Phytochemistry*, 49:1479-1507, 1998.

Desbene and Giorgi-Renault, "Drugs that Inhibit Tubulin Polymerization: The Particular Case of Podophyllotoxin and Analogues," *Curr. Med. Chem.—Anti-Cancer Agents*, 2:71-90, 2002.

(56) References Cited

OTHER PUBLICATIONS

Devi et al., "Antibodies to poly[(2→8)-α-N-Acetylneuraminic acid] and poly[(2→9)-α-N-Acetylneuraminic acid] are Elicited by Immunization of Mice with *Escherichia coli* K92 Conjugates: Potential Vaccines for Groups B and C Meningococci and *E. coli* K1," *PNAS*, 88:7175-79, 1991.
Dubertret et al., "In vivo imaging of quantum dots encapsulated in phospholipid micelles," *Science*, 298:1759-1762, 2002.
Fang and Casida, "Cube Resin Insecticide: Identification and Biological Activity of 29 Rotenoid Constituents," *J. Agric. Food Chem.*, 47:2130-2136, 1999.
Fattom et al., "Serum antibody response in adult volunteers elicited by injection of *Streptococcus pneumoniae* type 12F polysaccharide alone or conjugated to diphtheria toxoid," *Infect. Immun.*, 58:2309-12, 1990.
Gilham, "An addition reaction specific for uridine and guanosine nucleotides and its application to the modification of ribonuclease action," *J. Am. Chem. Soc.*, 84:687-688, 1962.
Gordaliza et al., "Podophyllotoxin: Distribution, Sources, Applications and New Cytotoxic Derivatives," *Toxicon*, 44:441-459, 2004.
Jaiswal et al., "Long-term multiple color imaging of live cells using quantum dot bioconjugates," *Nature Biotechnol.*, 21:47-51, 2003.
Lee et al., "Suppression of Reaginic Antibody Formation: III. Relationship Between Immunogenicity and Tolerogenicity of Hapten-Carrier Conjugates," *J. Immunol.*, 116:1711-18, 1976.
Masuda et al., "New biotinylating reagent utilizing carbodiimide function," *Nucleic Acids Symp. Ser.*, 34:69-70, 1995.
Meresse et al., "Etoposide: Discovery and Medicinal Chemistry," *Current Medicinal Chemistry*, 11:2443-2466, 2004.
Metz and Brown, "The investigation of nucleic acid secondary structure by means of chemical modification with a carbodiimide reagent. I. The reaction between N-cyclohexyl-N'-β-(4-methylmorphilinium)ethylcarbodiimide and model nucleosides," *Biochem.*, 8(6):2312-2328, 1969.
Mukumoto et al., "Investigation of ferrocenyl carbodiimide (FCDI) in the modification reaction of nucleic acids," *Nucleic Acids Symp. Ser. (Oxf.)*, 49:231-232, 2005.
Pavliakova et al., "Treatment with Succinic Anhydride Improves the Immunogenicity of *Shigella flexneri* Type 2a O-Specific Polysaccharide-Protein Conjugates in Mice," *Infect. Immun.*, 68:2161-66, 2000.
Pozsgay et al., "Protein conjugates of synthetic saccharides elicit higher levels of serum IgG lipopolysaccharide antibodies in mice than do those of the O-specific polysaccharide from *Shigella dysenteriae* type 1," *PNAS*, 96:5194-97, 1999.
Pujol et al., "Synthesis of Biological Activity of New Class of Dioxygenated Anticancer Agents," *Curr. Med. Chem.—Anti-Cancer Agents*, 5:215-237, 2005.
Rigby et al., "Labeling deoxyribonucleic acid to high specific activity in vitro by nick translation with DNA polymerase I," *J. Mol. Biol.*, 113:237-251, 1977.
Setzer and Setzer, "Plant-Derived Triterpenoids as Potential Antineoplastic Agents," *Mini Reviews in Medicinal Chemistry*, 3:540-556, 2003.
Singh et al., "Advances in Vaccine Adjuvants," *Nat. Biotechnol.*, 17:1075-1081, 1999.
Szu et al., "Relation between Structure and Immunologic Properties of the Vi Capsular Polysaccharide," *Infect. Immun.*, 59:4555-61, 1991.
Szu et al., "Vi Capsular Polysaccharide-Protein Conjugates for Prevention of Typhoid Fever," *J. Exp. Med.*, 166:1510-24, 1987.
Wu et al., "Immunofluorescent labeling of cancer marker Her2 and other cellular targets with semiconductor quantum dots," *Nature Biotech.*, 21:41-46, 2003.
You, "Podophyllotoxin Derivatives: Current Synthetic Approaches for New Anticancer Agents," *Current Pharmaceutical Design*, 11:1695-1717, 2005.
PCT International Search Report from the International Searching Authority dated Sep. 23, 2008.
Written Opinion of the International Searching Authority dated Sep. 23, 2008.
Bang et al., "Boiling heat transfer performance and phenomena of $Al_2O_3$-water nano-fluids from a plain surface in a pool," *International Journal of Heat and Mass Transfer* 48:2407-2419, 2005.
Bellon, "Quantitation and specific detection of collagenous proteins using an enzyme-linked immunosoret assay and an immunoblotting for cyanogens bromide peptides," *Analtyic Biochemistry* 150:188-202, 1985.
Böhlen et al., "Fluorometric Assay of Proteins in the Nanogram Range," *Archives of Biochemistry and Biophysics* 155:213-220, 1973.
Buongiorno et al., "Use of Nanofluids for Enhanced Economics and Safety of Nuclear Reactors," *COE-INES International Symposium*, 14 pages, Yokahama, Nov. 26-30, 2006.
Chan et al., "Quantum Dot Bioconjugates for Ultrasensitive Nonisotopic Detection," *Science* 281:2016-2018, Sep. 25, 1998.
Das et al., "Pool boiling characteristics of nano-fluids," *International Journal of Heat and Mass Transfer* 46:851-862, 2003.
Demers et al., "A Fluorescence-based method for determining the surface coverage and hybridization efficiency of thiol-capped oligonucleotides bound to gold thin films and nanoparticles," *Analytical Chemistry* 72:5535-5541, 2000.
Dong et al., "Study of Fluorescence Quenching and Dialysis Process of CdTe Quantum Dots, Using Ensemble Techniques and Fluorescence Correlation Spectroscopy," *J. Phys. Chem. B* 110:10069-10075, 2006.
Draper et al., "Attachment of reporter groups to specific, selected cytidine residues in RNA using a bisulfate-catalyzed transamination reaction," *Nucleic Acids Research* 12(2):989-1002, 1984.
Dubois et al., "A Versatile Strategy for Quantum Dot Ligand Exhange," *Journal of the American Chemical Society* 129(3):482-483, 2007.
Dyal et al., "Activity of *Candida rugosa* lipase Immobilized on $\gamma$-$Fe_2O_3$ Magnetic Nanoparticles," *Journal of the American Chemical Society* 125:1684-1685, 2003.
Eastman et al., "Anomalously increased effective thermal conductivities of ethylene glycol-based nanofluids containing copper nanoparticles," *Applied Physics Letters* 78(6):718-720, Feb. 5, 2001.
Gerardi, "Experimental Study of Boiling Crisis Phenomena in Nanofluids," *National Nuclear Society Student Conference*, 19 pages, Mar. 30, 2007.
Han et al., "Quantum-dot-tagged microbeads for multiplexed optical coding of biomolecules," *Nature Technology* 19:631-635, Jul. 2001.
Heafey et al., "Comparative study of the quenching of core and core-shell CdSe quantum dots by binding and non-binding nitroxides," *Photochemical and Photobiological Sciences* 6:580-584, 2007.
Heid et al., "Real time Quantitative PCR," *Genome Research* 6:986-994, 1996.
Hickman et al., "Combining Spontaneous Molecular Assembly with Microfabrication to Pattern Surfaces: Selective Binding of Isonitriles to Platinum Microwires and Characterization by Electrochemistry and Surface Spectroscopy," *Journal of the American Chemical Society* 111:7271-7272, 1989.
Hill et al., "The bio-barcode assay for the detection of protein and nucleic acid targets using DTT-induced ligand exchange," *Nature Protocols* 1(1):324-336, 2006.
Iijima et al., "Dispersion Behavior of Barium Titanate Nanoparticles Prepared by Using Various Polycarboxylic Dispersants," *Journal of the American Chemical Society* 90(9):2741-2746, 2007.
Jackson et al., "Characteristics of Nucleate Boiling with Gold Nanoparticles in Water," *Proceedings of IMECE 2006*, 2006 ASME International Mechanical Engineering Congress and Exposition, pp. 385-390, Chicago, Illinois, Nov. 5-10, 2006.
Kats et al., "Spectroscopic determination of protein concentrations from proteinase K digests," *Analytical Biochemistry* 307:212-218, 2002.
Kim et al., "A real-time PCR-based method for determining the surface coverage of thiol-capped oligonucleotides bound onto gold nanoparticles," *Nucleic Acids Research* 34(7):e54, 2006.

(56) References Cited

OTHER PUBLICATIONS

Kim et al., "Effects of nanoparticle deposition on surface wettability influencing boiling heat transfer in nanofluids," *Applied Physics Letters* 89(153107):1-3, 2006.
Kim et al., "Experimental studies on CHF characteristics of nano-fluids at pool boiling," *International Journal of Multiphase Flow* 33:391-706, 2007.
Kim et al., "Surface wettability change during pool boiling of nanofluids and its effect on critical heat flux," *International Journal of Heat and Mass Transfer* 50:4105-4116, 2007.
Koh et al., "Magnetic Iron Oxide Nanoparticles for Biorecognition: Evaluation of surface coverage and activity," *Journal of Physical Chemistry* 110:1553-1448, 2006.
Layne, "Spectrophotometric and turbidimetric methods for measuring proteins," *Methods in Enzymology* 3:447-454, 1957.
Link et al., "Size and Temperature Dependence of the Plasmon Absorption of Colloidal Gold Nanoparticles," *Journal of Physical Chemistry B* 103(21):4212-4217, 1999.
Matsui et al., "Synthesis of cerium oxide nanoparticles by hydrothermal crystallization with citric acid," *Journal of Materials Science Letters* 21:489-491, 2002.
Matteucci et al., "Synthesis of Deoxyoligonucleotides on a Polymer Support," *Journal of the American Chemical Society* 103:3185-3191, 1981.
Milanova et al., "Role of ions in pool boiling heat transfer of pure and silica nanofluids," *Applied Physics Letters* 87(233107):1-3, 2005.
Moreno et al., "Pool Boiling Heat Transfer of Alumina-Water, Zinc Oxide-Water and Alumina-Water+Ethylene Glycol Nanofluids," *Proceedings of HT2005, 2005 ASME Summer Heat Transfer Conference*, pp. 625-632, San Francisco, California, Jul. 17-22, 2005.
Mucic et al., "Synthesis and characterization of DNA with ferrocenyl groups attached to their 5'-termini: electrochemical characterization of a redox-active nucleotide monolayer," *Chem. Comm.*, pp. 555-557, 1996.
Otsuka et al., "Quantitative and Reversible Lectin-Induced Association of Gold Nanoparticles Modified with α-Lactosyl-ω-mercapto-poly(ethylene glycol)," *Journal of the American Chemical Society* 123(34):8226-8230, 2001.
Pathak et al., "Hydroxylated quantum dots as luminescent probes for in situ hybridization," *Journal of the American Chemical Society* 123:4103-4104, 2001.
Perkins, "Protein Volumes and hydration effects," *Eur. J. Biochem.* 157:169-180, 1986.
Rockenberger et al., "A New Nonhydrolytic Single-Precursor Approach in Surfactant-Capped Nanocrystals of Transition Metal Oxides," *Journal of the American Chemical Society* 121(49):11595-11596, 1999.
Santra et al., "Rapid and effective labeling of brain tissue using TAT-conjugated CdS:Mn/ZnS quantum dots," *Chemical Communications*, pp. 3144-3146, 2005.
Simonian, "Spectrophotometric Deteimination of Protein Concentration," *Current Protocols in Food Analytical Chemistry* B1.3.1-B.13.7, 2002.
Sun et al., "Shape-Controlled Synthesis of Gold and Silver Nanoparticles," *Science* 398:2176-2179, Dec. 13, 2002.
Thanh et al., "Development of an Aggregation-Based Immunoassay for Anti-Protein a Using Gold Nanoparticles," *Analytical Chemistry* 74(7):1624-1628, 2002.
Theofanous et al., "The boiling crisis phenomenon—Part I: nucleation and nucleate boiling heat transfer," *Experimental Thermal and Fluid Science* 26:775-792, 2002.
Theofanous et al., "The boiling crisis phenomenon—Part II: dryout dynamics and burnout," *Experimental Thermal and Fluid Science* 26:793-810, 2002.
Tsugita et al., "A rapid vapor-phase acid (hydrochloric acid and trifluoroacetic acid) hydrolysis of peptide and protein," *Journal of Biochemistry* 102:1593-1597, 1987.
Udenfriend et al., "Fluorescamine: A Reagent for Assay of Amino Acids, Peptides, Proteins and Primary Amines in the Picomole Range," *Science* 178:870-872, Nov. 24, 1972.
Vassallo et al., "Pool boiling heat transfer experiments in silica-water nano-fluids," *International Journal of Heat and Mass Transfer* 47:407-411, 2004.
Wang et al., "Effect of Surface Wettability on Active Nucleation Site Density During Pool Boiling of Water on a Vertical Surface," *Journal of Heat Transfer* 115:659-669, Aug. 1993.
Wen et al., "Experimental investigation into the pool boiling heat transfer of aqueous based γ-alumina nanofluids," *Journal of Nanoparticle Research* 7:265-274, 2005.
Woehrle et al., "Thiol-functionalized 1.5-nm gold nanoparticles through ligand exchange reactions: Scope and mechanism of ligand exchange," *Journal of the American Chemical Society* 127(7):2172-2183, 2005.
Xu et al., "Immunoassay using probe-labelling immungold nanoparticles with silver staining enhancement via surface-enhanced Raman scattering," *Analyst* 129:63-68, 2004.
Yi et al., "Water-Soluble $NaYF_4$:Yb,Er(Tm)/$NaYF_4$/Polymer Core/Shell/Shell Nanoparticles with Significant Enhancement of Upconversion Fluorescence," *Chemistry of Materials* 19:341-343, 2007.
You et al., "Effect of nanoparticles on critical heat flux of water in pool boiling heat transfer," *Applied Physics Letters* 83(16):3374-3376, Oct. 20, 2003.
Yu et al., "Water-soluble quantum dots for biomedical applications," *Biochemical and Biophysical Research Communications* 348:781-786, 2006.
International Search Report dated Aug. 24, 2005, from International Application No. PCT/US2004/042969.
International Search Report dated Sep. 23, 2008, from International Application No. PCT/US2007/023140.
International Search Report dated Dec. 16, 2009, from International Application No. PCT/US2009/045841.
Office action dated Sep. 17, 2008, from U.S. Appl. No. 11/800,360.
Office action dated Apr. 2, 2009, from U.S. Appl. No. 11/800,360.
Office action dated Dec. 19, 2008, from U.S. Appl. No. 11/982,627.
Office action dated Jul. 24, 2009, from U.S. Appl. No. 11/982,627.
Office action dated Aug. 17, 2010, from U.S. Appl. No. 12/658,092.
Canadian Office Action dated Aug. 10, 2011, in Canadian Patent Application No. 2,666,234.
European Patent Office Summons to Attend Oral Proceedings Pursuant to Rule 115(1) EPC dated Sep. 13, 2011, in European Patent Application No. 07867341.5.
Fong et al., "Clinical Pharmacology of IMPY by Radioimmunoassay," *Cancer Treatment Reports* 64(12):1253-1260, 1980.
Li et al., "Detection of Apoptosis and DNA Replication by Differential Labeling of DNA Strand Breaks with Fluorochromes of Different Color," *Experimental Cell Research* 222(1):28-37, 1996.
"Polyclonal Anti-Conjugated Rotenone Antibodies (rat)," *Gemacbio Data Sheet*, Code No. AP115, Apr. 5, 2006, 3 pages.
Extended European Search Report dated Oct. 17, 2012, from related European Patent Application No. 12150646.3.
Partial European Search Report dated Oct. 26, 2012, from related European Patent Application No. 12151520.9.
Partial European Search Report dated Oct. 26, 2012, from related European Patent Application No. 12151524.1.
Dintzis et al., "Molecular determinants of immunogenicity: The immunon model of immune response," *Proc. Natl. Acad. Sci. USA* 73(10):3671-3675 (1976).
Puttaiah et al., "Detection of dideoxyosone intermediates of glycation using a monoclonal antibody: Characterization of major epitope structures," *Archives of Biochemistry and Biophysics* 446:186-196, 2006.
Watkins et al., "The Synthesis of Haptenic Derivatives of Aminoimidazoazaarene Cooked-Food Mutagens," *Heterocycles* 26(8):2069-2072, 1987.

* cited by examiner

HAPTENS, HAPTEN CONJUGATES, COMPOSITIONS THEREOF AND METHOD FOR THEIR PREPARATION AND USE

CROSS-REFERENCE TO RELATED APPLICATIONS

This application is a divisional of U.S. patent application Ser. No. 11/982,627, filed Nov. 1, 2007 now U.S. Pat. No. 7,695,929, which claims the benefit of U.S. Provisional Application No. 60/856,133 filed on Nov. 1, 2006. The entire disclosures of these prior applications are incorporated herein by reference.

FIELD

This disclosure concerns haptens, hapten conjugates, and diagnostic and therapeutic compositions thereof. More particularly, this disclosure concerns haptens, hapten conjugates and anti-hapten antibody conjugates that can be utilized in various combinations for the simultaneous identification, visualization and/or quantitation of a plurality of targets in a sample, such as multiple protein and nucleic acid targets in a tissue sample.

BACKGROUND

Generally, only large molecules, infectious agents, and insoluble foreign matter can elicit an immune response in an animal. However, haptens, which are small molecules, can in certain instances be induced to elicit an immune response if they are first coupled to a large carrier (such as a protein) to form an immunogen. Haptens in combination with anti-hapten antibodies that are raised against the immunogens and isolated are useful for detecting particular molecular targets. For example, specific binding moieties such as primary antibodies and nucleic acid probes can be labeled with one or more hapten molecules, and once these specific binding moieties are bound to their molecular targets they can be detected using an anti-hapten antibody conjugate that includes a detectable label such as an enzyme or a fluorescent label. Binding of the detectable anti-hapten antibody conjugate to a sample indicates the presence of the target in a sample.

Digoxigenin, present exclusively in *Digitalis* plants as a secondary metabolite, is an example of a hapten that has been utilized in a variety of molecular assays. U.S. Pat. No. 4,469,797, entitled "Digoxigenin Immunogens, Antibodies, Label Conjugates and Related Derivatives," discloses using immunoassays to determine digoxin concentrations in blood samples based upon the specific binding of antidigoxin antibodies to the drug in the test sample. U.S. Pat. No. 5,198,537, entitled "Digoxigenin Derivatives and Use Thereof," describes a number of additional digoxigenin derivatives that have been used in immunological tests, such as immunoassays.

Other haptens have been developed for analytical procedures including biotin and fluorescein. However, each of these haptens has specific drawbacks that have made dioxigenin the hapten of choice for sensitive immunoassays. In the case of biotin, certain biological samples include endogenous biotin that can lead to background interference. Similarly, fluorescein, a fluorescent molecule, can lead to background fluorescence in a fluorescent immunoassay. For in situ assays such as immunohistochemical (IHC) assays and in situ hybridization (ISH) assays of tissue and cytological samples, especially multiplexed assays of such samples, it is highly desirable to identify and develop new haptens and anti-hapten antibodies (and conjugates thereof) to provide additional assay flexibility, especially since it is becoming clear that samples can best be characterized through simultaneous detection of multiple targets.

A primary goal of cancer therapy is to selectively kill, or inhibit uncontrolled growth of, malignant cells while not adversely affecting normal cells. Traditional chemotherapeutic drugs are highly cytotoxic, and while preferably having greater affinity for malignant cells than for normal cells, nevertheless typically adversely affect normal cells. New therapeutics are now being developed that target the growth factor and nutrient pathways that regulate cell growth and metabolism in response to intracellular and environmental cues. These signaling pathways often are altered or dysregulated in cancer. For example, certain growth factors (such as EGF, a growth factor that activates protein-receptor tyrosine kinase ("RTK") activity to initiate a signal transduction cascade resulting in changes in cell growth, proliferation and differentiation) are involved in the pathogenesis and progression of different cancers. Such pathways and associated signaling molecules provide attractive targets for therapeutic intervention, but it is becoming increasingly evident that different populations of patients have tumors that appear to be dysregulated in different manners. For example, a particular therapeutic target (or combination of therapeutic targets) may only be present in tumors from certain populations of patients, and thus identifying such certain populations having the target (or combination of targets) can be used to stratify patients into potential non-responders and potential non-responders to a therapeutic (or combination of therapeutics) directed toward the target (or targets). The use of companion diagnostics to stratify patients in this manner is a first step toward personalizing the treatment of cancer in individual patients. Increased individualization of treatments will certainly involve multiplexed assays for multiple therapeutic targets.

Unfortunately, in recent years there has been little research directed to developing additional classes of haptens against which sensitive and specific antibodies can be raised in order to enable highly multiplexed assays. Such highly multiplexed assays would be useful for monitoring the response of individuals to a given therapeutic regimen and for companion diagnostic applications. Identifying additional classes of haptens and methods for their use in analytical and therapeutic applications would substantially advance the state of the art in this field.

SUMMARY

Thus, based on the above, a need exists in the art for additional haptens, and hapten conjugates, that are useful for diagnostic and/or therapeutic applications. Accordingly, certain disclosed embodiments of the present invention concern new classes of haptens, hapten conjugates and compositions thereof.

Embodiments of a method for performing a multiplexed diagnostic assay, such as for two or more different targets in a sample, are described. One embodiment comprised contacting the sample with two or more specific binding moieties that bind specifically to two or more different targets. The two or more specific binding moieties are conjugated to different haptens, and at least one of the haptens is an oxazole, a pyrazole, a nitroaryl compound, a benzofurazan, a triterpene, a urea, a thiourea, a rotenoid, a coumarin or a cyclolignan. The sample is contacted with two or more different anti-hapten antibodies that can be detected separately. The two or more different anti-hapten antibodies may be conjugated to different detectable labels. In some embodiments, the two or more different anti-hapten antibodies are from different mammalian species. The method may further comprise contacting the two or more different anti-hapten antibodies with two or more anti-antibodies that specifically bind the two or more different anti-hapten antibodies. For such embodiments, the two or more anti-antibodies may be conjugated to different detectable labels.

Certain embodiments of the hapten are azoles having the following general chemical formula

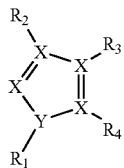

where $R_1$-$R_4$ independently are selected from hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, at least one of the $R_1$-$R_4$ substituents being bonded to a linker or is a reactive group suitable for coupling to a linker or a carrier molecule, X independently is nitrogen or carbon, Y is oxygen, sulfur or nitrogen, and if Y is oxygen or sulfur, then there is no $R_1$ group, and if Y is nitrogen, then there is at least one $R_1$ group. One specific example of such a hapten has the following structure.

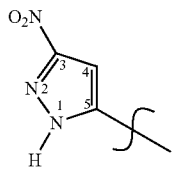

Another class of haptens is the nitroaryl compounds having the following general chemical formula

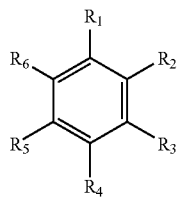

where at least one of $R_1$-$R_6$ is nitro, and the remaining $R_1$-$R_6$ ring substituents independently are selected from hydrogen, acyl, aldehydes, alkoxy, aliphatic heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, clic, heterocyclic, cyano, ester, ether, halogen, heteroaryl, hydroxyl, hydroxylamine, keto, sulfhydryl, sulfonyl, sulfoxide, exomethylene, or two or more of the $R_1$-$R_6$ substituents are atoms in a ring system, and at least one of the $R_1$-$R_6$ substituents is bonded to a linker or is a reactive group suitable for coupling to the linker.

Another class of haptens is the benzofurazans or derivatives thereof, such as compounds having a formula

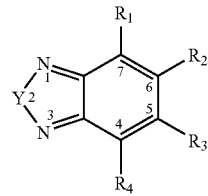

where the $R_1$-$R_4$ substituents independently are selected from hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, or two or more of the $R_1$-$R_4$ substituents are atoms in a ring system bonded or fused to the compounds having the illustrated general formula, at least one of the $R_1$-$R_4$ substituents being bonded to the linker or is the reactive group, and Y is oxygen, sulfur or a carbon atom having $R_5$ and $R_6$ substituents, where $R_5$ and $R_6$ are as stated for $R_1$-$R_4$. One specific example of such a hapten has the following structure.

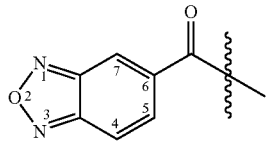

Another class of haptens is cyclic terpenes having a formula

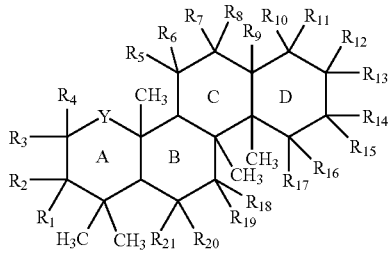

where $R_1$-$R_{21}$ independently are selected from hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, at least one of the $R_1$-$R_{21}$ substituents being bonded to a linker or is a reactive group suitable for coupling to the linker or a carrier molecule, and where two or more of $R_1$-$R_{21}$ substituents may be atoms in a ring system bonded or fused to the compounds having the illustrated general formula, Y is a bond, thereby defining a 5-membered ring, or is a carbon atom bearing $R_{22}$ and $R_{23}$ substituents, where $R_{22}$ and $R_{23}$ are as stated for $R_1$-$R_{21}$. One specific example of such a hapten has the following structure.

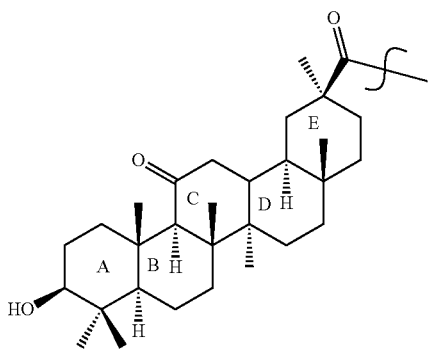

Another class of haptens is ureas and thioureas having a formula

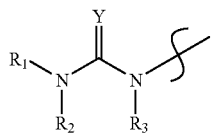

where $R_1$-$R_3$ independently are hydrogen, aliphatic, substituted aliphatic, cyclic, heterocyclic, aryl and heteroaryl, and Y is oxygen or sulfur. Particular examples of ureas or thioureas are aryl ureas or thioureas having a formula

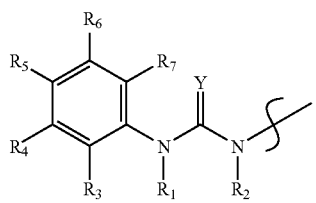

where $R_1$-$R_7$ independently are independently are selected from hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, at least one of the $R_1$-$R_7$ substituents is bonded to a linker or is a reactive group, and where two or more of $R_1$-$R_7$ substituents may be atoms in a ring system bonded or fused to the compounds having the illustrated general formula, and Y is oxygen or sulfur. One specific example of such a hapten has a formula

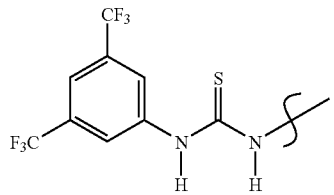

Another class of haptens is the rotenoids having a formula

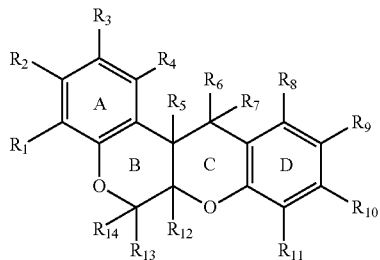

where $R_1$-$R_{14}$ independently are hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, at least one of the $R_1$-$R_{14}$ substituents is coupled to a linker or is a reactive group, and where two or more of $R_1$-$R_{14}$ substituents may be atoms in a ring system bonded or fused to the compounds having the illustrated general formula. One specific example of such a hapten has a formula

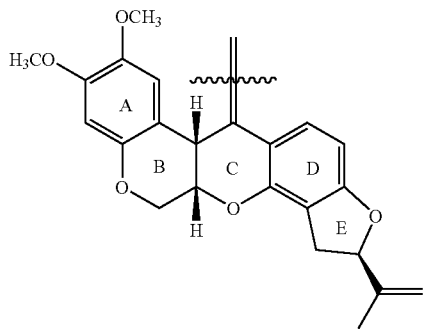

The rotenone haptens also include rotenone isoxazolines, which typically have a formula

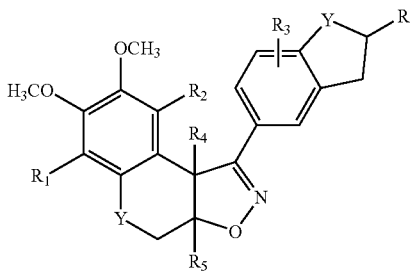

With reference to the rotenone isoxazolines, R-$R_5$ independently are hydrogen, aldehyde, alkoxy, aliphatic, particularly lower aliphatic, including all branched chain isomers, such as isoprene, and all stereoisomers, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto) amino, amino acid, amido, cyano (—CN), halogen, hydroxyl, hydroxylamine, oxime (HO—N═), oxime ether (e.g., methoxyimine, $CH_3$—O—N═) alkyl hydroxyl, particularly lower alkyl hydroxyl, carbonyl, keto, such as aliphatic ketones, nitro, sulfhydryl, sulfonyl, sulfoxide, carboxyl, carboxylate (and salts thereof, such as Group I metal or ammonium ion carboxylates) ester, alkyl ester, acyl, exomethylene, ether, cyclic, heterocyclic, aryl, alkyl aryl, such as benzyl, heteroaryl, polysaccharides, carbohydrate, monosaccharides, such as glucose and fructose, disaccharides, such as sucrose and lactose, oligosaccharides and polysaccharides, and combinations thereof. At least one of the $R$-$R_5$ substituents also is bonded to a linker or to a carrier molecule. Y is oxygen, nitrogen, or sulfur.

Another class of haptens is oxazoles or thiazoles having a formula

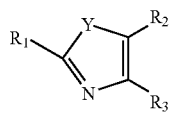

where $R_1$-$R_3$ independently are selected from hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, at least one of the $R_1$-$R_3$ substituents is coupled to a linker or is a reactive group, and where $R_2$-$R_3$ substituents may be atoms in a ring system bonded or fused to the compounds having the illustrated general formula, and Y is oxygen or sulfur. A specific example of such a hapten has the following chemical structure.

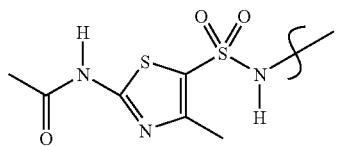

Another class of haptens is the coumarins or coumarin derivatives having a formula

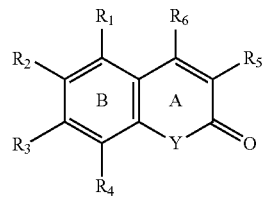

where $R_1$-$R_6$ independently are selected from hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, or two or more of the $R_1$-$R_6$ substituents available for forming such compounds also may be atoms in a ring system bonded or fused to the compounds having the illustrated general formula, at least one of the $R_1$-$R_6$ substituents is coupled to a linker or is a reactive group, and Y is oxygen, nitrogen or sulfur.

Another class of haptens is the cyclolignans having a formula

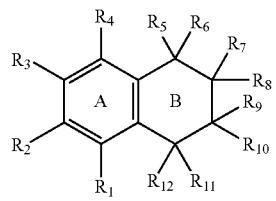

where $R_1$-$R_{12}$ independently are selected from hydrogen, acyl, aldehydes, alkoxy, aliphatic, substituted aliphatic, heteroaliphatic, oxime, oxime ether, alcohols, amido, amino, amino acid, aryl, alkyl aryl, carbohydrate, monosaccharides, disaccharides, oligosaccharides, polysaccharides, carbonyl, carboxyl, carboxylate, cyclic, cyano, ester, ether, exomethylene, halogen, heteroaryl, heterocyclic, hydroxyl, hydroxylamine, aliphatic ketones, nitro, sulfhydryl, sulfonyl, sulfoxide, and combinations thereof, or two or more of the $R_1$-$R_{12}$ substituents available for forming such compounds also may be atoms in a ring system bonded or fused to the compounds having the illustrated general formula, at least one of the $R_1$-$R_{12}$ substituents is coupled to a linker or is a reactive group. Specific examples of cyclolignan haptens include

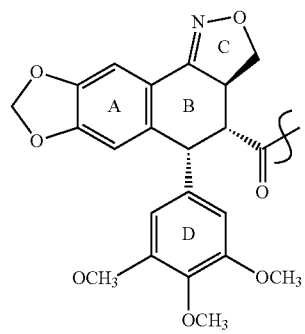

-continued

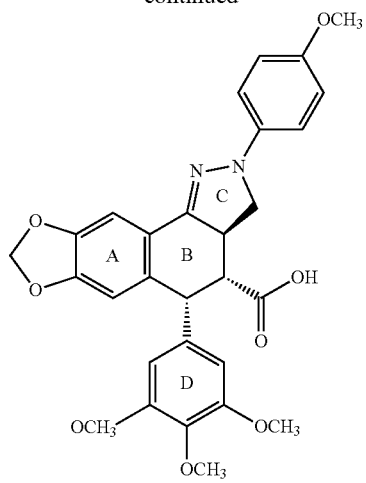

Another general class of haptens of the present invention is heterobicyclic/biaryl compounds, typically phenyl quinolines and quinoxalines. The heterobicyclic/biaryl compounds typically have a first general chemical formula as below.

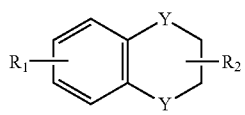

$R_1$-$R_2$ substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, alkoxy aryl, such as methoxy and ethoxy, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of the $R_1$-$R_2$ substituents, most typically plural $R_1$ substituents, also may be atoms, typically carbon atoms, in a ring system bonded or fused to the compounds having the illustrated general formula. At least one of the $R_1$-$R_2$ substituents is bonded to a linker or directly to a carrier. Y is oxygen, nitrogen or sulfur, typically nitrogen. If Y is nitrogen, then the formula also can include double bonds to the one or more nitrogen atoms.

Compounds having a single heteroatom are exemplified by phenylquinolines, as follows.

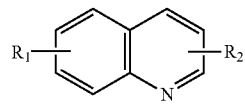

Compounds having two heteroatoms are represented by quinoxalines, as indicated by the general formula below.

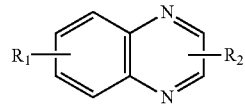

Particular examples include 2-(3,4-dimethoxyphenyl)quinoline-4-carboxylic acid)

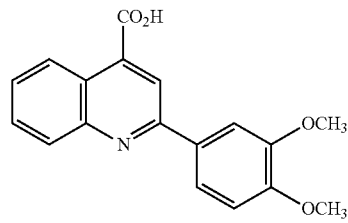 [SMILES: COc1ccc(-c2cc(C(=O)O)c3ccccc3n2)cc1OC]

and 3-hydroxy-2-quinoxalinecarbamide.

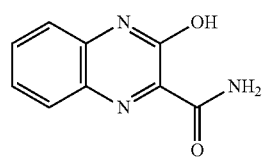 [SMILES: NC(=O)c1nc2ccccc2nc1O]

Another general class of haptens is azoaryl compounds, such as azobenzenes, having a first general chemical formula as below.

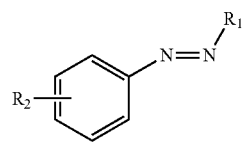

$R_1$-$R_2$ substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, alkoxy aryl, such as methoxy and ethoxy, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, sulfonyl, exomethylene, and combinations thereof. Two ore more $R_2$ substituents also may be atoms, typically carbon atoms, in a ring system bonded or fused to the compounds having the illustrated general formula. For example, 2 $R_2$ substituents may form a fused phenyl ring, or a fused heterocyclic or heteroaryl structure. A particular azoaryl haptens, 4-(dimethylamino)azobenzene-4'-sulfonyl chloride, has the formula provided below.

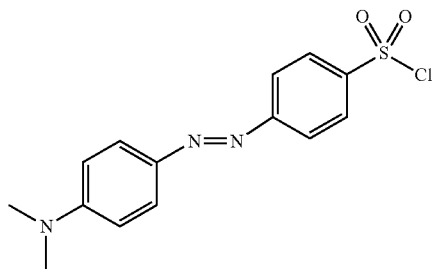

Another class of haptens is benzodiazepine having a first general formula as indicated below.

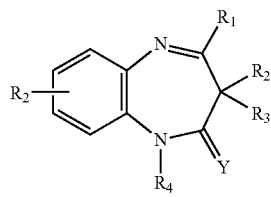

$R_1$-$R_5$ independently are selected from: acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, cyano (—CN), ester, ether, exomethylene, halogen, heteroaryl, heterocyclic, hydrogen, hydroxyl, hydroxylamine, oxime (HO—N=), keto, such as aliphatic ketones, nitro, sulfhydryl, sulfonyl, sulfoxide, sulfonyl, and combinations thereof. Two or more of the $R_5$ substituents also may be atoms, typically carbon atoms, in a ring system bonded or fused to the compounds having the illustrated general formula. At least one of the $R_1$-$R_5$ positions is bonded to a linker or is occupied by a functional group suitable for coupling to a linker or a carrier molecule. $R_1$-$R_5$ most typically are aliphatic, aryl, hydrogen, or hydroxyl, even more typically alkyl, hydrogen or phenyl. Y is oxygen or sulfur, most typically oxygen. A particular example of a benzodiazepine hapten, -(2-hydroxyphenyl)-1H-benzo[b][1,4]diazepine-2(3H)-one, is provided below.

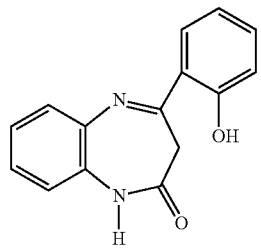 [SMILES: O=C1CC(c2ccccc2O)=Nc2ccccc2N1]

The present disclosure also provides embodiments of a compound having a formula (hapten)$_m$-(linker)$_n$-(reactive group)$_o$ where the hapten is an oxazole, pyrazole, thiazole, nitroaryl, benzofurazan, triterpene, urea, thiourea, rotenoid, coumarin, cycolignan, or combinations thereof, m is from 1 to about 200, n is 0 to about 200, and o is from 1 to 200. In certain embodiments m is 1 to about 100, n is from o to about 5, and o is from about 1 to about 5, and in other embodiments m, n and o are 1.

The present disclosure also describes hapten-carrier conjugates comprising a hapten coupled to a carrier where the hapten is an oxazole, pyrazole, thiazole, nitroaryl, benzofurazan, triterpene, urea, thiourea, rotenoid, coumarin, cycolignan, or combinations thereof. Certain embodiments of such conjugates have a formula (hapten)$_m$-(linker)$_n$-(carrier)$_p$ where m is from 1 to about 200, n is 0 to about 200 and p is from 1 to about 10. For other embodiments m is from 1 to about 100, n is 1 to 100, and p is from 1 to about 5, and yet other embodiments m, n, o and p are 1. For certain embodiments, the linker is heteroaliphatic, such as alkyl or alkylene oxides, with one particular embodiment comprising an ethylene glycol linker having from 1 to about 15 ethylene glycol units. The carrier may be a specific binding carrier, such as a protein, a nucleic acid, or an antibody. The carrier also may be an immunogenic carrier.

The present disclosure also concerns antibodies that specifically bind to a hapten selected from an oxazole, pyrazole, thiazole, nitroaryl, benzofurazan, triterpene, urea, thiourea, rotenoid, coumarin, or cycolignan.

Pharmaceutical compositions also are described. One embodiment of a pharmaceutical composition comprised diagnostically or therapeutically effective amounts of a hapten-carrier conjugate comprising a hapten coupled to a carrier where the hapten is an oxazole, pyrazole, thiazole, nitroaryl, benzofurazan, triterpene, urea, thiourea, rotenoid, coumarin, cycolignan, or combinations thereof. For such compositions, the hapten-carrier conjugate may have a formula (hapten)$_m$-(linker)$_n$-(reactive group)$_o$-(carrier)$_p$ where the hapten is an oxazole, pyrazole, thiazole, nitroaryl, benzofurazan, triterpene, urea, thiourea, rotenoid, coumarin, cycolignan, or combinations thereof.

Multiplexed arrays also are described. For example, disclosed embodiments of a multiplexed assay comprised a hapten selected from oxazoles, pyrazoles, thiazoles, nitroaryls, benzofurazans, triterpenes, ureas, thioureas, rotenones, coumarins, cycolignans, and combinations thereof.

Kits for use in an enzyme immunoassay are disclosed. Certain kit embodiments comprise a hapten-conjugated antibody or hapten conjugated to a nucleic acid probe, the hapten being selected from oxazoles, pyrazoles, thiazoles, nitroaryls, benzofurazans, triterpenes, ureas, thioureas, rotenones, coumarins, cyclolignans, and combinations thereof. Such kits also typically include an anti-hapten antibody conjugated to a detectable label.

Embodiments of an immunoassay process are described. For example, the immunoassay process may comprise providing a rective hapten conjugate suitable for performing the immunoassay, the hapten being selected from oxazoles, pyrazoles, thiazoles, nitroaryls, benzofurazans, triterpenes, ureas, thioureas, rotenones, coumarins, cyclolignans, and combinations thereof. The hapten conjugate is then used in at least one step of the immunoassay. The hapten conjugate may be a hapten-linker conjugate. Alternatively, the hapten conjugate may be a hapten-carrier conjugate, where the carrier might be an immunogenic carrier or a specific binding carrier.

A method for identifying a mammalian tumor is disclosed. One embodiment comprises assaying a sample obtained from the mammalian tumor to detect a pattern of expression, phosphorylation or both expression and phosphorylation, using a hapten conjugate where the hapten is selected from oxazoles, pyrazoles, thiazoles, nitroaryls, benzofurazans, triterpenes, ureas, thioureas, rotenones, coumarins, cyclolignans, and combinations thereof.

A method for assessing a response to drug therapy in an individual also is disclosed. One embodiment of the method comprised obtaining a first tissue or cell sample from the individual before exposing the individual to a drug therapy. A second tissue or cell sample is obtained from the individual after exposing the individual to the drug therapy. A biochemical product and/or process affected by the therapy is detected from the first sample and the second sample, where detecting comprises using a hapten conjugate having a hapten selected from oxazoles, pyrazoles, thiazoles, nitroaryls, benzofurazans, triterpenes, ureas, thioureas, rotenones, coumarins, cyclolignans, and combinations thereof. The results for the first sample are compared to the second sample to determine whether the drug therapy had a positive, negative or null effect.

A method for making a conjugate comprising a hapten also is disclosed. One embodiment of the method comprised providing a hapten selected from oxazoles, pyrazoles, thiazoles, nitroaryls, benzofurazans, triterpenes, ureas, thioureas, rotenones, coumarins, cyclolignans, and combinations thereof. The hapten is then coupled to a linker or a carrier.

A method for detecting a molecule of interest in a biological sample also is disclosed. One embodiment of the method comprised contacting the biological sample with a hapten-antibody conjugate comprising an antibody linked to the hapten using a heterobifunctional PEG linker, the hapten being selected from oxazoles, pyrazoles, thiazoles, nitroaryls, benzofurazans, triterpenes, ureas, thioureas, rotenones, coumarins, podophyllotoxin-based compounds, and combinations thereof. A signal generated by the hapten-antibody conjugate is detected after treatment with an anti-hapten antibody having at least one detectable label.

The foregoing and other objects, features, and advantages of the invention will become more apparent from the following detailed description, which proceeds with reference to the accompanying figures.

DETAILED DESCRIPTION

I. Terms and Introduction

Figure 1:
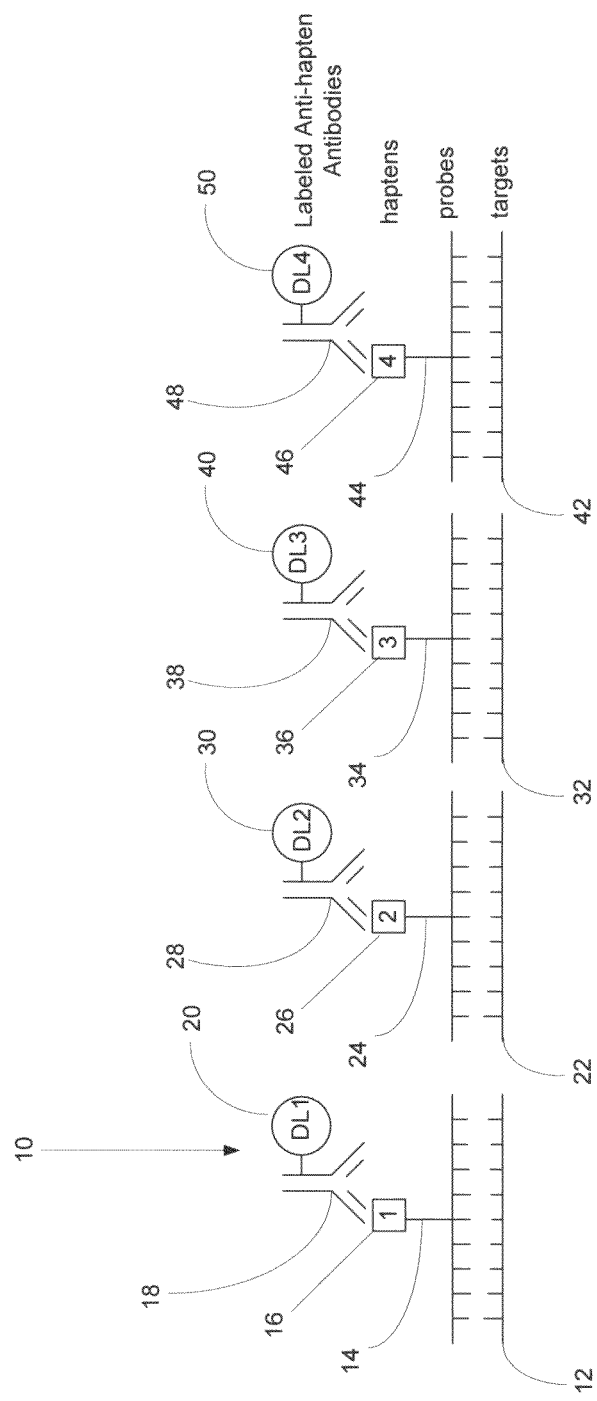
FIG. 1 is a schematic drawing illustrating one embodiment of a multiplexed in situ hybridization process.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts, such as aluminum hydroxide (Amphogel, Wyeth Laboratories, Madison, N.J.), and the MF59 microemulsion are the only vaccine adjuvants approved for human use. An aluminum hydrogel (available from Brentg Biosector, Copenhagen, Denmark is another common adjuvant).

In one embodiment, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199.

Amplification: Certain embodiments of the present invention allow a single target to be detected using plural visualization complexes, where the complexes can be the same or different, to facilitate identification and/or quantification of a particular target.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4 M^{-1}$ greater or at least $10^5 M^{-1}$ greater than a binding constant for other molecules in a biological sample.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art. Antibody fragments include proteolytic antibody fragments [such as $F(ab')_2$ fragments, Fab' fragments, Fab'-SH fragments and Fab fragments as are known in the art], recombinant antibody fragments (such as sFv fragments, dsFv fragments, bispecific sFv fragments, bispecific dsFv fragments, $F(ab)'_2$ fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079-5,874,541; 5,840,526; 5,800,988; and 5,759,808). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, $3^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

Antigen: A compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a *Bacillus* antigen, such as γPGA.

Avidin: Any type of protein that specifically binds biotin to the substantial exclusion of other small molecules that might be present in a biological sample. Examples of avidin include avidins that are naturally present in egg white, oilseed protein (e.g., soybean meal), and grain (e.g., corn/maize) and streptavidin, which is a protein of bacterial origin.

Binding affinity: The tendency of one molecule to bind (typically non-covalently) with another molecule, such as the tendency of a member of a specific binding pair for another member of a specific binding pair. A binding affinity can be measured as a binding constant, which binding affinity for a specific binding pair (such as an antibody/antigen pair or nucleic acid probe/nucleic acid sequence pair) can be at least $1 \times 10^5$ $M^{-1}$, such as at least $1 \times 10^6$ $M^{-1}$, at least $1 \times 10^7$ $M^{-1}$ or at least $1 \times 108$ $M^{-1}$. In one embodiment, binding affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity for an antibody/antigen pair is at least about $1 \times 10^8$ $M^{-1}$. In other embodiments, a high binding affinity is at least about $1.5 \times 10^8$ $M^{-1}$, at least about $2.0 \times 10^8$ $M^{-1}$, at least about $2.5 \times 10^8$ $M^{-1}$, at least about $3.0 \times 10^8$ $M^{-1}$, at least about $3.5 \times 10^8$ $M^{-1}$, at least about $4.0 \times 10^8$ $M^{-1}$, at least about $4.5 \times 10^8$ $M^{-1}$, or at least about $5.0 \times 10^8$ $M^{-1}$.

Carrier: A molecule to which a hapten or an antigen can be bound. Carrier molecules include immunogenic carriers and specific-binding carriers. When bound to an immunogenic carrier, the bound molecule may become immunogenic. Immunogenic carriers may be chosen to increase the immunogenicity of the bound molecule and/or to elicit antibodies against the carrier, which are diagnostically, analytically, and/or therapeutically beneficial. Covalent linking of a molecule to a carrier can confer enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups to which a reactant moiety can be attached. Specific binding carriers can by any type of specific binding moiety, including an antibody, a nucleic acid, an avidin, a protein-nucleic acid.

Examples of suitable immunogenic carriers are those that can increase the immunogenicity of a hapten and/or help elicit antibodies against the hapten which are diagnostically, analytically, and/or therapeutically beneficial. Useful carriers include polymeric carriers, which can be natural (such as proteins like ovalbumin or keyhole limpet hemocyanin) or derived from a natural polymer isolated from any organism (including viruses), semi-synthetic or synthetic materials containing one or more functional groups, for example primary and/or secondary amino groups, azido groups, hydroxyl groups, or carboxyl groups, to which a reactant moiety can be attached. The carrier can be water soluble or insoluble, and in some embodiments is a protein or polypeptide. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect. Immun.* 68:2161-66, 2000).

The immunogenic carrier can be a polypeptide, such as a polypeptide of a rotavirus, or of a virus other than a rotavirus. A non limiting, and far from exhaustive list of such other viruses includes Adeno-associated virus, Adenovirus, Avian infectious bronchitis virus, Baculovirus, Chicken pox, Corona virus, Cytomegalovirus, Distemper, Enterovirus, Epstein Barr virus, Feline leukemia virus, Flavivirus, Foot and mouth disease virus, Hepatitis A, Hepatitis B, Hepatitis C, Hepatitis E, Herpes species, Herpes simplex, Influenza virus, HIV-1, HIV-2, HTLV 1, Influenza A and B, Kunjin virus, Lassa fever virus, LCMV (lymphocytic choriomeningitis virus), lentivirus, Measles, Mengo virus, Morbillivirus, Myxovirus, Papilloma virus, Parovirus, Parainfluenza virus, Paramyxovirus, Parvovirus, Poko virus, Polio virus, Polyoma tumour virus, pseudorabies, Rabies virus, Reovirus, Respiratory syncytial virus, retrovirus, rhinovirus, Rinderpest, Rotavirus, Semliki forest virus, Sendai virus, Simian Virus 40, Sindbis virus, SV5, Tick borne encephalitis virus, Togavirus (rubella, yellow fever, dengue fever), Vaccinia virus, Venezuelan equine encephalomyelitis, Vesicular stomatis virus, metapneumovirus, norovirus, SARS virus, smallpox virus, picornaviruses, varicella zoster, and West Nile virus.

Alternatively, the immunogenic carrier polypeptide can be that of a bacteria or other pathogenic organism. Exemplary bacterial polypeptides include those of *Achromobacter xylosoxidans*, *Acinetobacter calcoaceticus*, preferably *A. anitratus*, *A. haemolyticus*, *A. alcaligenes*, and *A. lwoffi*, *Actinomyces israelii*, *Aeromonas hydrophilia*, *Alcaligenes* species, preferably *A. faecalis*, *A. odorans* and *A. denitrificans*, *Arizona hinshawii*, *Bacillus anthracis*, *Bacillus cereus*, *Bacteroides fragilis*, *Bacteroides melaminogenicus*, *Bordetella pertussis*, *Borrelia burgdorferi*, *Borrelia recurrentis*, *Brucella* species, preferably *B. abortus*, *B. suis*, *B. melitensis* and *B. canis*, *Calymmatobacterium granulomatis*, *Campylobacter coli* (e.g., the CjaA polypeptide), *Campylobacter fetus* ssp. *intestinalis*, *Campylobacter fetus* ssp. *jejuni*, *Chlamydia* species, preferably *C. psittaci* and *C. trachomatis*, *Chromobacterium violaceum*, *Citrobacter* species, preferably *C. freundii* and *C. diversus*, *Clostridium botulinum*, *Clostridium perfringens*, *Clostridium difficile*, *Clostridium tetani*, *Corynebacterium diphtheriae*, *Corynebacterium*, preferably *C. ulcerans*, *C. haemolyticum* and *C. pseudotuberculosis*, *Coxiella burnetii*, *Edwardsiella tarda*, *Eikenella corrodens*, *Enterobacter*, preferably *E. cloacae*, *E. aerogenes*, *E. hafniae* (also named *Hafnia alvei*) and *E. agglomerans*, *Erysipelothrix rhusiopathiae*, *Escherichia coli*, *Flavobacterium meningosepticum*, *Francisella tularensis*, *Fusobacterium nucleatum*, *Gardnerella vaginalis*, *Haemophilus ducreyi*, *Haemophilus influenzae*, *Helicobacter* species (e.g., the UreB polypeptide of *H. pylori*), *Klebsiella* species, preferably *K. pneumoniae*, *K. ozaenae* og *K. rhinoscleromatis*, *Legionella* species, *Leptospira interrogans*, *Listeria monocytogenes*, *Moraxella* species, preferably *M. lacunata* and *M. osloensis*, *Mycobacterium bovis*, *Mycobacterium leprae*, *Mycobacterium tuberculosis* (e.g., the CFP 10 polypeptide), *Mycoplasma* species, preferably *M. pneumoniae*, *Neisseria gonorrhoeae*, *Neisseria meningitidis*, *Nocardia* species, preferably *N. asteroides* and *N. brasiliensis*, *Pasteurella haemolytica*, *Pasteurella multocida*, *Peptococcus magnus*, *Plesiomonas shigelloides*, Pneumococci, *Proteus* species, preferably *P. mirabilis*, *P. vulgaris*, *P. rettgeri* and *P. morganii* (also named *Providencia rettgeri* and *Morganella morganii* respectively), *Providencia* species, preferably *P. akalifaciens*, *P. stuartii* and *P. rettgeri* (also named *Proteus rettgeri*), *Pseudomonas aeruginosa*, *Pseudomonas mallei*, *Pseudomonas pseudomallei*, *Rickettsia*, *Rochalimaia henselae*, *Salmonella* species, preferably *S. enteridis*, *S. typhi* and *S. derby*, and most preferably *Salmonella* species of the type *Salmonella* DT104, *Serratia* species, preferably *S. marcescens*, *Shigella dysenteriae*, *S. flexneri*, *S. boydii* and *S. sonnei*, *Spirillum minor*, *Staphylococcus aureus*, *Staphylococcus epidermidis*, *Staphylococcus saprophyticus*, *Streptobacillus moniliformis*, *Streptococcus*, preferably *S. faecalis*, *S. faecium* and *S. durans*, *Streptococcus agalactiae*, *Streptococcus pneumoniae*, *Streptococcus pyogenes* (e.g., the Sfb1 polypeptide), *Treponema carateum*, *Treponema pallidum*,

*Treponema pertenue*, preferably *T. pallidum, Ureaplasma urealyticum, Vibrio cholerae, Vibrio parahaemolyticus, Yersinia enterocolitica,* and *Yersinia pestis*.

Parasitic immunogenic carriers may for example be isolated and/or derived from Malaria (*Plasmodium falciparum, P. vivax, P. malariae*), *Schistosomes, Trypanosomes, Leishmania,* Filarial nematodes, Trichomoniasis, Sarcosporidiasis, *Taenia* (*T. saginata, T solium*), *Leishmania, Toxoplasma gondii,* Trichinelosis (*Trichinella spiralis*) or Coccidiosis (*Eimeria* species).

Illustrative fungal immunogenic carriers can be isolated and/or derived from a fungus selected from *Cryptococcus neoformans, Candida albicans, Aspergillus fumigatus* and Coccidioidomycosis.

Specific, non-limiting examples of water soluble polypeptide immunogenic carriers include, but are not limited to, natural, semi-synthetic or synthetic polypeptides or proteins from bacteria or viruses. In one embodiment, bacterial products for use as carriers include bacterial wall proteins and other products (for example, streptococcal or staphylococcal cell walls), and soluble antigens of bacteria. In another embodiment, bacterial products for use as carriers include bacterial toxins. Bacterial toxins include bacterial products that mediate toxic effects, inflammatory responses, stress, shock, chronic sequelae, or mortality in a susceptible host.

Specific, non-limiting examples of water insoluble polymeric carriers include, but are not limited to, aminoalkyl agarose (for example, aminopropyl or aminohexyl SEPHAROSE; Pharmacia Inc., Piscataway, N.J.), aminopropyl glass, cross-linked dextran, and the like, to which a reactive moiety can be attached. Other carriers can be used, provided that a functional group is available for covalently attaching a reactive group.

Chimeric antibody: An antibody that has framework residues from one species, such as human, and CDRs (which generally confer antigen binding) from another species, such as a murine antibody that specifically binds RET.

Conjugating, joining, bonding or linking: Covalently linking one molecule to another molecule to make a larger molecule. For example, making two polypeptides into one contiguous polypeptide molecule, or to covalently attaching a hapten or other molecule to a polypeptide, such as an scFv antibody. In the specific context, the terms include reference to joining a ligand, such as an antibody moiety, to an effector molecule ("EM"). The linkage can be either by chemical or recombinant means. "Chemical means" refers to a reaction between the antibody moiety and the effector molecule such that there is a covalent bond formed between the two molecules to form one molecule.

Coupled: When applied to a first atom or molecule being "coupled" to a second atom or molecule can be both directly coupled and indirectly coupled. A secondary antibody provides an example of indirect coupling. One specific example of indirect coupling is a rabbit anti-hapten primary antibody that is bound by a mouse anti-rabbit IgG antibody, that is in turn bound by a goat anti-mouse IgG antibody that is covalently linked to a detectable label.

Epitope: An antigenic determinant. These are particular chemical groups or contiguous or non-contiguous peptide sequences on a molecule that are antigenic, that is, that elicit a specific immune response. An antibody binds a particular antigenic epitope.

Hapten: A molecule, typically a small molecule that can combine specifically with an antibody, but typically is substantially incapable of being immunogenic except in combination with a carrier molecule.

Homopolymer: This term refers to a polymer formed by the bonding together of multiple units of a single type of molecular species, such as a single monomer (for example, an amino acid).

Humanized antibody: An antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Humanized immunoglobulin: an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences.

Immune Response: A response of a cell of the immune system, such as a B-cell, T-cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Immunogenic Conjugate or Composition: A term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed. One specific example of a type of immunogenic composition is a vaccine.

Immunogen: A compound, composition, or substance which is capable, under appropriate conditions, of stimulating the production of antibodies or a T-cell response in an animal, including compositions that are injected or absorbed into an animal.

Immunologically Effective Dose: An immunologically effective dose of the disclosed conjugates of the disclosure is therapeutically effective and will prevent, treat, lessen, or attenuate the severity, extent or duration of a disease or condition.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or Treating a Disease: Inhibiting the full development of a disease or condition, for example, in a subject who is at risk for a disease such as anthrax. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Detectable Label: A detectable compound or composition that is attached directly or indirectly to another molecule, such as an antibody or a protein, to facilitate detection of that molecule. Specific, non-limiting examples of labels include fluorescent tags, enzymes, and radioactive isotopes.

Linker peptide: A peptide within an antibody binding fragment (such as an Fv fragment) which serves to indirectly bond the variable heavy chain to the variable light chain. "Linker" can also refer to a peptide serving to link a targeting moiety, such as a scFv, to an effector molecule, such as a cytotoxin or a detectable label.

Mammal: This term includes both human and non-human mammals. Similarly, the term "subject" includes both human and veterinary subjects.

Molecule of interest or Target: A molecule for which the presence, location and/or concentration is to be determined. Examples of molecules of interest include proteins and nucleic acid sequences tagged with haptens.

Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

Multiplex, -ed, -ing: Embodiments of the present invention allow multiple targets in a sample to be detected substantially simultaneously, or sequentially, as desired, using plural different conjugates. Multiplexing can include identifying and/or quantifying nucleic acids generally, DNA, RNA, peptides, proteins, both individually and in any and all combinations. Multiplexing also can include detecting two or more of a gene, a messenger and a protein in a cell in its anatomic context.

Nanoparticle: A nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Neoplasia and Tumor: The process of abnormal and uncontrolled growth of cells. Neoplasia is one example of a proliferative disorder.

The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents. The term "pharmaceutically acceptable carrier" should be distinguished from "carrier" as described above in connection with a hapten/carrier conjugate or an antigen/carrier conjugate.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protein: A molecule, particularly a polypeptide, comprised of amino acids.

Purified: The term "purified" does not require absolute purity; rather, it is intended as a relative term. Thus, for example, a purified peptide, protein, conjugate, or other active compound is one that is isolated in whole or in part from proteins or other contaminants. Generally, substantially purified peptides, proteins, conjugates, or other active compounds for use within the disclosure comprise more than 80% of all macromolecular species present in a preparation prior to admixture or formulation of the peptide, protein, conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Quantum dot: A nanoscale particle that exhibits size-dependent electronic and optical properties due to quantum confinement. Quantum dots have, for example, been constructed of semiconductor materials (e.g., cadmium selenide and lead sulfide) and from crystallites (grown via molecular beam epitaxy), etc. A variety of quantum dots having various surface chemistries and fluorescence characteristics are commercially available from Invitrogen Corporation, Eugene, Oreg. (see, for example, U.S. Pat. Nos. 6,815,064, 6,682,596 and 6,649,138, each of which patents is incorporated by reference herein). Quantum dots are also commercially available from Evident Technologies (Troy, N.Y.). Other quantum dots include alloy quantum dots such as ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN quantum dots (Alloy quantum dots and methods for making the same are disclosed, for example, in US Application Publication No. 2005/0012182 and PCT Publication WO 2005/001889).

Reactive Groups: Formulas throughout this application refer to "reactive groups," which can be any of a variety of groups suitable for coupling a first unit to a second unit as described herein. For example, the reactive group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbodiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, mannich condensation products, iodination reaction products, and combinations thereof. Photoreactive chemical functional groups include aryl azides, halogenated aryl azides, benzophonones, diazo compounds, diazirine derivatives, and combinations thereof.

Sample: A biological specimen containing genomic DNA, RNA (including mRNA), protein, or combinations thereof, obtained from a subject. Examples include, but are not limited to, peripheral blood, urine, saliva, tissue biopsy, surgical specimen, amniocentesis samples and autopsy material. In one example, a sample includes a biopsy of an adenocarcinoma, a sample of noncancerous tissue, a sample of normal tissue (from a subject not afflicted with a known disease or disorder).

Specific binding moiety: A member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4$ $M^{-1}$ greater or $10^5$ $M^{-1}$ greater than a binding constant for either of the two members of the binding pair with other molecules in a biological sample). Particular examples of specific binding moieties include specific binding proteins (for example, antibodies, lectins, avidins such as streptavidins, and protein A), nucleic acids sequences, and protein-nucleic acids. Specific binding moieties can also include the molecules (or portions thereof) that are specifically bound by such specific binding proteins.

Therapeutically Effective Amount: A quantity of a specified agent sufficient to achieve a desired effect in a subject being treated with that agent. For example, this may be the amount of a conjugate useful in increasing resistance to, preventing, ameliorating, and/or treating infection and disease. Ideally, a therapeutically effective amount of an agent is an amount sufficient to increase resistance to, prevent, ameliorate, and/or treat infection and without causing a substantial cytotoxic effect in the subject. The effective amount of an agent useful for increasing resistance to, preventing, ameliorating, and/or treating infection and disease in a subject will be dependent on the subject being treated, the severity of the affliction, and the manner of administration of the therapeutic composition.

Vaccine: A vaccine is a pharmaceutical composition that elicits a prophylactic or therapeutic immune response in a subject. In some cases, the immune response is a protective response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a polysaccharide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

The antigenic polypeptide can be that of a rotavirus, or of a virus other than a rotavirus. A non limiting, and far from exhaustive list of such other viruses includes Adeno-associated virus, Adenovirus, Avian infectious bronchitis virus, Baculovirus, Chicken pox, Corona virus, Cytomegalovirus, Distemper, Enterovirus, Epstein Barr virus, Feline leukemia virus, Flavivirus, Foot and mouth disease virus, Hepatitis A, Hepatitis B, Hepatitis C, Hepatitis E, Herpes species, Herpes simplex, Influenza virus, HIV-1, HIV-2, HTLV 1, Influenza A and B, Kunjin virus, Lassa fever virus, LCMV (lymphocytic choriomeningitis virus), lentivirus, Measles, Mengo virus, Morbillivirus, Myxovirus, Papilloma virus, Parovirus, Parainfluenza virus, Paramyxovirus, Parvovirus, Poko virus, Polio virus, Polyoma tumour virus, pseudorabies, Rabies virus, Reovirus, Respiratory syncytial virus, retrovirus, rhinovirus, Rinderpest, Rotavirus, Semliki forest virus, Sendai virus, Simian Virus 40, Sindbis virus, SV5, Tick borne encephalitis virus, Togavirus (rubella, yellow fever, dengue fever), Vaccinia virus, Venezuelan equine encephalomyelitis, Vesicular stomatis virus, metapneumovirus, norovirus, SARS virus, smallpox virus, picornaviruses, varicella zoster, and West Nile virus.

Alternatively, the antigenic polypeptide can be that of a bacteria or other pathogenic organism. Exemplary bacterial polypeptides include those of *Achromobacter xylosoxidans*, *Acinetobacter calcoaceticus*, preferably *A. anitratus*, *A. haemolyticus*, *A. alcaligenes*, and *A. lwoffii*, *Actinomyces israelii*, *Aeromonas hydrophilia*, *Alcaligenes* species, preferably *A. faecalis*, *A. odorans* and *A. denitrificans*, *Arizona hinshawii*, *Bacillus anthracis*, *Bacillus cereus*, *Bacteroides fragilis*, *Bacteroides melaminogenicus*, *Bordetella pertussis*, *Borrelia burgdorferi*, *Borrelia recurrentis*, *Brucella* species, preferably *B. abortus*, *B. suis*, *B. melitensis* and *B. canis*, *Calymmatobacterium granulomatis*, *Campylobacter coli* (e.g., the CjaA polypeptide), *Campylobacter fetus* ssp. intestinalis, *Campylobacter fetus* ssp. *jejuni*, *Chlamydia* species, preferably *C. psittaci* and *C. trachomatis*, *Chromobacterium violaceum*, *Citrobacter* species, preferably *C. freundii* and *C. diversus*, *Clostridium botulinum*, *Clostridium perfringens*, *Clostridium difficile*, *Clostridium tetani*, *Corynebacterium diphtheriae*, *Corynebacterium*, preferably *C. ulcerans*, *C. haemolyticum* and *C. pseudotuberculosis*, *Coxiella burnetii*, *Edwardsiella tarda*, *Eikenella corrodens*, *Enterobacter*, preferably *E. cloacae*, *E. aerogenes*, *E. hafniae* (also named *Hafnia alvei*) and *E. agglomerans*, *Erysipelothrix rhusiopathiae*, *Escherichia coli*, *Flavobacterium meningosepticum*, *Francisella tularensis*, *Fusobacterium nucleatum*, *Gardnerella vaginalis*, *Haemophilus ducreyi*, *Haemophilus influenzae*, *Helicobacter* species (e.g., the UreB polypeptide of *H. pylori*), *Klebsiella* species, preferably *K. pneumoniae*, *K. ozaenae* og *K. rhinoscleromatis*, *Legionella* species, *Leptospira interrogans*, *Listeria monocytogenes*, *Moraxella* species, preferably *M. lacunata* and *M. osloensis*, *Mycobacterium bovis*, *Mycobacterium leprae*, *Mycobacterium tuberculosis* (e.g., the CFP10 polypeptide), *Mycoplasma* species, preferably *M. pneumoniae*, *Neisseria gonorrhoeae*, *Neisseria meningitidis*, *Nocardia* species, preferably *N. asteroides* and *N. brasiliensis*, *Pasteurella haemolytica*, *Pasteurella multocida*, *Peptococcus magnus*, *Plesiomonas shigelloides*, Pneumococci, *Proteus* species, preferably *P. mirabilis*, *P. vulgaris*, *P. rettgeri* and *P. morganii* (also named *Providencia rettgeri* and *Morganella morganii* respectively), *Providencia* species, preferably *P. alcalifaciens*, *P. stuartii* and *P. rettgeri* (also named *Proteus rettgeri*), *Pseudomonas aeruginosa*, *Pseudomonas mallei*, *Pseudomonas pseudomallei*, *Rickettsia*, *Rochalimaia henselae*, *Salmonella* species, preferably *S. enteridis*, *S. typhi* and *S. derby*, and most preferably *Salmonella* species of the type *Salmonella* DT 104, *Serratia* species, preferably *S. marcescens*, *Shigella dysenteriae*, *S. flexneri*, *S. boydii* and *S. sonnei*, *Spirillum minor*, *Staphylococcus aureus*, *Staphylococcus epidermidis*, *Staphylococcus saprophyticus*, *Streptobacillus moniliformis*, *Streptococcus*, preferably *S. faecalis*, *S. faecium* and *S. durans*, *Streptococcus agalactiae*, *Streptococcus pneumoniae*, *Streptococcus pyogenes* (e.g., the Sfb1 polypeptide), *Treponema carateum*, *Treponema pallidum*, *Treponema pertenue*, preferably *T. pallidum*, *Ureaplasma urealyticum*, *Vibrio cholerae*, *Vibrio parahaemolyticus*, *Yersinia enterocolitica*, and *Yersinia pestis*.

Parasitic haptens or antigens may for example be selected from Malaria (*Plasmodium falciparum*, *P. vivax*, *P. malariae*), Schistosomes, Trypanosomes, Leishmania, Filarial nematodes, Trichomoniasis, Sarcosporidiasis, *Taenia* (*T. saginata*, *T solium*), Leishmania, *Toxoplasma gondii*, Trichinelosis (*Trichinella spiralis*) or Coccidiosis (*Eimeria* species).

Illustrative fungal haptens or antigens could be derived a fungus selected from *Cryptococcus neoformans*, *Candida albicans*, *Aspergillus fumigatus* and Coccidioidomycosis.

The hapten or antigen may also be derived from any animal, including for example vertebrates. For example the hapten or antigen may comprise components derived from ovalbumin, keyhole limpet hemocyanin and sperm-whale myoglobulin.

Examples of suitable carriers are those that can increase the immunogenicity of the conjugate and/or elicit antibodies against the carrier which are diagnostically, analytically, and/or therapeutically beneficial. Useful carriers include polymeric carriers, which can be natural, semi-synthetic or synthetic materials containing one or more functional groups, for example primary and/or secondary amino groups, azido groups, hydroxyl groups, or carboxyl groups, to which a reactant moiety can be attached. The carrier can be water soluble or insoluble, and in some embodiments is a protein or polypeptide. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect. Immun.* 59:4555-61, 1991; Szu et al., *J. Exp. Med.* 166:1510-24, 1987; and Pavliakova et al., *Infect.*

*Immun.* 68:2161-66, 2000). A carrier can be useful even if the antibody that it induces is not of benefit by itself.

Specific, non-limiting examples of water soluble polypeptide carriers include, but are not limited to, natural, semisynthetic or synthetic polypeptides or proteins from bacteria or viruses. In one embodiment, bacterial products for use as carriers include bacterial wall proteins and other products (for example, streptococcal or staphylococcal cell walls), and soluble antigens of bacteria. In another embodiment, bacterial products for use as carriers include bacterial toxins. Bacterial toxins include bacterial products that mediate toxic effects, inflammatory responses, stress, shock, chronic sequelae, or mortality in a susceptible host.

Specific, non-limiting examples of water insoluble carriers include, but are not limited to, aminoalkyl agarose (for example, aminopropyl or aminohexyl SEPHAROSE; Pharmacia Inc., Piscataway, N.J.), aminopropyl glass, cross-linked dextran, and the like, to which a reactive moiety can be attached. Other carriers can be used, provided that a functional group is available for covalently attaching a reactive group.

II. Haptens

Disclosed embodiments of such haptens include pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof.

For the general formulas provided below, if no substituent is indicated, a person of ordinary skill in the art will appreciate that the substituent is hydrogen. A bond that is not connected to an atom, but is shown, for example, extending to the interior of a ring system, indicates that the position of such substituent is variable. A curved line drawn through a bond indicates that some additional structure is bonded to that position, typically a linker or the functional group or moiety used to couple the hapten to a carrier. Moreover, if no stereochemistry is indicated for compounds having one or more chiral centers, all enantiomers and diasteromers are included. Similarly, for a recitation of aliphatic or alkyl groups, all structural isomers thereof also are included.

1. Azoles

A first general class of haptens of the present invention is azoles, typically oxazoles and pyrazoles, more typically nitro oxazoles and nitro pyrazoles, having the following general chemical formula.

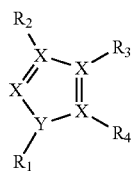

With reference to this general formula, n is 0-2, most typically 0 or 1. $R_1$-$R_4$ can be any organic group that does not interfere with, and potentially facilitates, the function as a hapten. More specifically, $R_1$-$R_4$ independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, cyano (—CN), ester, ether, exomethylene, halogen, heteroaryl, heterocyclic, hydroxyl, hydroxylamine, oxime (HO—N=), keto, such as aliphatic ketones, nitro, sulfhydryl, sulfonyl, sulfoxide, and combinations thereof. Two or more of these $R_1$-$R_4$ substituents also may be atoms, typically carbon atoms, in a ring system bonded or fused to the compounds having the illustrated general formula. At least one of the $R_1$-$R_4$ substituents is bonded to a linker or is a functional group suitable for coupling to a linker or a carrier molecule. $R_1$-$R_4$ most typically are aliphatic, hydrogen or nitro groups, even more typically alkyl, hydrogen or nitro, and still even more typically lower (10 or fewer carbon atoms) alkyl, hydrogen, nitro, or combinations thereof. The number of nitro groups can vary, but most typically there are 1 or 2 nitro groups. X independently is nitrogen or carbon. Y is oxygen, sulfur or nitrogen. If Y is oxygen or sulfur, then there is no $R_1$ group, and n=0. If Y is nitrogen, then there is at least one $R_1$ group.

A person of ordinary skill in the art will appreciate that, for compounds having 2 or more W groups, the relative positions thereof is variable. For example, a diazole could have nitrogen atoms at the 1 and 2 positions, or the 1 and 3 positions. Moreover, more than two heteroatoms also are possible, such as with triazines.

At least one of $R_1$-$R_4$ for these azole compounds is bonded to some other group or is a variable functional group. For example, the illustrated compounds can be coupled either directly to a carrier or to a linker at any of the suitable positions about the azole ring.

Working embodiments typically were mono- or dinitro pyrazole derivatives, such that at least one of $R_1$-$R_4$ is a nitro group, and perhaps two of $R_1$-$R_4$ are nitro groups, with the remaining $R_1$-$R_4$ being used to couple the hapten to a linker or a carrier.

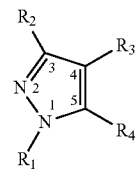

One particular compound had the following structure.

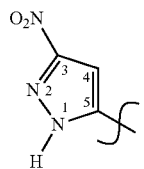

2. Nitroaryl

A second general class of haptens of the present invention are nitroaryl compounds. Exemplary nitroaryl compounds include, without limitation, nitrophenyl, nitrobiphenyl, nitrotriphenyl, etc., and any and all heteroaryl counterparts, having the following general chemical formula.

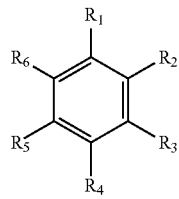

With reference to this general formula, such compounds have at least one, and optionally plural, nitro groups. Thus, at least one of $R_1$-$R_6$ is nitro. If more than one of $R_1$-$R_6$ is nitro, all combinations of relative ring positions of plural nitro substituents, or nitro substituents relative to other ring substituents, are included within this class of disclosed haptens. Dinitroaryl compounds are most typical. A person of ordinary skill in the art will appreciate that as the number of nitro groups increases, the number of remaining ring substituents in the general formula decreases. These substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer carbon atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, ether, halogen, heteroaryl, hydroxyl, hydroxlyamine, oxime (HO—N=), keto, such as aliphatic ketones, nitro, sulfhydryl, sulfonyl, sulfoxide, exomethylene, and combinations thereof. At least one of the $R_1$-$R_6$ substituents is bonded to a linker or is a functional group suitable for coupling to a linker or a carrier molecule.

Two or more of the $R_1$-$R_6$ substituents also may be atoms, typically carbon atoms, in a ring system, such as napthalene (shown below) or anthracene type derivatives. Ring systems other than 6-membered ring systems can be formed, such as fused 6-5 ring systems.

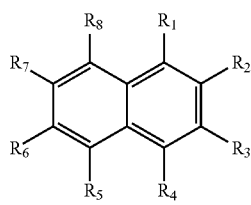

Again, at least on of the ring positions occupied by $R_1$-$R_8$ is bonded to a linker or is a variable functional group suitable for coupling, such as by covalent bonding, to a carrier molecule. For example, nitroaryl compounds of the present invention can include a functional group for coupling to a carrier, or to a linker, at various optional ring locations.

Working embodiments are exemplified by nitrophenyl compounds. Solely by way of example, mononitroaryl compounds are exemplified by nitrocinnamide compounds. One embodiment of a nitrocinnamide-based compound is exemplified by 4,5-dimethoxy-2-nitrocinnamide, shown below.

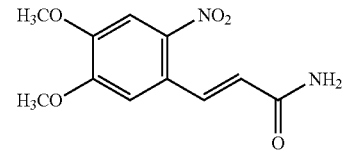 [SMILES: COc1cc(/C=C/C(N)=O)c([N+](=O)[O-])cc1OC]

The nitrophenyl class of compounds also is represented by dinitrophenyl compounds. At least one of the remaining carbon atoms of the ring positions not having a nitro group is bonded to a functional group, to a linker, or directly to a carrier. Any and all combinations of relative positions of these groups are included within the class of disclosed haptens.

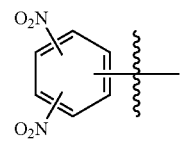

Working embodiments are more particularly exemplified by 2,4-dinitrophenyl compounds coupled to a linker, as illustrated below.

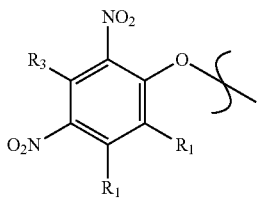

$R_1$-$R_3$ are as stated above.

3. Benzofurazans

Benzofurazans and derivatives thereof are another class of haptens within the scope of the present invention. A general formula for the benzofurazan-type compounds is provided below.

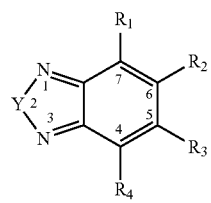

$R_1$-$R_4$ substituents independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of these $R_1$-$R_4$ substituents also may be atoms, typically carbon atoms, in a ring system bonded or fused to the compounds having the illustrated general formula. At least one of the $R_1$-$R_4$ substituents is bonded to a linker or directly to a carrier. Y is a carbon atom having $R_5$ and $R_6$ substituents, where $R_5$ and $R_6$ are as stated for $R_1$-$R_4$, oxygen or sulfur, typically oxygen.

Compounds where Y is oxygen are more particularly exemplified by compounds having the following structure, where $R_1$-$R_4$ are as stated above, and most typically are independently hydrogen and lower alkyl.

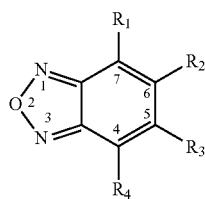

One working embodiment of a compound according to this class of haptens had the following chemical structure.

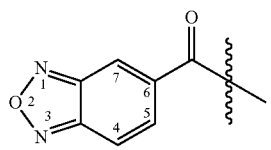 [SMILES: *C(=O)c1ccc2nonc2c1]

4. Triterpenes

Triterpenes are another class of haptens within the scope of the present invention. The basic ring structure common to the cyclic triterpenes has four six-membered fused rings, A-D, as indicated below.

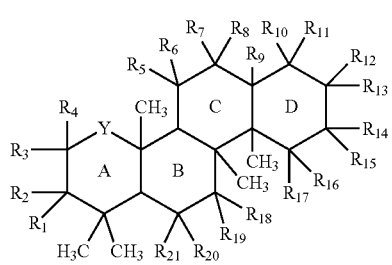

A number of publications discuss naturally occurring, semi-synthetic and synthetic triterpene species within the genus of triterpenes useful for practicing the present invention, including: J. C. Connolly and R. A. Hill, Triterpenoids, Nat. Prod. Rep., 19, 494-513 (2002); Baglin et al., A Review of Natural and Modified Beculinic, Ursolic and Echinocystic Acid Derivatives as Potential Antitumor and Anti-HIV Agents, Mini Reviews in Medicinal Chemistry, 3, 525-539; W. N. and M. C. Setzer, Plant-Derived Triterpenoids as Potential Antineoplastic Agents, Mini Reviews in Medicinal Chemistry, 3, 540-556 (2003); and Baltina, Chemical Modification of Glycyrrhizic Acid as a Route to New Bioactive Compounds for Medicine, Current Medicinal Chemistry, 10, 155-171 92003); each of which is incorporated herein by reference. Based on the present disclosure and working embodiments thereof, as well as disclosures provided by these prior publications, and with reference to this first general formula, $R_1$-$R_{21}$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of these $R_1$-$R_{21}$ substituents also may be atoms, typically carbon atoms, in a ring system bonded or fused to the compounds having the illustrated general formula. At least one of the $R_1$-$R_{21}$ substituents is bonded to a linker or is a functional group suitable for coupling to a linker or a carrier molecule. Y is a bond, thereby defining a 5-membered ring, or is a carbon atom bearing $R_{22}$ and $R_{23}$ substituents, where these R groups are as stated above.

Disclosed embodiments of triterpenes exemplifying this class of haptens also may include an E ring, and this E ring can be of various ring sizes, particularly rings having 5-7 atoms, typically carbon atoms, in the ring. For example, the E ring might be a 6-membered ring, as indicated by the following general formula, where $R_1$-$R_{31}$ are as stated above for $R_1$-$R_{21}$.

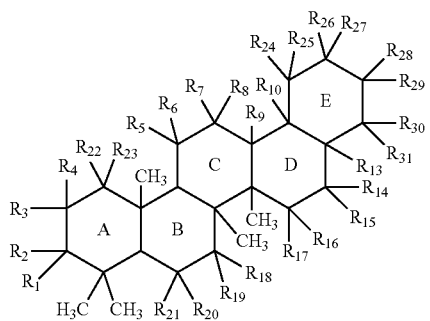

The following general formula indicates that the $R_{13}$ substituent may be an acyl group bearing an $R_{33}$ substituent selected from hydrogen, hydroxyl, ester, i.e. —$OR_{34}$ where $R_{34}$ is aliphatic, typically alkyl or substituted alkyl, and even more typically lower alkyl, amido, including primary amide (—$NH_2$), secondary amide (—$NHR_{35}$) and tertiary amide (—$NR_{35}R_{36}$), where $R_{35}$ and $R_{36}$ are aliphatic, typically lower aliphatic, more typically alkyl, substituted alkyl, and even more typically lower alkyl or substituted lower alkyl. This general formula also indicates that the $R_1$ substituent often is an $OR_{32}$ substituent, where $R_{32}$ is hydrogen or aliphatic, more typically alkyl or substituted alkyl, ane even more typically lower alkyl. The remaining R groups are as stated above with reference to the first general formula.

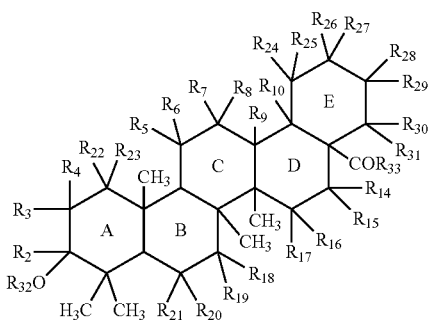

The E ring also may be a 5 membered ring, as indicated by the formula below where the $R_1$-$R_{29}$ groups are as stated above for $R_1$-$R_{21}$.

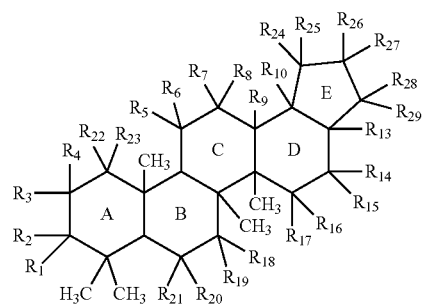

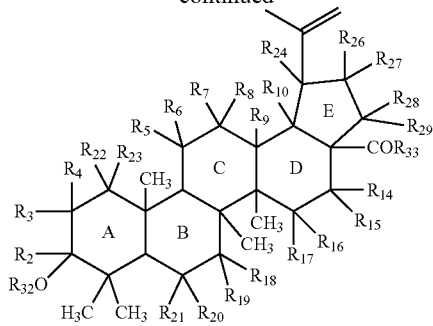

With reference to these general formulae, the $R_1$-$R_{29}$ groups are as stated above for $R_1$-$R_{21}$.

As with exemplary compounds where the E ring is a 6-membered ring, compounds where the E ring is a 5-membered ring also can include substituents at $R_1$ and $R_{13}$ as discussed above. Specifically, this general formula indicates that the $R_{13}$ substituent may be an acyl group bearing an $R_{33}$ substituent selected from hydrogen, hydroxyl, ester, i.e. —$OR_{34}$ where $R_{34}$ is aliphatic, typically alkyl or substituted alkyl, and even more typically lower alkyl, amido, including primary amide (—$NH_2$), secondary amide (—$NHR_{35}$) and tertiary amide (—$NR_{35}R_{36}$), where $R_{35}$ and $R_{36}$ are aliphatic, typically lower aliphatic, more typically alkyl, substituted alkyl, and even more typically lower alkyl or substituted lower alkyl. This general formula also indicates that the $R_1$ substituent often is an $OR_{32}$ substituent, where $R_{32}$ is hydrogen or aliphatic, more typically alkyl or substituted alkyl, ane even more typically lower alkyl.

Exemplary compounds also include 5-membered rings as both the A and the E ring. General formulae for such exemplary compounds are provided below, where the $R_1$-$R_{29}$ substituents are as stated above.

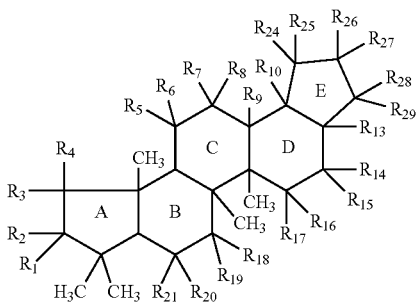

Again, the $R_1$ and $R_{13}$ substituents can be oxygen-based functional groups. The $R_{13}$ substituent may be an acyl group bearing an $R_{33}$ substituent selected from hydrogen, hydroxyl, ester, i.e. —$OR_{34}$ where $R_{34}$ is aliphatic, typically alkyl or substituted alkyl, and even more typically lower alkyl, amido, including primary amide (—$NH_2$), secondary amide (—$NHR_{35}$) and tertiary amide (—$NR_{35}R_{36}$), where $R_{35}$ and $R_{36}$ are aliphatic, typically lower aliphatic, more typically alkyl, substituted alkyl, and even more typically lower alkyl or substituted lower alkyl. This general formula also indicates that the $R_1$ substituent often is an $OR_{32}$ substituent, where $R_{32}$ is hydrogen or aliphatic, more typically alkyl or substituted alkyl, and even more typically lower alkyl.

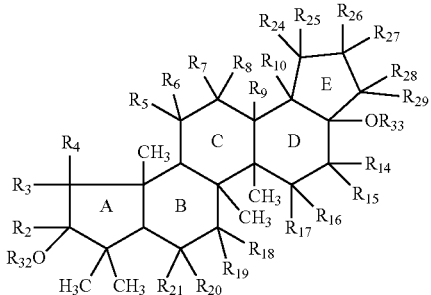

Exemplary triterpenes of the present invention also may include one or more sites of unsaturation in one or more of the A-E rings. Exemplary compounds often have at least one site of unsaturation in the C ring, such as the double bond in the C ring as indicated below.

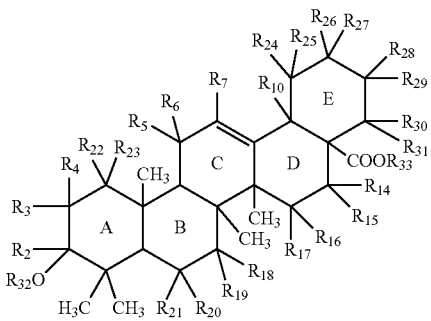

The site of unsaturation may be an alpha, beta unsaturated ketone, such as illustrated below for the C ring.

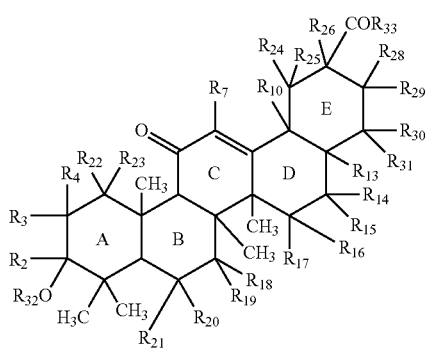

The triterpenes also have a number of stereogenic carbon atoms. A person of ordinary skill in the art will appreciate that particular enantiomers are most likely to occur naturally. While the naturally occurring enantiomer may be most available, and/or effective, for practicing disclosed embodiments, all other possible stereoisomers are within the scope of the present invention. Moreover, other naturally occurring triterpenes, or synthetic derivatives thereof, or fully synthetic compounds, may have (1) different stereochemistry, (2) different substituents, and further may be substituted at positions that are not substituted in the naturally occurring compounds. The general formulae provided above do not indicate stereochemistry at the chiral centers. This is to signify that both enantiomers at each chiral center, and all diastereomeric isomer combinations thereof, are within the scope of the present invention.

Particular working embodiments of the present invention are exemplified by the following general formula, in which the substituents are as stated above.

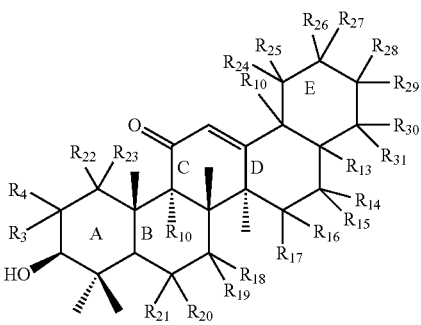

The stereochemistry and substituents for a naturally occurring triterpene useful as a hapten for practicing the present invention are shown below.

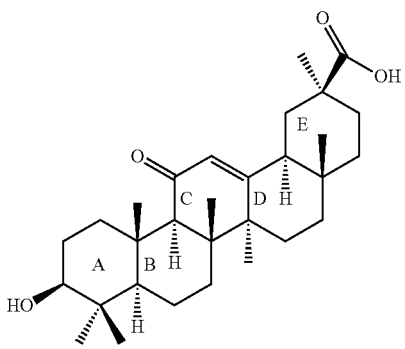

The hydroxyl group in the A ring typically is oxidized to a carbonyl functional group in working embodiments. As a result, the carbon atom bearing the carbonyl group is no longer a chiral center.

5. Ureas and Thioureas

Ureas and thioureas, particularly aryl and heteroaryl ureas and thioureas, are another class of haptens within the scope of the present invention. A general formula for urea-based haptens of the present invention is provided below.

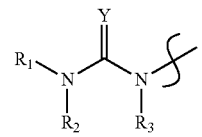

With reference to this general formula, $R_1$-$R_3$ are independently hydrogen, aliphatic, substituted aliphatic, typically alkyl, substituted alkyl, and even more typically lower alkyl and substituted lower alkyl, cyclic, heterocyclic, aryl and heteroaryl. More specifically, $R_1$ typically is aryl or aliphatic, often having at least one site of unsaturation to facilitate chromophoric activity. $R_2$ and $R_3$ most typically are independently hydrogen and lower alkyl. Y is oxygen (urea derivatives) or sulfur (thioureas).

Aryl derivatives typically have the following formula.

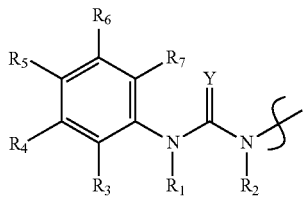

$R_1$-$R_7$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. At least one of the $R_3$-$R_7$ substituents also is bonded to a linker or to a carrier molecule. Two or more of these $R_3$-$R_7$ substituents available for such bonding also may be atoms, typically carbon atoms, in a ring system bonded or fused to the compounds having the illustrated general formula.

Additional rings also can be present, as indicated by the exemplary structures provided below. The R groups are as stated above for $R_1$-$R_7$ and Y is oxygen or sulfur.

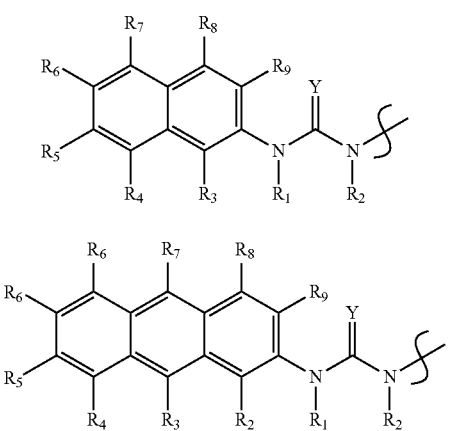

A particular subclass of thioureas is represented below.

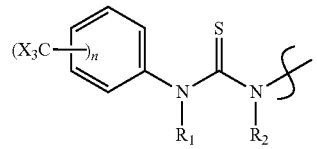

With reference to this general formula, n is 1 to 5, typically 1-2, $R_1$ and $R_2$ are independently hydrogen or lower alkyl, and X independently is a halide or combinations of different halides.

One example of a working embodiment of a phenyl thiourea is provided below.

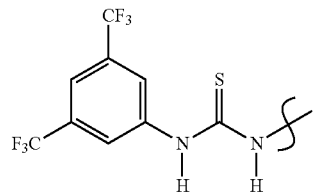 [SMILES: CNC(=S)Nc1cc(C(F)(F)F)cc(C(F)(F)F)c1]

The trifluoromethyl groups are shown in the 2 and 4 positions relative to the thiourea moiety. A person of ordinary skill in the art will appreciate that compounds having all relative positions for disubstituted compounds, such as 2,3, and compounds having more than two trihaloalkyl substituents, at all possible relative positions of such plural trihaloalkyl substituents, also are within the scope of the present invention. A particular example of a rhodamine thiourea hapten has the following formula.

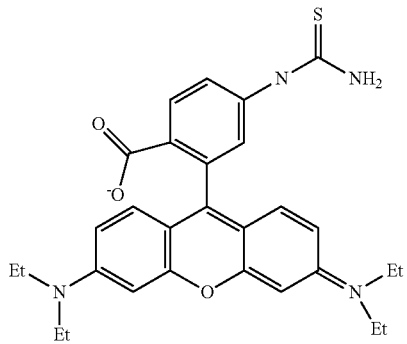

6. Rotenones

Rotenone and rotenone-based haptens, collectively referred to as rotenoids, provide another class of haptens within the scope of the present invention. A first general formula for rotenone, and rotenone-based haptens, is provided below.

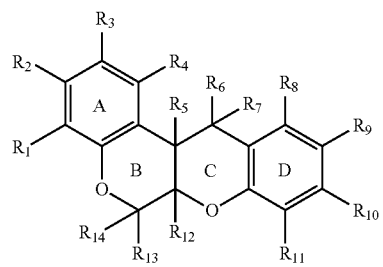

A number of publications discuss naturally occurring, semi-synthetic and synthetic rotenoids that are useful for describing the genus of rotenoids useful for practicing the present invention, including: Leslie Crombie and Donald Whiting, Biosynthesis in the Rotenoids Group of Natural Products: Application of Isotope Methodology, Phytochemistry, 49, 1479-1507 (1998); and Nianbai Fang, and John Casida, Cube Resin Insecticide: Identification and Biological Activity of 29 Rotenoid Constituents; each of which is incorporated herein by reference. Based on the present disclosure and working embodiments, as well as disclosures provided by these prior publications, and with reference to this first general formula, $R_1$-$R_{14}$ independently are hydrogen, aldehyde, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto) amino, amino acid, amido, cyano (—CN), halogen, hydroxyl, hydroxylamine, oxime oxime ether (e.g., methoxyimine, $CH_3$—O—N=) alkyl hydroxyl, particularly lower alkyl hydroxyl, carbonyl, keto, such as aliphatic ketones, nitro, sulfhydryl, sulfonyl, sulfoxide, carboxyl, carboxylate (and salts thereof, such as Group I metal or ammonium ion carboxylates) ester, alkyl ester, acyl, exomethylene, ether, cyclic, heterocyclic, aryl, alkyl aryl, such as benzyl, heteroaryl, polysaccharides, carbohydrate, monosaccharides, such as glucose and fructose, disaccharides, such as sucrose and lactose, oligosaccharides and polysaccharides, and combinations thereof. Two or more of these $R_1$-$R_{14}$ substituents also may be atoms, typically carbon atoms, in a ring system bonded or fused to the compounds having the illustrated general formula. At least one of the $R_1$-$R_{14}$ substituents also is bonded to a linker or to a carrier molecule.

While $R_6$ and $R_7$ can be as stated above, such substituents more typically independently are hydrogen, $OR_{15}$, where $R_{15}$ is hydrogen, aliphatic, substituted aliphatic, typically alkyl, substituted alkyl, and even more typically lower alkyl and substituted lower alkyl, such as lower alkyl halides, cyclic, heterocyclic, aryl and heteroaryl, —$NR_{21}$, where $R_{21}$ is hydrogen, aliphatic, substituted aliphatic, typically alkyl, substituted alkyl, and even more typically lower alkyl and substituted lower alkyl, such as lower alkyl halides, cyclic, heterocyclic, aryl and heteroaryl, or N-L-RG, where L is a linker or a reactive group, such as an amine, as discussed in more detail herein.

$R_6$ and $R_7$ also can form a double bond, such as a double bond to an oxygen to form a carbonyl. If $R_6$ and/or $R_7$ are not -L-RG, then at least one of the R substituents is bonded to a linker or to a carrier molecule.

The B ring also can include at least one additional site of unsaturation. For example, $R_5$ and $R_{12}$ can form a double bond.

$R_{10}$ and $R_{11}$ can be joined in a 5- or 6-membered ring. For example, $R_{10}$ and $R_{11}$ may define a pyran or furan ring, and more particularly is a substituted and/or unsaturated pyran or furan ring.

Certain exemplary rotenone-based haptens of the present invention also typically satisfy the following second general formula.

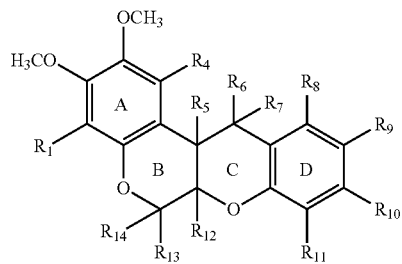

With reference to this second general formula, the R substituents are as stated above. If $R_6$ or $R_7$ is not -L-RG, then at least one of the remaining R groups is bonded to a linker or to a carrier.

$R_{10}$ and $R_{11}$ can be joined in a 5- or 6-membered ring, such as a pyran or furan, and more particularly a substituted and/or unsaturated pyran or furan ring. Thus, a third general formula useful for describing certain rotenone-based haptens of the present invention is provided below, where the R substituents are as stated above.

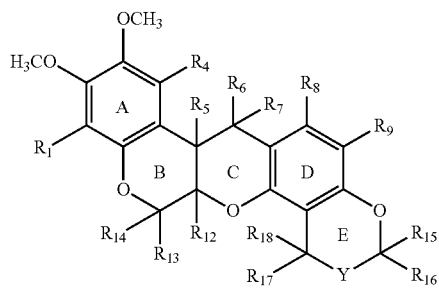

Y is a bond, thereby defining a 5-membered ring, or is a carbon atom in a 6-membered ring bearing $R_{19}$ and $R_{20}$ substituents, as shown below, where the R substituents are as stated above.

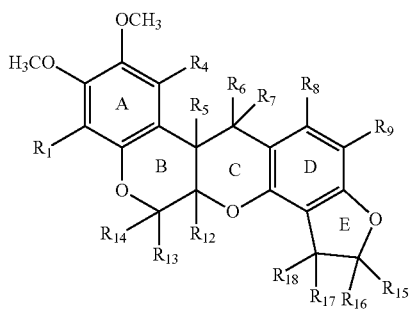

-continued

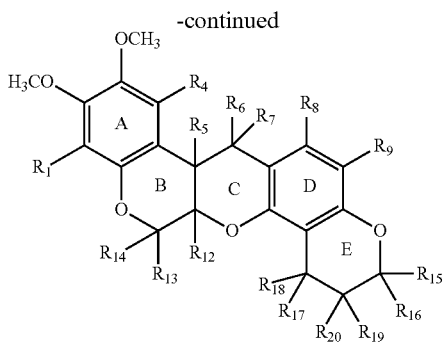

$R_5$ and $R_{12}$ at the ring juncture are shown without indicating particular stereochemistry. The naturally occurring compound has a cis-ring juncture, but racemic mixtures also are useful for practicing the present invention. Also, the trans stereoisomer likely quickly equilibrates to form the racemic mixture.

Working embodiments of compounds within this class more typically satisfy the following third general formula.

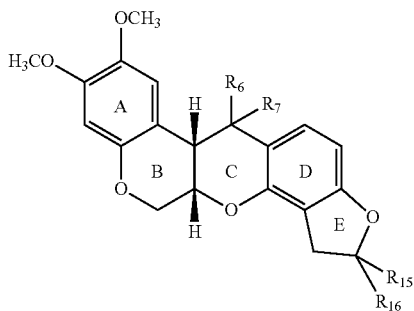

With reference to this general formula, $R_6$ and $R_7$ are hydrogen, alkyl, or define a double bond, such as to oxygen to form a carbonyl. $R_{15}$ and $R_{16}$ independently are hydrogen and aliphatic, typically lower aliphatic, such as alkenyl, one example of which is isoprene, as shown below.

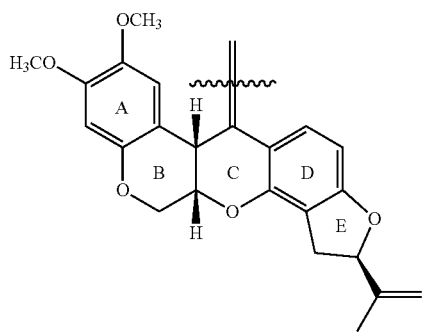

Again, a particular enantiomer is shown in the above formula, but a person of ordinary skill in the art will appreciate that the scope of the present invention is not limited to the particular enantiomer shown. Instead, all stereoisomers that act as haptens also are within the scope of the disclosure. All substitutions discussed above for this class of compounds applies to this particular compound. Other substitutions also are readily apparent to a person of ordinary skill in the art. For example, the methoxy groups on the A ring can be any alkoxy compound, particular lower alkoxy groups. The isoprene unit also provides an olefin that can be synthetically modified, perhaps to provide an alternative position, or at least a second position, for coupling the hapten to a linker or a carrier molecule. For example, the olefin could be converted to an alcohol by hydroboration. It also could be converted to a halide or an epoxide either for use as a hapten or as intermediates useful for further transformation.

A fourth general formula for describing rotenone-based haptens of the present invention is particularly directed to rotenone isoxazolines, as provided below.

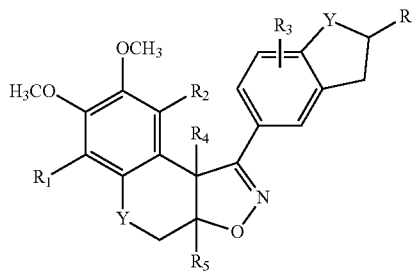

R-$R_5$ independently are hydrogen, aldehyde, alkoxy, aliphatic, particularly lower aliphatic, including all branched chain isomers, such as isoprene, and all stereoisomers, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto) amino, amino acid, amido, cyano (—CN), halogen, hydroxyl, hydroxylamine, oxime (HO—N=), oxime ether (e.g., methoxyimine, $CH_3$—O—N=) alkyl hydroxyl, particularly lower alkyl hydroxyl, carbonyl, keto, such as aliphatic ketones, nitro, sulfhydryl, sulfonyl, sulfoxide, carboxyl, carboxylate (and salts thereof, such as Group I metal or ammonium ion carboxylates) ester, alkyl ester, acyl, exomethylene, ether, cyclic, heterocyclic, aryl, alkyl aryl, such as benzyl, heteroaryl, polysaccharides, carbohydrate, monosaccharides, such as glucose and fructose, disaccharides, such as sucrose and lactose, oligosaccharides and polysaccharides, and combinations thereof. At least one of the R-$R_5$ substituents also is bonded to a linker or to a carrier molecule. Y is oxygen, nitrogen, or sulfur.

A particular working embodiment of a rotenone-based hapten satisfying this fourth general formula is provided below.

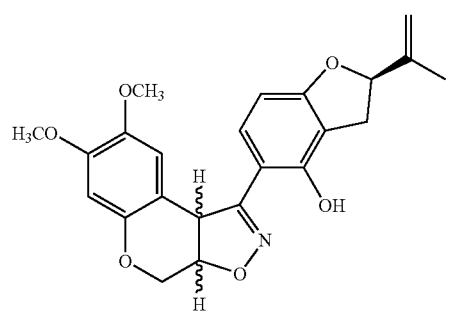

7. Oxazoles and Thiazoles

Oxazole and thiazole sulfonamides provide another class of haptens within the scope of the present invention. A general formula for oxazole and thiazole sulfonamides is provided below.

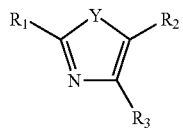

With reference to this first general formula $R_1$-$R_3$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of these $R_1$-$R_3$ substituents also may be atoms, typically carbon atoms, in a ring system bonded or fused to the compounds having the illustrated general formula. At least one of the $R_1$-$R_3$ substituents is bonded to a linker or is a functional group suitable for coupling to a linker or a carrier molecule. Y is oxygen or sulfur, typically sulfur.

For certain exemplary working embodiments, $R_1$ has been amido, such as the amide derivatives shown below. $R_2$ provides a position for coupling to a linker or to a carrier molecule, although the positions indicated by $R_1$ and $R_2$ also provide alternative or additional positions for coupling to a linker and/or carrier molecule. $R_2$, for certain working embodiments, has been —$SO_2$, and has been used to couple linkers by forming a sulfonamide. Thus, a second general formula for working embodiments of haptens exemplifying this class of haptens is indicated below, where the $R_3$-$R_6$ substituents and Y are as stated above.

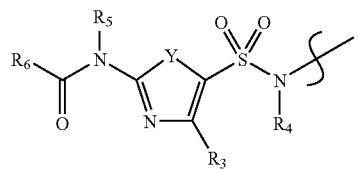

For certain working embodiments $R_6$ has been alkyl, particularly lower alkyl, such as methyl, and Y has been sulfur.

One working embodiment of a compound according to this class of haptens had the following chemical structure.

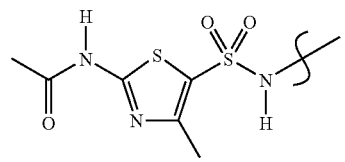 [SMILES: CCNS(=O)(=O)c1sc(NC(C)=O)nc1C]

The thiazole or oxazole might also be part of a larger ring system. For example, the 5-membered oxazole or thiazole might be coupled to at least one additional ring, such as a phenyl ring, as indicated below.

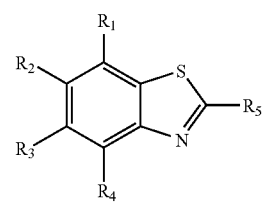

While the $R_1$-$R_5$ groups generally can be as stated above, such compounds also provide a position for coupling to a linker and/or to a carrier molecule, such as a $R_5$. One possible sulfonamide derivative is provided below.

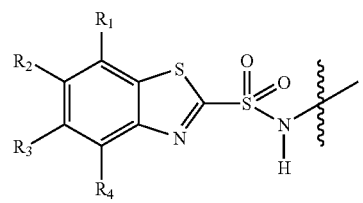

8. Coumarins

Coumarin and coumarin derivatives provide another class of haptens within the scope of the present invention. A general formula for coumarin and coumarin derivatives is provided below.

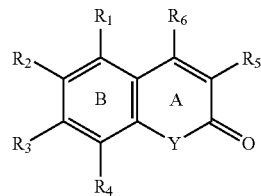

With reference to this general formula, $R_1$-$R_6$ independently are selected from: hydrogen, acyl, aldehydes, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. At least one of the $R_1$-$R_6$ substituents also typically is bonded to a linker or a carrier molecule. Certain working embodiments have used the position indicated as having an $R_5$ substituent for coupling to a linker or carrier molecule. The 4 position can be important if fluorescence is used to detect these compounds. Substituents other than hydrogen at the 4 position are believed to quench fluorescence, although such derivatives still may be chromophores. Y is oxygen, nitrogen or sulfur. Two or more of the $R_1$-$R_6$ substituents available for forming such compounds also may be atoms, typically carbon atoms, in a ring system bonded or fused to the compounds having the illustrated general formula. Exemplary embodiments of these types of compounds are provided below.

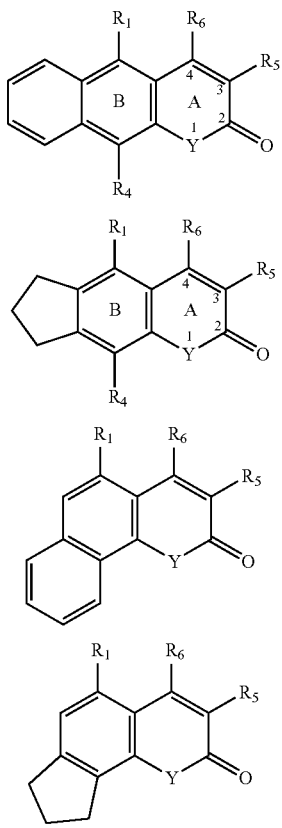

A person of ordinary skill in the art will appreciate that the rings also could be heterocyclic and/or heteroaryl.

Working embodiments typically were fused A-D ring systems having at least one carrier molecule coupling position, with one possible coupling position being indicated below.

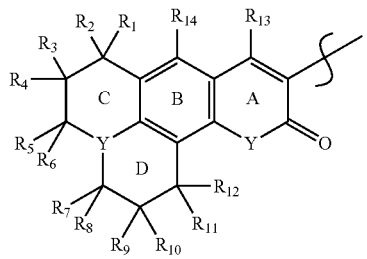

With reference to this general formula, the R and Y variable groups are as stated above. Most typically, $R_1$-$R_{14}$ independently are hydrogen or lower alkyl. Particular embodiments of coumarin-based haptens include 2,3,6,7-tetrahydro-11-oxo-1H,5H,11H-[1]benzopyrano[6,7,8-ij]quinolizine-10-carboxylic acid

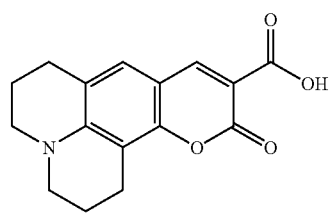

and diethyl coumarin

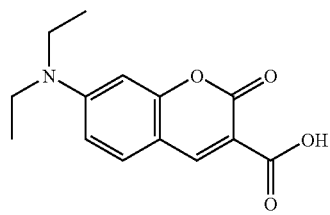 [SMILES: CCN(CC)c1ccc2cc(C(=O)O)c(=O)oc2c1]

9. Cyclolignans

Lignin-based compounds, particularly cyclolignans, such as Podophyllotoxin and derivatives thereof, provide another class of haptens within the scope of the present invention. A first general formula for these cyclolignin-based derivatives is provided below.

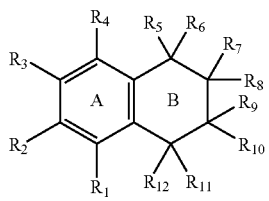

A number of publications discuss naturally occurring, semi-synthetic and synthetic cyclolignans that are useful for describing the genus of cyclolignans useful for practicing the present invention, including: Stephanie Desbene and Sylviane Giorgi-Renault, Drugs that Inhibit Tubulin Polymerization: The Particuar Case of Podophyllotoxin and Analogues, Curr. Med. Chem. Anti-Cancer Agents, 2, 71-90 (2002); M. Gordaliza et al., Podophyllotoxin: Distribution, Sources, Applications and New Cytotoxic Derivatives, Toxicon, 44, 441-459 (2004); Phillipe Meresse et al., Etoposide: Discovery and Medicinal Chemistry, Current Medicinal Chemistry, 11, 2443-2466 (2004); M. Pujol et al., Synthesis and Biological Activity of New Class of Dioxygenated Anticancer Agents, Curr. Med. Chem. Anti-Cancer Agents, 5, 215-237 (2005); and Youngjae You, Podophyllotoxin Derivatives: Current Synthetic Approaches for New Anticancer Agents, Current Pharmaceutical Design, 11, 1695-1717 (2005); each of which is incorporated herein by reference. Based on the present disclosure and working embodiments, as well as disclosures provided by these prior publications, and with reference to this first general formula, $R_1$-$R_{12}$ typically are selected from hydrogen, aldehyde, alkoxy, aliphatic, particularly lower aliphatic, such as isoprene, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto) amino, amino acid, amido, cyano (—CN), halogen, hydroxyl, hydroxylamine, oxime, oxime ether (e.g., methoxyimine, $CH_3$—O—N=) alkyl hydroxyl, particularly lower alkyl hydroxyl, carbonyl, keto, such as aliphatic ketones, nitro, sulfhydryl, sulfonyl, sulfoxide, carboxyl, carboxylate (and salts thereof, such as Group I metal or ammonium ion carboxylates) ester, alkyl ester, acyl, exomethylene, ether, cyclic, heterocyclic, aryl, alkyl aryl, such as benzyl, heteroaryl, polysaccharides, carbohydrate, monosaccharides, such as glucose and fructose, disaccharides, such as sucrose and lactose, oligosaccharides and polysaccharides, and combinations thereof. At least one of $R_1$-$R_{12}$ provides a position for coupling the compound to a linker or to a carrier molecule. Furthermore, certain of the R groups may be atoms in a ring system. For example, $R_2$ and $R_3$, as well as two of $R_7$-$R_{10}$, can be joined together in a ring system. At least one of $R_{12}$ and $R_{11}$ also often is an aryl group, such as a benzene ring or a substituted benzene ring.

Certain working embodiments also satisfied the following second general formula, where the R substituents are as stated above.

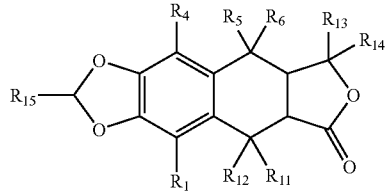

Exemplary compounds where at least one of $R_{11}$ and $R_{12}$ is an aryl group have the following general formula, where the R substituents are as stated above.

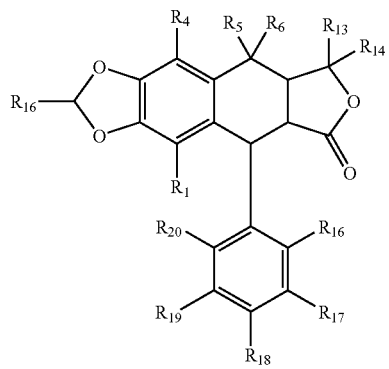

$R_{16}$-$R_{20}$ are generally as stated above, but more typically independently are hydrogen or alkoxy, typically lower alkoxy, such as methoxy, as shown below.

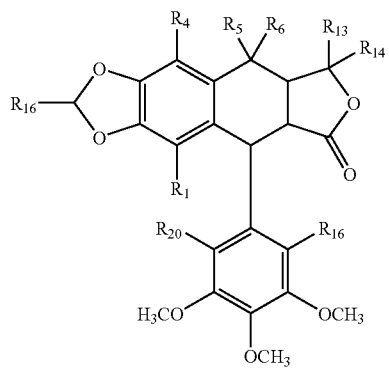

At least one of the R substituents typically is bonded to a linker, is a reactive functional group capable of reacting with a linker, or is -L-RG. For example, $R_5$ often is -L-RG.

$R_5$ and $R_6$ also may form a double bond, such as a double bond to oxygen to form a carbonyl functional group or a double bond to a nitrogen atom to form an imine. Certain exemplary compounds where $R_5$ and $R_6$ form a double bond had the following general formula, where the remaining R substituents are as stated above. Y is selected from nitrogen, oxygen or sulfur. If Y is nitrogen, then the nitrogen atom may further have bonded thereto hydrogen, or some atom, functional group or chemical moiety other than hydrogen. For example, the nitrogen may have an aliphatic substituent, such an alkyl group, an aryl or heteroaryl substituent, or a substituted aryl or heteroaryl substituent, such as alkyl and/or alkoxy substituted aryl or heteroaryl substituent.

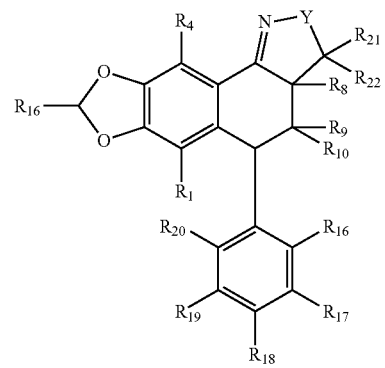

$R_{16}$-$R_{20}$ independently are selected from hydrogen and alkoxy, more typically lower alkoxy, such as methoxy, as indicated below.

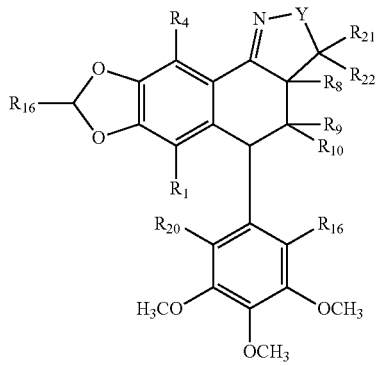

As with all hapten conjugates of the present invention, at least one of the R substituents typically is bonded to a linker, is a reactive functional group capable of reacting with a linker, is -L-RG, or is directly bonded to a carrier. For example, $R_9$ often is -L-RG.

The chemical structure for Podophyllotoxin, a compound exemplifying this cyclolignan class of haptens, is provided below.

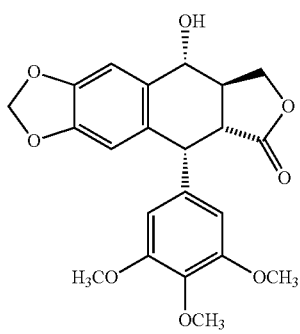 [SMILES: COc1cc([C@@H]2c3cc4c(cc3[C@H](O)[C@H]3COC(=O)[C@H]23)OCO4)cc(OC)c1OC]

Podophyllotoxin, also referred to as podofilox, is a non-alkaloid toxin having a molecular weight of 414.40 and a compositional formula of $C_{22}H_{22}O_8$. Podophyllotoxin is present at concentrations of 0.3 to 1.0% by mass in the rhizome of American Mayapple Podophyllum peltatum. The melting point of Podophyllotoxin is 183.3-184.0° C.

Accordingly, cyclolignans according to the present invention based substantially on the Podophyllotoxin structure have the following general formula, where Y is selected from nitrogen, oxygen or sulfur.

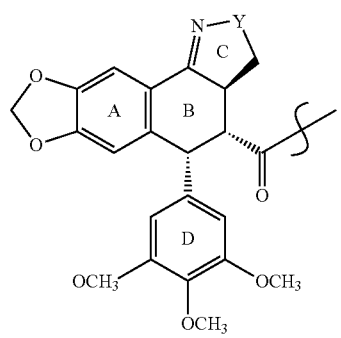

A specific example of a cyclolignan hapten according to the present invention is shown below.

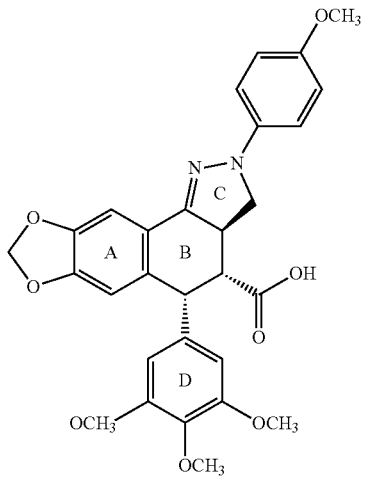

This compound was made starting with Podophyllotoxin. The hydroxyl group of Podophyllotoxin was oxidized to a ketone. The ketone was then reacted with a substituted hydrazine to produce the compound indicated above. The hydrazine reagent can be substituted as desired, including aliphatic and aryl substituents.

10. Heterobiaryl

Another general class of haptens of the present invention is heterobiaryl compounds, typically phenyl quinolines and quinoxalines. Disclosed heterobiaryl compounds have a first general chemical formula as below.

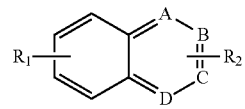

With reference to this general formula, A-D are selected from carbon, nitrogen, oxygen, and sulfur, and any and all combinations thereof. Most typically A-D are carbon or nitrogen. $R_1$-$R_2$ substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, alkoxy aryl, such as methoxy and ethoxy, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, exomethylene, and combinations thereof. Two or more of the $R_1$-$R_2$ substituents, most typically plural $R_1$ substituents, also may be atoms, typically carbon atoms, in a ring system bonded or fused to the compounds having the illustrated general formula. At least one of the $R_1$-$R_2$ substituents typically is bonded to a linker or directly to a carrier.

Particular embodiments of the heterobiaryl compounds have the following formula.

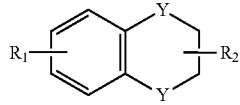

R1 and R2 are as stated above for the first general formula. Y is oxygen, nitrogen or sulfur, typically nitrogen. If Y is nitrogen, then the formula also can include double bonds to the one or more nitrogen atoms.

Compounds having a single heteroatom are exemplified by phenylquinolines, such as follows.

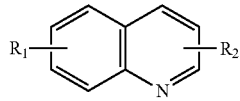

More particular embodiments include aryl substituted haptens, exemplified by the following general formula.

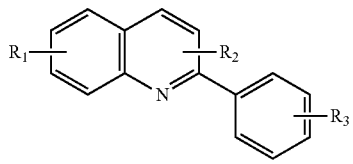

With reference to this general formula, $R_1$-$R_3$ are as indicated above. More typically, $R_1$ is hydrogen, $R_2$ is acyl, and $R_3$ is alkoxy. A particular example, 2-(3,4-dimethoxyphenyl)quinoline-4-carboxylic acid, is provided below.

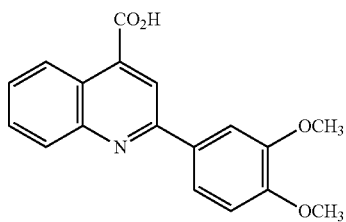

Compounds having two heteroatoms are represented by quinoxalines, as indicated by the general formula below.

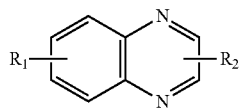

A particular example of biaryl-diheteroatom hapten of the present invention is exemplified by 3-hydroxy-2-quinoxalinecarbamide, below. Again, the $R_1$ and $R_2$ substituents are as stated above with respect to this class of haptens.

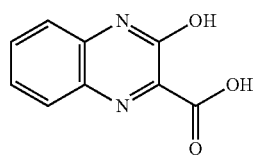 [SMILES: O=C(O)c1nc2ccccc2nc1O]

11. Azoaryl

Another general class of haptens of the present invention is azoaryl compounds, such as azobenzenes, having a first general chemical formula as below.

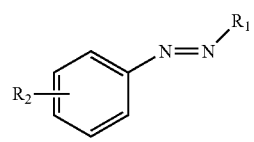

$R_1$-$R_2$ substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, alkoxy aryl, such as methoxy and ethoxy, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, alkyl ester, ether, halogen, heteroaryl, hydroxyl, hydroxylamine, oxime (HO—N=), keto, such as aliphatic ketones, nitro, sulfhydryl, sulfonyl, sulfoxide, sulfonyl, exomethylene, and combinations thereof. Two ore more $R_2$ substituents also may be atoms, typically carbon atoms, in a ring system bonded or fused to the compounds having the illustrated general formula. For example, 2 $R_2$ substituents may form a fused phenyl ring, or a fused heterocyclic or heteroaryl structure.

Certain disclosed azoaryl compounds have a first amine substituent and a second aryl substituent. These compounds typically have the following formula.

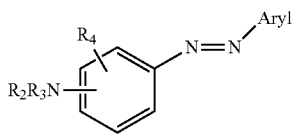

With reference to this general formula, $R_2$-$R_4$ are as stated above with respect to this class of haptens, with particular embodiments having $R_2$-$R_3$ aliphatic, particularly alkyl, more particularly lower alkyl, and $R_4$ hydrogen.

A third general formula for describing azoaryl compounds is provided below.

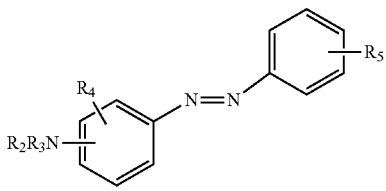

$R_2$-$R_5$ are as stated above for this particular class of haptens. At least one of $R_2$-$R_5$ defines a position for coupling a linker or carrier to the azoaryl hapten to form a conjugate. For example, $R_5$ may be a sulfonyl halide functional group. Sulfonyl halides, such as that shown below, are useful functional groups for coupling linkers to the azoaryl haptens.

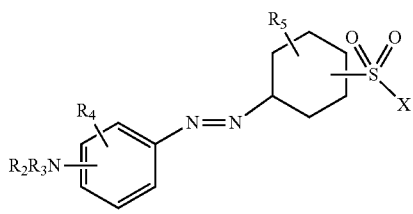

With reference to this formula, $R_2$-$R_5$ are as stated above. X is a halide. A particular embodiment of these azoaryl haptens, 4-(dimethylamino)azobenzene-4'-sulfonyl chloride, has the formula provided below.

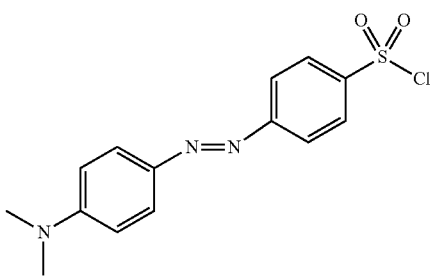 [SMILES: CN(C)c1ccc(/N=N/c2ccc(S(=O)(=O)Cl)cc2)cc1]

12. Benzodiazepines

Another class of haptens according to the present invention is the benzodiazepine haptens, having a first general formula as indicated below.

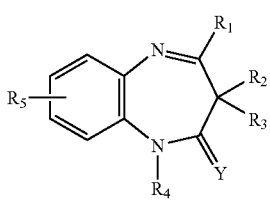

$R_1$-$R_5$ independently are selected from: acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer atoms, such as methyl, ethyl, propyl, isopropyl, and butyl, substituted alkyl, such as alkyl halide (e.g. —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, cyano (—CN), ester, ether, exomethylene, halogen, heteroaryl, heterocyclic, hydrogen, hydroxyl, hydroxylamine, oxime (HO—N=), keto, such as aliphatic ketones, nitro, sulfhydryl, sulfonyl, sulfoxide, and combinations thereof. Two or more of the $R_5$ substituents also may be atoms, typically carbon atoms, in a ring system bonded or fused to the compounds having the illustrated general formula. At least one of the $R_1$-$R_5$ positions is bonded to a linker or is occupied by a functional group suitable for coupling to a linker or a carrier molecule. $R_1$-$R_5$ most typically are aliphatic, aryl, hydrogen, or hydroxyl, even more typically alkyl, hydrogen or phenyl. Y is oxygen or sulfur, most typically oxygen.

Particular embodiments of the benzodiazepine haptens have $R_1$ aryl, as indicated below.

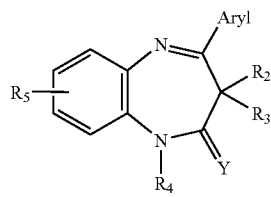

For these embodiments, $R_2$-$R_5$ are as stated above for this class of haptens, more typically such substituents are independently selected from aliphatic, particular alkyl, hydrogen and hydroxyl. Certain disclosed embodiments are phenyl compounds, as illustrated below.

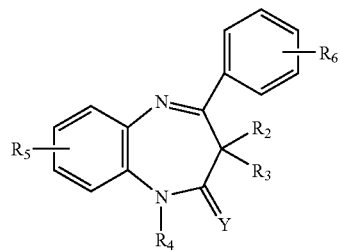

Again, $R_2$-$R_6$ are as stated above, but more typically such substituents are independently selected from aliphatic, particularly alkyl, hydrogen and hydroxyl. Certain disclosed embodiments are phenyl compounds, as illustrated below. A particular embodiment, 4-(2-hydroxyphenyl)-1H-benzo[b][1,4]diazepine-2(3H)-one, is provided below.

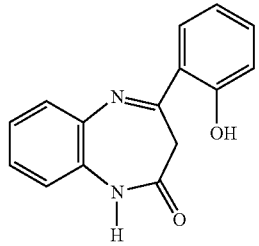 [SMILES: O=C1CC(c2ccccc2O)=Nc2ccccc2N1]

III. Linkers

1. General

As indicated by the general formula hapten-optional linker-carrier conjugates of the present application may include linkers. Any linker currently known for this purpose, or developed in the future, can be used to form conjugates of the present invention by coupling to the haptens disclosed herein. Useful linkers can either be homo- or heterobifunctional, but more typically are heterobifunctional.

2. Aliphatic

Solely by way of example, and without limitation, a first class of linkers suitable for forming disclosed hapten conjugates are aliphatic compounds, such as aliphatic hydrocarbon chains having one or more sites of unsaturation, or alkyl chains. The aliphatic chain also typically includes terminal functional groups, including by way of example and without limitation, a carbonyl-reactive group, an amine-reactive group, a thiol-reactive group or a photo-reactive group, that facilitate coupling to haptens and other desired compounds, such as specific binding moieties. The length of the chain can vary, but typically has an upper practical limit of about 30 atoms. Chain links greater than about 30 carbon atoms have proved to be less effective than compounds having smaller chain links. Thus, aliphatic chain linkers typically have a chain length of from about 1 carbon atom to about 30 carbon atoms. However, a person of ordinary skill in the art will appreciate that, if a particular linker has greater than 30 atoms, and still operates efficiently for linking the hapten to a carrier molecule coupling unit, and the conjugate still functions as desired, then such chain links are still within the scope of the present invention.

3. Alkylene Oxides

A second class of linkers useful for practicing the present invention are the alkylene oxides. The alkylene oxides are represented herein by reference to glycols, such as ethylene glycols. Hapten conjugates of the present invention have proved particularly useful if the hydrophilicity of the linker is increased relative to their hydrocarbon chains. As a result, the alkylene oxides, such as the glycols, have proved useful for practicing this invention. A person of ordinary skill in the art will appreciate that, as the number of oxygen atoms increases, the hydrophilicity of the compound also may increase. Thus, linkers of the present invention typically have a formula of $(-OCH_2CH_2O-)_n$ where n is from about 2 to about 15, but more particularly is from about 2 to about 8.

Heterobifunctional polyalkyleneglycol linkers useful for practicing certain disclosed embodiments of the present invention are described in assignee's co-pending applications, including "Nanoparticle Conjugates," U.S. patent application Ser. No. 11/413,778, filed Apr. 28, 2006; "Antibody Conjugates," U.S. application Ser. No. 11/413,415, filed Apr. 27, 2006; and "Molecular Conjugate," U.S. Provisional Patent Application No. 60/739,794, filed Nov. 23, 2005; all of which applications are incorporated herein by reference. A person of ordinary skill in the art will appreciate that the linkers disclosed in these applications can be used to link specific binding moieties, signal generating moieties and haptens in any and all desired combinations. Heterobifunctional polyalkyleneglycol linkers are disclosed below, and their use exemplified by reference to coupling specific binding moieties, such as antibodies and nucleic acids, to haptens and detectable labels. In particular, conjugates of anti-hapten antibodies and detectable labels and conjugates of primary antibodies or nucleic acids with haptens are exemplified below.

One particular embodiment of a linker for use with disclosed conjugates is a heterobifunctional polyalkyleneglycol linker having the general structure shown below:

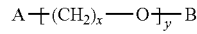

wherein A and B include different reactive groups, x is an integer from 2 to 10 (such as 2, 3 or 4), and y is an integer from 1 to 50, for example, from 2 to 30 such as from 3 to 20 or from 4 to 12. One or more hydrogen atoms can be substituted for additional functional groups such as hydroxyl groups, alkoxy groups (such as methoxy and ethoxy), halogen atoms (F, Cl, Br, I), sulfato groups and amino groups (including mono- and di-substituted amino groups such as dialkyl amino groups.

A and B of the linker can independently include a carbonyl-reactive group, an amine-reactive group, a thiol-reactive group or a photo-reactive grouHeerop, but are not the same. Examples of carbonyl-reactive groups include aldehyde- and ketone-reactive groups like hydrazine derivatives and amines. Examples of amine-reactive groups include active esters such as NHS or sulfo-NHS, isothiocyanates, isocyanates, acyl azides, sulfonyl chlorides, aldehydes, glyoxals, epoxides, oxiranes, carbonates, aryl halides, imidoesters, anhydrides and the like. Examples of thiol-reactive groups include non-polymerizable Michael acceptors, haloacetyl groups (such as iodoacetyl), alkyl halides, maleimides, aziridines, acryloyl groups, vinyl sulfones, benzoquinones, aromatic groups that can undergo nucleophilic substitution such as fluorobenzene groups (such as tetra and pentafluorobenzene groups), and disulfide groups such as pyridyl disulfide groups and thiols activated with Ellman's reagent. Examples of photo-reactive groups include aryl azide and halogenated aryl azides. Alternatively, A and/or B can be a functional group that reacts with a specific type of reactive group. For example, A and/or B can be an amine group, a thiol group, or a carbonyl-containing group that will react with a corresponding reactive group (such as an amine-reactive group, thiol-reactive group or carbonyl-reactive group, respectively) that has been introduced or is otherwise present on a hapten and/or a carrier. Additional examples of each of these types of groups will be apparent to those skilled in the art. Further examples and information regarding reaction conditions and methods for exchanging one type of reactive group for another are provided in Hermanson, "Bioconjugate Techniques," Academic Press, San Diego, 1996, which is incorporated by reference herein. In a particular embodiment, a thiol-reactive group is other than vinyl sulfone.

In some embodiments, a thiol-reactive group of the heterobifunctional linker is covalently attached to a specific-binding moiety and an amine-reactive group of the heterobifunctional linker is covalently attached to an amine-reactive group of a hapten derivative (such as an activated ester formed by reacting a carboxylic acid group with SMCC), the nanoparticle, or vice versa. For example, a thiol-reactive group of the heterobifunctional linker can be covalently attached to a cysteine residue (such as following reduction of cystine bridges) of the specific-binding moiety or a thiol-reactive group of the heterobifunctional linker can be covalently attached to a thiol group that is introduced to the specific-binding moiety, and the amine-reactive group is attached to an activated hapten derivative having an amine reactive group such as an activated ester. Where the conjugate includes an anti-hapten antibody conjugated to a detectable label, a thiol-reactive group of the heterobifunctional linker can be covalently attached to the antibody and an amine reactive group of the heterobifunctional linker can be covalently attached to the antibody and an amine reactive group of the heterobifunctional linker can be covalently attached to the detectable label or vice versa.

Alternatively, an aldehyde-reactive group of the heterobifunctional linker can be covalently attached to a specific binding moiety and a either a functional group or a different reactive group of the linker is attached to a hapten. Where the specific binding moiety is an anti-hapten antibody and the antibody is conjugated to a detectable label, an aldehyde-reactive group of the heterobifunctional linker can be covalently attached to the antibody and an amine-reactive group of the heterobifunctional linker can be covalently attached to the detectable label, or vice versa. In a particular embodiment, an aldehyde-reactive group of the heterobifunctional linker can be covalently attached to an aldehyde formed on a glycosylated portion of an anti-hapten antibody, and an amine-reactive group of the linker is attached to the detectable label. In yet other embodiments, an aldehyde-reactive group of the heterobifunctional linker is covalently attached to the anti-hapten antibody and a thiol-reactive group of the heterobifunctional linker is attached to the detectable label, or vice versa. In yet other embodiments, an aldehyde-reactive group of the heterobifunctional linker is covalently attached to the specific-binding moiety and a thiol-reactive group of the heterobifunctional linker is attached to the nanoparticle, or vice versa.

In some embodiments the heterobifunctional linker has the formula:

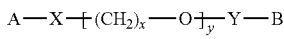

wherein A and B are different reactive groups and are as stated above; x and y are as stated above, and X and Y are additional spacer groups, for example, spacer groups having between 1 and 10 carbons such as between 1 and 6 carbons or between 1 and 4 carbons, and optionally containing one or more amide linkages, ether linkages, ester linkages and the like. Spacers X and Y can be the same or different, and can be straight-chained, branched or cyclic (for example, aliphatic or aromatic cyclic structures), and can be unsubstituted or substituted. Functional groups that can be substituents on a spacer include carbonyl groups, hydroxyl groups, halogen (F, Cl, Br and I) atoms, alkoxy groups (such as methoxy and ethoxy), nitro groups, and sulfate groups.

In particular embodiments, the heterobifunctional linker comprises a heterobifunctional polyethylene glycol linker having the formula:

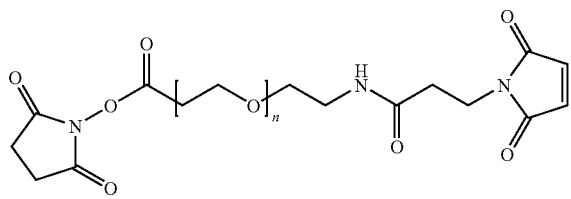

wherein n=1 to 50, for example, n=2 to 30 such as n=3 to 20 or n=4 to 12. In more particular embodiments, a carbonyl of a succinimide group of this linker is covalently attached to an amine group on a detectable label and a maleimide group of the linker is covalently attached to a thiol group of an anti-hapten antibody, or vice versa. In other more particular embodiments, an average of between about 1 and about 10 specific-binding moieties are covalently attached to a nanoparticle, such as semiconductor nanocrystals (such as quantum dots, obtained for example, from Invitrogen Corp., Eugene, Oreg.; see, for example, U.S. Pat. Nos. 6,815,064, 6,682,596 and 6,649,138, each of which patents is incorporated by reference herein), paramagnetic nanoparticles, metal nanoparticles, and superparamagnetic nanoparticles.

In other particular embodiments, the heterobifunctional linker comprises a heterobifunctional polyethylene glycol linker having the formula:

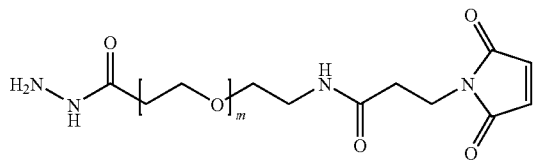

wherein m=1 to 50, for example, m=2 to 30 such as m=3 to 20 or m=4 to 12. In more particular embodiments, a hydrazide group of the linker is covalently linked with an aldehyde group of an anithapten antibody and a maleimide group of the linker is covalently linked with a thiol group of a detectable label, or vice versa. In even more particular embodiments, the aldehyde group of the specific-binding moiety is an aldehyde group formed in an Fc portion of an anti-hapten antibody by oxidation of a glycosylated region of the Fc portion of the antibody. In other even more particular embodiments, an average of between about 1 and about 10 anti-hapten antibodies are covalently attached to a nanoparticle. Briefly, maleimide/hydrazide PEG-linkers of the formula above can be synthesized from corresponding maleimide/active ester PEG linkers (which are commercially available, for example, from Quanta Biodesign, Powell, Ohio) by treatment with a protected hydrazine derivative (such as a Boc-protected hydrazine) followed by treatment with acid.

A conjugate of a specific binding moiety (SBM) and one or more of the disclosed haptens is provided. The SBM in these conjugates can include, for example, an antibody, a nucleic acid, a lectin or an avidin such as streptavidin. If the SBM includes an antibody, the antibody can specifically bind any particular molecule or particular group of highly similar molecules, for example, an antibody that specifically binds a particular protein that may be present in a sample. Alternatively, the antibody can be an anti-antibody antibody that can be used as a secondary antibody in an immunoassay. For example, the antibody can comprise an anti-IgG antibody such as an anti-mouse IgG antibody, an anti-rabbit IgG antibody or an anti-goat IgG antibody.

In particular embodiments, a disclosed antibody conjugate has the formula:

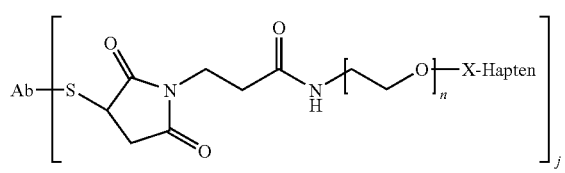

wherein Ab is an antibody, n=1 to 50 (such as n=2 to 30, n=3 to 20 or n=4 to 12) and j=1 to 10 (such as j=2 to 6 or j=3 to 4). X is a spacer group suitable for spacing the hapten from the remainder of the conjugate and allowing the hapten to be coupled to the remainder of the conjugate. For example, a spacer group may be an aliphatic or aromatic group, typically an aliphatic group, and even more typically an alkyl or substituted alkyl group having from about 1 to about 10 carbon atoms, such as between 1 and 6 carbons or between 1 and 4 carbons. The spacer also may include atoms other than carbon, such as heteroatoms, including but not limited to, halides, nitrogen, oxygen, sulfur, and combinations thereof. Such additional atoms can define functional groups. For example, the spacer group optionally may include one or more amide linkages, ether linkages, ester linkages, amine linkages and the like. The structure of the spacer will depend on the chemistry used to couple the hapten to the linker, and specific examples of such linkages are later discussed with regard to specifically disclosed haptens, but in general the group X can, for example, be formed by reacting an amine on the linker with an amine reactive group added to the hapten (or vice versa) or a carbonyl on the linker with a carbonyl reactive group added to the hapten (or vice versa.

Alternatively a conjugate of an antibody with one or more of the disclosed haptens can have the following formula:

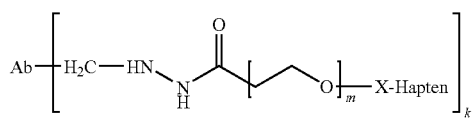

wherein Ab is an antibody, m=1 to 50 (such as m=2 to 30, m=3 to 20 or n=4 to 12) and k=1 to 10 (such as k=2 to 6 or kj=3 to 4) and X is again a spacer group, for example, a spacer group having between 1 and 10 carbon atoms, such as between 1 and 6 carbons or between 1 and 4 carbons, and optionally containing one or more amide linkages, ether linkages, ester linkages, amine linkages and the like.

In other embodiments, the specific binding moiety linked to one or more haptens is a nucleic acid. In a particular embodiment, such a conjugate can have the formula:

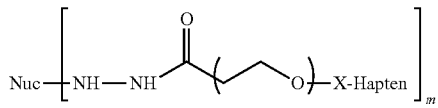

wherein Nuc is any nucleic acid base containing compound, including a nucleoside, nucleotide, nucleotide phosphate (such as a nucleotide triphosphate), an oligonucleotide, or a polynucleotide, and m can be, for example, from about 1 to 500 such as m=1 to 100 or m=1 to 50) and X is yet again a spacer group, for example, a spacer group having between 1 and 10 carbon atoms, such as between 1 and 6 carbons or between 1 and 4 carbons, and optionally containing one or more amide linkages, ether linkages, ester linkages, amine linkages and the like.

Also provided is a conjugate of an antibody that specifically binds a disclosed hapten. In particular embodiments, such a conjugate can have the following formula:

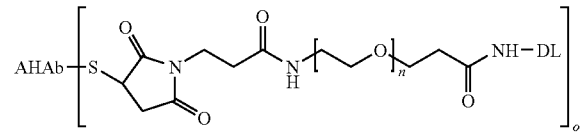

wherein AHAb is an anti-hapten antibody, DL is a detectable label such as an enzyme, n=1 to 50 (such as n=2 to 30, n=3 to 20 or n=4 to 12) and o=1 to 10 (such as o=2 to 6 or o=3 to 4); or

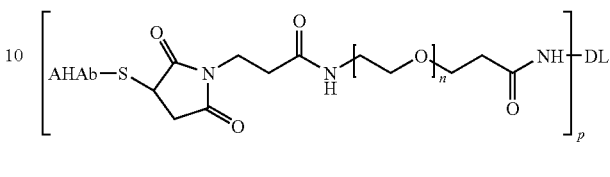

wherein AHAb is an anti-hapten antibody, DL is a detectable label such as a nanoparticle, n=1 to 50 (such as n=2 to 30, n=3 to 20 or n=4 to 12) and p=1 to 10 (such as p=2 to 6 or p=3 to 4).

In yet other particular embodiments, a disclosed conjugate comprises a conjugate having the formula:

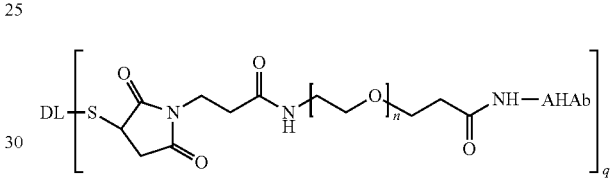

wherein AHAb is an anti-hapten antibody, DL is a detectable label such as a nanoparticle, n=1 to 50 (such as n=2 to 30, n=3 to 20 or n=4 to 12) and q=1 to 10 (such as q=2 to 6 or q=3 to 4); or

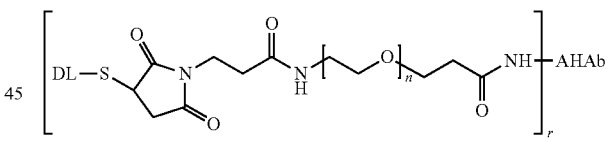

wherein AHAb is an anti-hapten antibody, DL is a detectable label such as an enzyme and n=1 to 50 (such as n=2 to 30, n=2 to 20 or n=4 to 12) and r=1 to 10 (such as r=2 to 6 or r=3 to 4).

In still other particular embodiments, a heterobifunctional PEG-linked specific-binding moiety-nanoparticle conjugate comprises a conjugate having the formula:

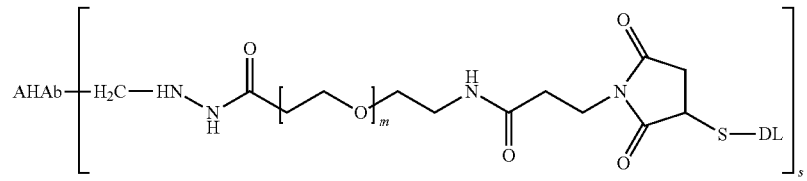

wherein AHAb is an anti-hapten antibody, DL is a detectable label such as an enzyme, m=1 to 50 (such as m=2 to 30, m=3 to 20 or m=4 to 12) and s=1 to 10 (such as s=2 to 6 or s=3 to 4); or

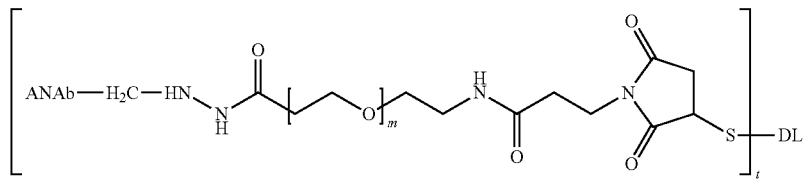

wherein AHAb is an anti-hapten antibody, DL is a detectable label such as a nanoparticle, m=1 to 50 (such as m=2 to 30, 2 to 20 or 4 to 12) and t=1 to 10 (such as t=2 to 6 or t=3 to 4).

In still further particular embodiments, a heterobifunctional PEG-linked specific-binding moiety-nanoparticle conjugate comprises a conjugate having the formula:

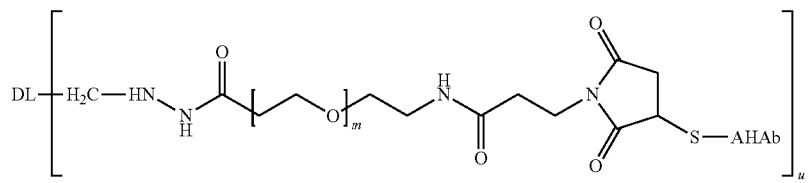

wherein AHAb is an antihapten antibody, DL is a detectable label, m=1 to 50 (such as m=2 to 30, m=3 to 20 or m=4 to 12) and u=1 to 10 (such as u=2 to 6 or u=3 to 4); or

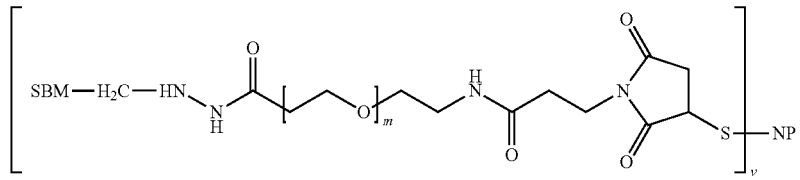

wherein SBM is a specific-binding moiety, NP is a nanoparticle, m=1 to 50 (such as m=2 to 30, m=2 to 20 or m=4 to 12) and v=1 to 10 (such as v=2 to 6 or v=3 to 4).

Disclosed conjugates can be utilized for detecting one or more molecules of interest in a biological sample in any type of assay, including immunohistochemical assays and in situ hybridization assays. In one embodiment, the disclosed conjugates are used as a hapten-labeled antibody in an immunoassay, for example, a hapten-labeled primary antibody directed to a particular molecule that is then contacted with an anti-hapten antibody conjugate including a detectable label. Alternatively, a hapten-labeled nucleic acid probe bound to a target nucleic acid is then contacted with an anti-hapten antibody conjugate including a detectable label. The biological sample can be any sample containing biomolecules (such as proteins, nucleic acids, lipids, hormones etc.), but in particular embodiments, the biological sample includes a tissue section (such as obtained by biopsy) or a cytology sample (such as a Pap smear or blood smear). Other types of assays in which the disclosed conjugates can be used are readily apparent to those skilled in the art, and particular examples are discussed below.

In another aspect, a method is disclosed for preparing a specific-binding moiety-hapten conjugate, the method including forming a thiolated specific-binding moiety from a specific-binding moiety; reacting a hapten having an amine group with a maleimide/active ester bifunctional linker to form an activated hapten; and reacting the thiolated specific-binding moiety with the activated hapten to form the specific-binding moiety-hapten conjugate.

A thiolated specific-binding moiety can be formed by reacting the specific-binding moiety with a reducing agent to form the thiolated specific-binding moiety, for example, by reacting the specific-binding moiety with a reducing agent to form a thiolated specific-binding moiety having an average number of thiols per specific-binding moiety of between about 1 and about 10. The average number of thiols per specific-binding moiety can be determined by titration. Examples of reducing agents include reducing agents selected from the group consisting of 2-mercaptoethanol, 2-mercaptoethylamine, DTT, DTE and TCEP, and combinations thereof. In a particular embodiment the reducing agent is selected from the group consisting of DTT and DTE, and combinations thereof, and used at a concentration of between about 1 mM and about 40 mM.

Alternatively, forming the thiolated specific-binding moiety includes introducing a thiol group to the specific-binding moiety. For example, the thiol group can be introduced to the specific-binding moiety by reaction with a reagent selected from the group consisting of 2-Iminothiolane, SATA, SATP, SPDP, N-Acetylhomocysteinethiolactone, SAMSA, and cystamine, and combinations thereof (see, for example, Hermanson, "Bioconjugate Techniques," Academic Press, San Diego, 1996, which is incorporated by reference herein). In a more particular embodiment, introducing the thiol group to the specific-binding moiety includes reacting the specific-binding moiety with an oxidant (such as periodate) to convert a sugar moiety (such as in a glycosylated portion of an antibody) of the specific-binding moiety into an aldehyde group and then reacting the aldehyde group with cystamine. In another more particular embodiment, the specific binding moiety includes streptavidin and introducing the thiol group comprises reacting the streptavidin with 2-iminothiolane (Traut reagent).

In other particular embodiments, reacting the hapten with a maleimide/active ester bifunctional linker to form an activated nanoparticle includes reacting the hapten with a PEG maleimide/active ester having the formula:

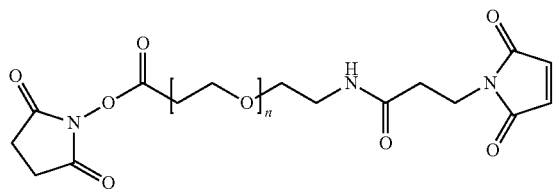

wherein n=1 to 50, for example, n=2 to 30 such as n=3 to 20 or n=4 to 12.

In a further aspect, a method is disclosed for preparing a specific-binding moiety-hapten conjugate composition that includes reacting a specific-binding moiety with an oxidant to form an aldehyde-bearing specific-binding moiety; reacting the aldehyde-bearing specific-binding moiety with a maleimide/hydrazide bifunctional linker to form a thiol-reactive specific-binding moiety; and reacting the thiol-reactive specific-binding moiety with a thiolated hapten to form the specific-binding moiety-nanoparticle conjugate. In a particular embodiment, the specific-binding moiety is an antibody and reacting the specific-binding moiety with an oxidant to form the aldehyde-bearing specific-binding moiety includes oxidizing (such as with periodate, $I_2$, $Br_2$, or a combination thereof, or neuramidase/galactose oxidase) a glycosylated region of the antibody to form the aldehyde-bearing antibody. In a more particular embodiment, reacting an antibody with an oxidant to form an aldehyde-bearing antibody includes introducing an average of between about 1 and about 10 aldehyde groups per antibody. In a more particular embodiment, the maleimide/hydrazide bifunctional linker has the formula:

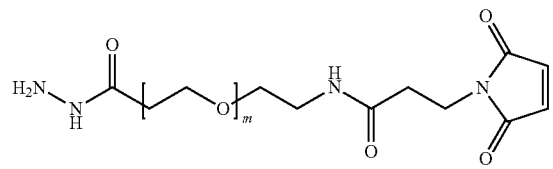

wherein m=1 to 50, for example, m=2 to 30 such as m=3 to 20 or m=4 to 12. A thiolated hapten can be formed from a hapten by introducing a thiol group to the hapten (for example, by reacting a hapten with a reagent selected from the group consisting of 2-Iminothiolane, SATA, SATP, SPDP, N-Acetylhomocysteinethiolactone, SAMSA, and cystamine, and combinations thereof).

In other embodiments, a hapten-linker conjugate having a hydrazide reactive group is reacted with a carbonyl group of an aldehyde formed on an antibody to form a hapten-linker-antibody conjugate. Hapten-linker conjugates having hydrazide reactive group are discussed further below.

4. Commercially Available Linkers

Additional linkers also are commercially available. Pierce Biotechnology Inc., of Rockford, Ill., provides certain linkers that are useful for practicing the present invention. For example, Pierce provides sulfosuccinimidyl-4-(N-maleimidomethyl)cyclohexane-1-carboxylate(sulfo-SMCC). Pierce also sells a sulfonamidyl compound without the sulfo group, referred to as SMCC, which also is a useful linker. Sulfo-SMCC is a water soluble, non-cleavable membrane, impermeable cross-linker. NH esters of this compound can react readily with primary amines at pH 7-9 to form stable amide bonds. Malemides react with sulfhydryl groups at pH between about 6 to 8, more typically from about 6.5 to about 7.5, to form stable thioether bonds. For use in coupling the haptens to a carrier comprising a free amine, the sulfo-SMCC can react with the free amine of the carrier to provide a malemide-activated carrier. The carrier type compound then can be reacted with a hapten, such as a hapten having a free sulfhydryl group or hydroxyl group, to form a conjugate according to the present invention.

Pierce also provides additional exemplary linkers, as well as additional information concerning the length for each potentially suitable for practical use. For example, for functional groups reactive with amines, Pierce provides the following compounds: EGS (ethylene glycol bis[succinimidylsuccinate]); Sulfo-EGS (ethylene glycol bis[sulfosuccinimidylsuccinate]); DTSSP (3,3'-dithiobis[sulfosuccinimidylpropionate]); DSS (disuccinimidyl suberate); BS (bis[sulfosuccinimidyl] suberate); DSG (disuccinimidyl glutarate); and MSA (methyl N-succinimidyl adipate. Examples of sulfhydryl reactive linkers include DPDPB (1,4-di-[3'-(2'-pyridyldithio)-propionamido]butane); BM[PEO]$_3$(1,1'-bis-maleimidotriethyleneglycol); BMH (bis-maleimidohexane); BM[PEO]$_2$(1,8-bis-maleimidodiethyleneglycol); HBVS (1,6-hexane-bis-vinylsulfone); DTME (dithio-bis-maleimidoethane); BMDB (1,4-bis-maleimidyl-2,3-dihydroxybutane); BMB (1,4-bis-maleimidiobutane; and BMOE (bis-maleimidoethane). Photoreactive compounds also are available from Pierce, including BASED (bis-[b-(4-azidosalicylamido)ethyl]disulfide) and APG (p-azidophenyl glyoxal monohydrate).

5. Carbodiimide Coupling

Carbodiimides [R—N=C=N—R$_1$] can be used to couple haptens directly to target molecules, including amino acids, proteins, nucleotides, and oligonucleotides. See, for example, *New Biotinylating Reagent Utilizing Carbodiimide Function*, Nucleic Acid Symposiums Series, No. 34, 69-70 (1995), which is incorporated herein by reference. Alternatively, carbodiimide functionalities can be incorporated into or coupled to a linker as discussed above for forming hapten-linker conjugates. A general synthetic scheme for making hapten-dPEGx-carbodiimides is provided below in the working examples. Using this general synthetic scheme, several working embodiments of hapten-carbodiimides have been made, including nitropyrazole-dPEGx-carbodiimide, benzofurazan-dPEGx-carbodiimide, dinitrophenyl-dPEGx-carbodiimide, thiazolesulfonamide-dPEGx-carbodiimide and rotenoid-dPEGx-carbodiimide.

IV. Hapten-Linker Conjugates

Compounds of the present invention, also referred to as conjugates, typically comprise a hapten typically coupled to a linker. The hapten conjugate also may include a carrier, such as a polypeptide, protein, mononucleotide, dinucleotide, trinucleotide, oligonucleotide, or nucleic acid(s), either coupled directly to the hapten, or coupled to linker. Particular examples of carriers include immunogenic carriers, antibodies and nucleic acid probes. The hapten, carrier and/or linker may include one or more functional groups or moieties, typically electrophiles and electrophile/nucleophile pairs that are useful for coupling a hapten to a carrier, either directly or indirectly through a linker. Thus, a first general formula describing certain embodiments of the present disclosure is hapten-carrier. Such compounds also optionally, and most typically, include a linker. Embodiments having a linker satisfy the formula hapten-linker-carrier. A combined formula therefore is (hapten)$_k$-(linker)$_m$-carrier$_n$ where k is 1, m and n are 0 or 1, and at least one of m or n is 1. A person of ordinary skill in the art will understand that, for the general formula, k=1, m=1 or n=1 implies no limitation on the number or structure of the hapten, the linker or the carrier. For example, a carrier can have multiple linkers attached and the multiple linkers can be attached to multiple haptens to provide a conjugate of the combined formula. Furthermore, a linker can include plural subunits or be formed from various subcomponents. For example, both a carrier and a hapten can include attached linkers, wherein the linkers can then be reacted to couple the hapten and the carrier together.

In a particular embodiment, a conjugate according to the disclosure has the general structure (specific-binding moiety)-linker-hapten, and more particularly (specific-binding moiety)-(linker-hapten)$_p$ where p=1-200, for example p=1-50 such as 1-10. In one example, the linker comprises a PEG linker. In more particular embodiments, the specific binding moiety is an antibody or a nucleic acid. In another example, the specific-binding moiety is an antibody and the linker includes a carbonyl reactive group covalently linked to an aldehyde group of an oxidized sugar moiety of an Fc region of the antibody. In yet another example, the specific-binding moiety is an antibody and the linker includes a sulfhydryl reactive group covalently linked to a thiol group of the antibody, wherein the thiol group is generated by reducing a disulfide bond in the antibody. In still another example, the specific binding moiety is a nucleic acid and the linker includes a carbonyl reactive group covalently linked to a cytosine residue of the nucleic acid.

In another particular embodiment, a conjugate according to the disclosure has the general structure hapten-linker-RG, wherein RG refers to a reactive group, such as a carbonyl reactive group, a thiol reactive group or an amine reactive group. Although typically one hapten will be linked to one linker bearing a reactive group, it is possible to have multiple haptens attached to one linker having a reactive group, or to have multiple linkers having reactive groups attached to one hapten. Hapten linker conjugates such as these are particularly useful for attaching a hapten to an antibody (such as discussed in the previous paragraph) and also for attaching a hapten to an immunogenic carrier such as KLH to provide an immunogen that can be used to stimulate an animal to produce an antibody that specifically binds to the hapten. Thus, an antibody that specifically binds to a hapten is an aspect of the disclosure.

In yet another aspect, a conjugate is disclosed that includes an anti-hapten antibody (such as can be produced using a disclosed immunogen) and a detectable label (such as a quantum dot or enzyme). Thus, a general formula for this type of conjugate is (anti-hapten antibody)$_t$-(detectable label)$_s$ where t and s can each independently be 1-100, but more typically, t=1 and s=1-10. Conjugates of anti-hapten antibodies with detectable labels can be used in conjunction with other hapten-carrier conjugates (such as hapten labeled nucleic acid probes for target genomic sequences and hapten-labeled primary antibodies that specifically bind to target proteins) to allow multiplexed assays of multiple targets in a single sample.

Conjugates of the present invention may be formed by coupling a disclosed exemplary linker or linkers to a disclosed hapten or haptens. Many of the haptens have plural locations to which a linker may be coupled. Suitable linker positions with respect to the general formulae provided for disclosed haptens are indicated below, as are general formulae for hapten-linker conjugates. Particular hapten-linker conjugates are provided by reference to PEG linkers, as are protocols for synthesizing these compounds.

1. Oxazoles and Pyrazoles

A first general class of haptens of the present invention are oxazoles and pyrazoles, most typically nitro oxazoles and nitro pyrazoles, having the following general chemical formula, as discussed in more detail herein.

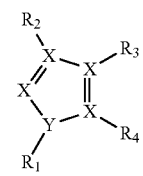

Any one or more of the R$_1$-R$_4$ positions can be coupled to a linker. The position occupied by the R$_2$ substituent is quite suitable for coupling linkers to this class of haptens, as indicated below, where L is a linker and RG is a reactive functional group.

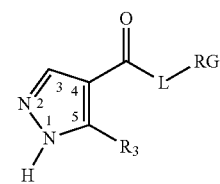

Hapten-linker conjugates have been formed using PEG-based linkers. One example of such a compound, 5-nitro-3-pyrazole carbamide, is shown below. For this and subsequent embodiments, X is from about 2 to about 24, typically from about 4 to about 12.

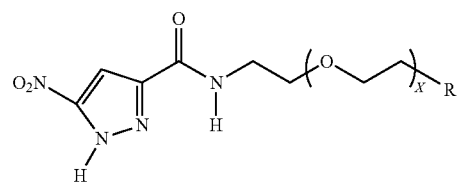

A particular embodiment where X is 4 is provided below.

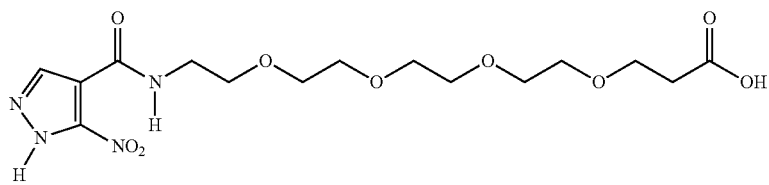 [SMILES: O=C(O)CCOCCOCCOCCOCCNC(=O)c1cn[nH]c1[N+](=O)[O-]]

This example satisfies the formula hapten-L-RG where L is a PEG 4 (4 ethylene oxy units) and the reactive group is a carboxylic acid functional group. The carboxylic acid functional group has been converted to other reactive functional groups in working embodiments. For example, the carboxylic acid functional group can be converted to an activated ester, such as an NHS ester, as shown below.

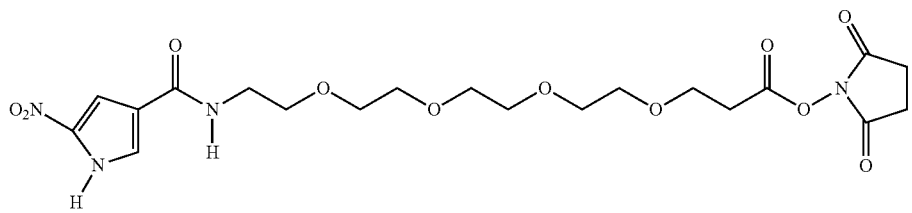 [SMILES: O=C(CCOCCOCCOCCOCCNC(=O)c1c[nH]c([N+](=O)[O-])c1)ON1C(=O)CCC1=O]

And, the activated ester can be converted to other useful reactive functional group, such as a hydrazide, as illustrated below.

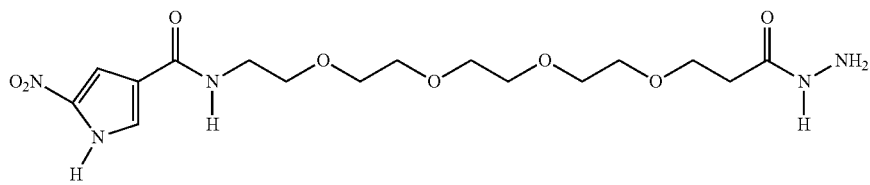 [SMILES: NNC(=O)CCOCCOCCOCCOCCNC(=O)c1c[nH]c([N+](=O)[O-])c1]

2. Nitroaryl

A second general class of haptens of the present invention are nitroaryl compounds having the following general chemical formula.

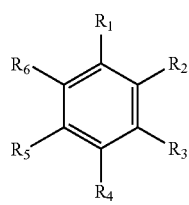

Such compounds have at least one, and optionally plural, nitro groups so that at least one of $R_1$-$R_6$ is nitro. Any of the $R_1$-$R_6$ positions not coupled to a nitro group is a potential position for coupling linkers to the aryl ring. Mononitrophenyl compounds are represented by nitrocinnamide hapten conjugates as illustrated below.

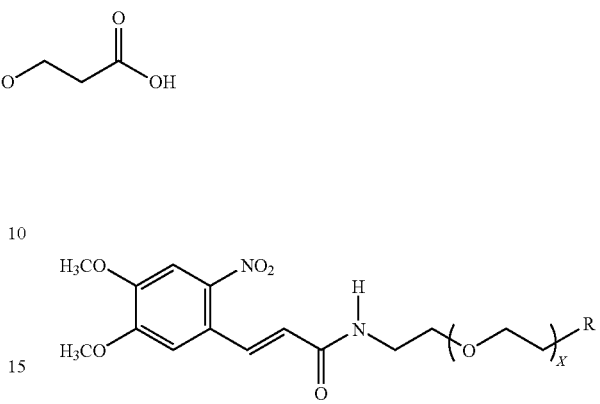

Working embodiments also are exemplified by 2,4-dinitrophenyl compounds. Exemplary hapten conjugates of this class are illustrated below, where $R_1$-$R_3$ are as stated above.

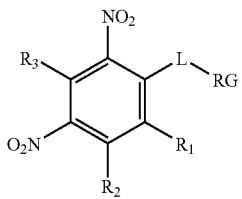

Hapten-linker conjugates have been formed using PEG-based linkers. One example of such a compound is shown below.

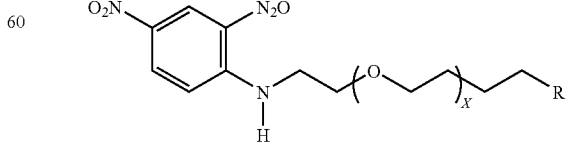

A particular embodiment had the following structure.

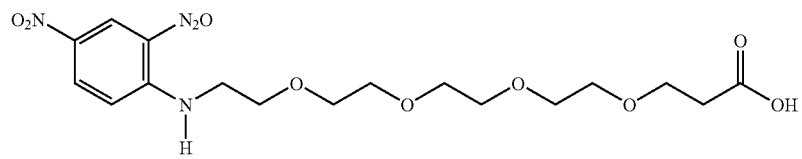

This example therefore satisfies the formula hapten-L-RG where L is a PEG 4 (4 ethylene oxy units) and the reactive group is a carboxylic acid functional group. The carboxylic acid functional group has been converted to other reactive functional groups in working embodiments. For example, the carboxylic acid functional group can be converted to an activated ester, such as an NHS ester, as shown below.

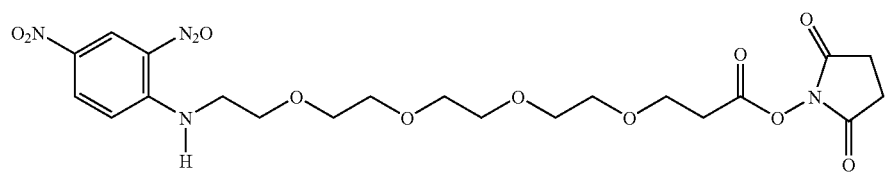

The activated ester can be converted to other useful reactive functional group, such as a hydrazide, as illustrated below.

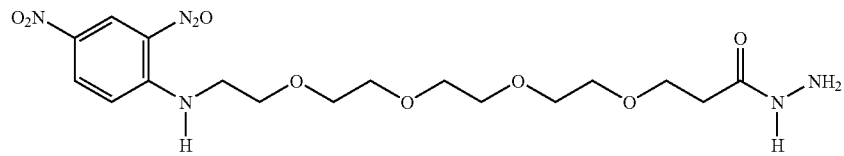

3. Benzofurazan and Related Compounds

Benzofurazans and derivatives thereof are in another class of haptens of the present invention. A general formula for the benzofurazan-type compounds is provided below.

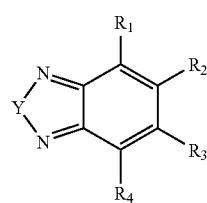

The $R_1$-$R_4$ and Y substituents are as stated above. At least one of the $R_1$-$R_4$ substituents is bonded to a linker, to a carrier, or is a functional group suitable for coupling to a linker or a carrier. The $R_2$ and $R_3$ positions are most likely used to couple the linker to this class of haptens ($R_2$ and $R_3$ may be substantially identical in terms of reactivity, particularly if $R_1$ and $R_4$ are the same). Such hapten conjugates are exemplified by the general formula provided below.

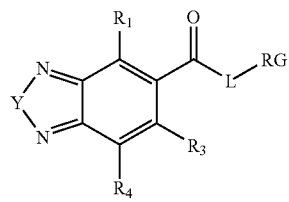

Hapten-linker conjugates have been formed using PEG-based linkers. One example of such a compound, 2,1,3-benzoxadiazole-5-carbamide, is shown below.

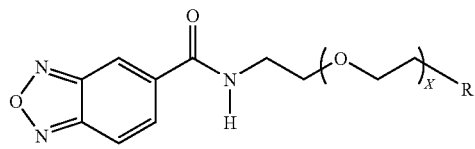

A particular embodiment had the following formula.

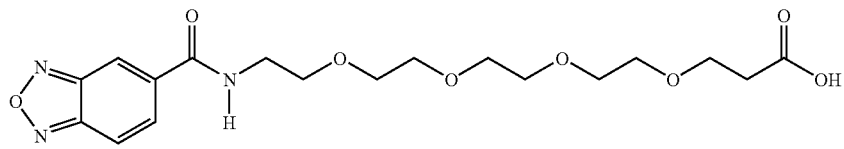 [SMILES: O=C(O)CCOCCOCCOCCOCCNC(=O)c1ccc2nonc2c1]

This example satisfies the formula hapten-L-RG where L is a PEG 4 (4 ethylene oxy units) and the reactive group is a carboxylic acid functional group. The carboxylic acid functional group has been converted to other reactive functional groups in working embodiments. For example, the carboxylic acid functional group can be converted to an activated ester, such as an NHS ester, as shown below.

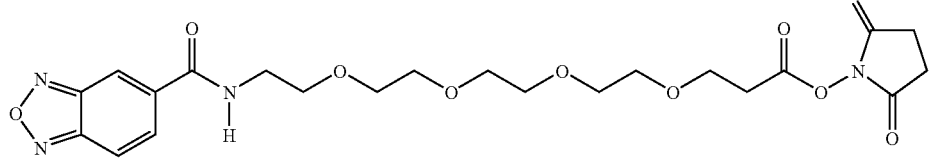

The activated ester can be converted to other useful reactive functional group, such as a hydrazide, as illustrated below.

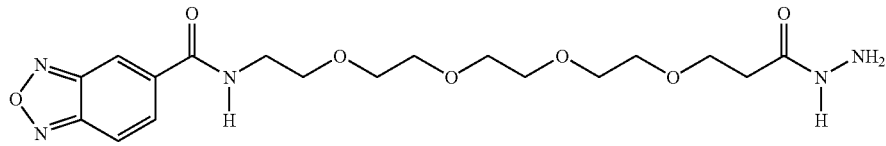 [SMILES: NNC(=O)CCOCCOCCOCCOCCNC(=O)c1ccc2nonc2c1]

4. Triterpenes

Triterpenes are another class of haptens within the scope of the present invention. The basic ring structure common to the triterpenes has four six-membered fused rings, A-D, as indicated below, where the $R_1$-$R_{21}$ and Y substituents are as stated above.

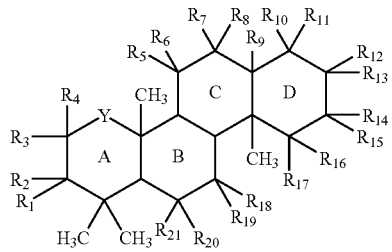

Disclosed embodiments of triterpenes exemplifying this class of haptens also may include an E ring, that can be of various ring sizes. For example, the E ring might be a 5- or 6-membered ring. Quite often, these compounds include an alpha-beta unsaturated ketone, such as illustrated below for the C ring.

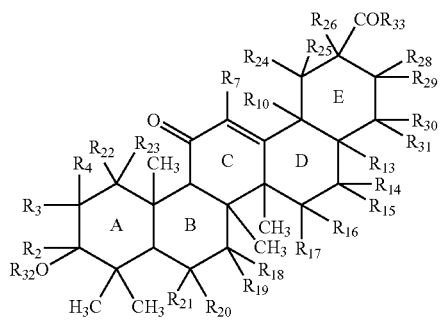

A person of ordinary skill in the art will appreciate that many of the positions occupied by the R groups in these general formulae may be useful for coupling the haptens to a linker to form a reactive conjugate. With reference to the alpha-beta unsaturated compounds, particular linker positions are indicated below using arrows.

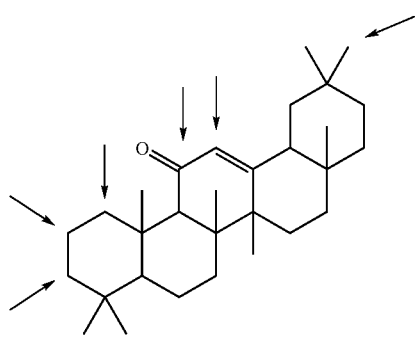

For example, hapten conjugates of the present invention A particular reactive conjugate according to this class has the following formula.

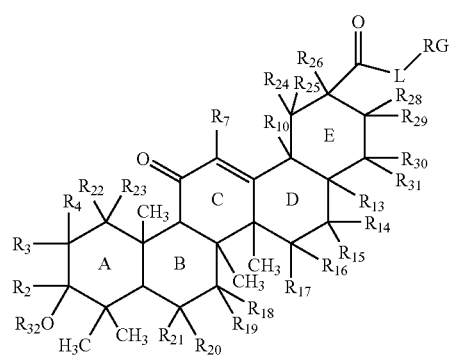

Other exemplary triterpene structures and potential linker coupling positions are provided below.

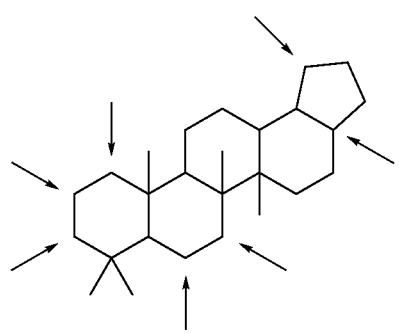

Betulinic, Ursolic and Echinocystic Acid Core Structures

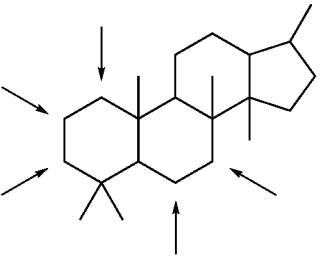

Cucurbitacin Core

Hapten-linker conjugates have been formed using PEG-based linkers. One example of such a compound is shown below.

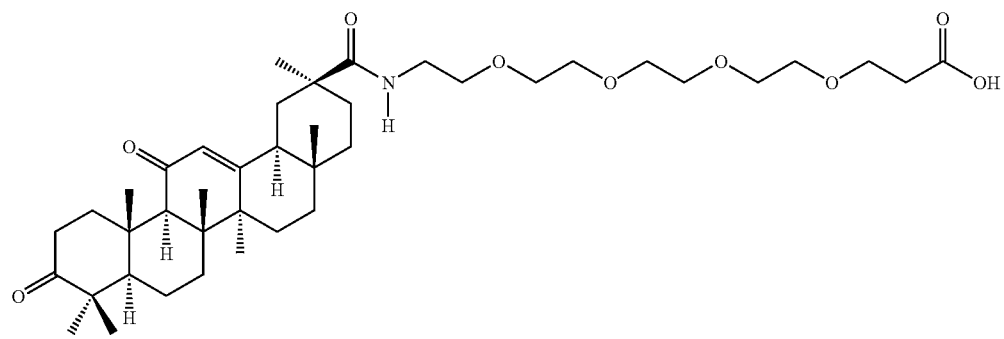

This example therefore satisfies the formula hapten-L-RG where L is a PEG 4 (4 ethylene oxy units) and the reactive group is a carboxylic acid functional group. The carboxylic acid functional group can be converted to an activated ester, such as an NHS ester, as shown below.

At least one of the $R_3$-$R_7$ substituents also may be bonded to a linker, to a carrier, or is a functional group suitable for coupling to a linker and/or to a carrier molecule. Alternatively, the urea/thiourea functional group can be used to couple a linker to this class of disclosed haptens. An exem-

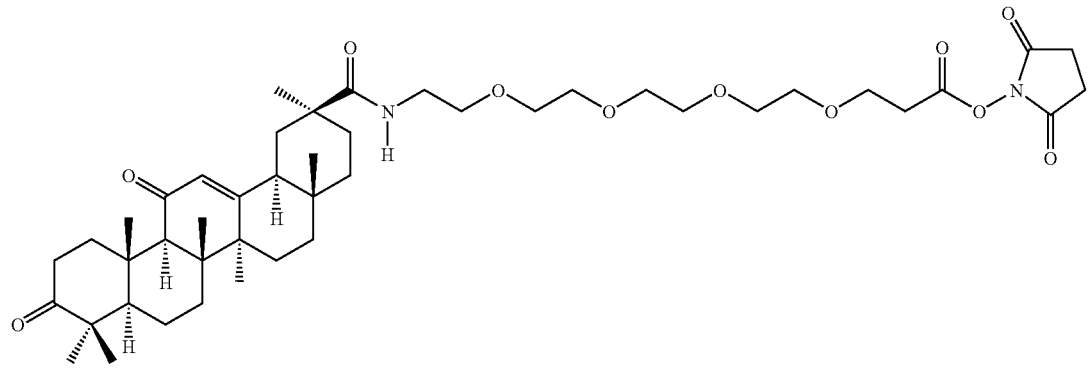

The illustrated activated ester has been coupled directly to a protein carrier. Alternatively, the activated ester could be converted into a different reactive functional group, such as a hydrazide by treatment with a protected, e.g. a BOC-protected hydrazine reagent, if desired.

5. Ureas and Thioureas

Ureas/thioureas, particularly aryl and heteroaryl ureas and thioureas, is another class of haptens within the scope of the present invention. Aryl derivatives typically have the following formula.

plary hapten conjugate, with particular reference to thioureas, is provided below.

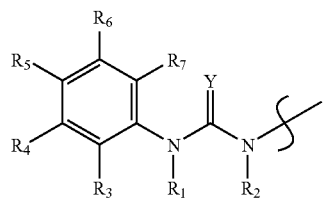

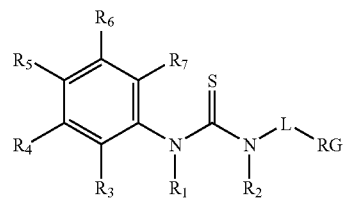

Hapten-linker conjugates have been formed using PEG-based linkers. One example of such a compound is shown below.

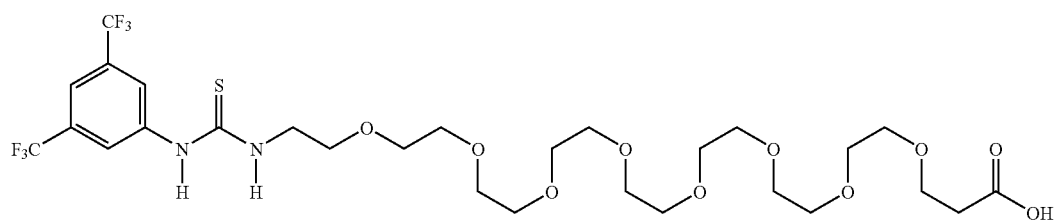 [SMILES: O=C(O)CCOCCOCCOCCOCCOCCOCCOCCOCCNC(=S)Nc1cc(C(F)(F)F)cc(C(F)(F)F)c1]

This example therefore satisfies the formula hapten-L-RG where L is a PEG 8 (8 ethylene oxy units) and the reactive group is a carboxylic acid functional group. The carboxylic acid functional group can be converted to an activated ester, such as an NHS ester, as shown below.

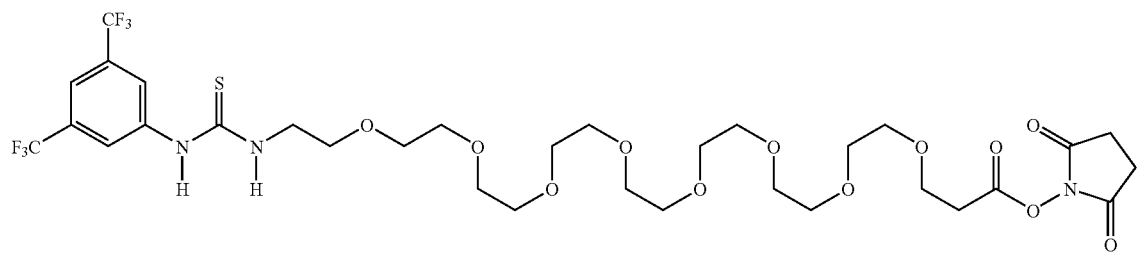 [SMILES: O=C(CCOCCOCCOCCOCCOCCOCCOCCOCCNC(=S)Nc1cc(C(F)(F)F)cc(C(F)(F)F)c1)ON1C(=O)CCC1=O]

The activated ester can be converted to other useful reactive functional group, such as a hydrazide, as illustrated below.

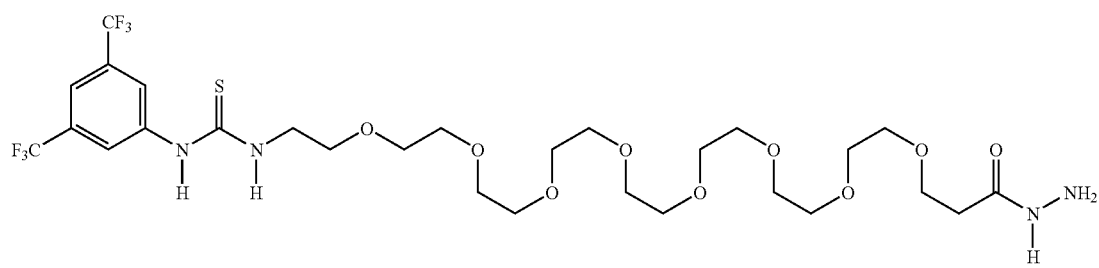 [SMILES: NNC(=O)CCOCCOCCOCCOCCOCCOCCOCCOCCNC(=S)Nc1cc(C(F)(F)F)cc(C(F)(F)F)c1]

Rhodamine thiourea hapten conjugates according to the present invention typically have the following formula.

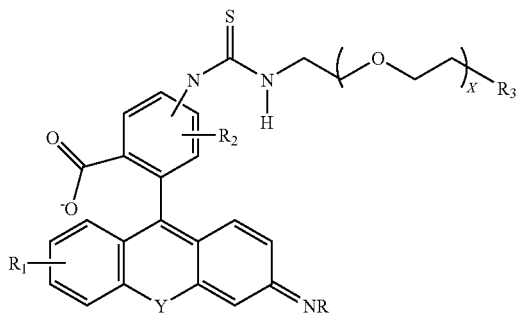

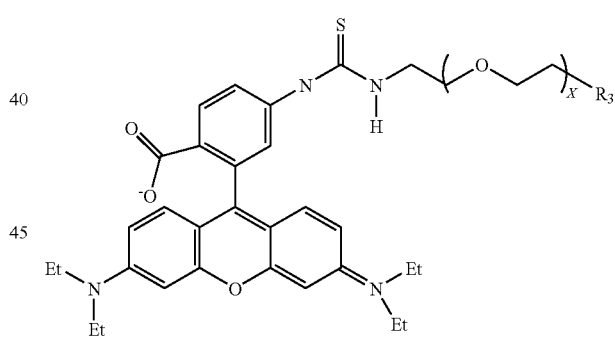

With reference to this formula, R typically is independently selected from hydrogen, aliphatic, particularly alkyl, heteroaliphatic, substituted aliphatic, such as alkyl halide, aryl, heteroaryl, and combinations thereof. $R_1$ typically is independently selected from hydrogen, aliphatic, particularly alkyl, heteroaliphatic, substituted aliphatic, such as alkyl halide, alcohol, amine, substituted amine, such as lower alkyl amine, one example being diethyl amine, aryl, heteroaryl, halogen, hydroxyl, and combinations thereof. $R_2$ typically is independently selected from hydrogen, aliphatic, particularly alkyl, heteroaliphatic, substituted aliphatic, such as alkyl halide, alcohol, amine, substituted amine, aryl, heteroaryl, halogen, hydroxyl, and combinations thereof. Y is oxygen, nitrogen or sulfur. A particular embodiment of a rhodamine B thiourea had the following formula.

6. Rotenone and Rotenone-Based Haptens

Rotenone, and rotenone-based haptens, define another class of haptens within the scope of the present invention. General formulas for rotenone, and rotenone-based haptens, are provided below.

Formula 1

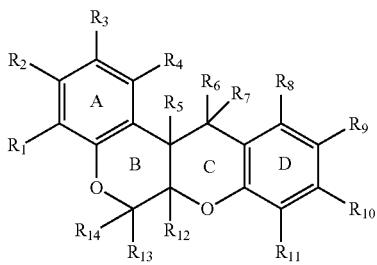

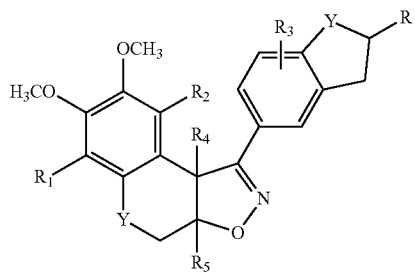

Formula 2

Any of the $R_1$-$R_{14}$ positions can be used to couple linkers to this class of haptens. Certain particular compounds of Formula 1 have $R_6$ and $R_7$ form a double bond, such as a double bond to oxyten to form a carbonyl or a double bond to an nitrogen to form an imine. Specific exemplary linker coupling positions with reference to these hapten conjugates is provided below.

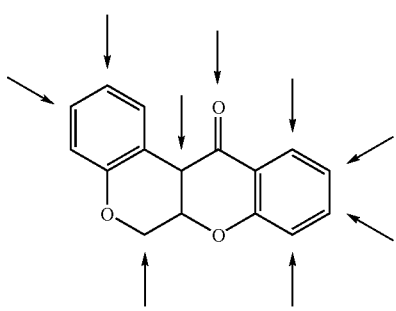 [SMILES: O=C1c2ccccc2OC2COc3ccccc3C12]

A person of ordinary skill in the art will appreciate that the carbonyl compound can be used to bond to the linker. This class of exemplary hapten conjugates is exemplified by the general formulas provided below.

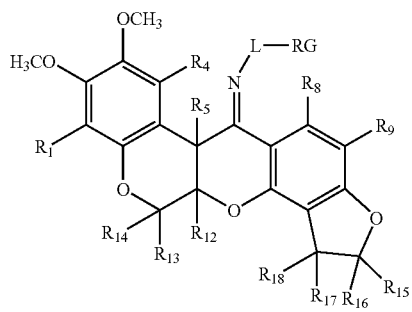

the general formulas provided below.

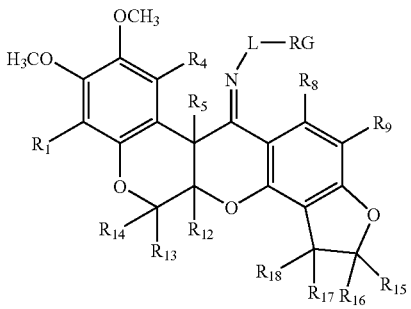

One example of a hapten-linker conjugate having a PEG-based linker is shown below.

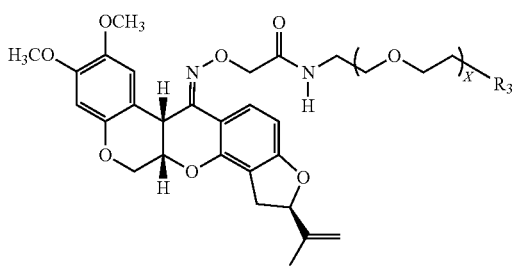

A particular embodiment had the following formula.

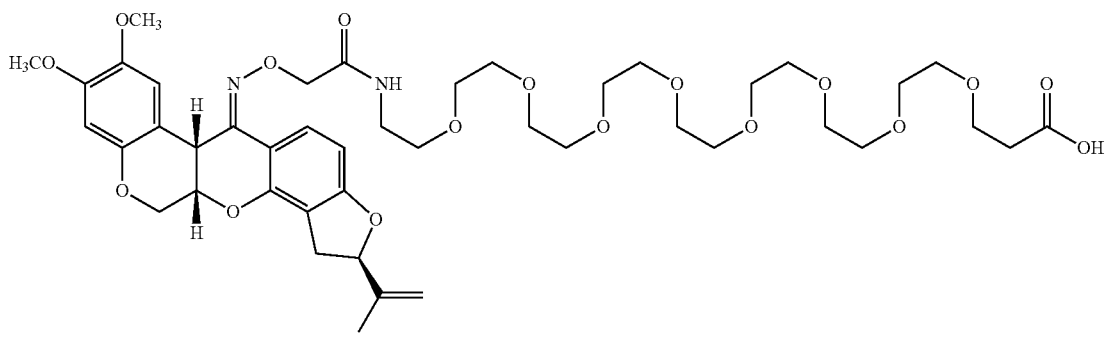 [SMILES: C=C(C)[C@H]1Cc2c(ccc3c2O[C@@H]2COc4cc(OC)c(OC)cc4[C@@H]2/C3=N/OCC(=O)NCCOCCOCCOCCOCCOCCOCCOCCOCCC(=O)O)O1]

This example satisfies the formula hapten-L-RG where L is a PEG 8 (8 ethylene oxy units) and the reactive group is a carboxylic acid functional group. The carboxylic acid functional group can be converted into a different reactive functional group, as desired, such as an activated ester, including the NHS ester shown below.

conjugates. For certain exemplary working embodiments, $R_1$ has been amido, such as the amide derivatives shown below. For these compounds, the $R_2$ and $R_3$ positions are suitable for coupling to a linker. $R_2$, for certain working embodiments, has been —$SO_2$, and has been used to couple linkers by

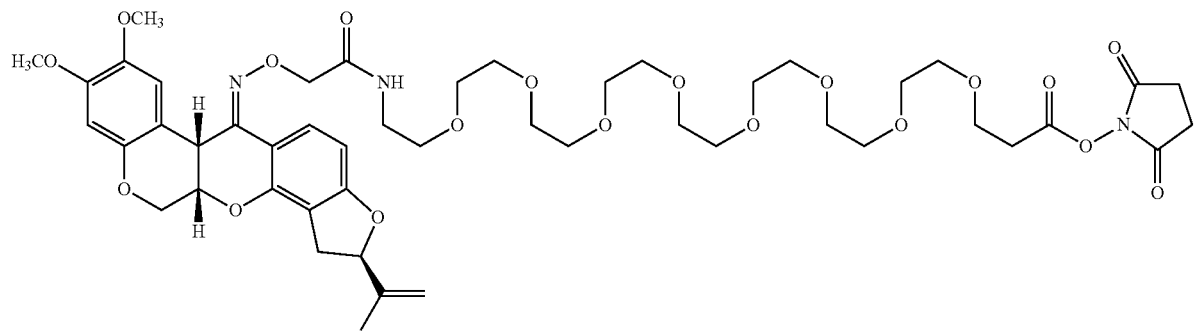 [SMILES: C=C(C)[C@H]1Cc2c(ccc3c2O[C@@H]2COc4cc(OC)c(OC)cc4[C@@H]2/C3=N/OCC(=O)NCCOCCOCCOCCOCCOCCOCCOCCOCCC(=O)ON2C(=O)CCC2=O)O1]

The activated ester can be converted to other useful reactive functional group, such as a hydrazide, as illustrated below.

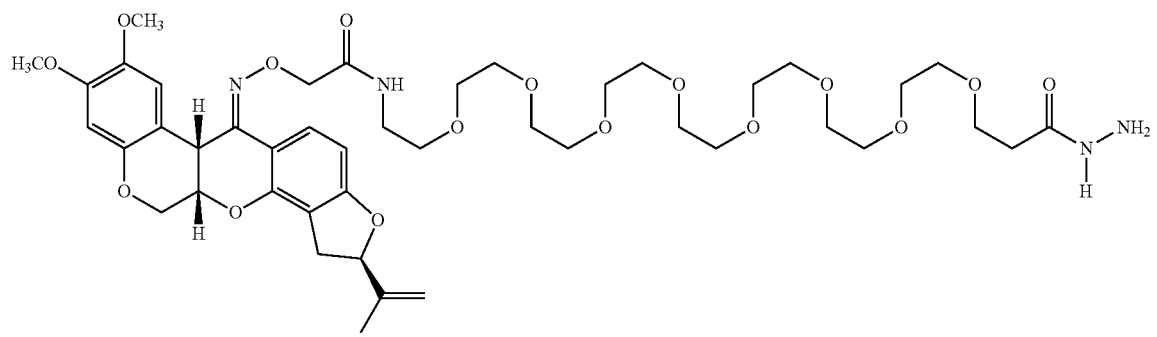 [SMILES: C=C(C)[C@H]1Cc2c(ccc3c2O[C@@H]2COc4cc(OC)c(OC)cc4[C@@H]2/C3=N/OCC(=O)NCCOCCOCCOCCOCCOCCOCCOCCOCCC(=O)NN)O1]

For rotenone isoxazolines, exemplary hapten-linker conjugates had the following formula.

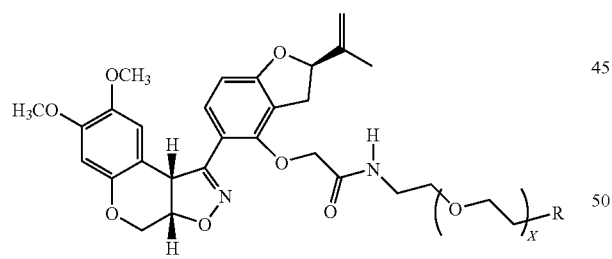

7. Oxazole and Thiazole Sulfonamides

Oxazole and thiazole sulfonamides provide another class of haptens within the scope of the present invention. A general formula for oxazole and thiazole sulfonamides is provided below.

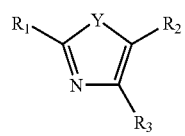

Any one or more of the $R_1$-$R_3$ positions can be used to couple a linker or carrier to this class of haptens to form hapten forming a sulfonamide. Thus, a second general formula for working embodiments of haptens exemplifying this class of haptens is indicated below.

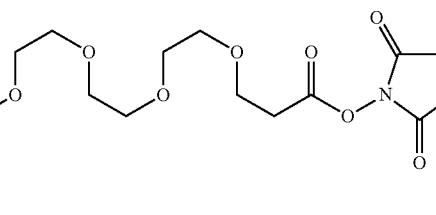

Exemplary hapten conjugates based on this general formula include those having the following formula.

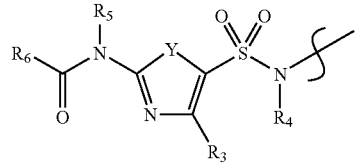

Hapten-linker conjugates have been formed using PEG-based linkers. One example of such a compound, 2-acetamido-4-methyl-5-thiazolesulfonamide, is shown below.

A particular embodiment had the following structure.

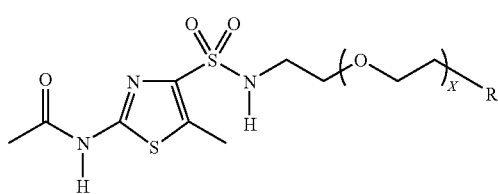

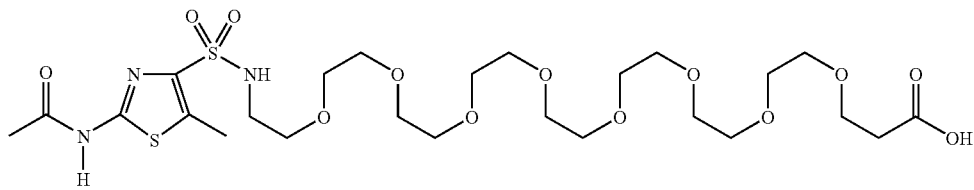 [SMILES: CC(=O)Nc1nc(S(=O)(=O)NCCOCCOCCOCCOCCOCCOCCOCCOCCC(=O)O)c(C)s1]

This example satisfies the formula hapten-L-RG where L is a PEG 8 (8 ethylene oxy units) and the reactive group is a carboxylic acid functional group. The carboxylic acid functional group can be converted into a different reactive functional group, as desired, such as an activated ester, including the NHS ester shown below.

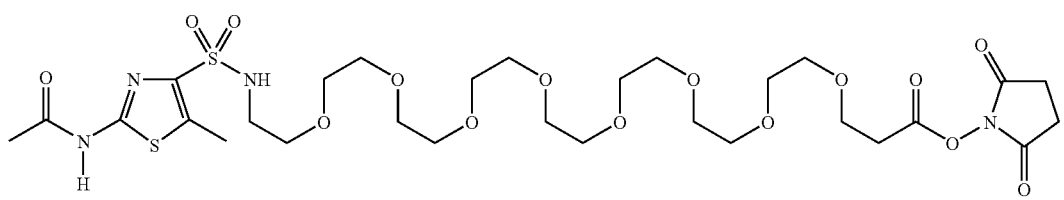 [SMILES: CC(=O)Nc1nc(S(=O)(=O)NCCOCCOCCOCCOCCOCCOCCOCCOCCC(=O)ON2C(=O)CCC2=O)c(C)s1]

The activated ester can be converted to other useful reactive functional group, such as a hydrazide, as illustrated below.

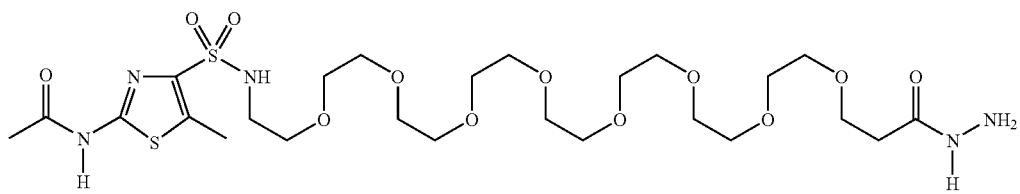 [SMILES: CC(=O)Nc1nc(S(=O)(=O)NCCOCCOCCOCCOCCOCCOCCOCCOCCC(=O)NN)c(C)s1]

8. Coumarins

Coumarin and coumarin derivatives provide another class of haptens within the scope of the present invention. A general formula for coumarin and coumarin derivatives is provided below.

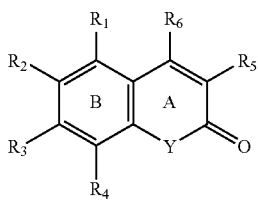

Any of the $R_1$-$R_6$ positions also typically is bonded to a linker, to a carrier or is a functional group suitable for coupling to a linker or a carrier molecule. Certain working embodiments have used the position indicated as having an $R_5$ substituent for coupling to linkers. The position occupied by the $R_6$ substituent can be important if fluorescence is used to detect these compounds. Substituents other than hydrogen at the position occupied by $R_6$ in the general formula are believed to quench fluorescence, although such derivatives still may be chromophores. Exemplary hapten conjugates made using this formula have the following general formula.

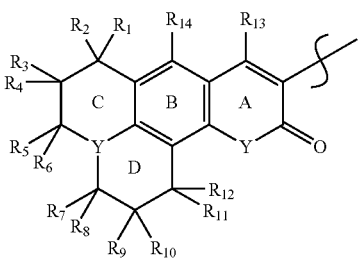

Working embodiments typically were fused A-D ring systems, as indicated below.

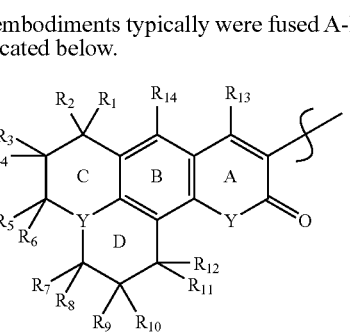

Hapten conjugates exemplifying this class are provided below.

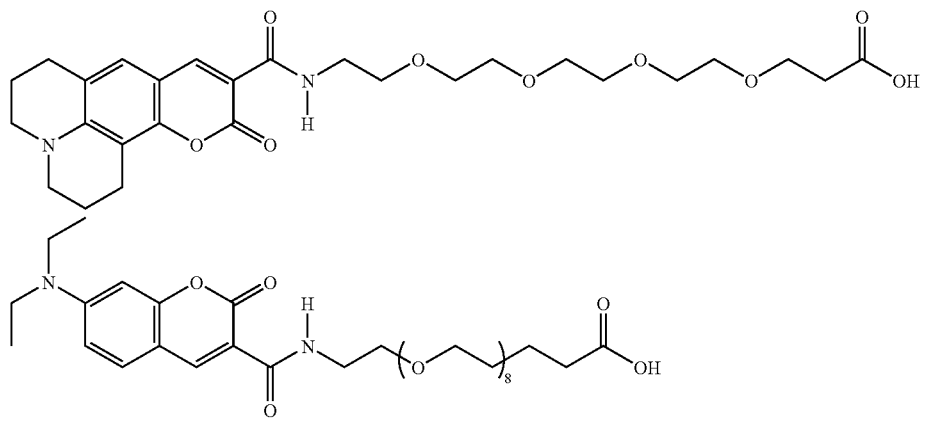

These examples satisfy the formula hapten-L-RG where L is a PEG linker and the reactive group is a carboxylic acid functional group. The carboxylic acid functional group can be converted into a different reactive functional group, as desired, such as an activated ester, including the NHS esters shown below.

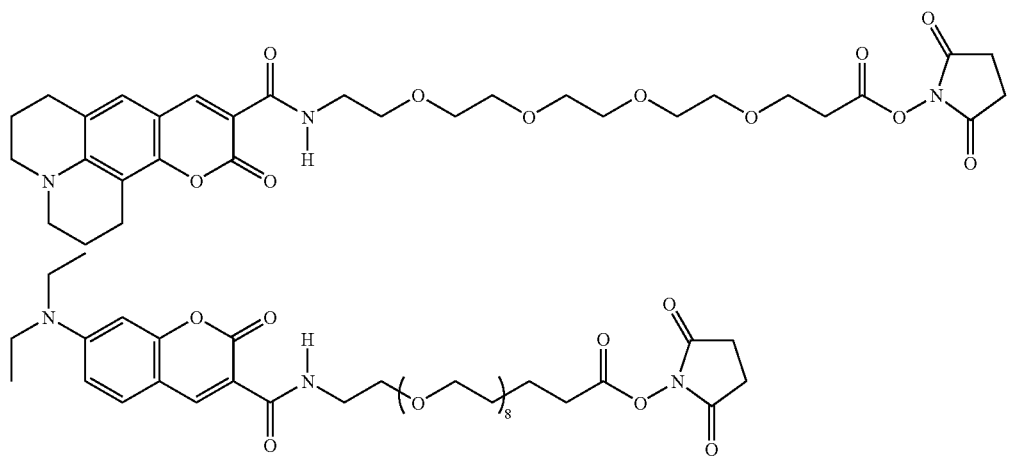

The NHS esters can be converted to other useful reactive functional group, such as a hydrazide, as illustrated below.

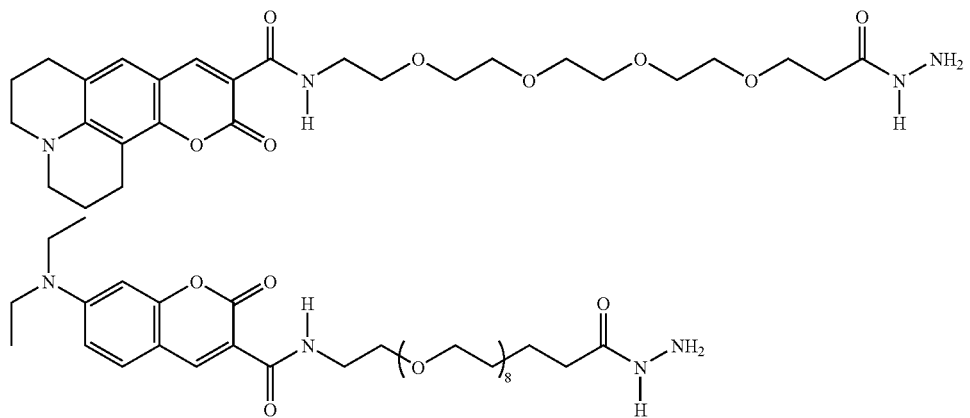

9. Cyclolignans

Cyclolignans provide another class of haptens within the scope of the present invention. A first general formula, discussed herein in detail, is provided below.

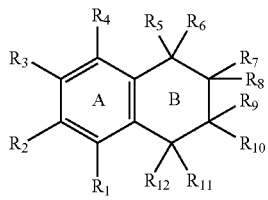

At least one of the $R_1$-$R_{12}$ substituents typically is bonded to a linker or to carrier, or is a reactive functional group capable of reacting with a linker or carrier. At least one of $R_{12}$ and $R_{11}$ also often is an aryl group, such as a benzene ring or a substituted benzene ring. Exemplary compounds where at least one of $R_{11}$ and $R_{12}$ is an aryl group typically have the following general formula, where the R substituents are as stated above.

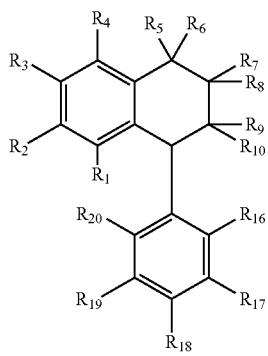

$R_9$ often is -L-RG, and $R_{16}$-$R_{20}$ independently are hydrogen and alkoxy, typically lower alkoxy, such as methoxy, as shown below. The following general molecular formula indicates likely positions for coupling linkers to this class of haptens.

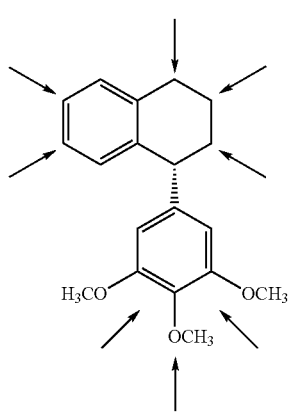 [SMILES: COc1cc([C@H]2CCCc3ccccc32)cc(OC)c1OC]

Another general formula useful for describing species of compounds within this class is as follows.

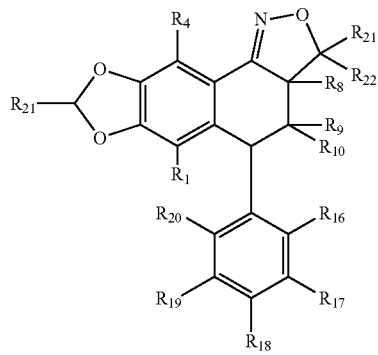

As with all hapten conjugates of the present invention, at least one of the R substituents typically is bonded to a linker, is a reactive functional group capable of reacting with a linker, or is -L-RG. For example, $R_9$ often is -L-RG, as indicted below.

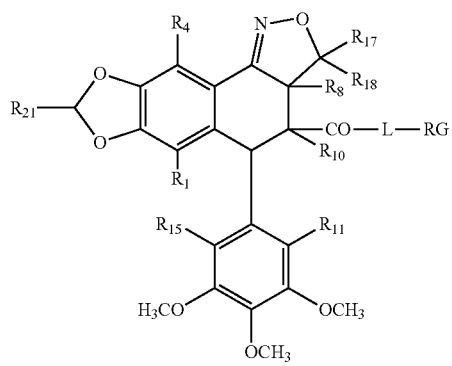

Hapten-L-RG conjugates exemplifying this class are provided below.

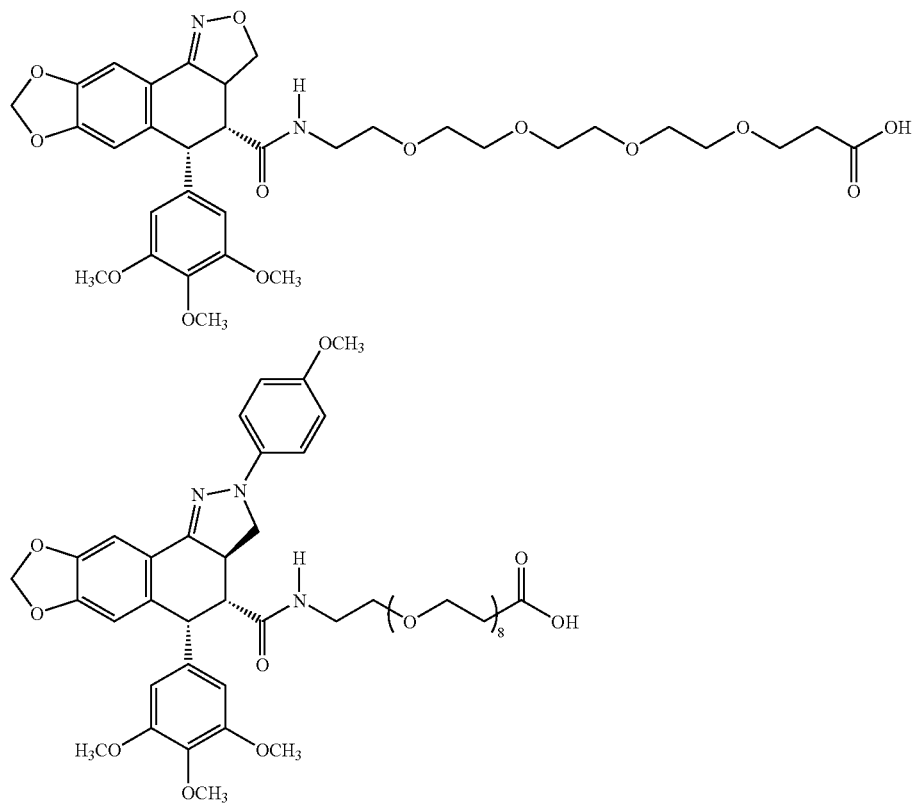
These examples satisfy the formula hapten-L-RG where L is a PEG linker and the reactive group is a carboxylic acid functional group. The carboxylic acid functional group can be converted into a different reactive functional group, as desired, such as an activated ester, including the NHS esters shown below.
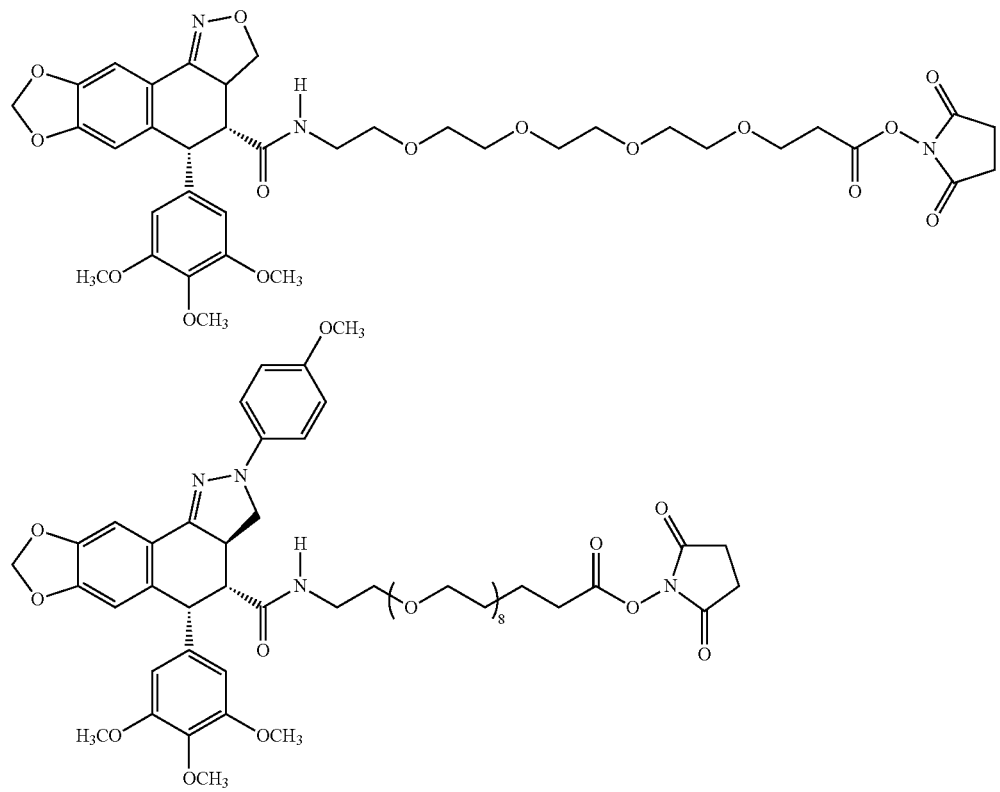

The NHS esters can be converted to other useful reactive functional groups, such as a hydrazide, as illustrated below.

suitable for directly labeling biomolecules. The carboxyl group can be activated, such as by formation of the acid halide

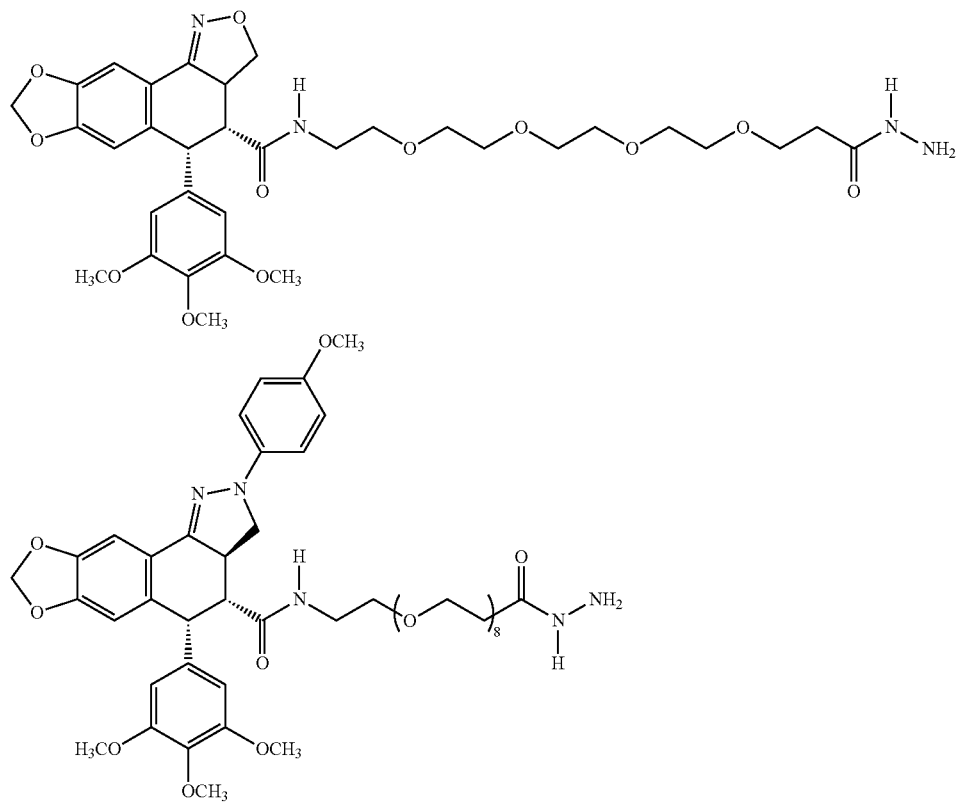

10. Heterobiaryl Hapten Conjugates

Heterobiaryl hapten conjugates provide another class of haptens within the scope of the present invention. This general class of haptens has a first general chemical formula as below.

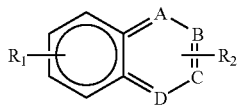

With reference to this general formula, A-D are selected from carbon, nitrogen, oxygen, and sulfur, and most typically are carbon or nitrogen.

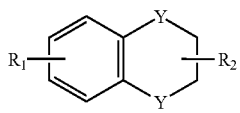

At least one of the $R_1$-$R_2$ substituents typically is bonded to a linker or to carrier, or is a reactive functional group capable of reacting with a linker or carrier.

A particular example of a monoheteroatombiaryl hapten conjugate is illustrated below. R typically is hydroxyl or carboxyl. For hydroxyl conjugates, the hydroxyl group can be converted to a halide, and subsequently displaced using an aminocarbodiimide to produce a carbodiimide compound or NHS ester for further reaction, such as with a protected hydrazide. The synthesis of these compounds is described in further detail below.

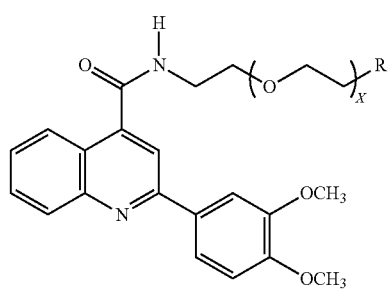

Another general class of haptens of the present invention is heterobicyclic/biaryl compounds, typically phenyl quinolines and quinoxalines, having a first general chemical formula as below.

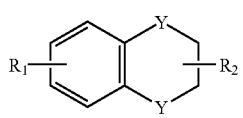

$R_1$-$R_2$ substituents are as stated above for this class of haptens. A particular example of a diheteroatombiaryl hapten conjugate is illustrated below.

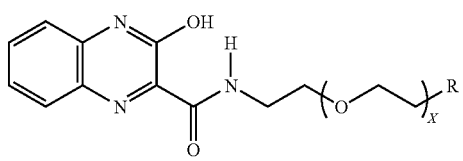

As with the monoheteroatom derivatives, R typically is hydroxyl or carboxyl. These functional groups can be used to form additional conjugates as disclosed herein. R typically is hydroxyl or carboxyl. For hydroxyl conjugates, the hydroxyl group can be converted to a halide, and subsequently displaced using an aminocarbodiimide to produce a carbodiimide compound suitable for directly labeling biomolecules. The carboxyl group can be activated, such as by formation of the acid halide or NHS ester for further reaction, such as with a protected hydrazide. The synthesis of these compounds is described in further detail below.

11. Azoaryl Conjugates

Certain disclosed embodiments of azoaryl hapten conjugates had a formula as provided below.

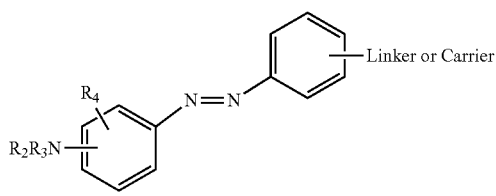

$R_2$-$R_4$ are as stated above. The linker or carrier may be, for example, coupled to the azoaryl hapten by reaction with a sulfonyl halide. One embodiment of such a conjugate, 4-(dimethylamino)azobenzene-4'-sulfonamide, has the formula provided below.

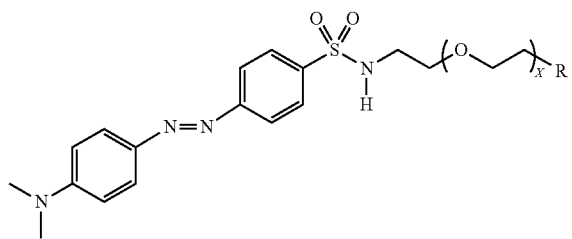

12. Benzodiazepine Conjugates

Particular embodiments of the benzodiazepine haptens have $R_1$ aryl, as indicated below, where a linker or carrier is coupled to the aryl group. For example, benzodiazepine hapten linker conjugates have a formula as indicated below.

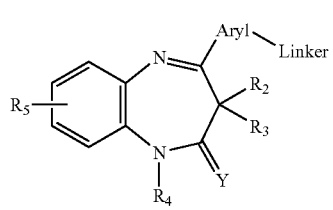

$R_2$-$R_5$ are as stated above. More typically such substituents are independently selected from aliphatic, particular alkyl, hydrogen and hydroxyl. Certain disclosed embodiments are phenyl compounds, as illustrated below.

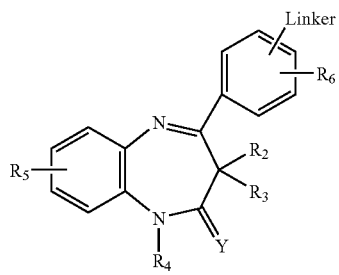

Again, $R_2$-$R_6$ are as stated above. A particular embodiment, (E)-2-(2(2-oxo-2,3-dihydror-1H-benxo[b][1,4]diazepin-4yl)phenoxy)acetamide, is provided below.

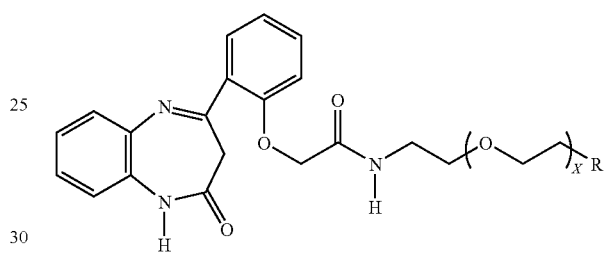

R typically is hydroxyl or carboxyl. These functional groups can be used to form additional conjugates as disclosed herein. R typically is hydroxyl or carboxyl. For hydroxyl conjugates, the hydroxyl group can be converted to a halide, and subsequently displaced using an aminocarbodiimide to produce a carbodiimide compound suitable for directly labeling biomolecules. The carboxyl group can be activated, such as by formation of the acid halide or NHS ester for further reaction, such as with a protected hydrazide. The synthesis of these compounds is described in further detail below.

V. Carriers

A person of ordinary skill in the art will recognize that the hapten linker conjugates of the present application also may include a carrier that is coupled to the hapten, or hapten-linker, by a suitable functional group. Carriers can be, by way of example, and without limitation, amino acids, polypeptides, proteins, and portions thereof; nucleosides, nucleotides, nucleotide chains, nucleic acids, DNA, RNA, mRNA, etc.; and combinations thereof. Typically carrier molecules are proteins, DNA, RNA, or combinations thereof.

Suitable carriers also are disclosed in published patent documents. For example, Waggoner et al., U.S. patent application number 2004/0057958, which is incorporated herein by reference, discloses additional suitable carriers. Carriers may be used to enhance the immunogenicity of a hapten, or any other antigenic compound that is immunogenic, non-immunogenic, or weakly immunogenic when not associated with the carrier. Certain properties of potential carriers also can be considered when selecting a particular carrier, such as physiochemical qualities including being non-immunogenic, non-allergenic, non-antigenic, being metabolizable, molecular weight, solubility, particularly in aqueous physiological solutions, such as phosphate buffered saline, for example, and capable of being conjugated (e.g., covalently bound) or associated (e.g., admixed with or associated through charge-charge interactions) with the antigenic compound.

A single carrier can be used, as well as mixtures of different carriers. Different carriers include, for example, polymers of different lengths, such, as, for example, two or more different length homopolymers, as well as mixtures of two or more different carriers or polymers of the invention. Using a single carrier requires produding only one carrier-hapten complex, whereas using multiple carriers obviously is more difficult. Using more than one carrier may be advantageous if the immune response generated against a particular hapten or epitope varies, such as in magnitude or specificity, for example, depending upon the particular carrier used, and the most optimal carrier is not known or has not yet been experimentally determined.

The carrier may be a synthetic or natural polymer, substantially antigenic, substantially non-antigenic or biodegradable, or both. Examples of suitable polymers useful as carriers include, but are not limited to, poly(diene), a poly(alkene), a poly(acrylic), a poly(methacrylic), a poly(vinyl ether), a poly(vinyl alcohol), a poly(vinyl ketone), a poly(vinyl halide), a poly(vinyl nitrile), a poly(vinyl ester), a poly(styrene), a poly(carbonate), a poly(ester), a poly(orthoester), a poly(esteramide), a poly(anhydride), a poly(urethane), a poly (amide), a cellulose ether, a cellulose ester, a poly(saccharide), poly(lactide-co-glycolide), a poly(lactide), a poly(glycolide), a copolyoxalate, a polycaprolactone, a poly(lactide-co-caprolactone), a poly(esteramide), a polyorthoester, a poly (a-hydroxybutyric acid), a polyanhydride or a mixture thereof. In another embodiment, the polymers may be a polymer or oligomer derived from the polymerization or oligomerization of at least one monomer selected from an alpha hydroxycarboxylic acid or acids (such as alpha hydroxycarboxylic acid comprises glycolic acid, lactic acid, a-hydroxy butyric acid, a-hydroxyisobutyric acid, a-hydroxyvaleric acid, a-hydroxyisovaleric acid, a-hydroxy caproic acid, a-hydroxy-a-ethylbutyric acid, a-hydroxyisocaproic acid, a-hydroxy-3-methylvaleric acid, a-hydroxyheptanoic acid, a-hydroxyoctanoic acid, a-hydroxydecanoic acid, a-hydroxymysristic acid, a-hydroxystearic acid, a-hydroxyligoceric acid), a lactone (3-propiolactone, tetramethyleneglycolide, b-butyrolactone, 4-butyrolactone, pivalactone), a diene, an alkene, an acrylate, a methacrylate, a vinyl ether, a vinyl alcohol, a vinyl ketone, a vinyl halide, a vinyl nitrile, a vinyl ester, styrene, a carbonate, an ester, an orthoester, an esteramide, an anhydride, a urethane, an amide, a cellulose ether, a cellulose ester, a saccharide, an alpha hydroxycarboxylic acid, a lactone, an esteramide, or a mixture thereof.

The polymer may be derived from one or more amino acids, including both homopolymers and heteropolymers thereof. For example, polyglutamate derived from L-glumatic acid, D-glumatic acid or mixtures, e.g., racemates, of these L and D isomers are used. L and/or D glutanyl, aspartly, glycyl, seryl, threonyl, and cysteinyl are all examples of amino acids that may be used. The polymer also may be a block, graft or random copolymer. These include, for example, copolymers containing at least one other amino acid, such as aspartic acid, serine, tyrosine, glycine, ethylene glycol, ethylene oxide, (or an oligomer or polymer of any of these) or polyvinyl alcohol. Glutamic acid may, of course, carry one or more substituents and the polymers include those in which a proportion or all of the glutamic acid monomers are substituted. Particular polymer examples include, but are not limited to, poly(l-glutamic acid), poly(d-glutamic acid), poly(dl-glutamic acid), poly(l-aspartic acid), poly(d-aspartic acid), poly(dl-aspartic acid), poly(l-serine), poly(d-serine), poly(dl-serine), poly(l-tyrosine), poly(d-tyrosine), poly(dl-tyrosine), poly(l-glysine), poly(d-glysine), poly(dl-glysine), poly(l-threonine), poly(d-threonine), poly(dl-threonine), poly(d-cysteine), poly(l-cysteine), and poly(dl-cysteine). In further embodiments, the polymers are copolymers, such as block, graft or random copolymers, of the above listed poly (amino acids) with polyethylene glycol, polycaprolactone, polyglycolic acid and polylactic acid, as well as poly(2-hydroxyethyl 1-glutamine), chitosan, carboxymethyl dextran, hyaluronic acid, human serum albumin and alginic acid, with poly-glutamic acids being particularly preferred.

The molecular weight of suitable polymers may vary. Typically, however, the molecular weight is from about 1,000 kilodaltons molecular weight to less than 10,000,000 kilodaltons.

Working embodiments exemplifying protein carriers included bovine thyroglobulin, keyhole limpet hemocyanin, or bovine serum albumin.

Hapten conjugates of the present application include a reactive functional groups for coupling the hapten to a carrier, or the hapten to a linker to form a hapten-linker compound. For protein coupling, proteins include various functional groups, typically nucleophiles, that can be coupled to suitable electrophilic functional groups to form hapten conjugates. For example, a free amine (—NH$_2$) or secondary amine can be used to couple the protein to the hapten or hapten-linker compound to form amides by reaction with carboxylic acids or carboxylic acid derivatives, such as acid halides (—CO), succinimide ester, etc.; alkyl halides can be used to form amines; carbonyl compounds, such as ketones and aldehydes, can be used to form imines; and combinations thereof. Certain amino acids include other reactive functional groups suitable for coupling carriers of haptens, including reactive hydroxyl and/or sulfhydryl groups. Exemplary couplings include ester and lactone formation by reaction with a carboxylic acid or carboxylic acid derivative; ether formation; and combinations thereof.

VI. Signal Generating Moieties

Conjugates comprising signal generating moieties, such as conjugates of specific-binding moieties and signal-generating moieties, can be used in assays for detecting specific target molecules in biological samples. The signal-generating portion is utilized to provide a detectable signal that indicates the presence/and or location of the target. Examples of signal-generating moieties include, by way of example and without limitation: enzymes, such as horseradish peroxidase, alkaline phosphatase, acid phosphatase, glucose oxidase, β-galactosidase, β-glucuronidase or β-lactamase. Horseradish peroxidase is widely used as a label for immunoglobulins in many different immunochemistry applications including ELISA, immunoblotting and immunohistochemistry. In addition to other possible disclosed embodiments, HRP can be conjugated to antibodies by several different methods including glutaraldehyde, periodate oxidation, through disulfide bonds, and also via amino and thiol directed cross linkers. HRP is the smallest and most stable of the three most popular enzyme labels (HRP, alkaline phosphatase, and B-galactosidase) and its glycosylation leads to lower non-specific binding; fluorescent molecules (such as fluoresceins, coumarins, BODIPY dyes, resorufins, rhodamines; additional examples can be found in *The Handbook—A Guide to Fluorescent Probes and Labeling Technologies*, Invitrogen Corporation, Eugene, Oreg.), detectable constructs (such as fluorescent constructs like quantum dots, which can be obtained, for example, from Invitrogen Corporation, Eugene, Oreg.; see, for example, U.S. Pat. Nos. 6,815,064, 6,682,596 and 6,649,138, each of which patents is incorporated by reference herein), metal chelates (such as DOTA and DPTA chelates of radioactive or paramagnetic metal ions like $Gd^{3+}$) and liposomes (such as liposomes sequestering fluorescent molecules.

When the signal-generating moiety includes an enzyme, a chromagenic compound, fluorogenic compound, or luminogenic compound can be used to generate a detectable signal (a wide variety of such compounds are available, for example, from Invitrogen, Eugene Oreg.). Particular examples of chromogenic compounds include di-aminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitorphenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

Labeled secondary antibodies can be purchased from a number of sources, such as, but not limited to, Pierce Co. Amersham and Evident Technologies provide a broad range of conjugated antibody possibilities. CyDye, EviTag Quantum Dot, fluorescein (FITC), and rhodamine can be utilized. These conjugates span a variety of applications, colors, and emission ranges. The EviTag Quantum Dots from Evident Technologies offer photo-stability and multicolor fluorescence in a variety of wavelengths, with the advantage over organic fluorophores of improved photostability, color multiplexing, and single source excitation. Each Evitag generates a sharp emission wavelength making them ideal for multiplexing in intact cell environments.

The Amersham CyDyes offer superior photostability over a broad range of pH values. For a tutorial on fluorescent markers, with the chemical structures of the labels, see: http://www.hmds.org.uk/fluorochrome.html. See the following link on how to label with haptens: http://probes.invitrogen.com/handbook/boxes/2020.html One type of detectable conjugate is a covalent conjugate of an antibody and a fluorophore. Directing photons toward the conjugate that are of a wavelength absorbed by the fluorophore stimulates fluorescence that can be detected and used to qualitate, quantitate and/or locate the antibody. A majority of the fluorescent moieties used as fluorophores are organic molecules having conjugated pi-electron systems. While such organic fluorophores can provide intense fluorescence signals, they exhibit a number of properties that limit their effectiveness, especially in multiplex assays and when archival test results are needed.

Organic fluorophores can be photo-bleached by prolonged illumination with an excitation source, which limits the time period during which maximal and/or detectable signals can be retrieved from a sample. Prolonged illumination and/or prolonged exposure to oxygen can permanently convert organic fluorophores into non-fluorescent molecules. Thus, fluorescence detection has not been routinely used when an archival sample is needed.

Chromophoric and/or fluorescent semiconductor nanocrystals, also often referred to as quantum dots, can be used for identifying complexes. Nanocrystalline quantum dots are semiconductor nanocrystalline particles, and without limiting the present invention to use with particle light emitters of a particular size, typically measure 2-10 nm in size (roughly the size of typical proteins). Quantum dots typically are stable fluorophores, often are resistant to photo bleaching, and have a wide range of excitation, wave-length and narrow emission spectrum. Quantum dots having particular emission characteristics, such as emissions at particular wave-lengths, can be selected such that plural different quantum dots having plural different emission characteristics can be used to identify plural different targets. Quantum dot bioconjugates are characterized by quantum yields comparable to the brightest traditional dyes available. Additionally, these quantum dot-based fluorophores absorb 10-1000 times more light than traditional dyes. Emission from the quantum dots is narrow and symmetric, which means overlap with other colors is minimized, resulting in minimal bleed through into adjacent detection channels and attenuated crosstalk, in spite of the fact that many more colors can be used simultaneously. Symmetrical and tuneable emission spectra can be varied according to the size and material composition of the particles, which allows flexible and close spacing of different quantum dots without substantial spectral overlap. In addition, their absorption spectra are broad, which makes it possible to excite all quantum dot color variants simultaneously using a single excitation wavelength, thereby minimizing sample autofluorescence.

Furthermore, it has been found that pegylation, the introduction of polyethylene glycol groups onto the quantum dot conduits, can substantially decrease non-specific protein: quantum dot interaction. Certain quantum dots are commercially available, such as from Quantum Dot Corp., of Hayward, Calif., and Invitrogen.

Standard fluorescence microscopes are an inexpensive tool for the detection of quantum dot bioconjugates. Since quantum dot conjugates are virtually photo-stable, time can be taken with the microscope to find regions of interest and adequately focus on the samples. Quantum dot conjugates are useful any time bright photo-stable emission is required and are particularly useful in multicolor applications where only one excitation source/filter is available and minimal crosstalk among the colors is required. For example, quantum dots have been used to form conjugates of Streptavidin and IgG to label cell surface markers and nuclear antigens and to stain microtubules and actin (Wu, X. et al. (2003). Nature Biotech. 21, 41-46).

As an example, fluorescence can be measured with the multispectral imaging system Nuance™ (Cambridge Research & Instrumentation, Woburn, Mass.). As another example, fluorescence can be measured with the spectral imaging system SpectrView™ (Applied Spectral Imaging, Vista, Calif.). Multispectral imaging is a technique in which spectroscopic information at each pixel of an image is gathered and the resulting data analyzed with spectral image-processing software. For example, the Nuance system can take a series of images at different wavelengths that are electronically and continuously selectable and then utilized with an analysis program designed for handling such data. The Nuance system is able to obtain quantitative information from multiple dyes simultaneously, even when the spectra of the dyes are highly overlapping or when they are co-localized, or occurring at the same point in the sample, provided that the spectral curves are different. Many biological materials autofluoresce, or emit lower-energy light when excited by higher-energy light. This signal can result in lower contrast images and data. High-sensitivity cameras without multispectral imaging capability only increase the autofluorescence signal along with the fluorescence signal. Multispectral imaging can unmix, or separate out, autofluorescence from tissue and, thereby, increase the achievable signal-to-noise ratio.

Haptens can be conjugated to quantum dots, and quantum dot fluorescence can be stimulated, such as by using fluorescence resonance energy transfer (FRET) whereby low-wavelength light stimulates quantum dot fluorescence. Invitrogen has determined that biotin-conjugated quantum dots had a 100-fold lower limit of detection for the biotin derivative biocytin than anti-biotin Alexa Fluor. Fully biotinylated quantum dots were 10-fold less sensitive than quantum dots with 25 percent biotin coverage.

Quantum dot use has so far been limited by their lack of biocompatibility. New advances in surface coating chemistry, however, have helped to overcome these problems. See, for example, Wu, X. et al. Immunofluorescent labeling of cancer marker Her2 and other cellular targets with semiconductor quantum dots, *Nature Biotechnol.* 21, 41-46 (2003); Jaiswal, J. K., Mattoussi, H., Mauro, J. M. & Simon, S. M. Long-term multiple color imaging of live cells using quantum dot bioconjugates, *Nature Biotechnol.* 21, 47-51 (2003); and Dubertret, B. et al. In vivo imaging of quantum dots encapsulated in phospholipid micelles. *Science* 298, 1759-1762 (2002).

Quantum dots also have been conjugated to biorecognition molecules, Id., such as streptavidin. These conjugates have been used on both fixed cells and tissue sections. In addition, cell-surface proteins and the endocytic compartments of live cells have been labelled with quantum dot bioconjugates.

Fluorescent proteins also can be used as a carrier, or can be coupled to a carrier, to facilitate visualization. For example, green fluorescent protein (GFP) was originally isolated from the light-emitting organ of the jellyfish *Aequorea victoria*. Chimeric GFP fusions can be expressed in situ by gene transfer into cells, and can be localized to particular sites within the cell by appropriate targeting signals. Spectral variants with blue, cyan and yellowish-green emissions have been successfully generated from the *Aequorea* GFP, but only exhibit emission maxima longer than 529 nm. GFP-like proteins have been isolated from *Anthozoa* (coral animals) that significantly expanded the range of colors available for biological applications. The family of 'GFP-like proteins' deposited in sequence databases now includes approximately 30 significantly different members. Fluorescent proteins refers to proteins that can become spontaneously fluorescent through the autocatalytic synthesis of a chromophore.

Proteins that fluoresce at red or far-red wavelengths (red fluorescent proteins or RFPs) are known. RFPs can be used in combination with other fluorescent proteins that fluoresce at shorter wavelengths for both multicolour labelling and fluorescence resonance energy transfer (FRET) experiments. Commercially available RFPs are derived from two wild-type GFP-like proteins. DsRed (drFP583) has excitation and emission maxima at 558 nm and 583 nm, respectively. A far-red fluorescent protein was generated by mutagenesis of a chromoprotein that absorbs at 571 nm. HcRed1 (Clontech) has excitation and emission maxima at 588 nm and 618 nm, respectively. The fluorescent protein that emits fluorescence at the longest wavelength (without any mutations being introduced) is eqFP611, cloned from the sea anemone *Entacmaea quadricolor*. This protein absorbs at 559 nm and emits at 611 nm. As many spectral variants have emerged, more investigators are becoming interested in the simultaneous imaging of multiple fluorophores and/or FRET signals.

Fusion proteins also can be used to form hapten conjugates of the present invention. There are at least three points to consider when creating a functional fluorescent protein: the fluorescent protein must fold correctly to fluoresce; the host protein must fold correctly to be functional; and the integrity of the chimeric protein must be maintained.

The length and sequence of any linker between the fluorescent protein and host protein should be optimized for each specific application. The most widely used linker designs have sequences that primarily consist of glycine (Gly) and serine (Ser) stretches, Ser residues being interspersed to improve the solubility of a poly-Gly stretch.

The decision of whether to fuse a fluorescent protein to the amino or carboxyl terminus of a protein depends on the properties of the protein. For example, a particular terminus might need to be preserved to retain proper protein function or to ensure correct localization. This decision might also be made on the basis of structural aspects of the particular fluorescent protein. For example, *Aequorea* GFP has a floppy carboxyl terminal tail of approximately ten amino acids, which makes its fusion to the amino terminus of other proteins possible without the addition of a linker. By contrast, DsRed is more successfully fused to the carboxyl terminus of proteins of interest, because the amino termini project fully from a tetrameric complex of DsRed. If neither end of a host protein can be modified, it is possible to insert the fluorescent protein into the middle of the protein.

Citrine and Venus, two bright versions of a yellow-emitting mutant of GFP (YFP) that mature efficiently, have recently been developed.

Two recently developed varieties of DsRed, known as T1 and E57, display improved maturation, making them preferable for use in dual-color experiments.

Fluorescence of some GFP variants can be 'photoactivated' by specific illumination, which provides the advantage that fluorescence can be turned on at a chosen time point. Three fluorescent proteins that undergo photochemical modification in or near the chromophore have been developed, PA-GFP, Kaede and KFP1, that enable selective activation of fluorescence signals after specific illumination, and can be used to fluorescently mark individual cells, organelles or proteins.

Table 1 provides additional examples of signal generating moieties and conjugates comprising such moieties.

TABLE 1

Exemplary Antibody-Detectable Label Conjugates

| Antibody Conjugate Label | Recommended for ... | Emitted Color | Label Excitation (nm) | Label Emission (nm) |
|---|---|---|---|---|
| Lake Placid Blue (EviTag™ Quantum Dot) | Flow cytometry, immunoblots, and fluorescent microscopy | | <450 | 490 |
| Fluorescein (i.e. FITC) | Flow cytometry, incl. BD FACS systems and Guava System, and fluorescent microscopy | | 494 | 518 |
| Adirondack Green (EviTag™ Quantum Dot) | Flow cytometry, immunoblots, and fluorescent microscopy | | <450 | 520 |
| Rhodamine Green | Fluorescent microscopy | | 502 | 527 |
| Catskill Green (EviTag™ Quantum Dot) | Fluorescent microscopy | | <450 | 540 |
| Rhodamine 6G | Flow cytometry, immunoblots, and fluorescent microscopy | | 525 | 555 |
| Hops Yellow (EviTag™ Quantum Dot) | Flow cytometry, immunoblots, and fluorescent microscopy | | <450 | 560 |
| Amersham Cy3 | Fluorescent microscopy | | 550 | 565 |
| R-Phycoerythrin (PE) | Flow cytometry, Luminex® and Guava systems, FRET assays, and capillary electrophoresis; use with FITC for double labeling | | (495)565 | 575 |
| Rhodamine Red | Flow cytometry, fluorescent microscopy | | 560 | 580 |
| Birch Yellow (EviTag™ Quantum Dot) | Fluorescent microscopy | | <450 | 580 |
| Amersham Cy3.5 | Fluorescent microscopy | | 581 | 596 |
| Fort Orange (EviTag™ Quantum Dot) | Flow cytometry, immunoblots, and fluorescent microscopy | | <450 | 600 |
| SulfoRhodamine (Alias Texas Red®) | Flow cytometry and fluorescent microscopy | | 596 | 615 |
| Amersham Cy5 | Immunoblot, incl. Amersham Typhoon System, and immunofluorescent applications | | 650 | 670 |
| Allophycocyanin (APC) | FRET assays and HTRF assays | | 652 | 670 |
| Amersham Cy5.5 | Immunoblot, especially LI-COR Odyssey systems | | 675 | 694 |
| Biotin | Flow cytometry and other fluorescent applications | | - | |

Many of these labels can be used with multiple antibodies that do not cross-react to create custom multiplexed assays.

VII. Processes for Forming Hapten Conjugates—Reaction Schemes

The following schemes provide exemplary embodiments of a method useful for making conjugates of the present invention. Other synthetic methodologies also are useful for making such conjugates, and the following schemes should not be construed to limit the method to the particular synthetic methodologies depicted.

1. Nitropyrazole Conjugates

Scheme 1 illustrates one method suitable for coupling exemplary nitropyrazole haptens to an alkylene oxide linker, and subsequently to a protein carrier.

Scheme 1

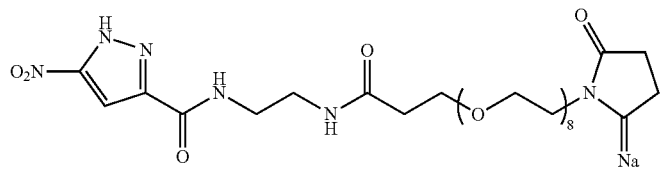

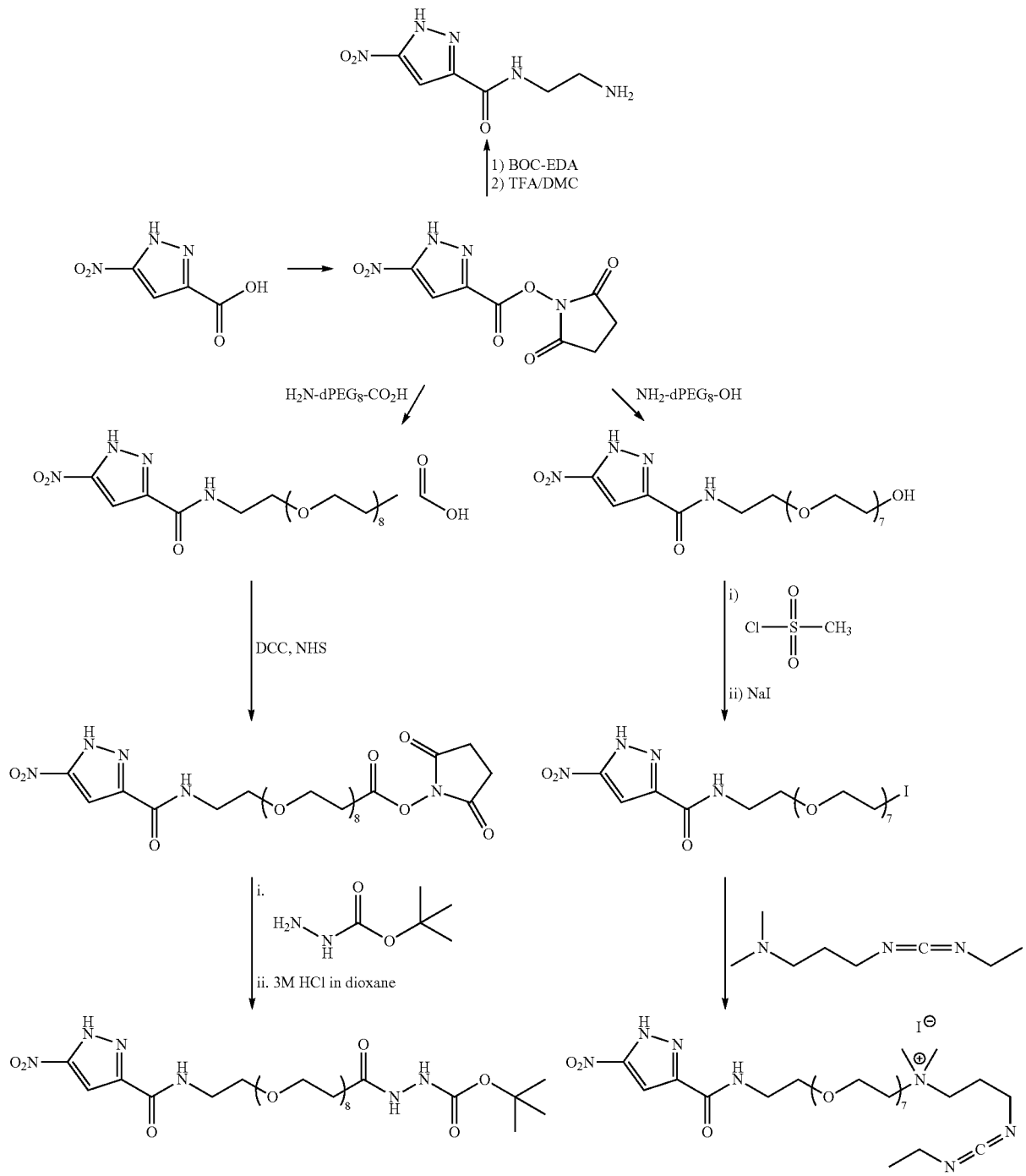

Scheme 1 illustrates coupling the exemplary nitropyrazole hapten is to an exemplary ethylene glycol linker via the pendent carboxylic acid functional group. The first step is forming an N-hydroxysuccinimide (NHS) ester from nitropyrazole. This "activates" the ester for subsequent reaction with a nucleophile. Formation of the NHS ester was achieved in working embodiments using dicyclohexylcarbodiimide (DCC) as a coupling reagent. Dichloromethane was used as the solvent, and triethylamine was added as a base. The NHS ester is then ready for coupling to a nucleophile.

A first possible synthetic path is reacting the activated ester with a diamine to produce an amide having a terminal amine. The diamine can be a protected diamine, as illustrated in Scheme 1 where the BOC-ethylene diamine compound is used. The BOC-protected amide is then deprotected using trifluoroacetic acid (TFA) in dichloromethane. The deprotected compound can then be reacted with a maleimide-PEG-NHS ester to couple a linker to the hapten. The linker also includes a reactive functional group at the terminal end.

As another alternative, the hapten having an activated ester can be coupled to a linker to form an amide having either a terminal carboxylic acid functional group or a terminal hydroxyl group. A second DCC coupling reaction can be performed to again activate the carboxylic acid functional group, which is reacted with the illustrated protected hydrazine reagent. Deprotection in hydrochloric acid produced the illustrated hydrazide. Alternatively, nitropyrazole hapten-PEG linker having an activated ester pendent functional group is suitable for reacting with a carrier protein to form an immunogen.

Another alternative synthetic path is illustrated using the hapten-PEG linker having a terminal hydroxyl group. The hydroxyl terminated compound can be reacted with mesyl chloride, followed by reaction with iodide to provide the iodo-substituted derivative. This compound can be reacted with the illustrated dimethyl amine carbodiimide to produce a compound useful for direct labeling of a biomolecule.

2. Nitrophenyl Conjugates

Scheme 2 illustrates exemplary dinitrophenyl haptens coupled to an alkylene oxide (PEG) linker. These hapten-linker conjugates subsequently can be derivatized as desired or directly coupled to a carrier.

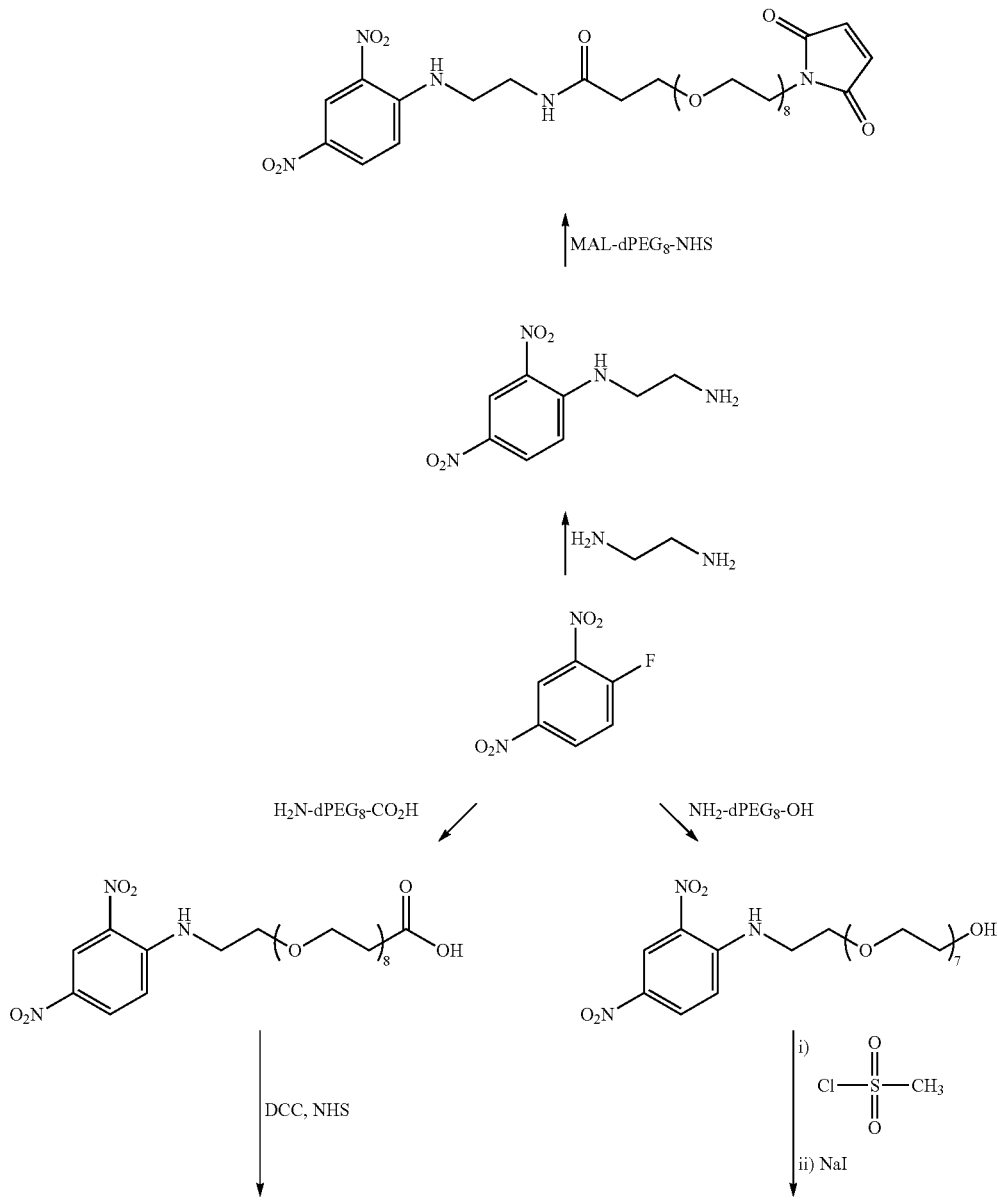

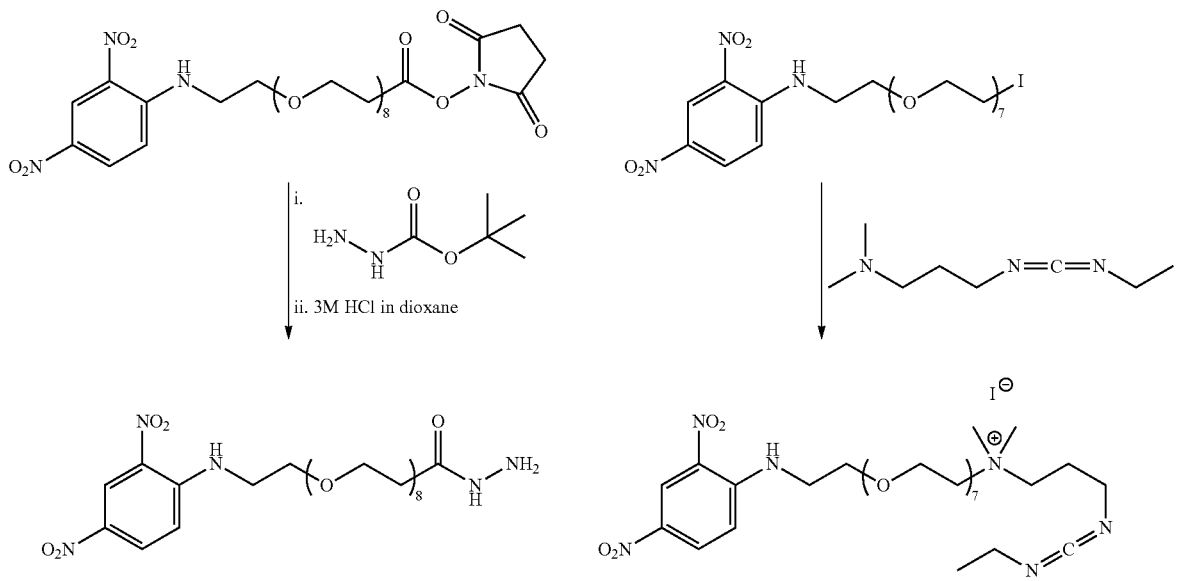

The exemplary dinitrophenyl hapten was coupled to an alkylene oxide linker, namely a bifunctional polyethylene glycol having both a pendent free acid and amine. In a first approach, the dinitrophenyl hapten was coupled to ethylene diamine via substitution, with the ring position occupied by fluorine being activated for nucleophilic substitution by the presence of the ortho and para nitro groups. The resulting compound includes a terminal nucleophilic amine for coupling to a maleimide-PEG-NHS ester.

Alternatively, the dinitrophenyl hapten can be reacted with an amino-PEG compound having either a terminal carboxylic acid or hydroxyl group. With reference to the carboxylic acid derivative, this compound was reacted with the dinitrophenyl hapten to substitute for fluorine. An NHS ester was then formed using DCC in dichloromethane. The activated ester is suitable for derivatizing as desired, such as by reaction with the illustrated protected hydrazine reagent, followed by deprotection using an acid, such as hydrochloric or trifluoracetic acid. Alternatively, the activated ester is suitable for coupling to a carrier protein to form an immunogen.

As yet another alternative, the dinitrophenyl hapten can be reacted with an amino-PEG linker to produce a compound having a terminal hydroxyl group. The hydroxyl terminated compound can be reacted with mesyl chloride, followed by reaction with iodide to provide an iodo-substituted derivative. This compound can be reacted with the illustrated dimethyl amine carbodiimide to produce a compound useful for direct labeling of a biomolecule.

A second example of a synthetic pathway for making cinnamide-based conjugates is provided below in Scheme 3. The exemplary nitrophenyl hapten was converted to the corresponding NHS ester using DCC. The NHS ester was reacted with ethylene diamine. The resulting compound includes a terminal nucleophilic amine for coupling to a maleimide-PEG-NHS ester.

Alternatively, the nitrophenyl hapten can be reacted with an amino-PEG compound having either a terminal carboxylic acid or hydroxyl group. With reference to the carboxylic acid derivative, this compound was reacted with the nitrophenyl. An NHS ester was then formed using DCC in dichloromethane. The activated ester is suitable for derivatizing as desired, such as by reaction with the illustrated protected hydrazine reagent, followed by deprotection in hydrochloric acid. Alternatively, the activated ester is suitable for coupling to a carrier protein to form an immunogen.

As yet another alternative, the nitrophenyl hapten can be reacted with a amino-PEG linker to produce a compound having a terminal hydroxyl group. The hydroxyl terminated compound can be reacted with mesyl chloride, followed by reaction with iodide to provide an iodo-substituted derivative. This compound can be reacted with the illustrated dimethyl amine carbodiimide to produce a compound useful for direct labeling of a biomolecule.

Scheme 3

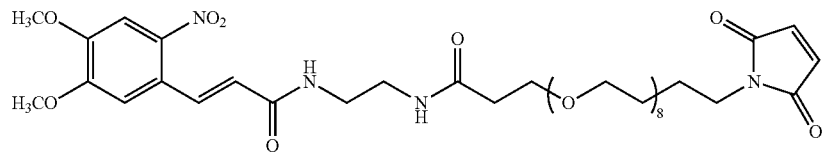

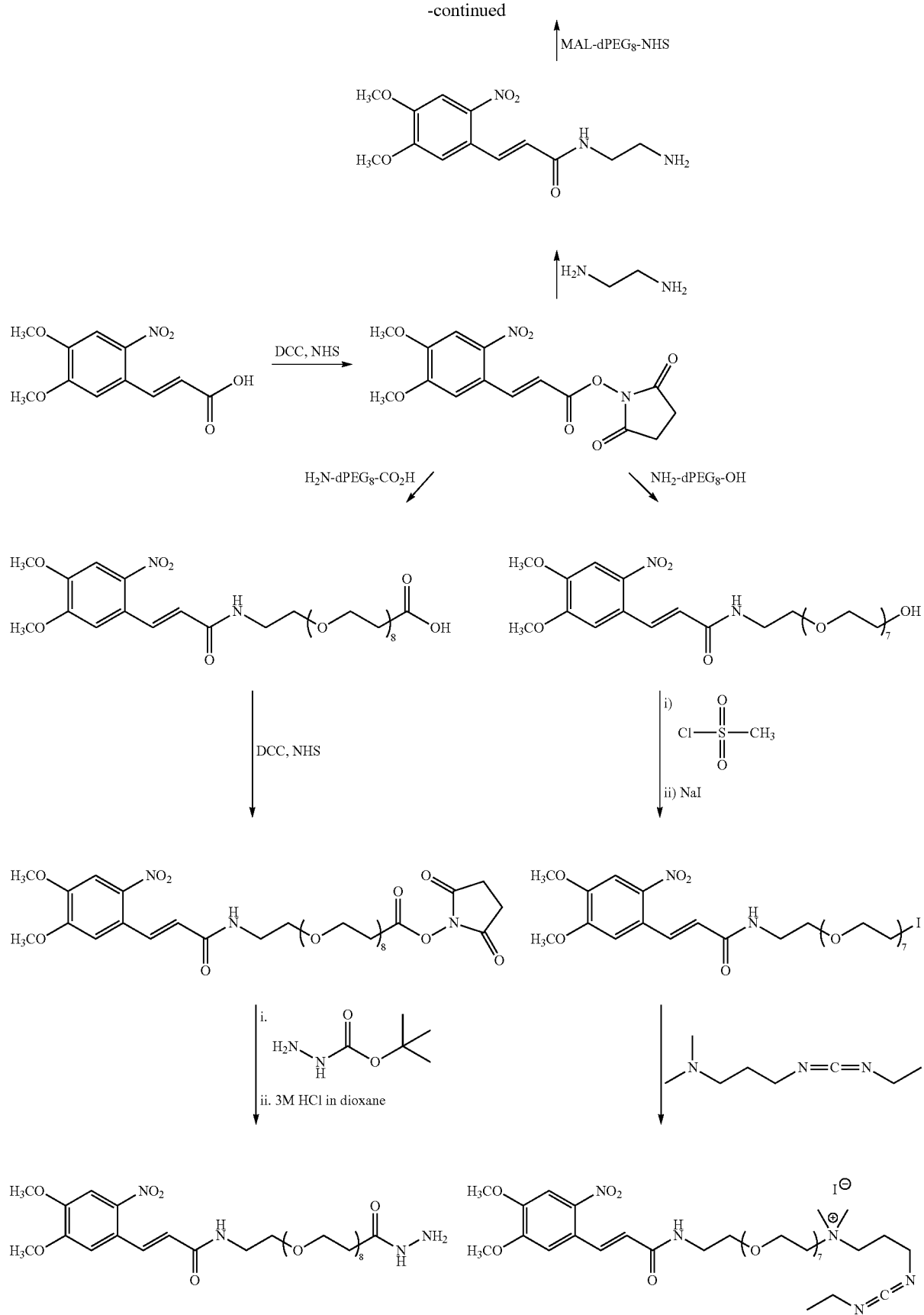

3. Benzofurazan Conjugates

Scheme 4 illustrates synthetic methodologies suitable for coupling exemplary benzofurazan haptens to an alkylene oxide linker.

With reference to Scheme 4, the exemplary benzofurazan hapten includes a carboxylic acid functional group. The first step is activation of the carboxylic acid functional group by reaction with NHS using DCC as a coupling agent to form an

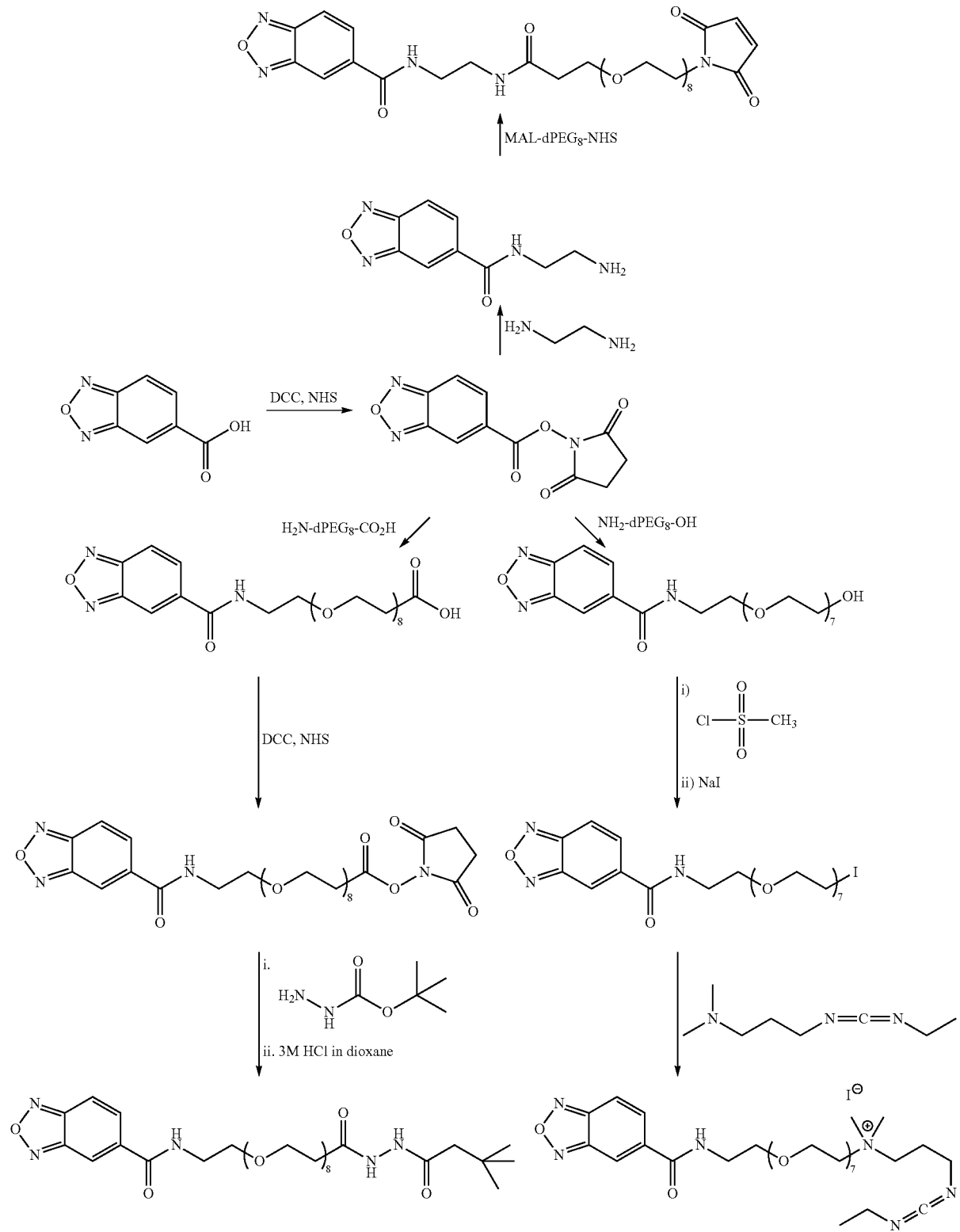

Scheme 4 activated ester, or by formation of an acid chloride. As a first option, the activated ester can be reacted with a diamine to produce a terminal amine. In certain embodiments, the diamine is a protected diamine, such as a BOC-protected diamine, as illustrated below in Scheme 5. Following the coupling reaction, the BOC protecting group can be removed in acid, such as trifluoroacetic acid. The deprotected compound is then reacted with a maleimide-PEG-NHS ester to couple a linker to the hapten.

As a second alternative illustrated by Scheme 4, the activated ester is now ready for coupling with a linker, if desired, such as the exemplary bifunctional alkylene oxide linkers, i.e. PEG linkers. Exemplary PEG linkers may have both an amine and a carboxylic acid group or an amine and a hydroxyl group. Reaction of activated ester compound with linker provides either a carboxylic acid terminated compound or a hydroxyl group terminated compound. The carboxylic acid can be converted to an activated ester by reaction with NHS using DCC as a coupling agent. This activated ester can be reacted with the illustrated protected hydrazine reagent, followed by deprotection in hydrochloric acid.

Alternatively, the hydroxyl terminated compound can be reacted with mesyl chloride, followed by reaction with iodide to provide the iodo-substituted compound. This compound can be reacted with the illustrated dimethyl amine carbodiimide to produce a compound useful for direct labeling of a biomolecule.

Another alternative synthesis path for making a maleimide-dPEG$_8$ conjugate is provided below in Scheme 5. The acid chloride is then treated with a BOC-protected hydrazide, followed by deprotection using trifluoroacetic acid. The hydrazide is then reacted with maleimide-dPEG8-NHS to produce the illustrated conjugate.

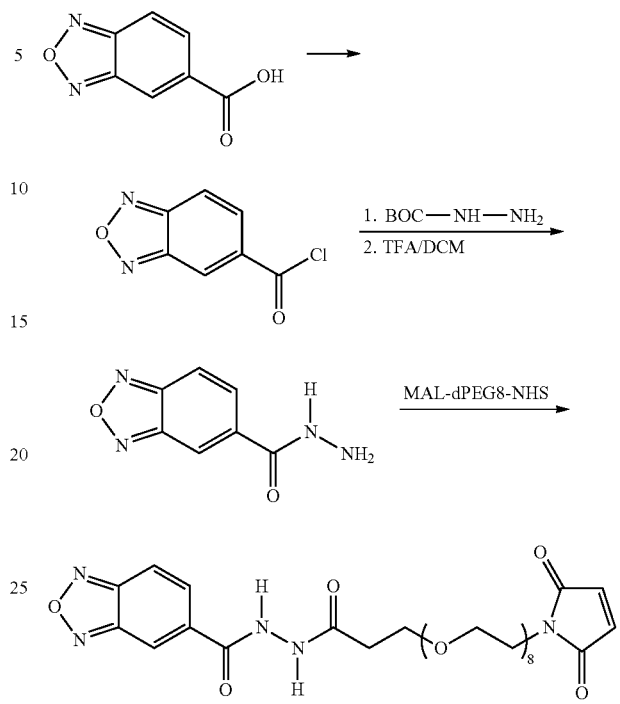

Scheme 5

4. Triterpene-Linker Conjugates and Triterpene Immunogens

Scheme 6 illustrates one method suitable for coupling exemplary triterpene haptens to an alkylene oxide linker to form hapten-linker conjugates. The hapten-linker conjugates can be further derivatized as desired, or can be directly coupled to a protein carrier molecule.

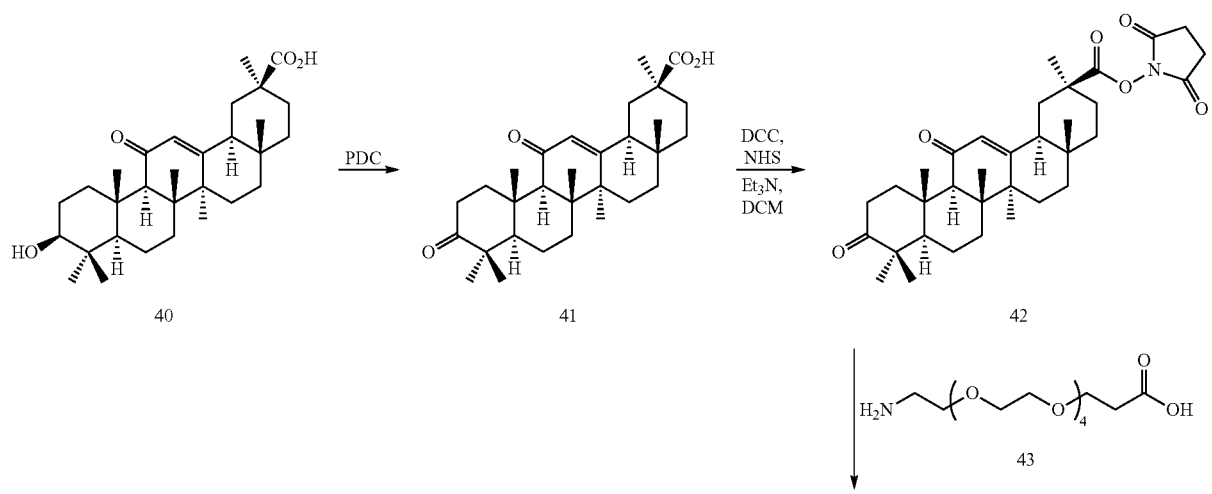

Scheme 6

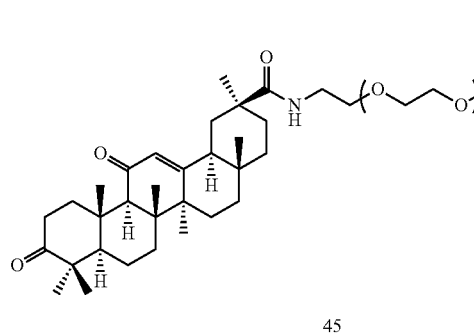

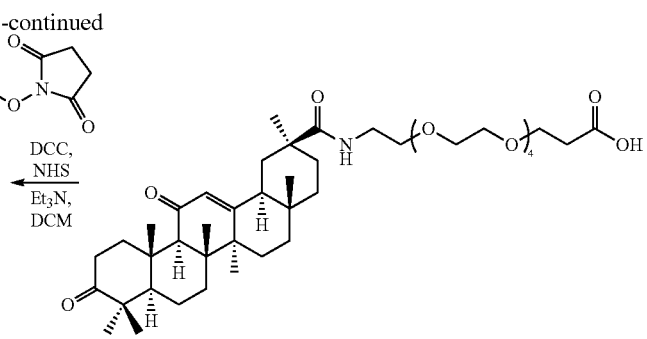

With reference to Scheme 6, starting compound 40 was oxidized to ketone 41 using pyridinium dichromate (PDC). The NHS activated ester 42 was then formed using DCC coupling in dichloromethane. Activated ester 42 was then reacted with a bifunctional PEG-4 linker 43 comprising both an amine and carboxylic acid functional group to form amide 44. The carboxylic acid functional group of compound 44 was converted to the activated ester 45 again using NHS and DCC. Activated ester 45 was then coupled to an immunogenic protein carrier to form immunogen 46.

5. Urea- and Thio Urea-Based Hapten-Linker Conjugates and Immunogens

Scheme 7 illustrates one method suitable for coupling exemplary urea and thioureas-based haptens to an alkylene oxide linker, and subsequently to a protein carrier molecule.

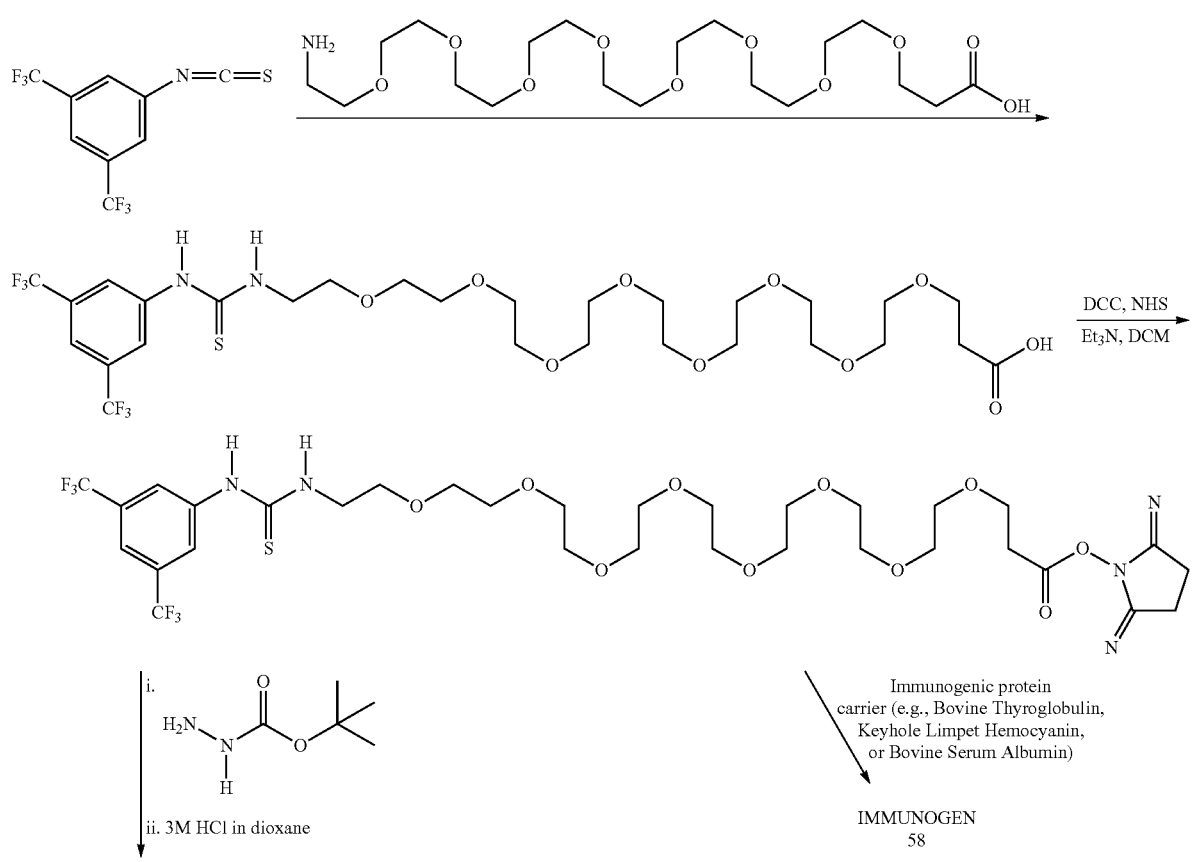

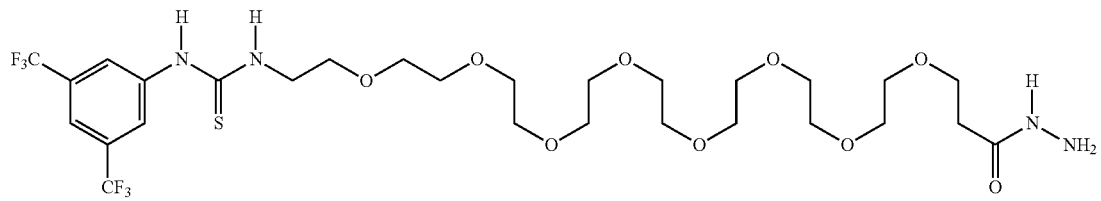

With reference to Scheme 7, starting isothiocyanate compound 51 was reacted with a PEG-4 linker 52 comprising both an amine and a carboxylic acid functional group to form thiourea 53. The carboxylic acid functional group of compound 53 was converted to the activated ester 54 using NHS and DCC. Activated ester 54 was then coupled to protected hydrazine reagent 55, followed by deprotection in 3M hydrochloric acid, to form compound 56. Alternatively, activated ester 54 can be coupled to a carrier to form immunogen 58.

6. Rotenone-Based Hapten-Linker Conjugates and Immunogens

Scheme 8 illustrates one method suitable for coupling exemplary rotenone-based haptens to an alkylene oxide linker, and subsequently to a protein carrier molecule

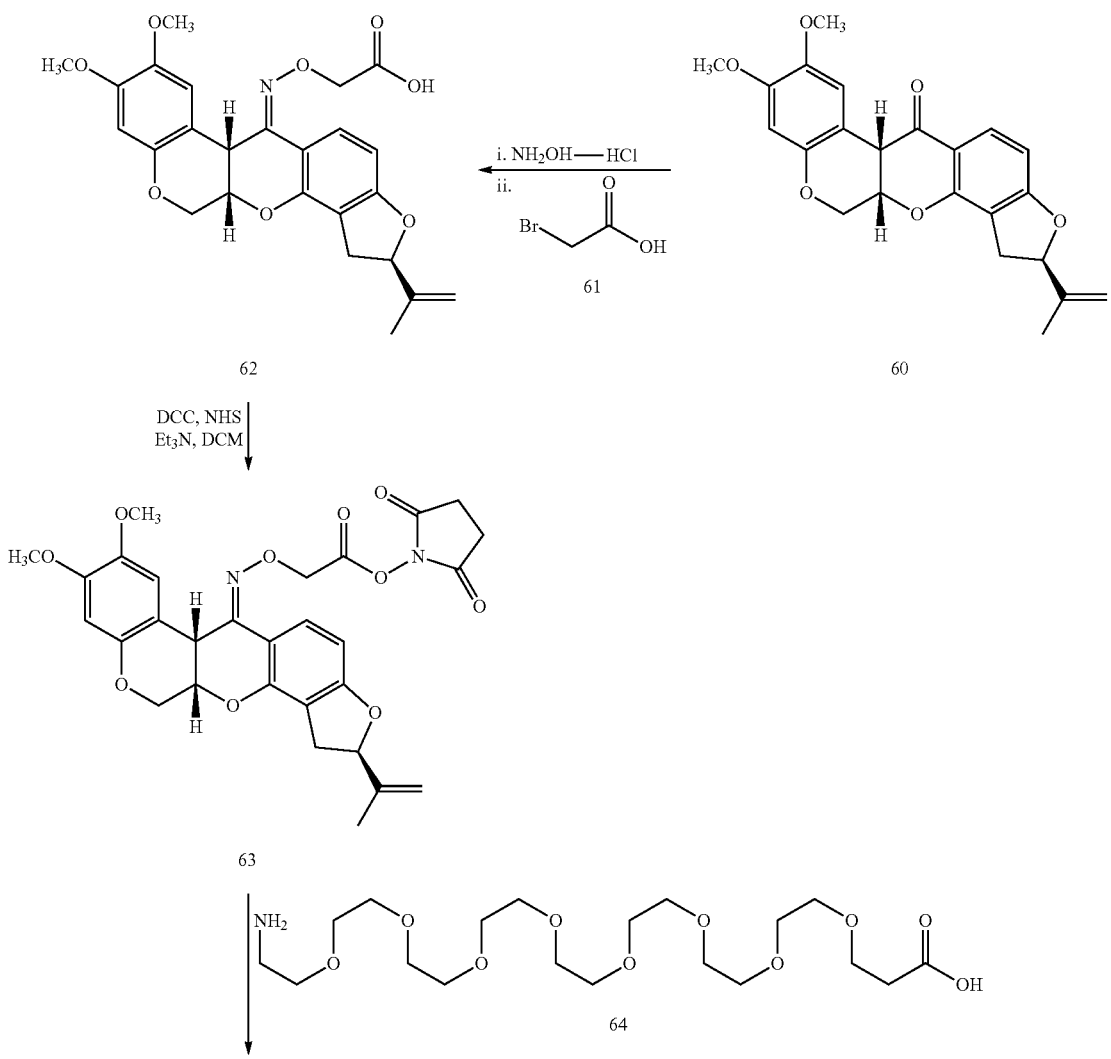

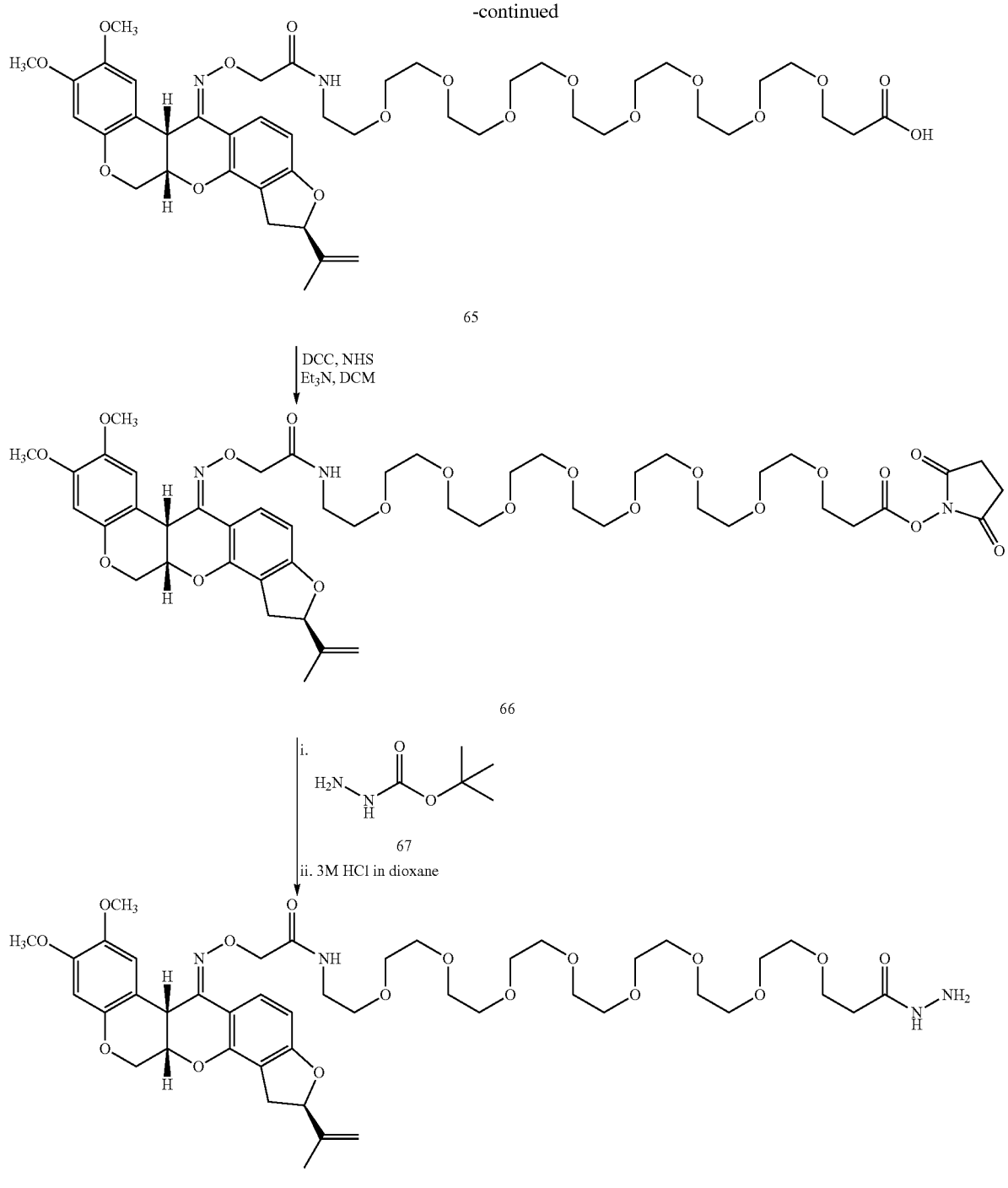

Starting compound 60 was treated with NH₂OH—HCl to form an intermediate oxime, which was then reacted with alpha bromoacetic acid, compound 61, to form oxime 62. The carboxylic acid functional group of compound 62 was converted into an NHS ester using DCC to form compound 63. Compound 63 was then coupled to an exemplary PEG-4 linker 64, having both an amine and a carboxylic acid functional group, to produce compound 65. The carboxylic acid functional group of compound 65 was converted to the NHS ester 66 by reaction with NHS using DCC as a coupling agent. Compound 66 was then treated with BOC-protected hydrazine compound 67, and then deprotected using 3M hydrochloric acid in dioxane, to produce compound 68. A person of ordinary skill in the art will appreciate that compound 66 also could be coupled to a carrier, such as a protein carrier, as disclosed herein to form an immunogen.

Scheme 9 illustrates synthetic paths used with rotenone isoxazolines.

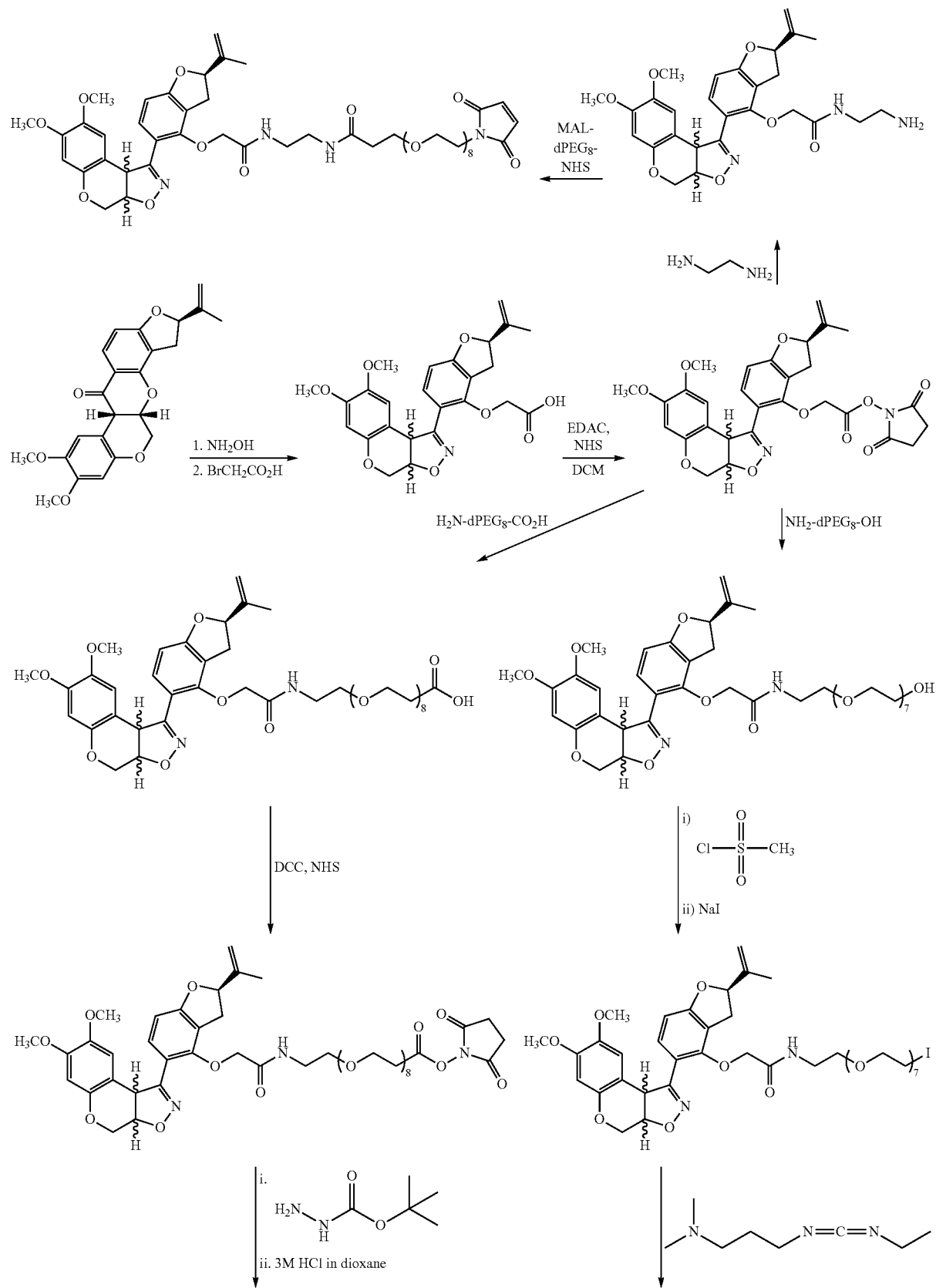

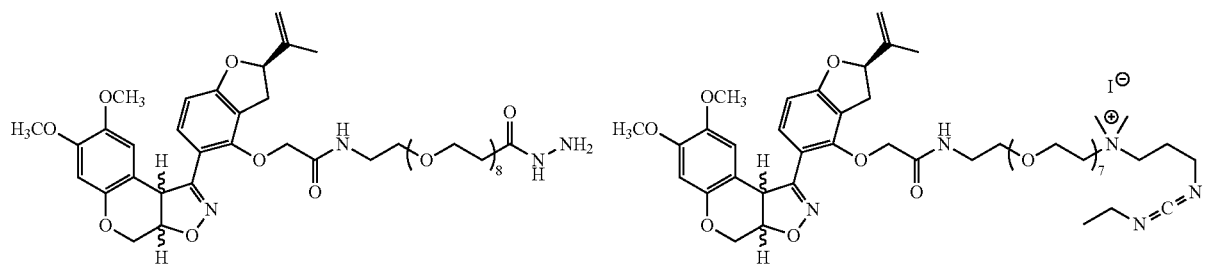

Scheme 9 illustrates making rotenone isoxazoline conjugates by sequentially treating the starting compound with ammonium hydroxide, followed by bromoacetic acid. This results in ring rearrangement to produce rotenone isoxazolines having a terminal carboxylic acid functional group. The NHS ester was produced using N-3-dimethylaminopropyl-N'-ethylcarbodiimide (EDAC). As a first option, the NHS ester can be reacted with a diamine to produce an amide having a terminal amine. This compound can then be reacted with a maleimide-PEG-NHS ester to couple to the hapten a PEG linker having a reactive terminus.

As a second alternative illustrated by Scheme 9, the NHS ester is ready for coupling with a linker, if desired, such as the exemplary bifunctional alkylene oxide linkers, i.e. PEG linkers. These exemplary PEG linkers have plural reactive functional groups, such as an amine and a carboxylic acid group or an amine and a hydroxyl group. Reacting the NHS ester with a linker provides either a carboxylic acid-terminated compound or a hydroxyl group-terminated compound. The carboxylic acid can be converted to an NHS ester using DCC as a coupling agent. The NHS ester can be reacted with the illustrated protected hydrazine reagent, followed by deprotection in hydrochloric acid, to produce the amino-terminated amide.

Alternatively, the hydroxyl terminated compound can be reacted with mesyl chloride, followed by reaction with a halide, such as iodide, to provide the halide-substituted compound. This compound can be reacted with the illustrated dimethyl amine carbodiimide to produce a compound useful for direct labeling of a biomolecule.

7. Oxazole- and Thiazole-Based Conjugates

Scheme 10 illustrates one method suitable for coupling exemplary oxazole- and thiazole-based haptens to an exemplary alkylene oxide linker. The hapten-linker conjugate then can be derivatized as desired, or can be directly coupled to a protein carrier molecule to form an immunogen.

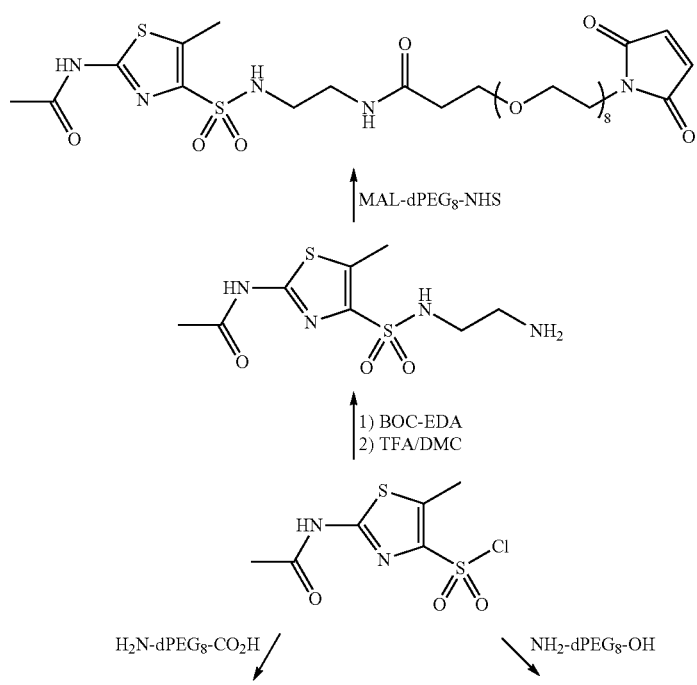

-continued

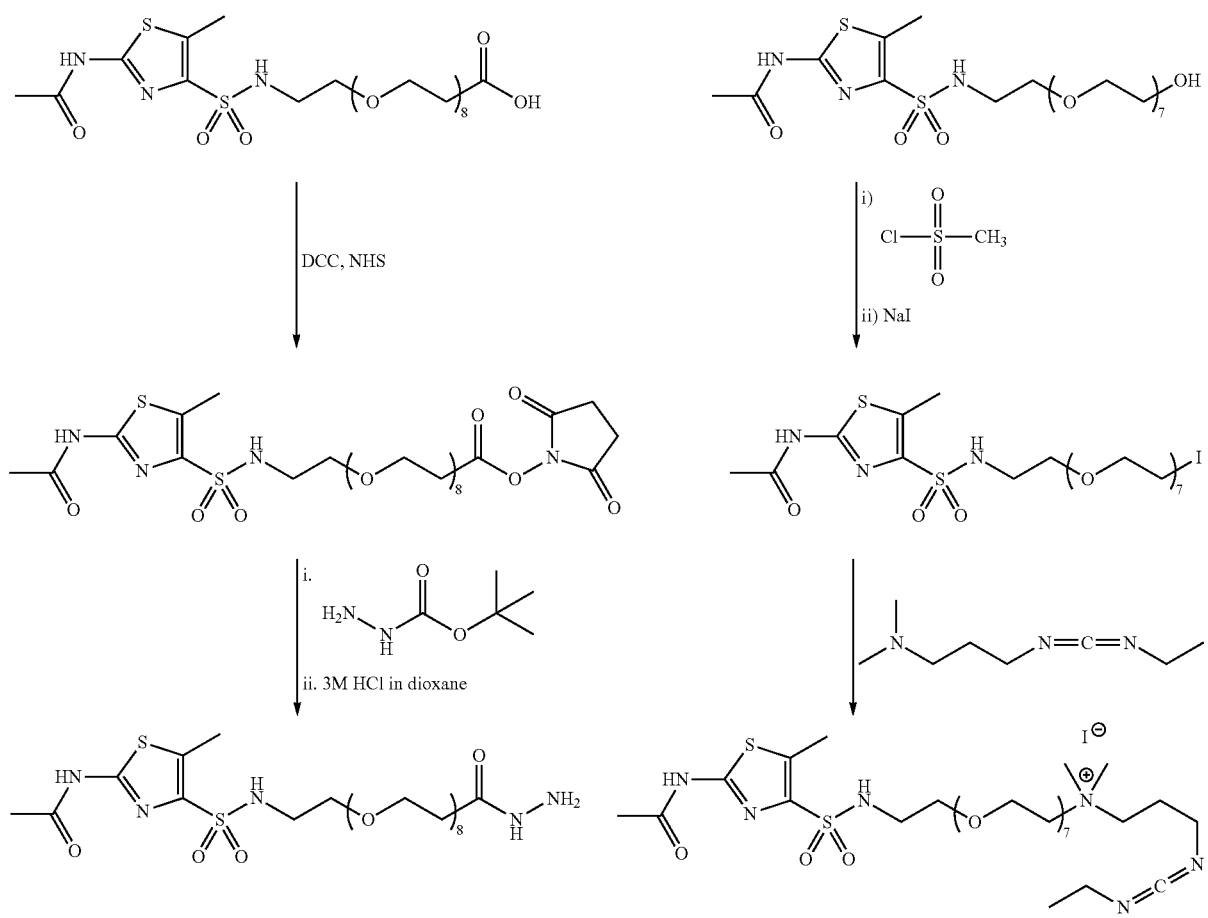

With reference to Scheme 10, the exemplary thiazole hapten, having a reactive sulfonyl chloride functional group, was reacted with either ethylene diamine or an exemplary bifunctional PEG$_8$ linker. As a first option, the thiazole can be reacted with a BOC-protected ethylene diamine, followed by deprotection using TFA, to produce an amide having a terminal amine. This compound can then be reacted with a maleimide-PEG-NHS ester to couple a linker to the hapten. Alternatively, the compound can be coupled to directly to carrier protein to form an immunogen.

Alternatively, the thiazole hapten can be reacted with a amino-dPEG linker having either a terminal hydroxyl group or a terminal carboxylic acid group. The carboxylic acid-terminated linker can be converted to the NHS ester using DCC, followed by reaction with a BOC protected hydrazide.

The BOC group can be removed using an acid, such as 3M HCl, to form the hydrazide terminated conjugate.

The hydroxyl-terminated thiazole sulfonamide PEG conjugate can be reacted with mesyl chloride, followed by reaction with a halide, such as iodide, to provide the halide-substituted compound. This compound can be reacted with the illustrated dimethyl amine carbodiimide to produce a compound useful for direct labeling of a biomolecule.

8. Coumarin-Based Hapten-Linker Conjugates and Immunogens

Scheme 11 illustrates one method suitable for coupling exemplary coumarin-based haptens to an exemplary alkylene oxide linker. The resulting hapten-linker conjugate can be derivatized further as desired, or can be coupled to a carrier, such as a protein carrier, to form an immunogen.

Scheme 11

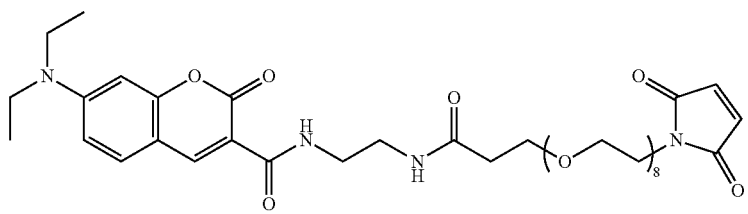

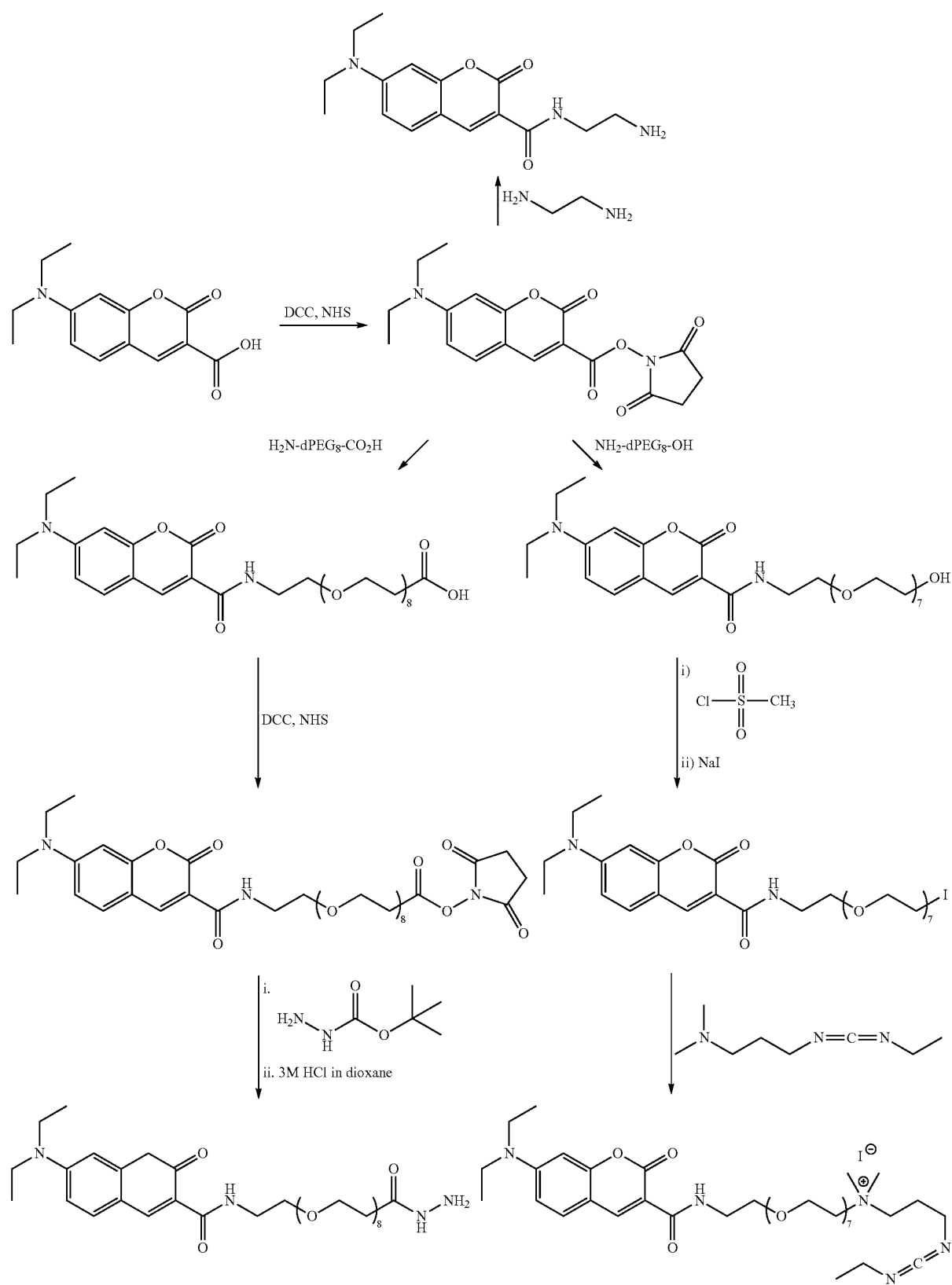

With reference to Scheme 11, the starting compound includes a carboxylic acid functional group that was converted to an NHS using DCC as a coupling agent. As a first option, the NHS ester can be reacted with ethylene diamine to produce an amide having a terminal amine. This compound can then be reacted with a maleimide-PEG-NHS ester to couple to the hapten a linker having a reactive terminal functional group.

Alternatively, the NHS ester can be coupled with the exemplary bifunctional $PEG_8$ to produce amides having either a terminal carboxylic acid or hydroxyl functional group. The carboxylic acid functional group can be converted to an NHS ester using DCC as a coupling agent. The NHS ester was then reacted with the protected hydrazine compound, followed by deprotection in 3M hydrochloric acid in dioxane, to produce the hydrazide. Alternatively, the NHS ester can be coupled to an immunogenic protein to produce an immunogen.

The hydroxyl-terminated coumarin PEG conjugate can be reacted with mesyl chloride, followed by reaction with a halide, such as iodide, to provide the halide-substituted compound. This compound can be reacted with the illustrated dimethyl amine carbodiimide to produce a compound useful for direct labeling of a biomolecule.

9. Cyclolignan-Linker Conjugates and Immunogens

Scheme 12 illustrates one method suitable for coupling exemplary Podophyllotoxin-based haptens to an exemplary alkylene oxide linker. The hapten-linker conjugate then can be further derivatized as desired, or directly coupled to a carrier molecule, such as a protein carrier molecule.

Scheme 12

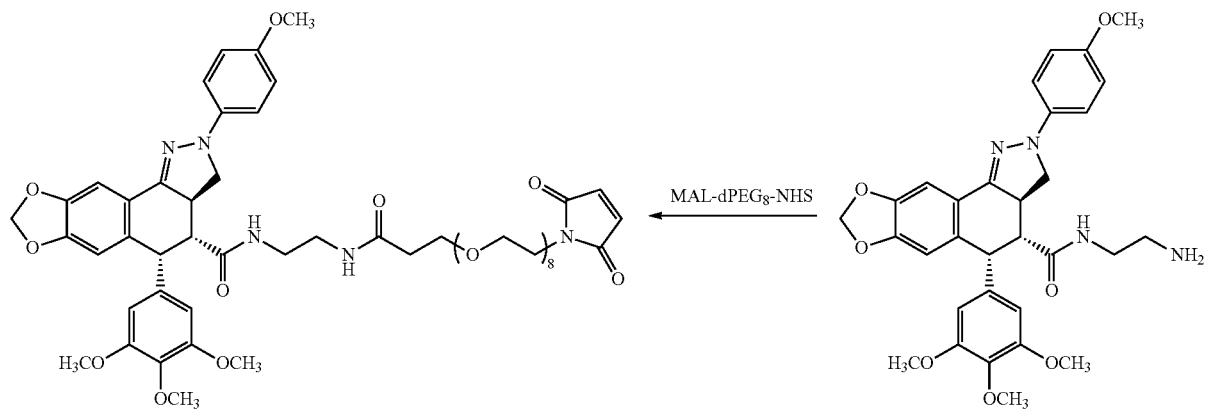

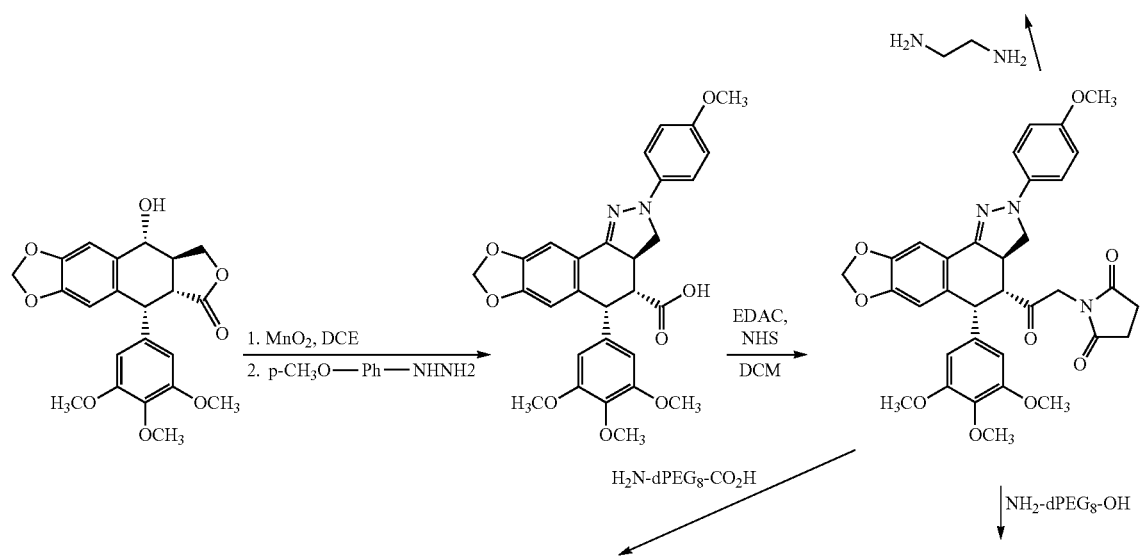

133
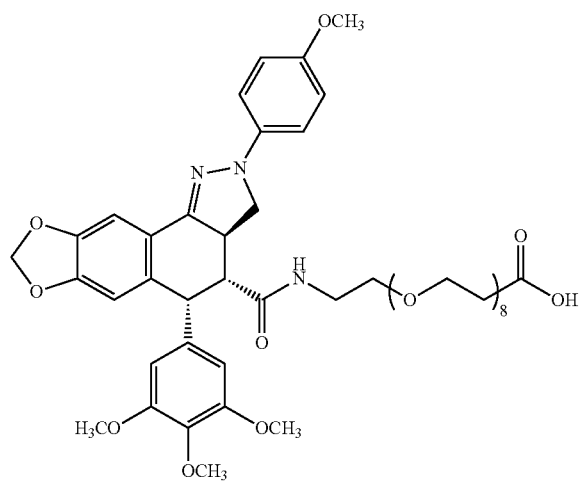
| DCC, NHS
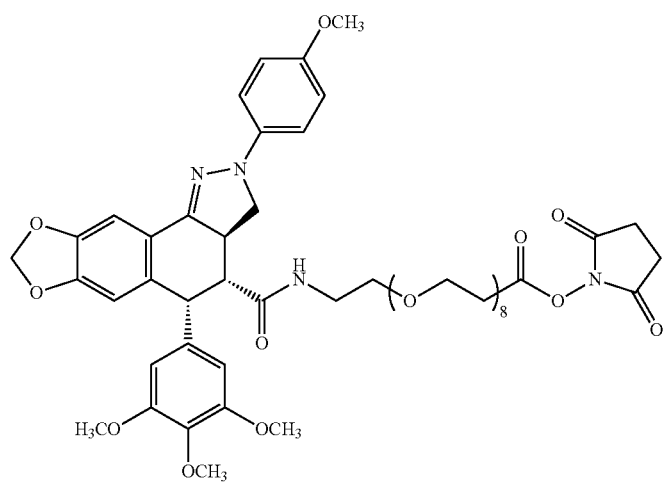
i.
<br>H₂N-NH-C(O)-O-C(CH₃)₃
<br>ii. 3M HCl in dioxane
134
-continued
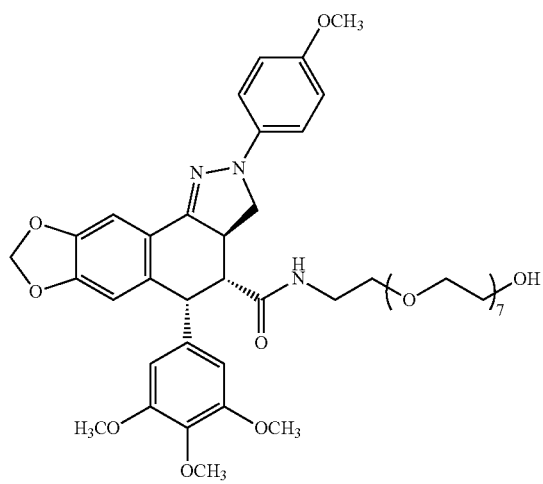
i) Cl-S(O)₂-CH₃
<br>ii) NaI
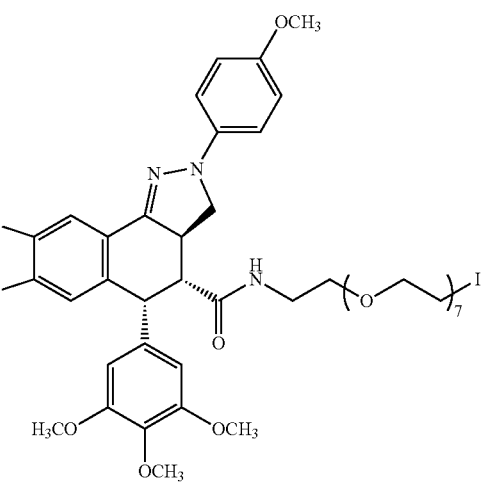
(CH₃)₂N-(CH₂)₃-N=C=N-CH₂CH₃

135

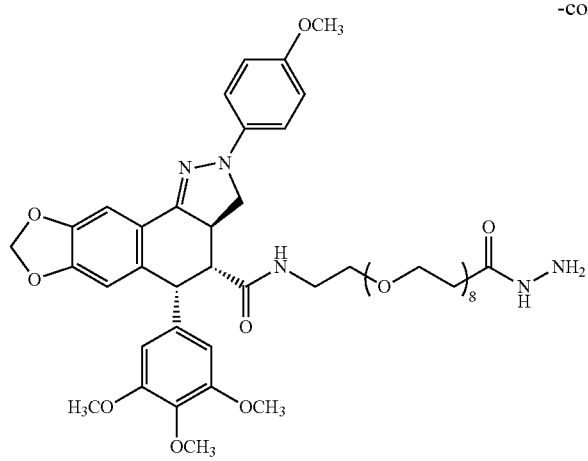

136

-continued

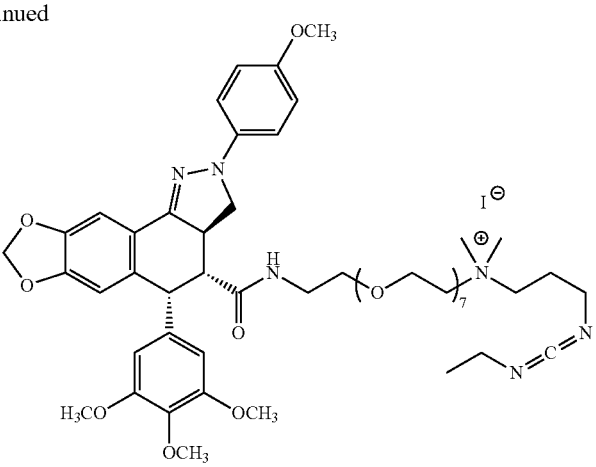

With reference to Scheme 12, the starting alcohol was oxidized to the corresponding ketone using manganese dioxide oxidation in dichloroethane. The ketone was then converted to an intermediate oxime (not shown), followed by ring rearrangement to the 5-membered heterocycle, thereby producing a compound having a carboxylic acid functional group by ring opening of the lactone. This compound was converted to the NHS ester, using either DCC or EDAC. As a first option, the NHS ester can be reacted with ethylene diamine to produce an amide having a terminal amine. This compound can then be reacted with a maleimide-PEG-NHS ester to couple a linker to the hapten.

Alternatively, the NHS ester was coupled with a $PEG_8$ linker to produce an amide having either a terminal carboxylic acid or hydroxyl functional group. The carboxylic functional group of the amide was converted to the NHS ester.

This compound was then coupled to a protein carrier to produce an immunogen. Alternatively, the NHS ester was reacted with a BOC-protected hydrazine reagent, followed by deprotection in 3M hydrochloric acid in dioxane, to produce the hydrazide.

The hydroxyl-terminated PEG conjugate can be reacted with mesyl chloride, followed by reaction with a halide, such as iodide, to provide the halide-substituted compound. This compound can be reacted with the illustrated dimethyl amine carbodiimide to produce a compound useful for direct labeling of a biomolecule.

10. Heteroaryl Conjugates

Schemes 13 and 14 illustrate one method suitable for coupling exemplary heteroaryl-based haptens to an exemplary alkylene oxide linker. The hapten-linker conjugate then can be further derivatized as desired, or directly coupled to a carrier molecule, such as a protein carrier molecule.

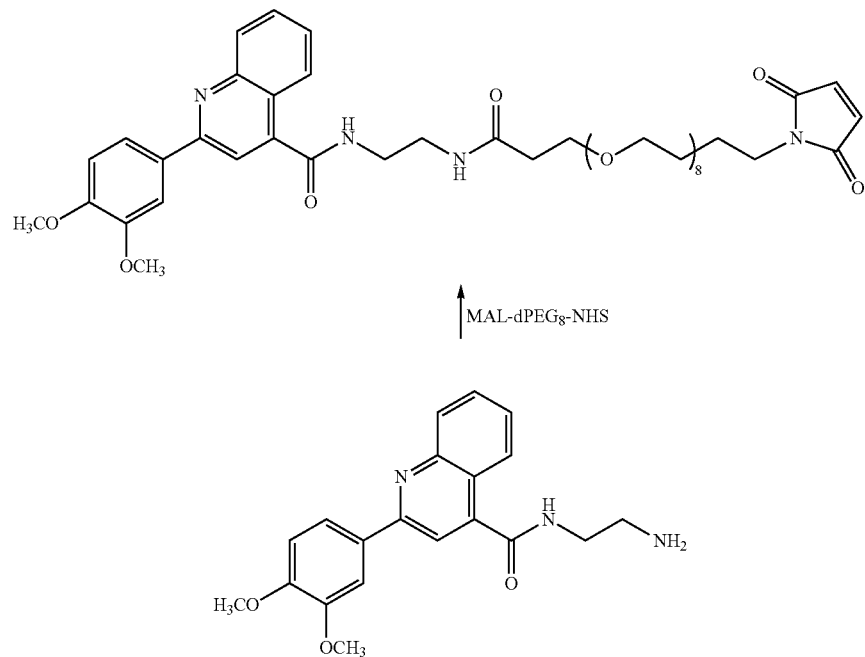

Scheme 13

137 138
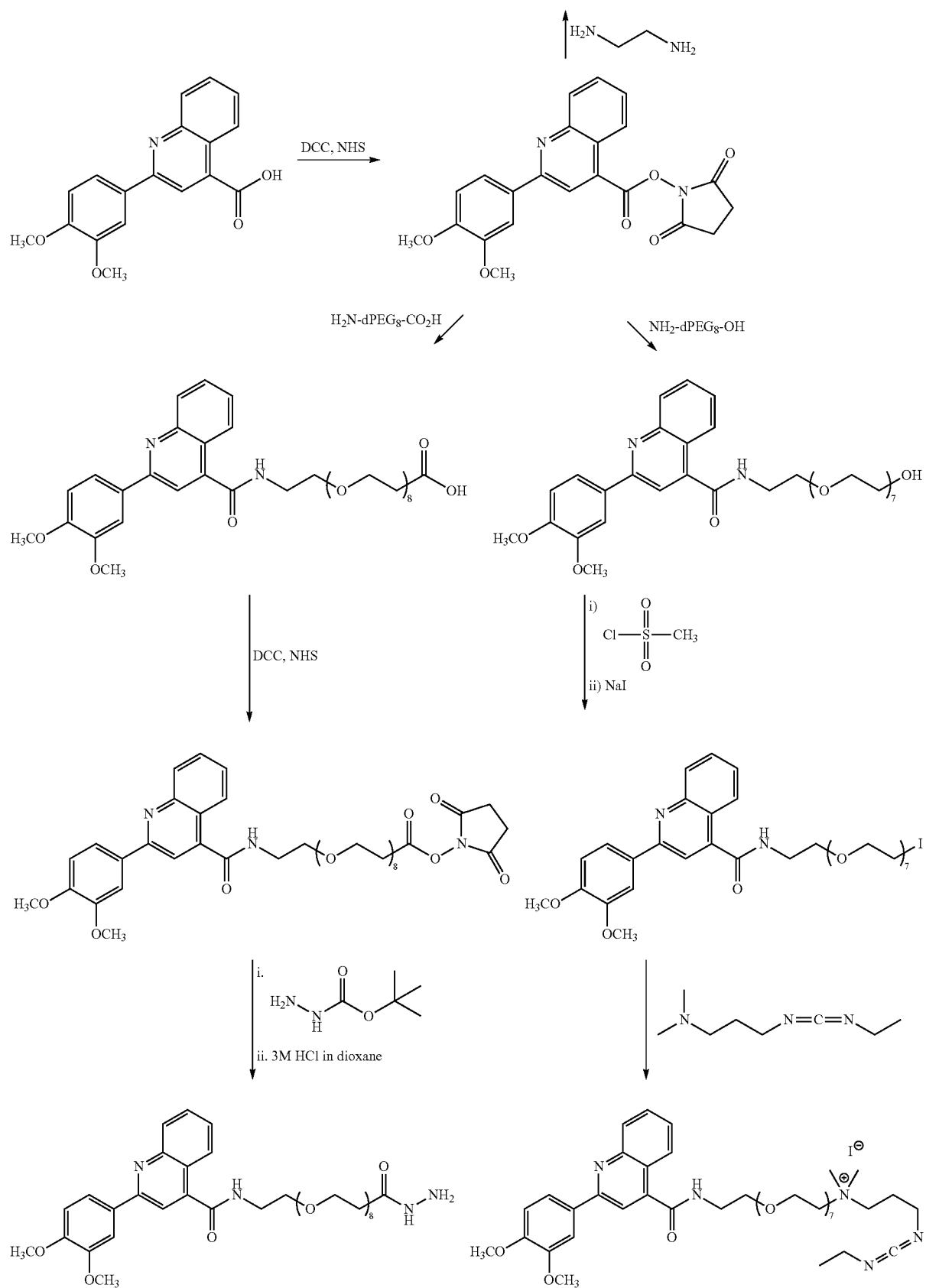

Scheme 14
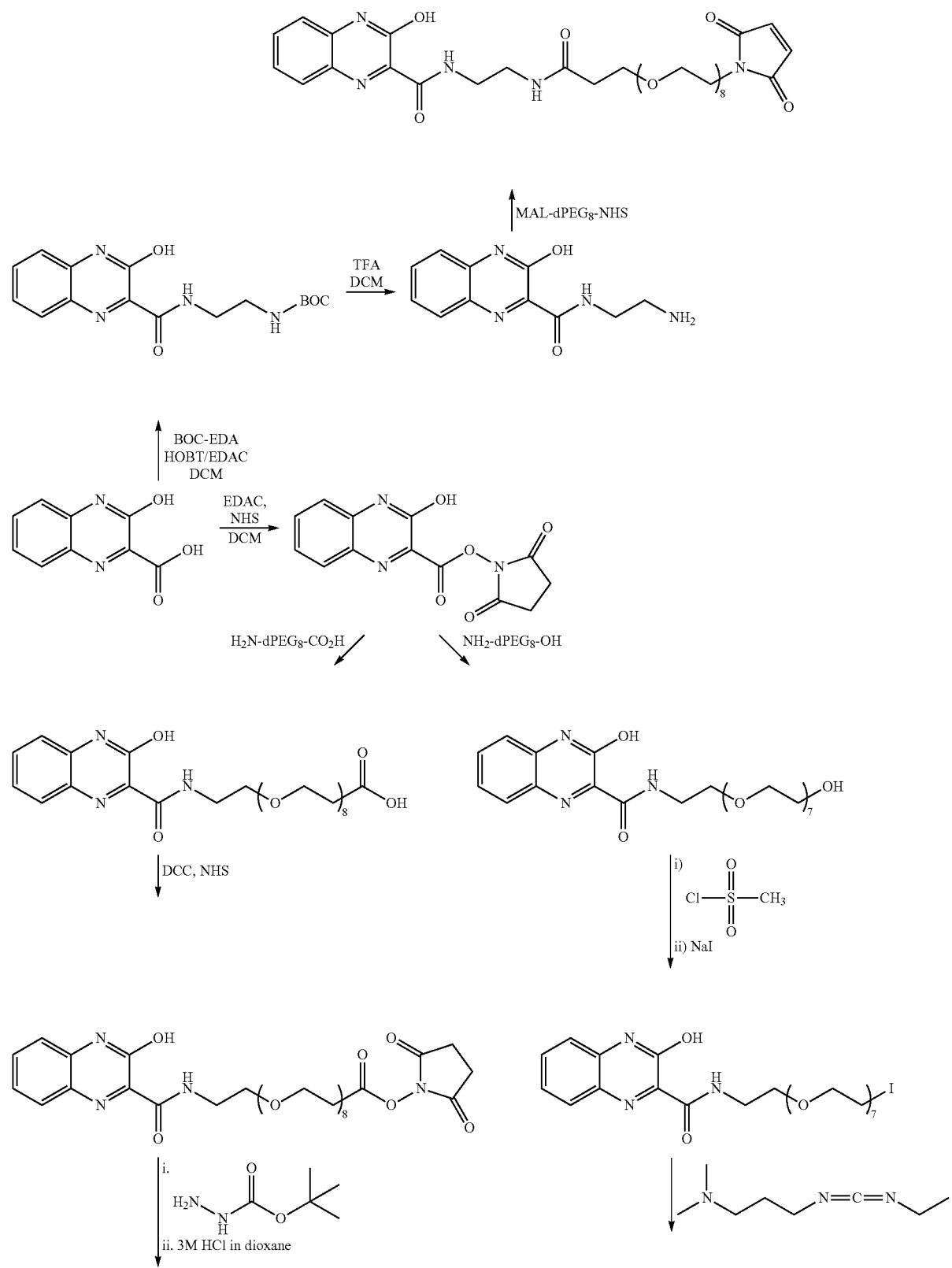

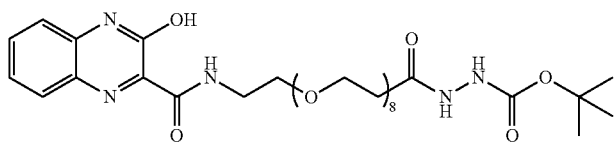 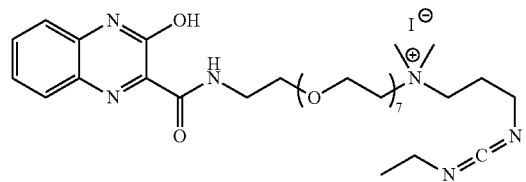

With reference to Schemes 13 and 14, the starting compounds each include a carboxylic acid functional group. In a first approach, the carboxylic acid can be converted to an ethyleneamino amide by reaction with BOC-protected ethylene diamine using HOBT/EDAC. The BOC protecting group is removed using an acid, such as TFA in dichloromethane. This compound can then be reacted with a maleimide-PEG-NHS ester to couple a linker to the hapten.

Alternatively, the NHS ester can be coupled to a $PEG_8$ linker to produce an amide having either a terminal carboxylic acid or hydroxyl functional group. The carboxylic functional group of the amide can be converted to an NHS ester using DCC as coupling agent. The NHS ester was reacted with a BOC-protected hydrazine reagent, followed by deprotection in 3M hydrochloric acid in dioxane, to produce the hydrazide. Alternatively, the NHS ester can be coupled to a protein carrier to produce an immunogen.

The hydroxyl-terminated PEG conjugate can be reacted with mesyl chloride, followed by reaction with a halide, such as iodide, to provide the halide-substituted compound. This compound can be reacted with the illustrated dimethyl amine carbodiimide to produce a compound useful for direct labeling of a biomolecule.

11. Azoaryl Conjugates

Scheme 15 illustrates one method suitable for coupling exemplary azoaryl-based haptens to an exemplary alkylene oxide linker. The hapten-linker conjugate then can be further derivatized as desired, or directly coupled to a carrier molecule, such as a protein carrier molecule.

Scheme 15
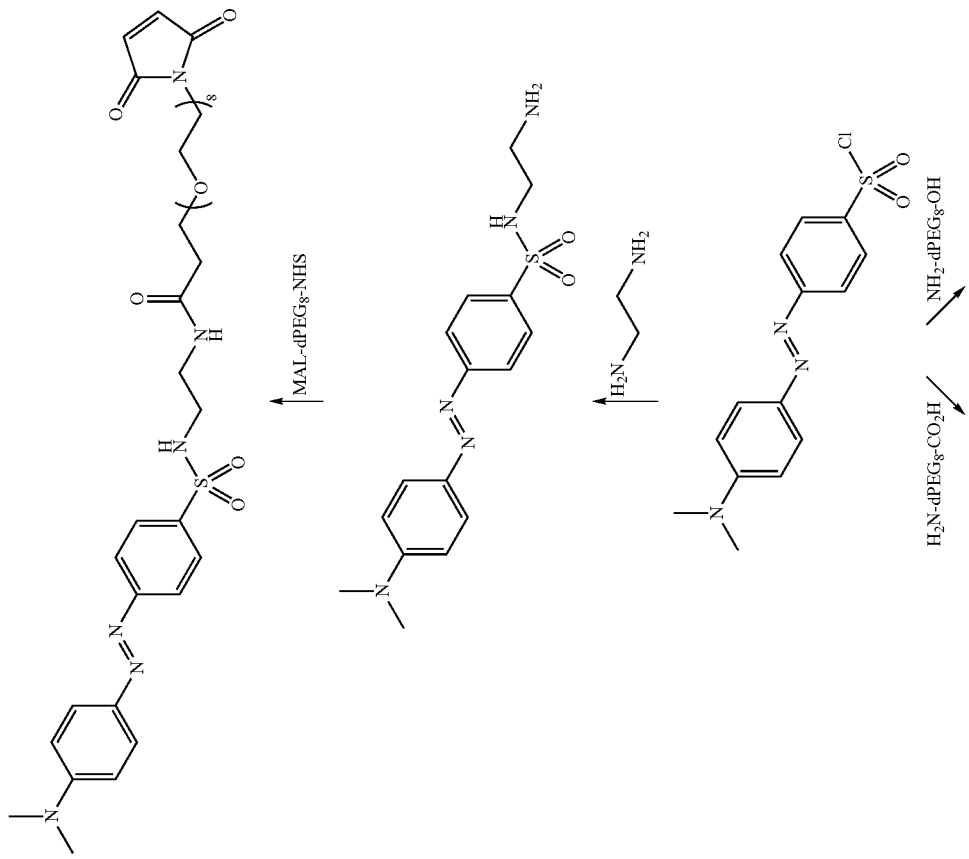

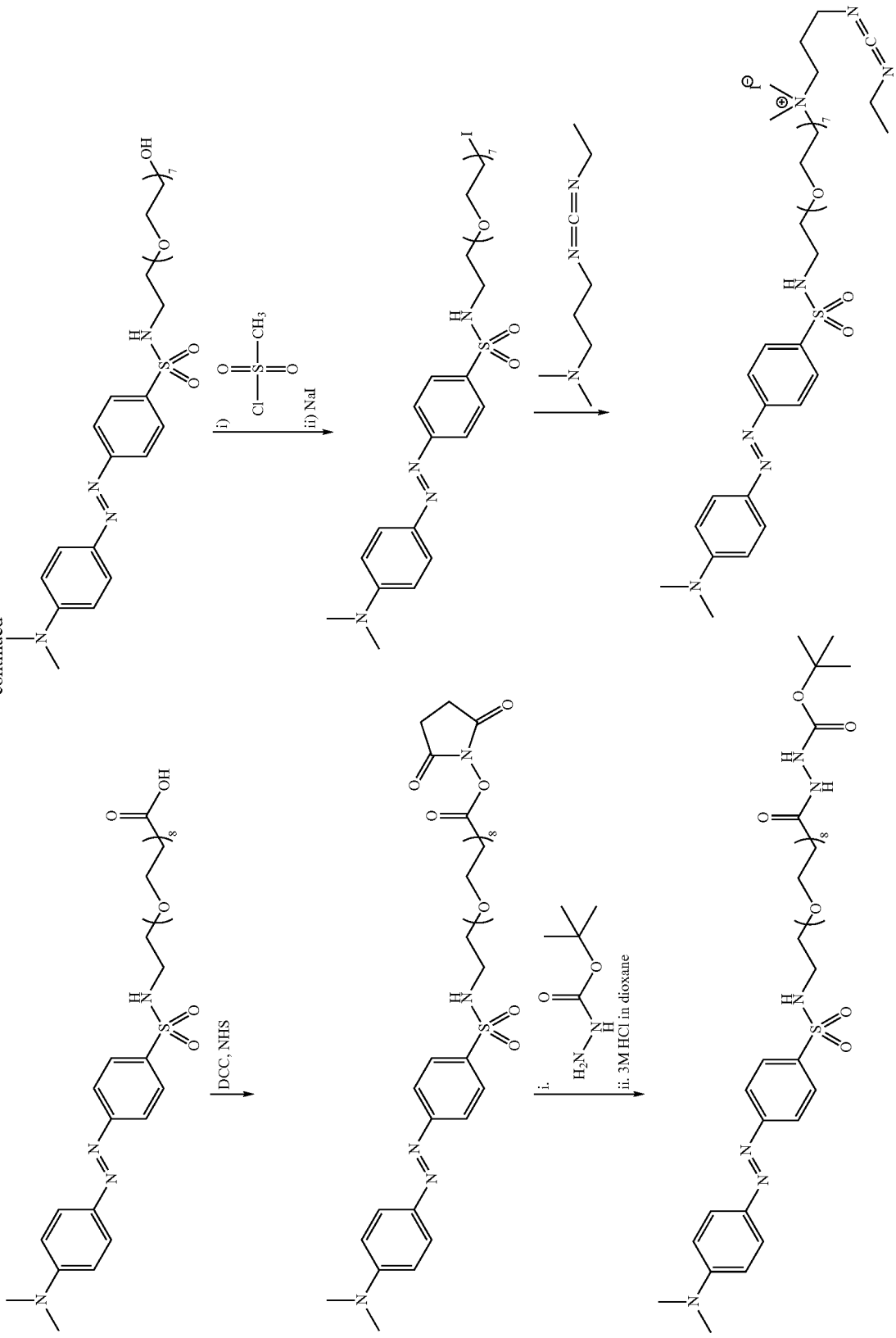

With reference to Scheme 15, the exemplary azoaryl hapten, having a reactive sulfonyl chloride functional group, was reacted with either ethylene diamine or an exemplary bifunctional $PEG_8$ linker. As a first option, the azoaryl compound can be reacted with ethylene diamine to produce a sulfamide having a terminal amine. This compound can then be reacted with a maleimide-PEG-NHS ester to couple to the hapten a linker having a reactive terminal functional group.

Alternatively, the reactive sulfonyl chloride can be reacted with a $PEG_8$ linker to produce a sulfamide having either a terminal carboxylic acid or hydroxyl functional group. The carboxylic functional group of the amide can be converted to an NHS ester using DCC as coupling agent. The NHS ester was reacted with a BOC-protected hydrazine reagent, followed by deprotection in 3M hydrochloric acid in dioxane, to produce the hydrazide. Alternatively, the NHS ester can be coupled to a protein carrier to produce an immunogen.

The hydroxyl-terminated PEG conjugate can be reacted with mesyl chloride, followed by reaction with a halide, such as iodide, to provide the halide-substituted compound. This compound can be reacted with the illustrated dimethyl amine carbodiimide to produce a compound useful for direct labeling of a biomolecule.

12. Benzodiazepine Conjugates

Scheme 16 illustrates one method suitable for coupling exemplary benzodiazepine-based haptens to an exemplary alkylene oxide linker. The hapten-linker conjugate then can be further derivatized as desired, or directly coupled to a carrier molecule, such as a protein carrier molecule.

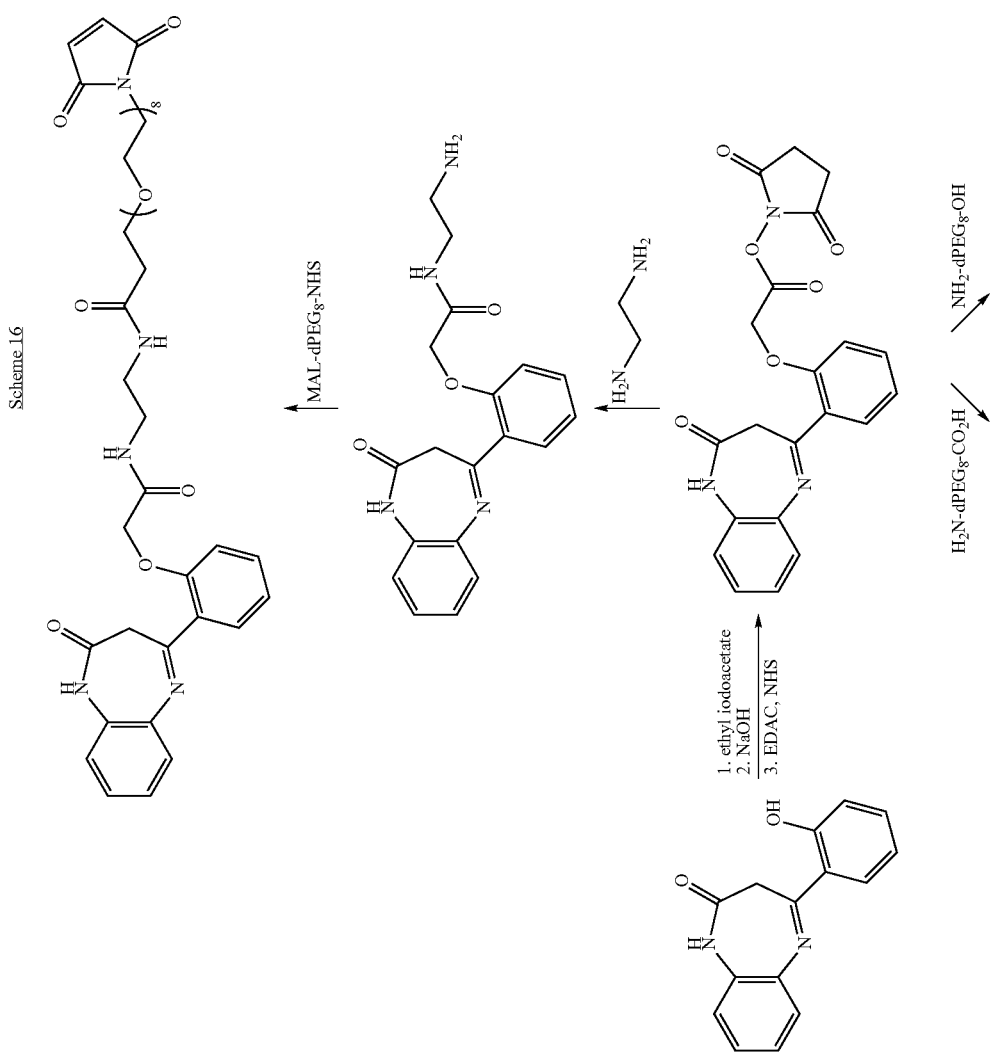

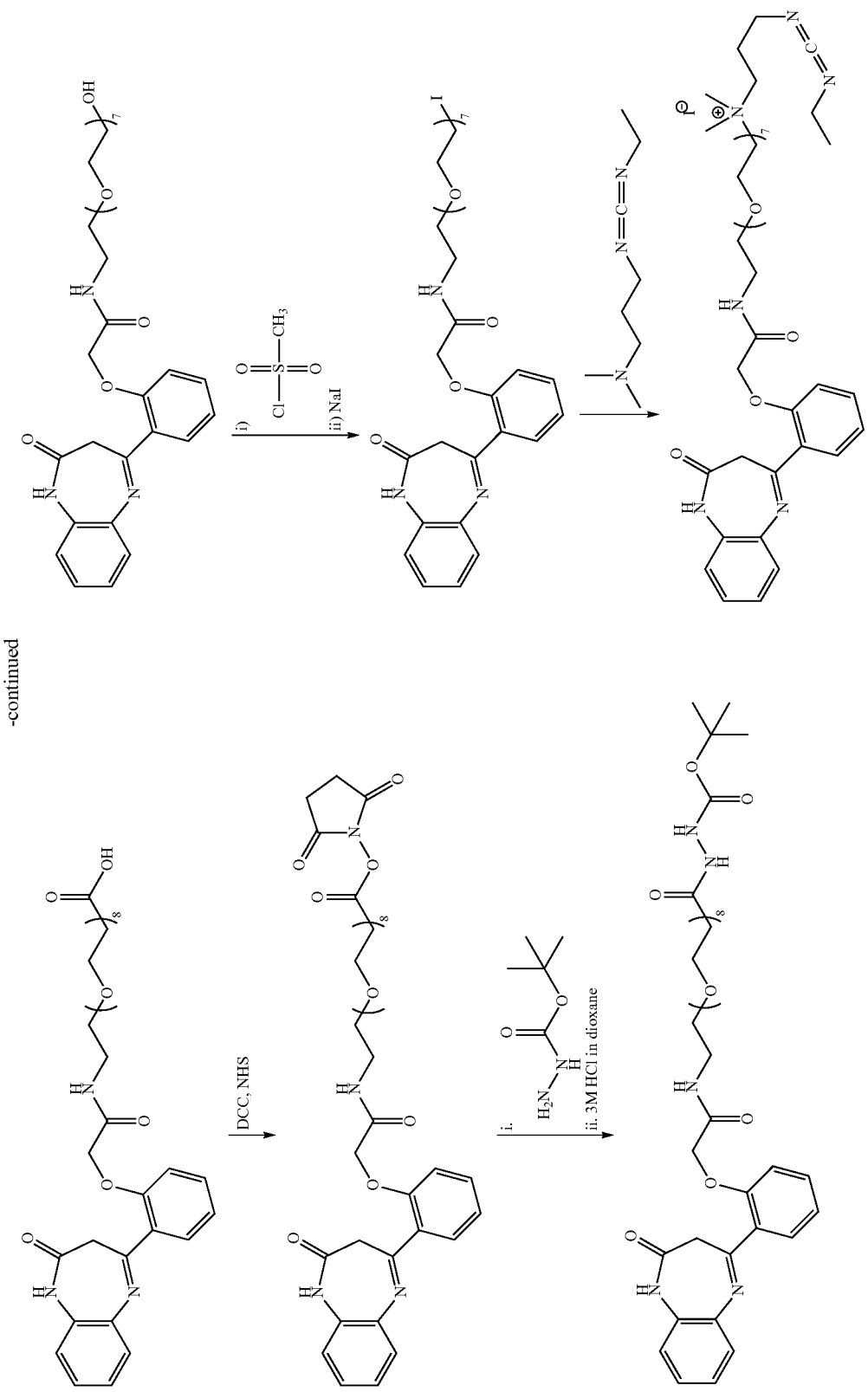

With reference to Scheme 16, the exemplary benzodiazepine hapten includes a hydroxyl group. This group was reacted with ethyliodoacetate, followed by treatment with sodium hydroxide to produce a compound having a terminal carboxylic acid functional group. The carboxylic acid was converted to an NHS ester using EDAC as a coupling agent. The NHS ester was reacted with either ethylene diamine or an exemplary bifunctional $PEG_8$ linker. As a first option, the azoaryl compound can be reacted with ethylene diamine to produce an amide having a terminal amine. This compound can then be reacted with a maleimide-PEG-NHS ester to couple a linker to the hapten.

Alternatively, the reactive NHS ester can be reacted with a $PEG_8$ linker to produce an amide having either a terminal carboxylic acid or hydroxyl functional group. The carboxylic functional group of the amide can be converted to an NHS ester using DCC as coupling agent. The NHS ester was reacted with a BOC-protected hydrazine reagent, followed by deprotection in 3M hydrochloric acid in dioxane, to produce the hydrazide. Alternatively, the NHS ester can be coupled to a protein carrier to produce an immunogen.

The hydroxyl-terminated PEG conjugate can be reacted with mesyl chloride, followed by reaction with a halide, such as iodide, to provide the halide-substituted compound. This compound can be reacted with the illustrated dimethyl amine carbodiimide to produce a compound useful for direct labeling of a biomolecule.

13. Maleimide/Hydrazide PEG-Linker Synthesis

Scheme 17 shows a general method for preparing maleimide/hydrazide heterobifunctional PEG linkers. Briefly, a maleimide/active ester PEG linker 102 (such as obtained from Quanta Biodesign) is reacted with a protected hydrazine derivative 104 to produce compound 106. Compound 106 was then deprotected with acid to yield the maleimide/hydrazide PEG linker 108.

Scheme 17

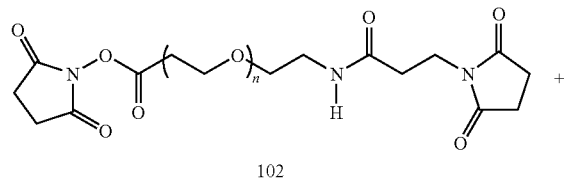

102

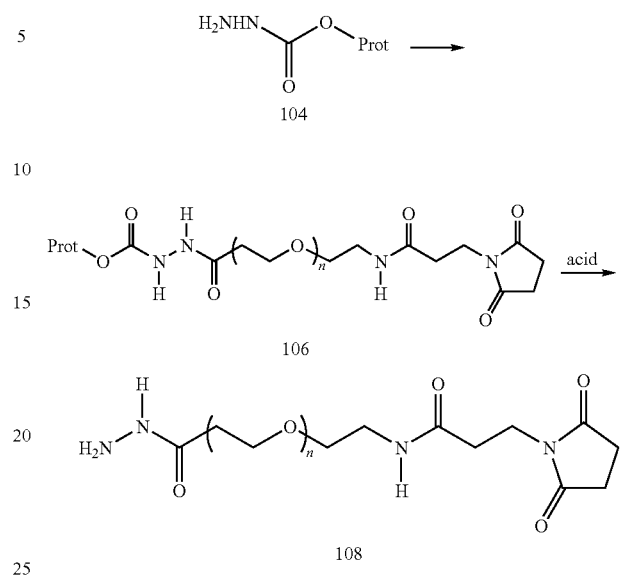

A specific synthesis of a maleimide/hydrazide $PEG_4$ linker is outlined in Scheme 16 below. To the active ester 110 (116 mg, 1.0 eq.) in 5 ml dry dioxane was added 30 mg (1.0 eq.) of the Boc protected hydrazine 112 in 5 ml of dry dioxane over 1 hour. The reaction was then stirred at ambient temperature under dry nitrogen for 16 hours. The reaction mixture was fractionated by HPLC utilizing a Waters Delta 600 HPLC fitted with a 2996 photo-diode array detector and a Phenomenex luna 10μ, C18(2), 100 A, 250×30 mm column. The column was eluted with 30-60% ACN/water over 30 min at a flow rate of 12 mL/min. The desired Boc protected-$PEG_4$-maleimide 114 eluted at 38 minutes giving 50 mg of a thick yellow oil after drying under high vacuum. The final deprotected hydrazide 116 was then obtained by stirring the residue with 6 ml of anhydrous 2 N HCL/dioxane under dry nitrogen for 45 minutes. Concentration via rotory evaporation then gave 55 mg of the hydrazide-$PEG_4$-maleimide HCL salt.

Scheme 18

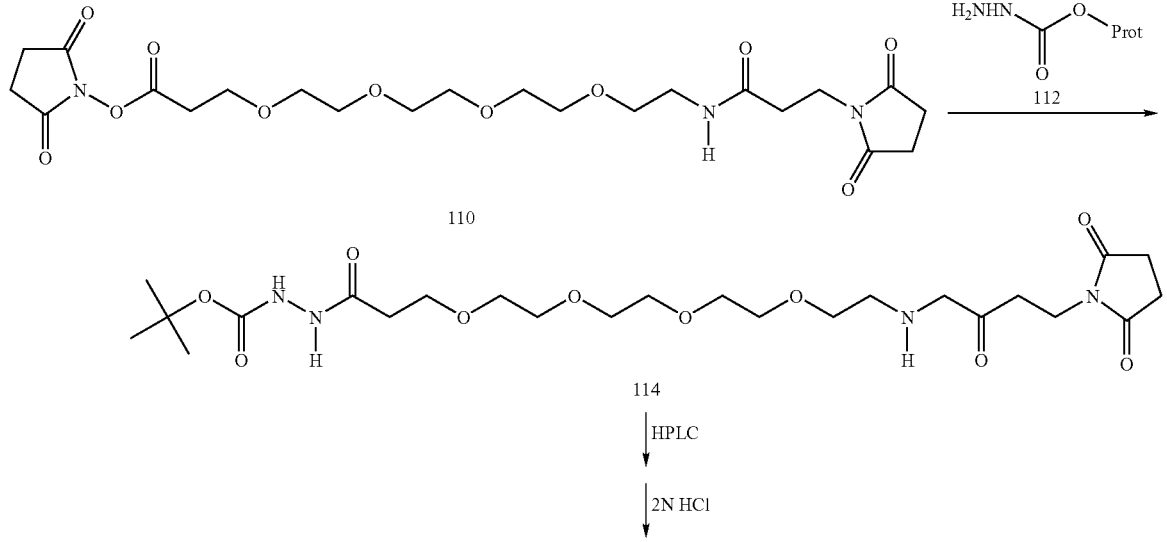

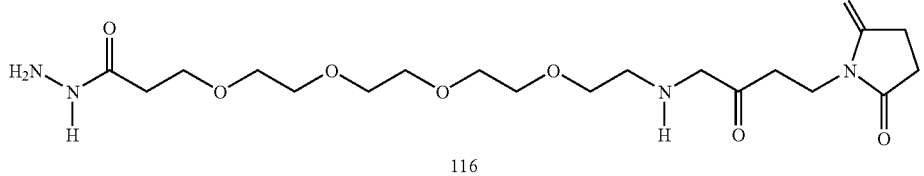

116

14. Linker-Detectable Label Conjugates

Certain embodiments of the present invention concern forming conjugates using linkers. The following non-limiting examples are provided to illustrate embodiments of the method by reference to embodiments for forming detectable label conjugates using maleimide PEG active esters to exemplify the process. A person of ordinary skill in the art will appreciate that the illustrated embodiments can be used to form other types of conjugates as disclosed herein.

In one embodiment, a disclosed specific-binding moiety nanoparticle conjugate is prepared according to the processes described in Schemes 19 to 22 below, wherein the heterobifunctional polyalkylene glycol linker is a polyethylene glycol linker having an amine-reactive group (active ester) and a thiol-reactive group (maleimide). As shown in Scheme 19, a nanoparticle (such as a quantum dot) that has one or more available amine groups is reacted with an excess of the linker to form an activated nanoparticle.

Scheme 19

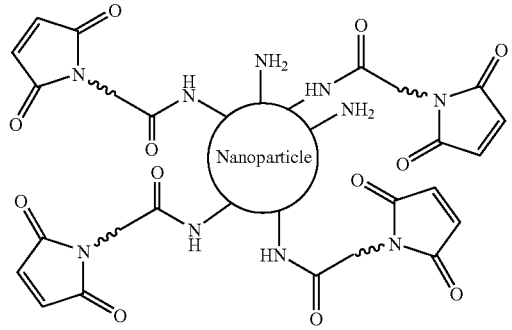

-continued

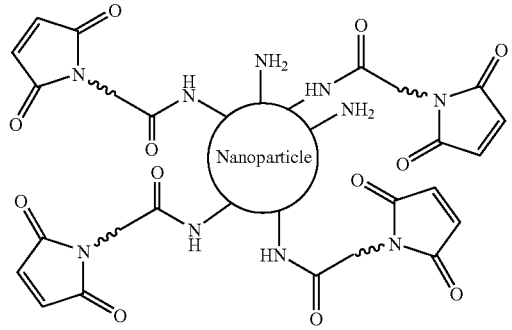

Thiol groups may be introduced to the antibody by treating the antibody with a reducing agent such as DTT as shown in Scheme 20. For a mild reducing agent such as DTE or DTT, a concentration of between about 1 mM and about 40 mM, for example, a concentration of between about 5 mM and about 30 mM and more typically between about 15 mM and about 25 mM, is utilized to introduce a limited number of thiols (such as between about 2 and about 6) to the antibody while keeping the antibody intact (which can be determined by size-exclusion chromatography). A suitable amount of time for the reaction with a solution of a particular concentration can be readily determined by titrating the number of thiols produced in a given amount of time, but the reaction is typically allowed to proceed from 10 minutes to about one day, for example, for between about 15 minutes and about 2 hours, for example between about 20 minutes and about 60 minutes.

Scheme 20

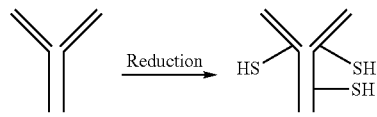

The components produced according to Schemes 19 and 20 are then combined to give a conjugate as shown in Scheme 21.

Scheme 21

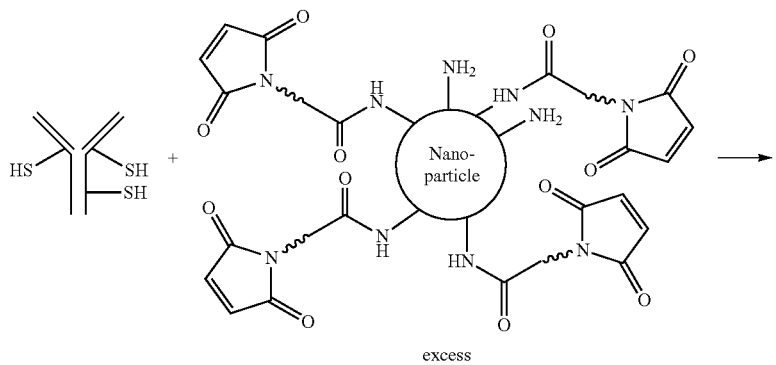

-continued

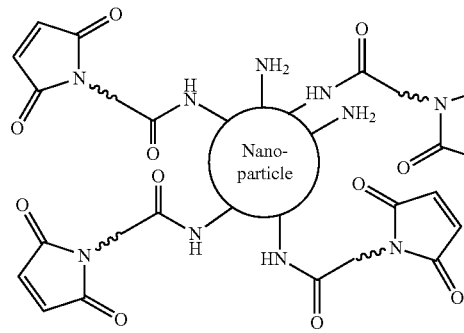
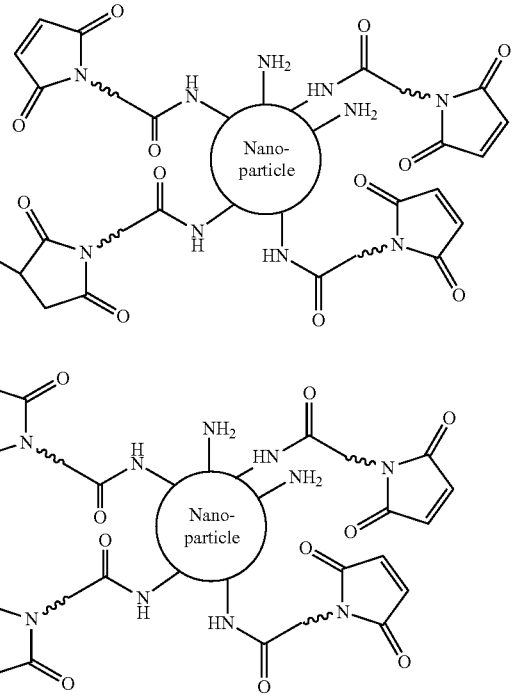

Although Schemes 19-21 illustrate an optimal process for maleimide PEG active esters, wherein the nanoparticle is first activated by reacting an amine group(s) with the active ester of the linker to form an activated nanoparticle, it also is possible to first activate the antibody by reacting either an amine(s) or a thiol(s) on the antibody with the linker and then react the activated antibody with the nanoparticle [having either a thiol(s) or an amine(s) to react with the remaining reactive group on the linker as appropriate].

Thus, in an alternative embodiment, an antibody is activated for conjugation and then conjugated to a nanoparticle as shown in Schemes 22 and 23 below. In Scheme 23, the antibody is activated instead of the nanoparticle as was shown in Scheme 19. In the particular embodiment of Scheme 22, a sugar moiety (such as located in a glycosylated region of the Fc portion of the antibody) is first oxidized to provide an aldehyde group, which is then reacted with an aldehyde-reactive group of the linker (such as a hydrazide group of the illustrated maleimide/hydrazide PEG linker).

Scheme 22

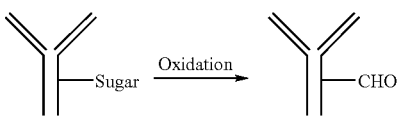

-continued

Then, as shown in Scheme 23, a thiol-reactive group of the linker portion of the activated antibody (such as a maleimide group as illustrated) is then reacted with a thiol group on the nanoparticle. Again, the process can be reversed, wherein the linker is first reacted with an aldehyde group on the nanoparticle (formed, for example, by oxidation of a sugar moiety) to form an activated nanoparticle, and then the activated nanoparticle can be reacted with a thiol group on the antibody.

Scheme 23

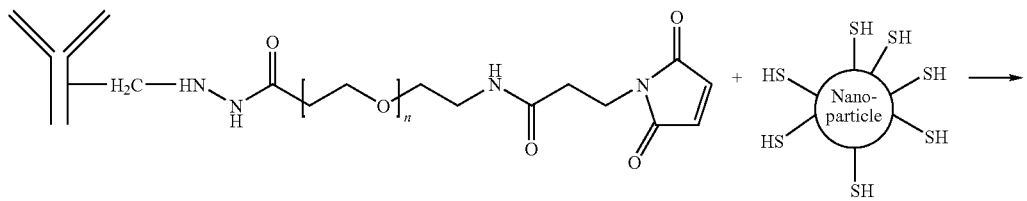

-continued

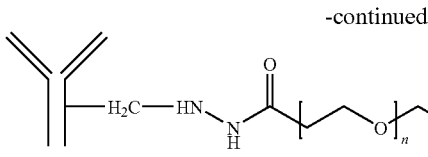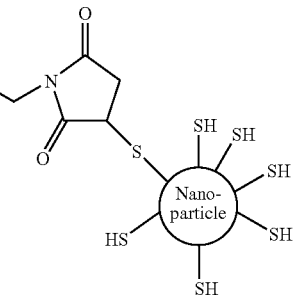

Although schemes 17-2 above and 22 that follows show particular examples of conjugates for illustrative purposes, it is to be understood that the ratio of specific-binding moiety (in this case, antibody) to nanoparticle in the disclosed conjugates can vary from multiple (such as 5, 10, 20 or more) specific binding moieties per nanoparticle to multiple nanoparticles per specific-binding moiety (such as 5, 10, 20 or more).

15. Introduction of Thiols to Antibodies

To activate an antibody for conjugation, for example, an anti-mouse IgG or anti-rabbit IgG antibody, the antibody can be incubated with 25 mmol DTT at ambient temperature (23-25° C.) for about 25 minutes. After purification across a PD-10 SE column, DTT-free antibody, typically with two to six free thiols, is obtained (Scheme 2). The exemplary procedure outlined for preparing goat anti-mouse IgG thiol is generally applicable to other antibodies. The number of thiols per antibody can be determined by titration, for example, by using the thiol assay described in U.S. Provisional Patent Application No. 60/675,759, filed Apr. 28, 2005, which application is incorporated by reference herein.

16. Conjugates of Immunoglobulins and Streptavidin with CdSe/ZnS Quantum Dots for Ultrasensitive (and Multiplexed) Immunohistochemical and In Situ HybridizationDetection in Tissue Samples.

Figure 45:
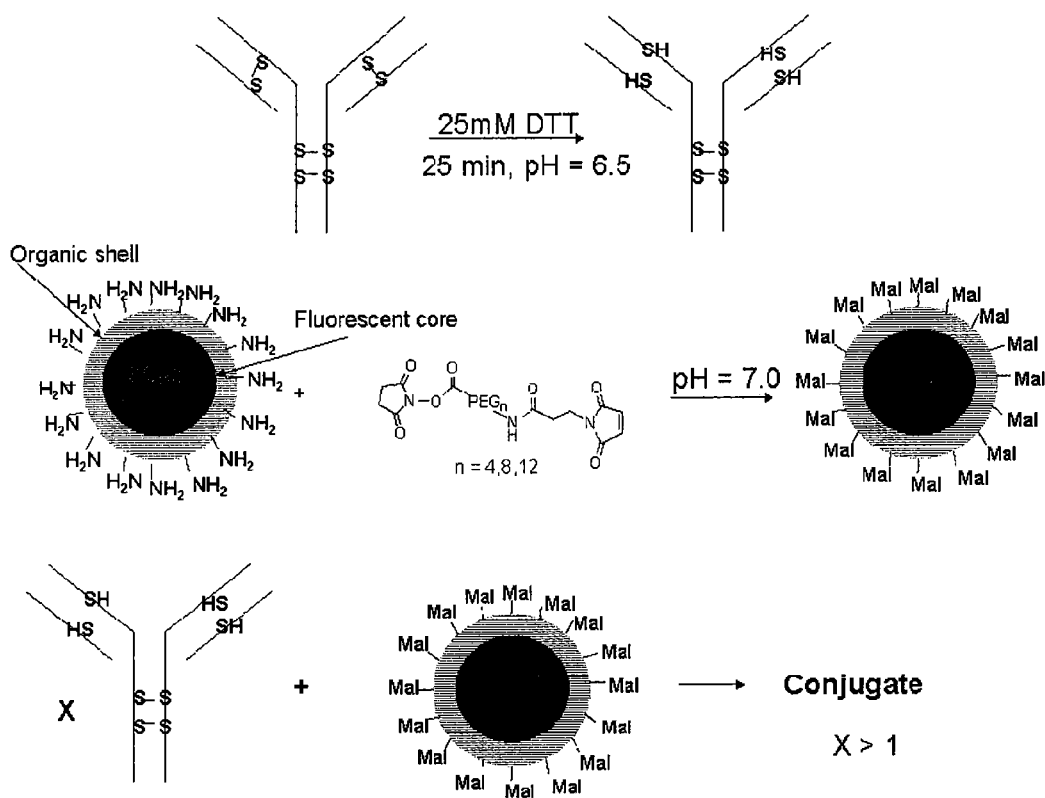
FIG. 45 illustrates one embodiment of the method for incorporating an immunoglobulin into a quantum dot shell.

One embodiment of a method for incorporating an immunoglobulin into a quantum dot shell is described in this example. This embodiment involves: 1) functionalization of amine-terminated quantum dot capping groups with a suitable heterobifunctional NHS ester-(PEG)x-maleimide; (x=4, 8, 12) 2) reduction of native disulfides by treatment with dithiothreitol (DTT); 3) derivatizing maleimide-terminated quantum dots with these thiolated immunoglobulins; and 4) purifying the conjugates using suitable techniques, such as size-exclusion chromatography. The process is depicted in FIG. 45.

A streptavidin conjugate can be made by substituting a thiolated streptavidin for the thiolated immunoglobulin in the process. For example, a streptavidin molecule treated with 2-iminothiolane.

The quantum dots used in this example were protected by an electrostatically bound shell of trioctyl phosphine oxide (TOPO) and an intercalating amphiphilic polymer to induce water solubility. This polymer has approximately 30 terminal amine groups for further functionalization. See E. W. Williams, et. al. "Surface-Modified Semiconductive and Metallic Nanoparticles Having Enhanced Dispersibility in Aqueous Media", U.S. Pat. No. 6,649,138 (incorporated by reference, herein). In order to form highly sensitive quantum dot conjugates, antibodies were attached to the quantum dots with varying ratios. The chemistry is similar to that described in U.S. Provisional Patent Application No. 60/675,759, filed Apr. 28, 2005, which is incorporated by reference herein.

This methodology is advantageous due to the need for few reagents because native disulfides are used. Additionally, the antibody remains discrete and does not form fragments. This allows for two binding sites from each tethered antibody. Furthermore, highly stable and bright conjugates are produced. The brightness surpasses commercially available streptavidin-QD conjugates (Invitrogen Corporation, Eugene, Oreg.) on the same tissue. Goat anti-biotin and rabbit anti-DNP antibodies conjugated to quantum dots of differing wavelengths of emission were produced, thereby permitting multiplex assays. HPV detection through FISH was demonstrated with the disclosed quantum dot conjugates.

VIII. Embodiments of a Method for Using Disclosed Haptens, Hapten Conjugates, and Compositions Thereof A. In Situ Hybridization Certain exemplary embodiments of the present invention are disclosed herein with reference to the attached drawings. FIG. 1 illustrates one embodiment of an in situ hydridization scheme 10 that can be implemented with various embodiments of disclosed haptens. A sample having a target 12, such as a protein, is selected. A probe 14 useful for detecting the target 12, such as an antibody, also is selected. At least one hapten 16 of the classes of haptens disclosed herein is conjugated to the probe 14. Target 12 is treated with the probe 14 conjugated to the hapten 16 in a manner effective to form a complex that can be visualized using any suitable means. FIG. 1 depicts treating the target 12 complexed with the probe-hapten conjugate with an anti-hapten antibody 18 having a detectable label 20. A person of ordinary skill in the art will appreciate that the detectable label 20 can be any of the variety of signal generating moieties disclosed herein or that would be known to a person of ordinary skill in the art, or combinations thereof, such as an enzyme, an organic chromophore, such as a flourphore, chromophoric nanoparticles, such as fluorescent quantum dots, etc. The detectable label 20 is used to visualize the complex. For example, if the detectable label 20 is an enzyme, a substrate for the enzyme is provided, thereby producing a uniquely identifiable precipitate, such as a colored precipitate.

FIG. 1 also illustrates using at least one, and typically plural probes, where the probe or probes is conjugated to at least one hapten, and potentially plural different haptens, to simultaneously visualize multiple targets in a sample. FIG. 1 illustrates a sample having a particular target 22 that is recognized by a probe 24. Hapten 26 is conjugated to the probe 24. Hapten 26 may be the same or different from hapten 16. The sample is then treated with an anti-hapten antibody 28 conjugated to a detectable label 30. This process can continue, as illustrated for targets 32 and 42.

Signal generating moieties 20, 30, 40 and 50 as illustrated in FIG. 1 can be the same label, such as an enzyme. In this situation, the process may comprise adding anti-hapten antibodies 18, 28, 38 and 48 sequentially. After each application a different precipitate is formed by adding a different substrate. Substrates used for previous visualization reactions are washed from the samples before second and subsequent substrates are added.

Figure 2:
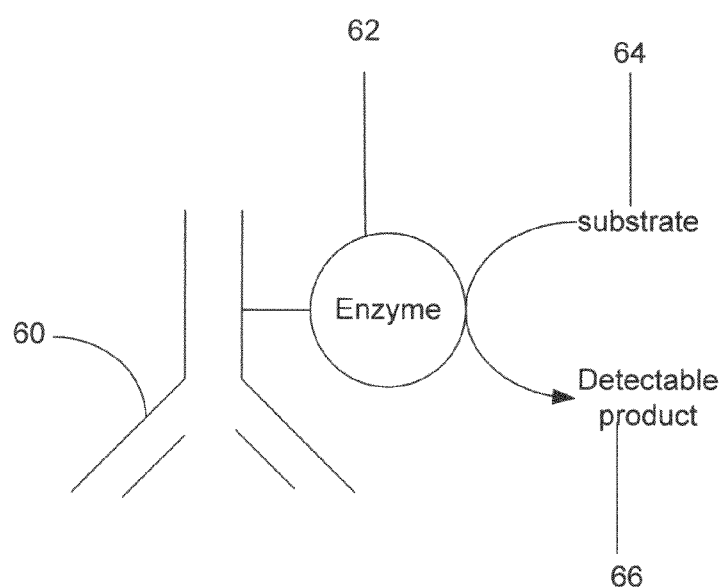
FIG. 2 is a schematic drawing illustrating one embodiment of a method for using enzymes as signal generating moieties.

FIG. 2 illustrates antibody 60 coupled to detectable label, such as an enzyme 62. An enzyme substrate 64 is added to produce a detectable enzymatic product 66. One specific embodiment of this process is Silver In Situ Hydridization (SISH). One suitable enzyme 62 for SISH is horseradish peroxidase, using silver ions and hydrogen peroxide as a substrate. The detectable product 66 is elemental silver particles.

As another example, enzyme 62 might be alkaline phosphatase. Substrate 64 is a source of silver ions and a phosphate-protected reductant. Again, the visually detectable product 66 is elemental silver. Silver can be detected by any suitable means, including bright field microscopy.

The embodiment illustrated in FIG. 2 also can be used to implement Chromogenic In Situ Hydridization. In this process, an enzyme 62 is again selected, with suitable examples including those disclosed herein or are otherwise known to those of ordinary skill in the art, with horseradish peroxidase and alkaline phosphatase being used to exemplify particular embodiments. A substrate is then selected suitable for producing a colored precipitate product 66 that can be detected using techniques known in the art, including bright field microscopy. The chromogenic compound can be fluorogenic. Suitable fluorogenic compounds are commercially available from various sources. For example, beta-lactamase and fluorogenic beta-lactamase substrates are available from Invitrogen Detection. The substrate can be made fluorogenic by the enzymatic action, or a fluorogenic substrate can be rendered non-fluorescent. Quantum dots also can be used to visualize immunohistochemical interactions too. Fluorescent probes and quantum dots typically are monitored using a fluorescence microscope.

Figure 3:
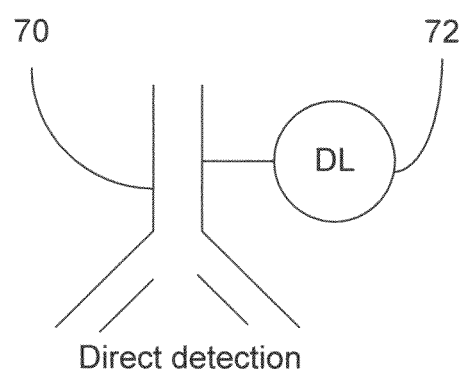
FIG. 3 is a schematic drawing illustrating direct detection of a target using a primary antibody comprising a detectable signal generating label.

FIG. 3 illustrates one embodiment of a direct detection process. For this process, a primary antibody 70 is selected for a particular target. For example, the primary antibody 70 might be a monoclonal antibody, such as mouse monoclonal IgG antibody. Primary antibody 70 also typically includes a detectable label 72, as discussed above.

Figure 4:
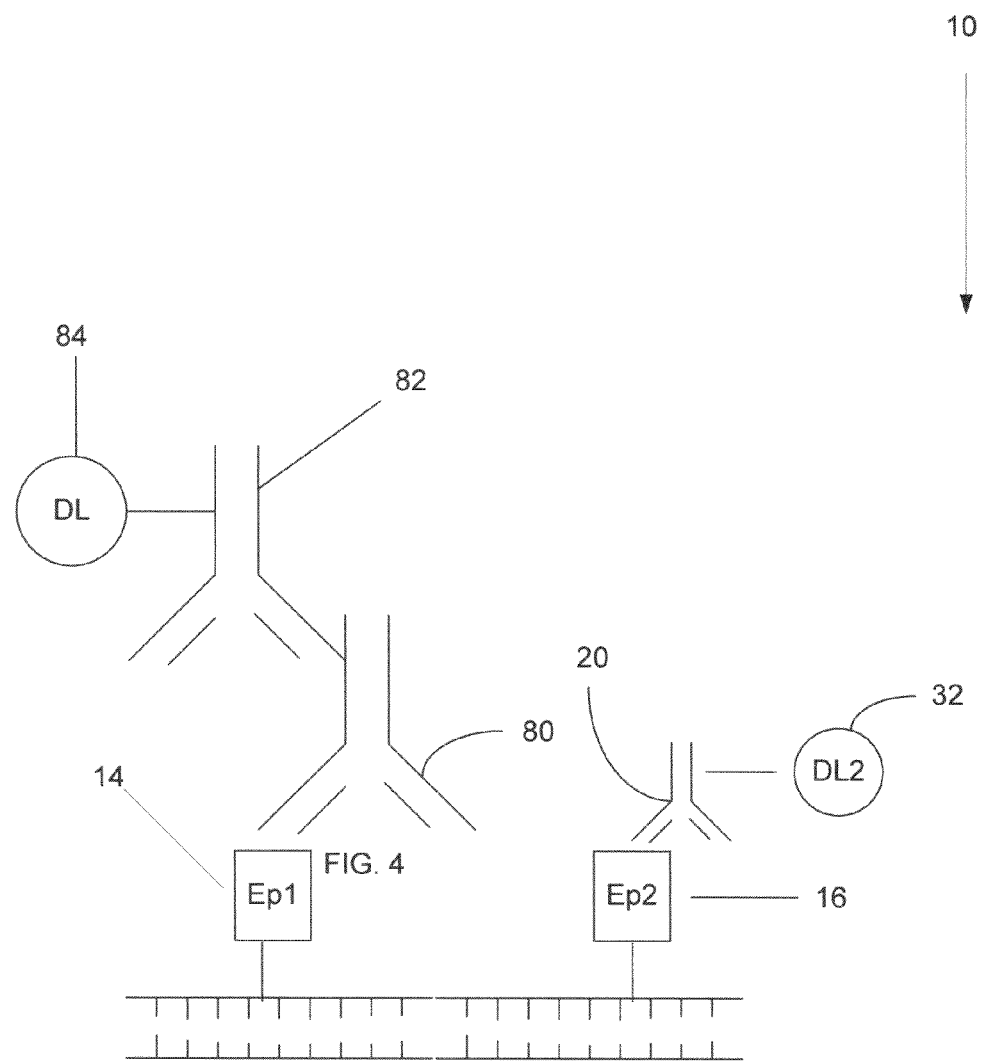
FIG. 4 is a schematic diagram illustrating one embodiment of a method for amplifying detection signals.

Alternatively, an amplification process can be used, as is illustrated schematically in FIG. 4. This embodiment also can be used for diagnostic tests. A target is selected. A primary antibody 80 is added to the sample in a manner to allow complexation of the target and primary antibody. A secondary antibody 82 against the primary antibody 80 is added to the sample. Antibody 82 includes a detectable label that can be used to identify, particularly visually or by visual means, such as microscopy, the complexed target using a substrate, as discussed herein. Antibody 82 can be any suitable antibody, including by way of example and without limitation, a labeled rabbit anti-mouse IgG antibody. Moreover, a secondary antibody 86 to the primary antibody 80 also can be added to the sample. Antibody 86 can be any suitable antibody against the primary antibody, such as an antibody from a different species. For example, antibody 86 might be, by way of example and without limitation, a goat antibody raised against the primary antibody, such as a mouse IgG antibodies. FIG. 4 illustrates adding at least one additional anti-antibody 88 having a detectable label 90 to the sample to amplify the signal produced by the detected target. In this exemplary process, the antibody 88 might be a labeled rabbit anti-goat IgG antibody. Antibody 88 can be added simultaneously with, or subsequent to, as the labeled antibody 84.

Figure 5:
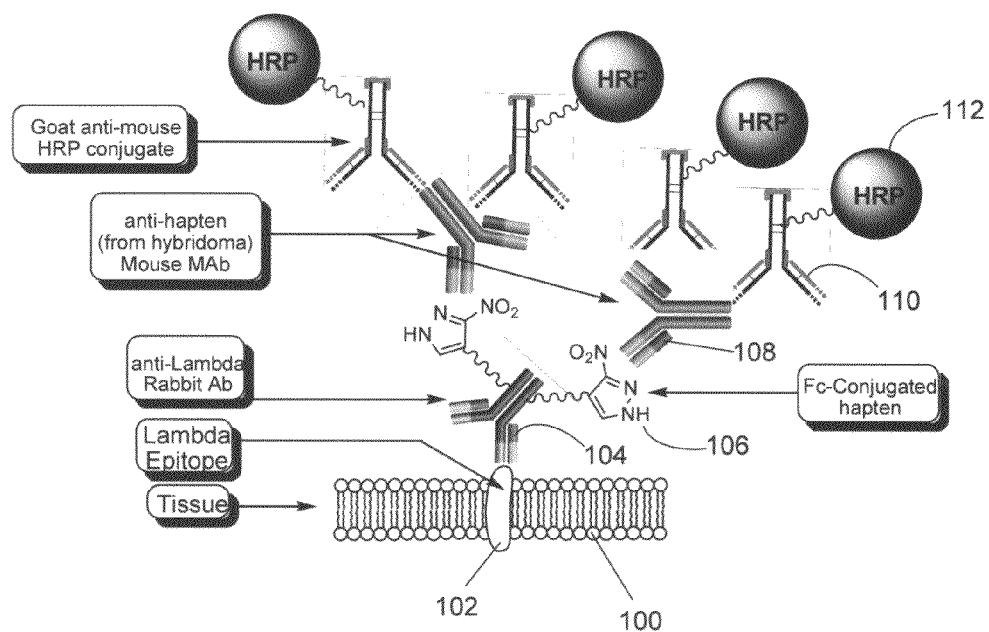
FIG. 5 is a schematic drawing illustrating one embodiment of hapten-quantum dot immunohistochemistry detection according to the present invention.

Certain embodiments of the present invention are facilitated by using anti-hapten monoclonal antibodies. FIG. 5 schematically represents one embodiment of the present invention useful for hybridoma screening. As with preceding examples, a particular target is selected. For example, a target situated in a tissue 100, such as the illustrated lambda epitope 102, is identified. A primary antibody 104 directed to the target 102 is administered in a manner effective for the antibody to recognize the target. One example of a suitable primary antibody 104 for the illustrated system is anti-Lambda rabbit antibody. As indicted in FIG. 5, antibody 104 has at least one, and potentially plural, haptens 106 conjugated thereto, as with the illustrated embodiment. A person of ordinary skill in the art will recognize first that the number of haptens conjugated to the antibody can vary, but this number typically is from 1 to about 5 haptens, but more typically is 2 to 3. Furthermore, a person of ordinary skill in the art will appreciate that the haptens conjugated to the primary antibody can be the same or different.

Tissue sample 100 is treated with anti-hapten antibodies 108. For example, in the embodiment illustrated in FIG. 5, haptens 106, coupled to the primary antibody 104, then effectively become coupled to an anti-haptenantibody 108, such as may be provided from a hybridoma mouse monoclonal antibody. Thus, for each hapten 106 coupled to the primary antibody 104, there will be a secondary antibody 108. The complex formed by the anti-hapten antibody 108, such as a mouse monoclonal antibody, then must be identified. One method is to now treat the composition with an antibody that recognizes the mouse antibody, such as a goat antibody. In the illustrated embodiment of FIG. 5, goat antibodies 110 are conjugated to a detectable label, such as an enzyme, including the illustrated horseradish peroxidase (HRP) enzymes 112. This complex is then incubated with an HRP substrate, as is known to persons of ordinary skill in the art, to form detectable, e.g. colored, precipitates. This process can be used for screening, such as hybridoma screening.

To screen for antihapten monoclonal antibodies, a tissue sample, such as normal human tonsil tissue is obtained. The sample may be embedded in paraffin, and if so, the tissue sample is deparaffinized, such as by using VMSI EZPrep solution. Cell conditioning and antigen retrieval is then performed using VMSI CC1. A primary polyclonal antibody, such as human anti-lamba (available from Dako), was conjugated to embodiments of haptens disclosed in the present application. Conjugation typically occurred at the Fc region of the antibody. Conjugating to the Fc region reduces the likelihood that the binding will affect the antibody specificity. A solution comprising an effective amount of the primary antibody is applied to the tissue for an effective period of time. For working embodiments the effective concentration has been about 10 μg/ml of the primary antibody, and the effective time period has been about 60 minutes. The tissue sample is then washed. Thereafter, a potential anti-hapten antibody (e.g. KLH-CGT1-1.1+5-27F09-02E01) is applied to the tissue sample for an effective period of time, such as about 60 minutes. The antibody is then detected using any suitable means, such as VMSI Omni Map DAB stain.

Automated immunohistochemistry (IHC) screening of potential anti-hapten antibodies was performed using a VMSI Discovery XT and formalin-fixed, paraffin-embedded human tonsil tissue on glass slides. Tissue samples first undergo de-pariffination, antigen retrieval, followed by the addition of a primary antibody linked to the hapten of interest, the potential anti-hapten antibody and a detection antibody. The detection antibody is visualized using a chromogen detection reagent from VMSI. Stained slides were manually screened under a microscope. Samples having a correct primary antibody staining pattern were selected as potential anti-hapten candidates. To test for selectivity and specificity, candidate anti-hapten cell fusion products are further screened using primary antibodies conjugated to a hapten of a different chemical class under the same staining method detailed above.

Figure 6:
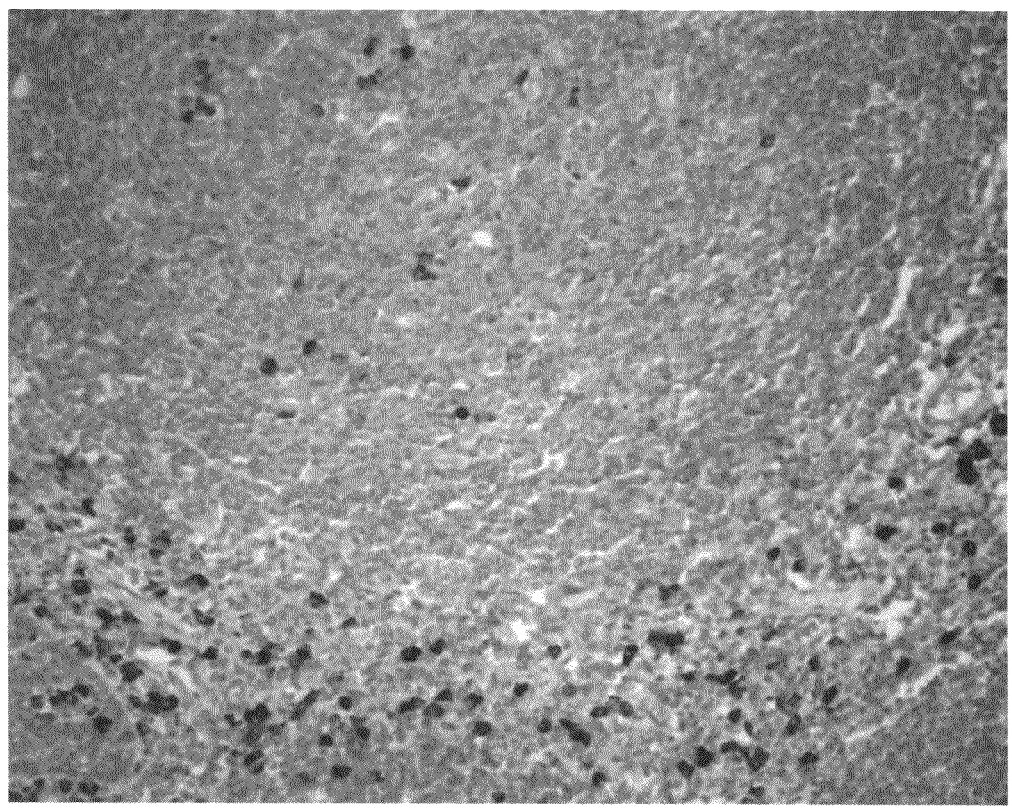
FIG. 6 is a photomicrograph depicting IHC positive staining of anti-hapten antibody detection using a primary antibody conjugated to a disclosed embodiment of a class of haptens according to the present invention.

FIG. 6 is a photomicrograph depicting IHC positive staining of anti-hapten antibody detection using a primary antibody conjugated to a disclosed embodiment of a nitropyrazole hapten according to the present invention. FIG. 6 clearly demonstrates visualization of a target in a sample using haptens according to the present invention coupled to a detectable label.

Figure 7:
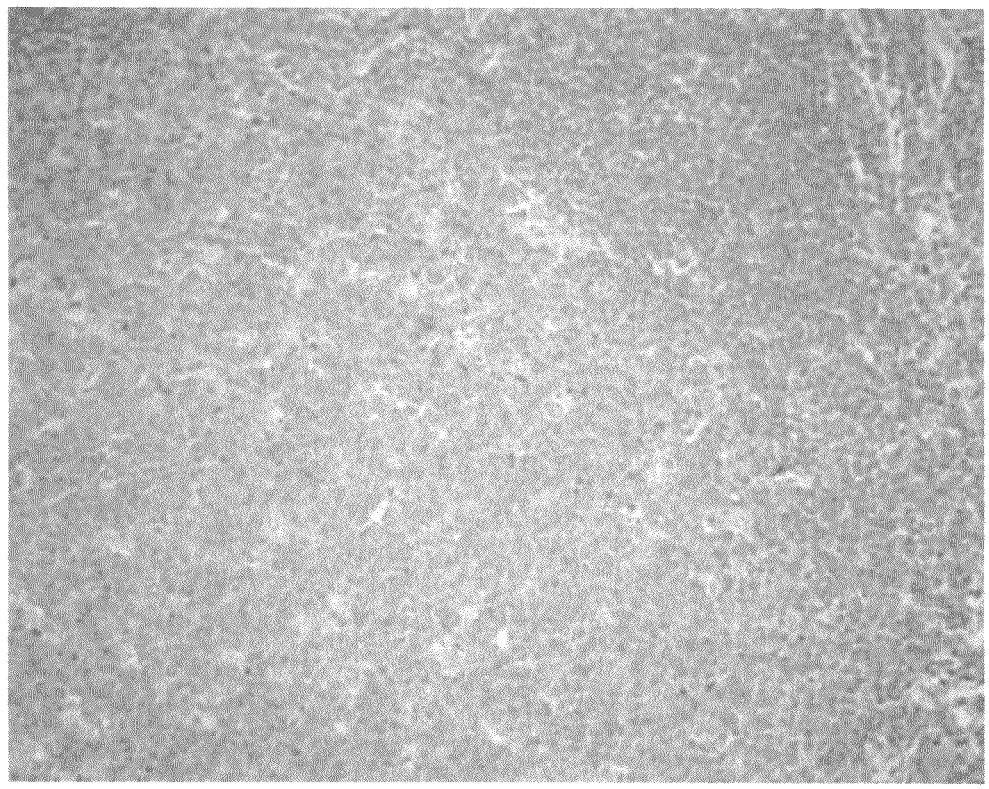
FIG. 7 is a photomicrograph depicting IHC negative staining using an anti-hapten antibody using a primary antibody conjugated to a disclosed embodiment of a class of haptens according to the present invention.

FIG. 7 is a photomicrograph depicting IHC negative staining using an anti-hapten antibody, such as an anti-nitropyrazole antibody, and a primary antibody conjugated to a disclosed embodiment of a class of haptens according to the present invention, such as a phenylthiourea. FIG. 7 clearly demonstrates visualization of a target in a sample using haptens according to the present invention coupled to a detectable label.

Figure 8:
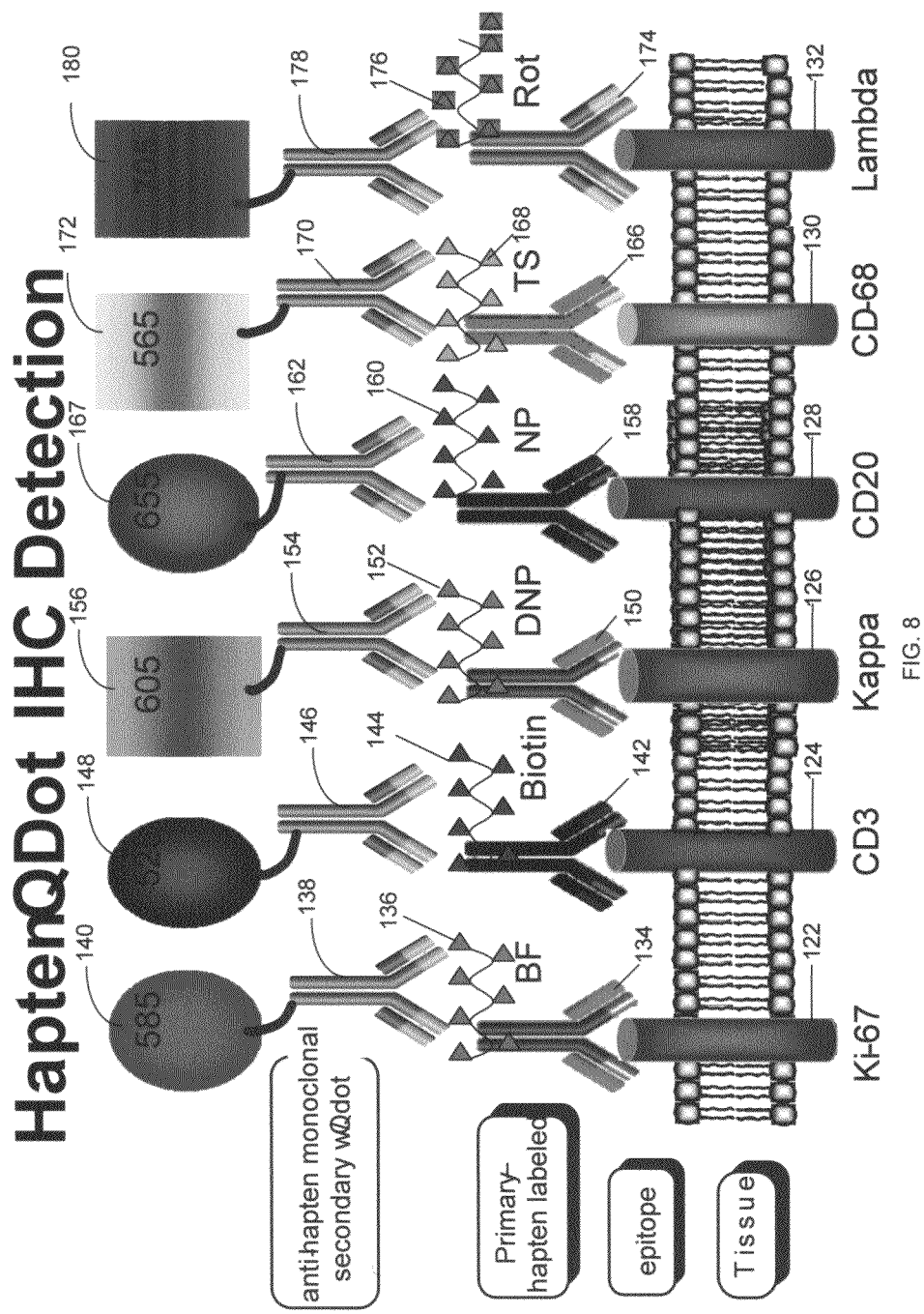
FIG. 8 is a schematic diagram illustrating one embodiment of a disclosed method for multiplexed detection of multiple targets in a sample using plural different haptens and plural different signal generating moieties to generate plural different detectable signals.

Embodiments of the present invention are useful for multiplexing, i.e. simultaneous detection of multiple targets in a sample. One embodiment of this approach is illustrated schematically in FIG. 8. FIG. 8 illustrates that a sample, such as tissue sample 120, may have multiple targets, including: Ki-67 (122) [a protein antigen that accumulates from G1-phase to mitosis, where it is found at its highest content. During interphase the Ki-67 protein is predominantly associated with the nucleoli. During mitosis it shows a close association with the chromosomes. Ki-67 is present in nuclei of proliferating (G1-, S-, G2-phase and mitosis) cells, but not in nuclei of quiescent or resting cells (G0-phase). Recently it was demonstrated that the Ki-67 protein belongs to the family of MPM-2 antigens and that phosphorylation of the Ki-67 protein during mitosis is associated with the condensation of the chromosomes and the separation of sister chromatids. A C-terminal domain of Ki-67 protein can bind to all three members of the mammalian heterochromatin protein 1 (HP1) family in vitro and in vivo suggesting a role for Ki-67 protein in the control of higher order chromatin structure; CD3 antigen (124) [CD3 is a protein complex composed of three distinct chains (CD3γ, CD3δ and CD3ε) in mammals, that associate with T-cell receptors (TCR) to generate an activation signal in T-lymphocytes. The TCR, ζ-chain and CD3 molecules together comprise the TCR complex. The CD3γ, CD3δ and CD3ε chains are highly related cell surface proteins]; Kappa protein (126); CD20 (128) [an antigen expressed on normal and malignant human B cells that is thought to function as a receptor during B cell activation]; CD-68 antigen (130) [a 110 kDa highly glycosylated transmembrane protein which is mainly located in lysosomes]; and lambda protein (132). An antibody for each of the targets 122, 124, 126, 128, 130 and 132 is then selected, and added to the tissue sample 120 in a manner effective to allow antibody recognition of the target. For example, Ki-67 (122) may be recognized by a primary antibody 134 conjugated to BF hapten 136. An anti-BF monoclonal antibody 138 is then added to the sample in a manner effective to allow recognition of the BF hapten by the anti-BF antibody 138. Anti-BF monoclonal antibody 138 includes a detectable label 140, such as Qdot 585. Color emission spectra for various Qdots are provided at www.niaid.nih.gov/vrc/pdf/fig3_qdot_spectra.pdf. Qdot 585 produces a yellow-orange light. A person of ordinary skill in the art will appreciate that this process can be varied from that described. For example, hapten 136 need not be BF, nor does the detectable label 140 need to be Qdot 585, nor even a Qdot. Rather, all various combinations of haptens and signal generating moieties as described herein and as would be known to a person of ordinary skill in the art can be used to practice the invention.

With continued reference to FIG. 7, CD3 (124) may be recognized by a primary antibody 142 conjugated to biotin 144. This feature illustrates another embodiment of the present invention where known agents, such as biotin, can be used in combination with disclosed embodiments of haptens, hapten conjugates, and compositions thereof. An anti-biotin monoclonal antibody 146 is then added to the sample in a manner effective to allow recognition of biotin by the anti-biotin antibody 146. Anti-biotin monoclonal antibody 146 includes a detectable label 148, such as Qdot 525, which produces a bluish green color.

Kappa (126) may be recognized by a primary antibody 150 conjugated to dinitrophenyl hapten 152. An anti-DNP monoclonal antibody 154 is then added to the sample in a manner effective to allow recognition of the DNP hapten by the anti-DNP antibody 154. Anti-biotin monoclonal antibody 154 includes a detectable label 156, such as Qdot 605, which produces an orange color.

CD20 (128) may be recognized by a primary antibody 158 conjugated to nitrophenyl hapten 160. An anti-NP monoclonal secondary antibody 162 is then added to the sample in a manner effective to allow recognition of NP 160 by the anti-NP antibody 162. Anti-NP monoclonal antibody 162 includes a detectable label 164, such as Qdot 655, which produces a light red color.

CD-68 (130) may be recognized by a primary antibody 166 conjugated to TS hapten 168. An anti-TS monoclonal secondary antibody 170 is then added to the sample in a manner effective to allow recognition of TS 168 by the anti-TS antibody 170. Anti-TS monoclonal antibody 170 includes a detectable label 172, such as Qdot 565, which produces a light green color.

Lambda (132) may be recognized by a primary antibody 174 conjugated to rotenone hapten 176. An anti-Rot monoclonal secondary antibody 178 is then added to the sample in a manner effective to allow recognition of Rot 176 by the anti-Rot antibody 178. Anti-Rot monoclonal antibody 178 includes a detectable label 180, such as Qdot 705, which produces a dark red color. Thus, by using different signal generating moieties, several different sample targets can be visualized substantially simultaneously, or sequentially, as may be desired.

Figure 9:
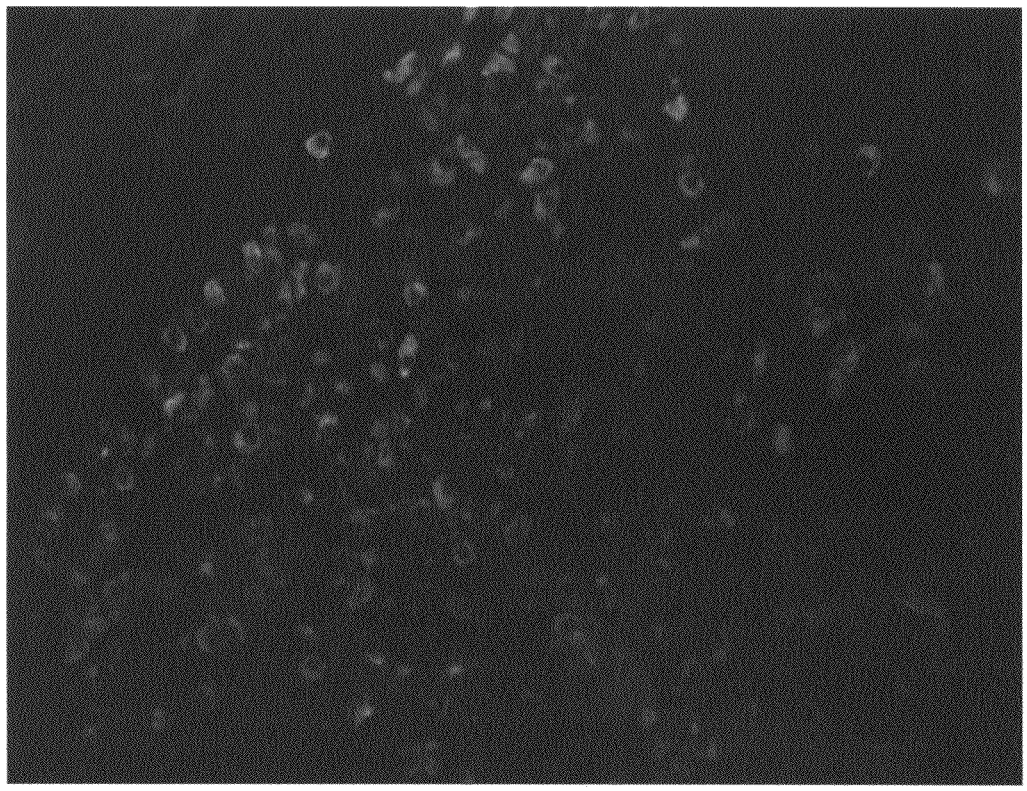
FIG. 9 is a photomicrograph depicting using multiple haptens and antibodies thereto, such as antibiotin and antidinitrophenyl, for detection of sample, such as a protein, in tissue.

Working embodiments have used multiple different haptens, and antibodies thereto, to visualize a detectable target. FIG. 9 illustrates the results of such an approach. FIG. 9 is a staining image produced using multiple haptens and antibodies thereto. FIG. 9 clearly shows visualization of the protein.

Embodiments of the present invention also are useful for implementing a different type of multiplexing, i.e. simultaneous detection of multiple different types of targets, such as protein and nucleic acid targets, in a sample. This is illustrated schematically in FIG. 10 with reference to Her2 (human epidermal growth factor receptor 2). Her2 is a gene that helps control how cells grow, divide, and repair themselves. The Her2 proto-oncogene encodes a transmembrane glycoprotein of 185 kDa with intrinsic tyrosine kinase activity. Amplification of the Her2 gene and overexpression of its product induce cell transformation. Numerous studies have demonstrated the prognostic relevance of p185(Her2), which is overexpressed in 10% to 40% of human breast tumors.

Figure 10:
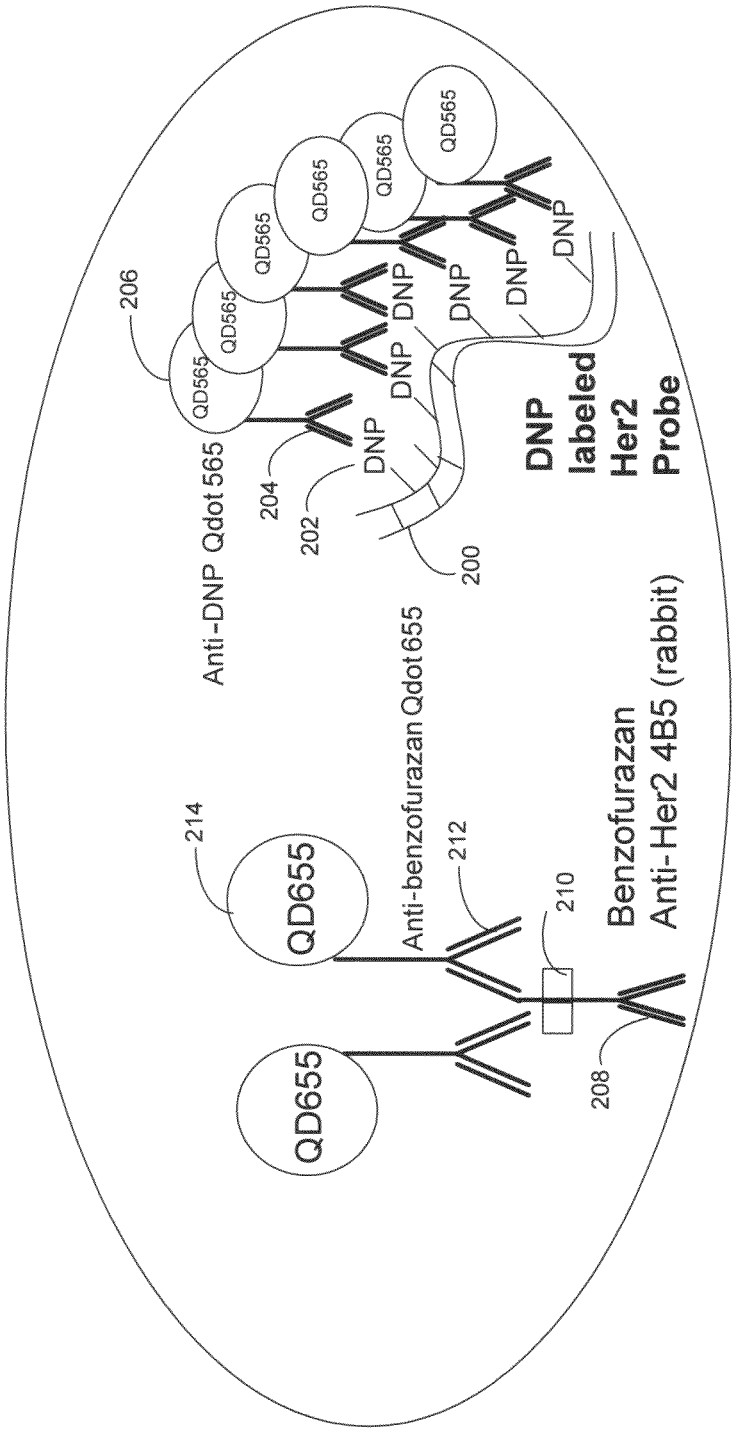
FIG. 10 schematically illustrates one embodiment of multiplexed detection of two different classes of targets, namely gene and protein targets.

FIG. 10 illustrates fluorescent imaging. As illustrated in FIG. 10, a hapten labeled Her2 probe 200 is added to a sample in a manner effective to allow the probe to complex with the Her2 gene. Probe 200 includes a hapten 202 that can be any known hapten, including embodiments of haptens disclosed herein. FIG. 10 illustrates using dinitrophenyl hapten 202. The complexed gene is then treated with an anti-hapten antibody 204. Anti-hapten antibody 204 includes detectable label 206, such as Qdot 565.

An anti-Her2 protein antibody 208, such as Anti-her2 4B5 rabbit antibody, is added to the sample in a manner effective to allow recognition of the Her2 protein. The anti-Her2 antibody 208 includes at least one hapten 210, and potentially plural haptens 210, which may be the same or different. The embodiment illustrated in FIG. 10 illustrates the process using biotin. An anti-hapten secondary antibody 212 is then added to the sample in a manner effective to allow complexation of the secondary antibody 212 and hapten(s) 210. Anti-hapten secondary antibody 212 includes a detectable label 214, such as a Qdot 655. Thus, the embodiment illustrated in FIG. 10 allows multiplexed detection of gene and gene product.

Figure 11:
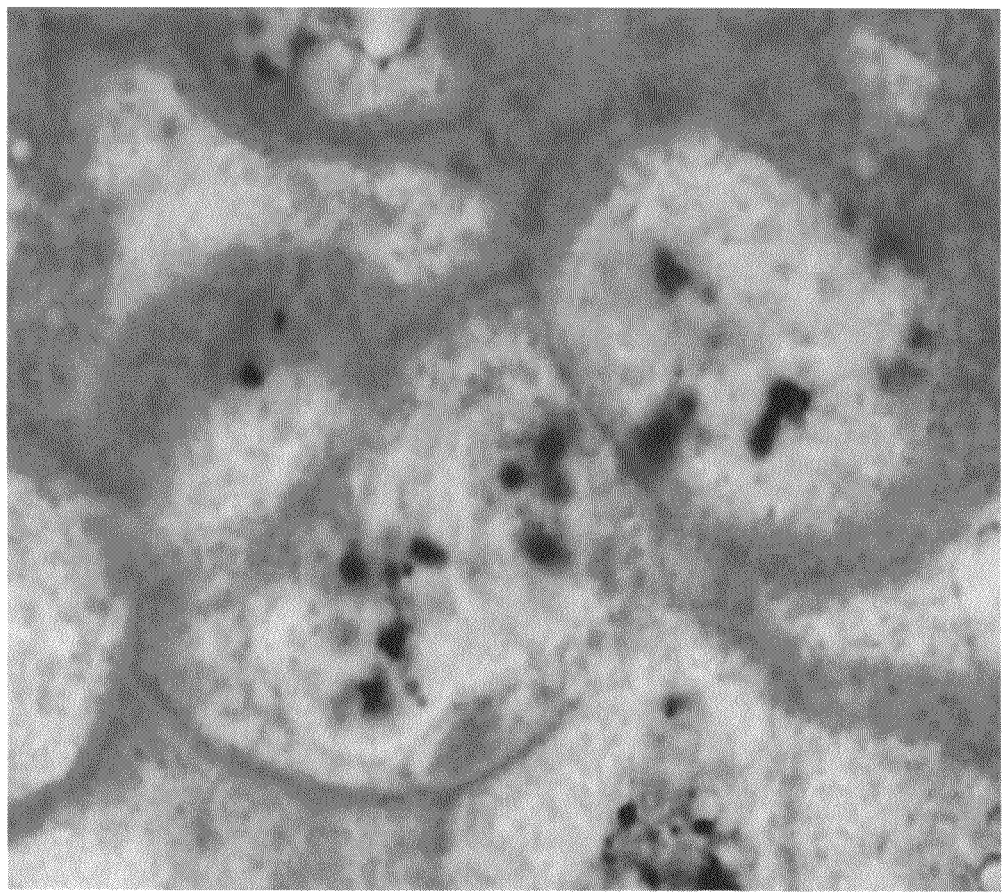
FIG. 11 is a photomicrograph depicting detection of protein and 2 genes, such as by using an antidinitrophenyl antibody.
Figure 12:
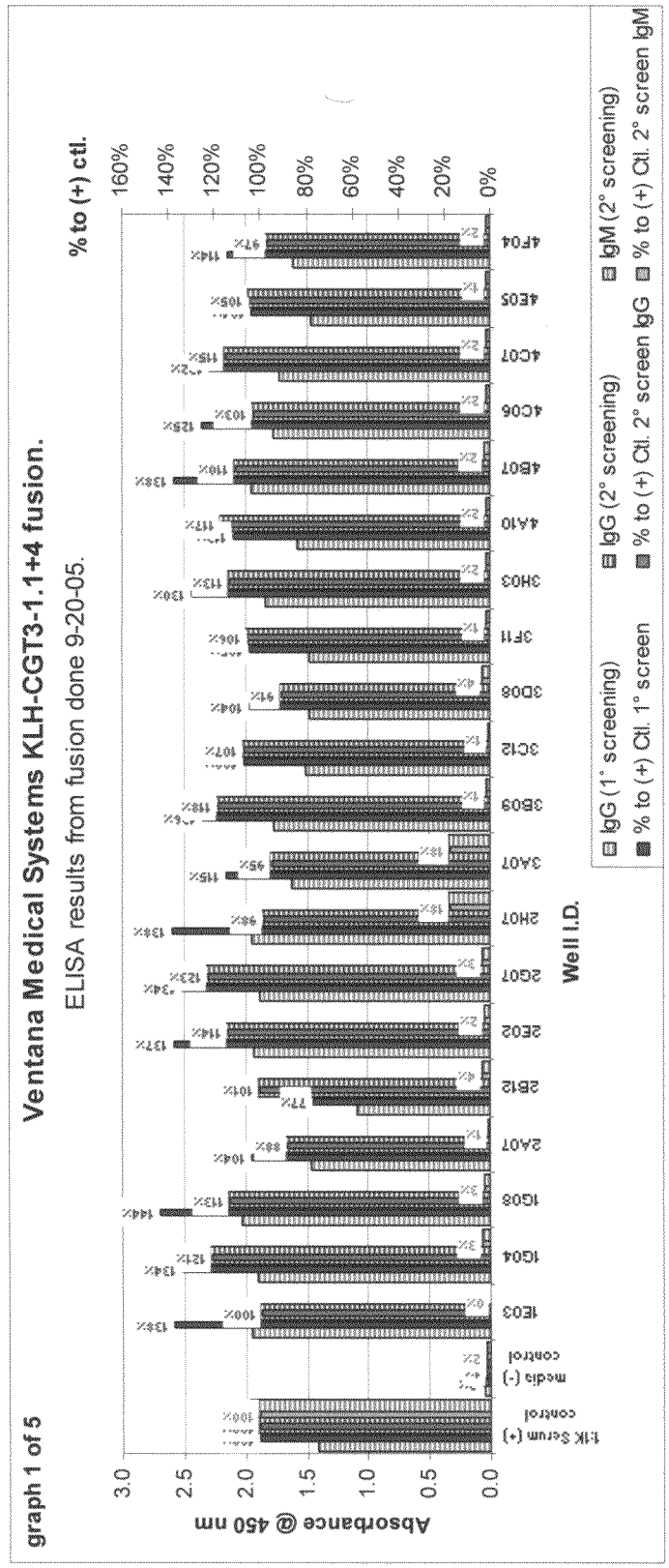
FIG. 12 illustrates hybridoma fusion product ELISA results for mouse IgG monoclonal antibodies against one embodiment of a disclosed benzofurazan hapten.
Figure 13:
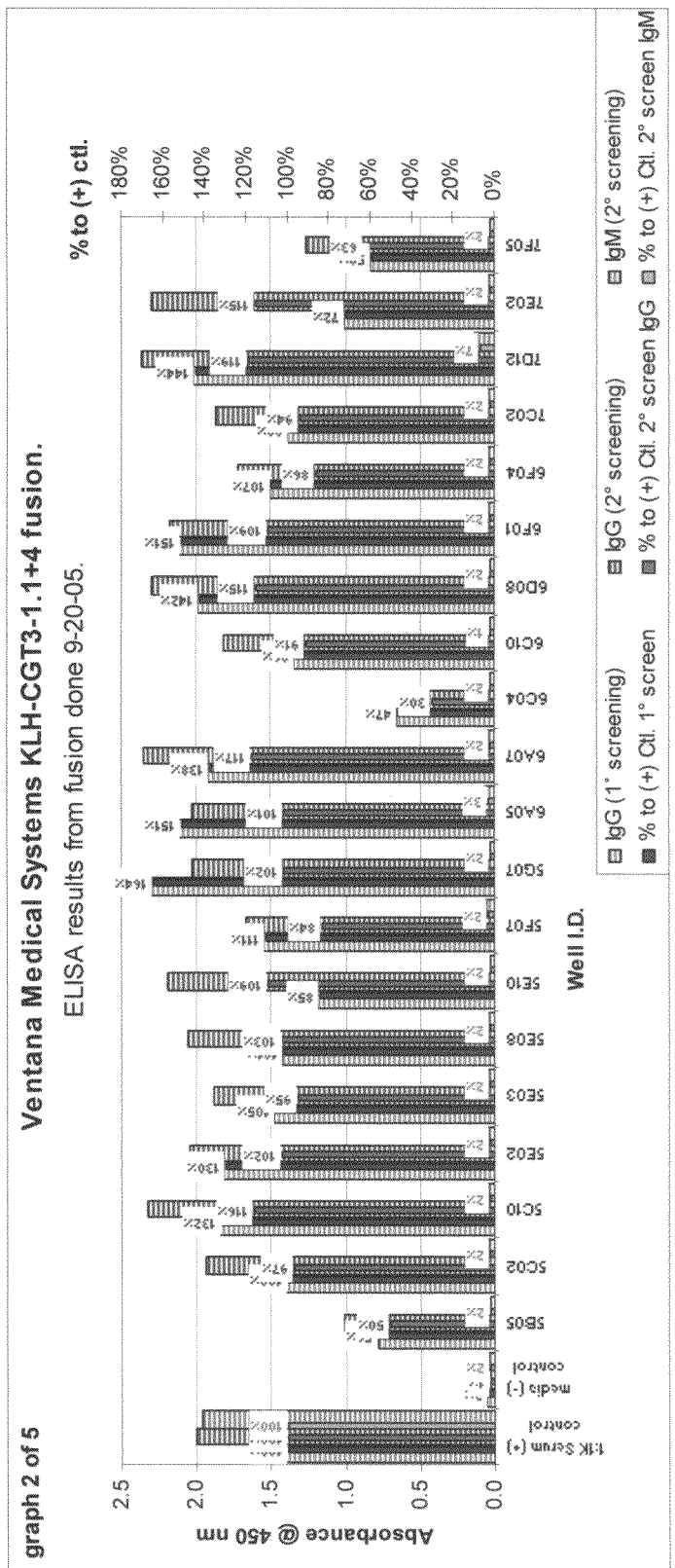
FIG. 13 illustrates hybridoma fusion product ELISA results for mouse IgG monoclonal antibodies against one embodiment of a disclosed benzofurazan hapten.
Figure 14:
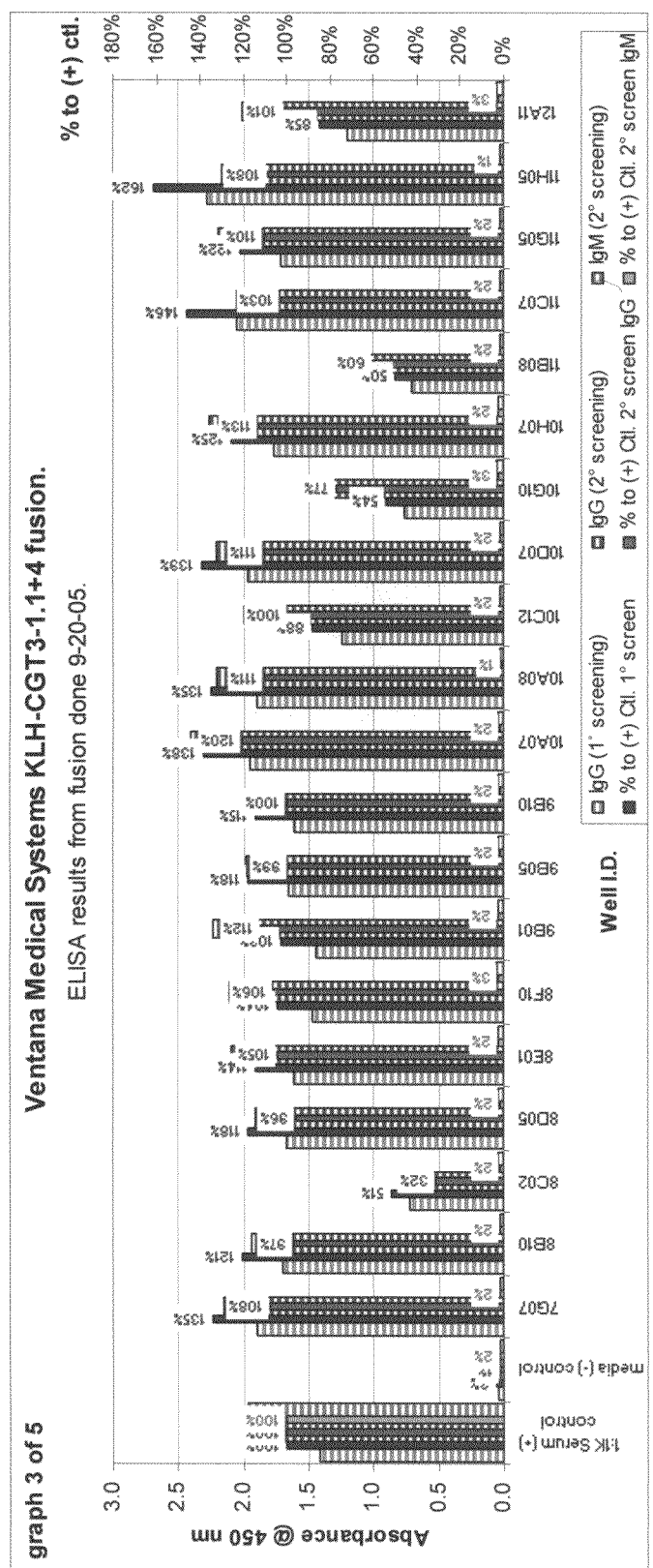
FIG. 14 illustrates hybridoma fusion product ELISA results for mouse IgG monoclonal antibodies against one embodiment of a disclosed benzofurazan hapten.
Figure 15:
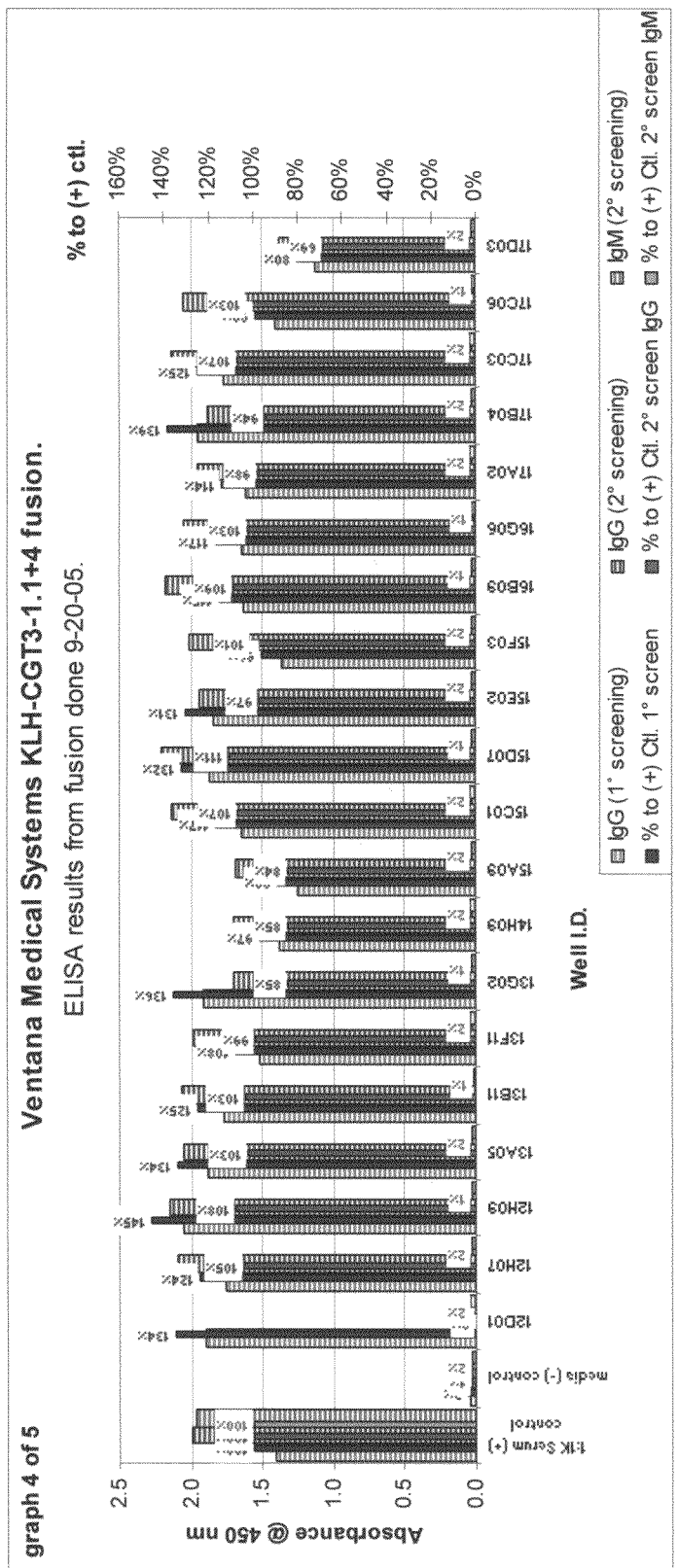
FIG. 15 illustrates hybridoma fusion product ELISA results for mouse IgG monoclonal antibodies against one embodiment of a disclosed benzofurazan hapten.
Figure 16:
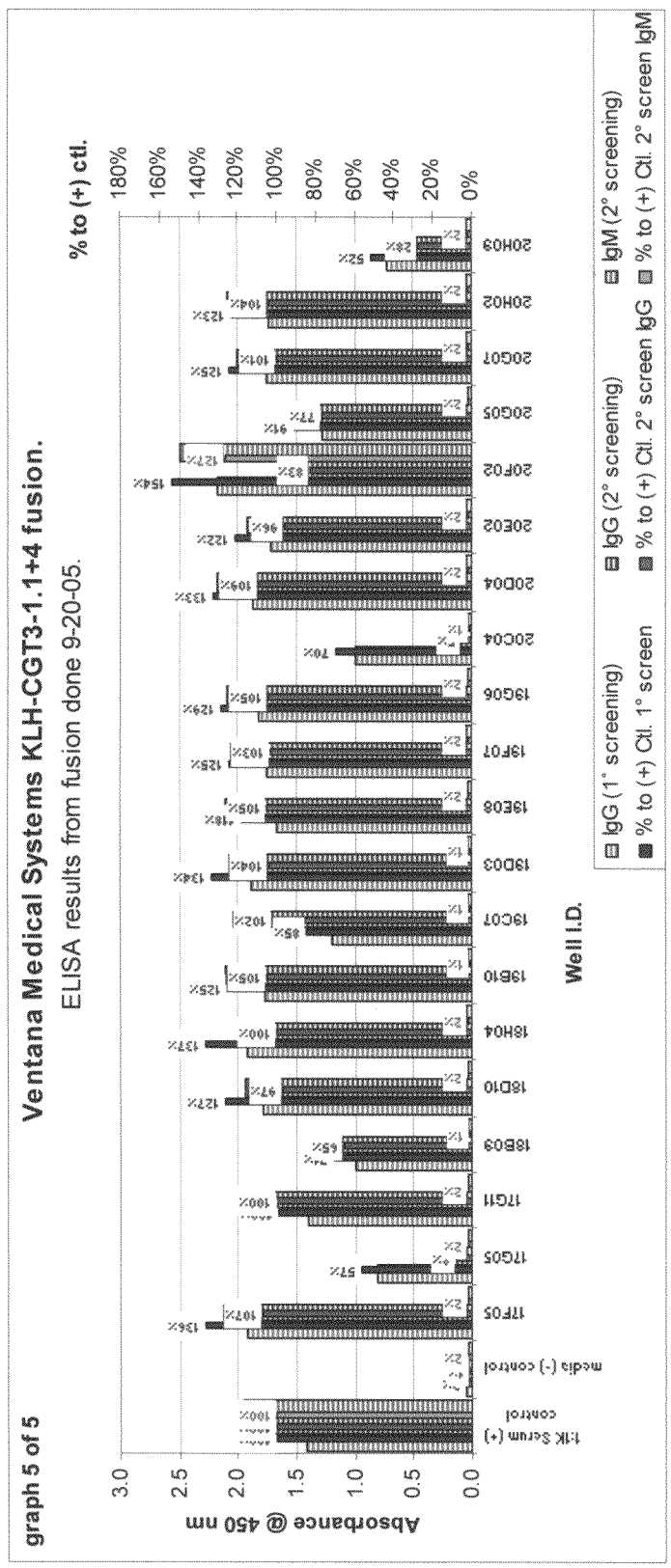
FIG. 16 illustrates hybridoma fusion product ELISA results for mouse IgG monoclonal antibodies against one embodiment of a disclosed benzofurazan hapten.

FIG. 11 illustrates the results of such a multiplexed chromogenic detection. FIG. 11 is a staining image depicting detection of protein and 2 genes, such as by using anti-biotin and anti-dinitrophenyl antibodies.

IX. Test Kits

Disclosed embodiments of the present invention provide, in part, kits for carrying out various embodiments of the method of the invention. Examples of such kits include those useful for cholesterol analyses, pregnancy kits, cancer diagnostic kits, etc. Test kits of the present invention typically have a hapten conjugate according to the present invention, such as at least one hapten-specific binding molecule conjugate, including hapten-antibody conjugates and/or hapten-nucleic acid probe conjugates, and an anti-hapten antibody, particularly an anti-hapten antibody conjugated to a detectable label As a specific example, kits are provided for characterizing a mammalian tumor's responsiveness to drug therapies, such as inhibitors. Particular examples include, without limitation, an inhibitor of the mTOR pathway or a dual mTOR pathway inhibitor and an EGR pathway inhibitor comprising at least two reagents, preferably antibodies, that can detect the expression, phosphorylation, or both of polypeptides in the EGF pathway, the mTOR pathway, or both. For example, the kit can contain at least two, three, or four reagents that bind to a phosphorylated form of ERK, that bind to the phosphorylated form of MEK, that bind to HIF-1α, or that bind to mTOR. Further, the kit can include additional components other then the above-identified reagents, including but not limited to additional antibodies. Such kits may be used, for example, by a clinician or physician as an aid to selecting an appropriate therapy for a particular patient.

X. Automated Embodiments

A person of ordinary skill in the art will appreciate that embodiments of the method disclosed herein for using hapten conjugates can be automated. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. published application Nos. 20030211630 and 20040052685, each of which is incorporated herein by reference.

Particular embodiments of hapten staining procedures were conducted using various automated processes. Additional detail concerning exemplary working embodiments are provided in the working examples.

XI. Working Examples

The following examples are provided to illustrate certain specific features of working embodiments. The scope of the present invention is not limited to those features exemplified by the following examples.

Materials

DTT was purchased from Aldrich and quantum dots were purchased from Quantum Dot, Co. and used as received. $NH_2$-dPEG$_8$-CO$_2$H, $NH_2$-dPEG$_8$-OH, NHS-dPEG$_{12}$-MAL and NHS-dPEG$_4$-MAL were purchased from Quanta BioDesign. Goat anti-biotin was received lyophilized from Sigma. Antibody concentrations were calculated using $\epsilon_{280}=1.4$ ml mg$^{-1}$ cm$^{-1}$. Quantum dot concentrations were determined using $\epsilon_{601(\pm 3)}=650\,000$ M$^{-1}$ cm$^{-1}$ for 605 nm emitting quantum dots (QD$_{605}$) and $\epsilon_{645(\pm 3)}=700\,000$ M$^{-1}$ cm$^{-1}$ for QD 655. Deionized water was passed through a Milli-Q Biocel System to reach a resistance of 18.2 MΩ. Buffer exchange was performed on PD-10 columns (GE Biosciences). Size-exclusion chromatography (SEC) was performed on Akta purifiers (GE Biosciences) which was calibrated with protein standards of known molecular weight. The flow rate was 0.9 ml/min on a Superdex 200 GL 10/300 (GE Biosciences) running PBS, pH 7.5.

Example 1

This example concerns the synthesis of Rotenone isoxazoline.

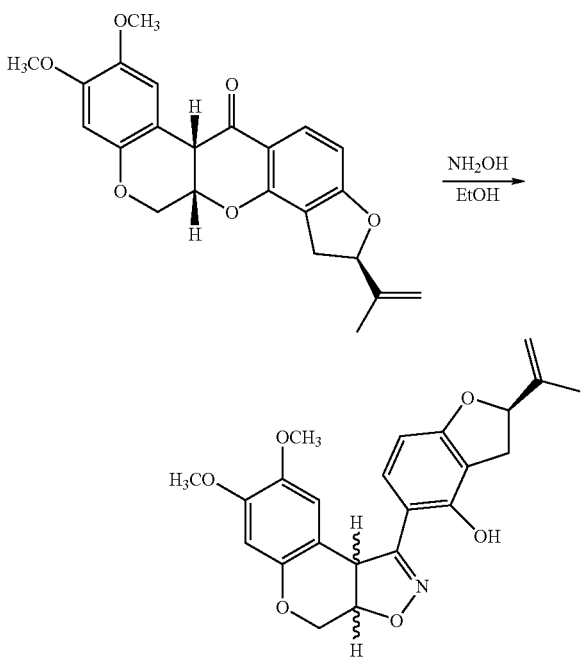

Rotenone (20.00 g, 50.7 mmol, 1.0 eq.) and hydroxylamine hydrochloride (35.20 g, 507 mmol, 10.0 eq.) were suspended/ dissolved in absolute ethanol (600 mL). A solution of sodium hydroxide (24.30 g, 608 mmol, 12 eq.) in water (120 mL) was added to the stirred suspension and refluxed for three hours. After the reaction was cooled to room temperature, the solution was filtered and the filtrate reduced in vacuo to approximately 150 mL volume. The reduced filtrate was diluted with water (200 mL) and extracted three times with methylene chloride (200 mL each). The methylene chloride washes were combined, dried over anhydrous magnesium sulfate, filtered and the solvent removed under vacuum. The resulting material (20 g) was taken up in methylene chloride (10 mL) and purified by flash chromatography (Isco Combiflash) using a 330 gram column and eluting using a methylene chloride to 20% methanol/methylene chloride gradient. The desired compound (6.17 g, 30%) was isolated as the earlier eluting fraction. Purity was determined by HPLC and structure by $^1H/^{13}C$-NMR and MS.

Example 2

This example concerns the synthesis of Rotenone isoxazoline acetic acid.

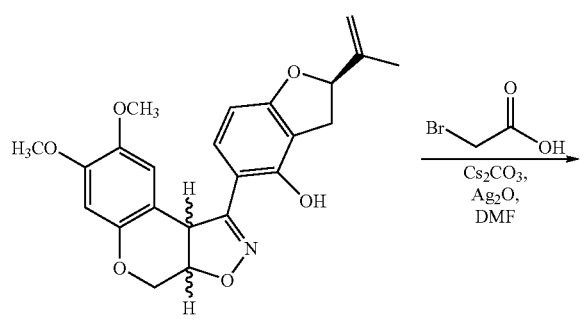

Rotenone isoxazoline (3.53 g, 8.62 mmol, 1.0 eq.) was stirred/suspended in anhydrous dimethylformamide (80 mL). Bromoacetic acid (28.10 g, 86.2 mmol, 10.0 eq.) was added under nitrogen. Cesium carbonate (28.1 g, 86.2 mmol, 10.0 eq.) and silver oxide (2.99 g, 12.9 mmol, 1.5 eq.) were added and the reaction stirred under nitrogen at ambient temperature for 21 hours. The reaction mixture was diluted with methylene chloride (120 mL), filtered and the solvent removed in vacuo. The residue was taken up in methylene chloride (15 mL) and chromatographed (Isco CombiFlash) using a 120 gram Redisep column with a 0 to 10% methanol gradient in methylene chloride. The fractions containing the desired compound were combined and concentrated under vacuum to give 2.98 g (74%). Purity was determined by HPLC and structure by $^1H/^{13}C$-NMR and MS.

Example 3

This example concerns the synthesis of diazapinone ester.

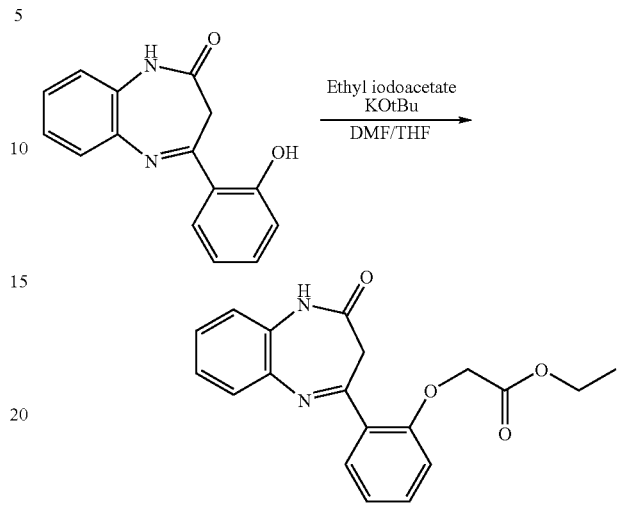

1,3-Dihydro-4-(2-hydroxyphenyl)-2H-1,5-benzodiazapin-2-one (2.837 g, 11.2 mmol, 1.0 eq) was stirred-suspended in 40 mL of DMF, 34 mL (34 mmol, 3.0 eq) of a 1.0 M (in THF) solution of potassium tert-butoxide added, 1.6 mL (13.5 mmol, 1.2 eq) of ethyl iodoacetate added, and reaction stirred under N2 for 3 hours. Then an additional 1.6 mL (13.5 mmol, 1.2 eq) of ethyl iodoacetate was added, and stirring continued for 2 hours. The reaction was then poured into 100 mL of water and extracted with EtOAc (3×100 mL). The EtOAc extracts were combined, dried over MgSO$_4$, solvent removed in vacuo, and resulting oil purified by flash chromatography, eluting with EtOAc/Hexane (20/80). Obtained 806 mg (21% yield). Purity was determined by HPLC and structure by NMR and MS.

Example 4

This example concerns the synthesis of diazapinone acid.

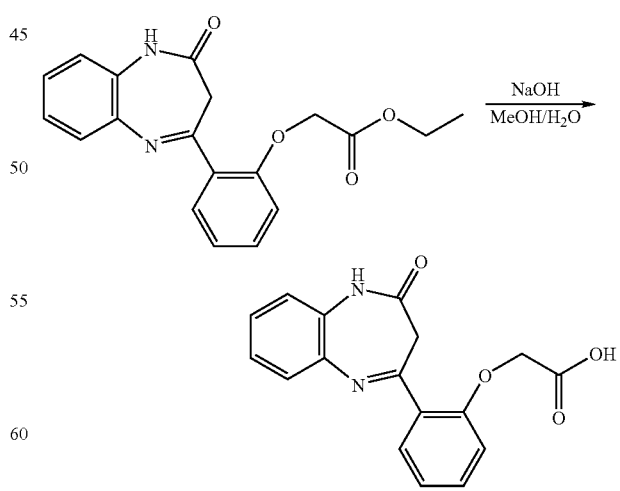

The diazapine ester (999 mg, 2.95 mmol, 1.0 eq) was dissolved in 30 mL of MeOH, 944 mg (23.6 mmol, 8.0 eq) of sodium hydroxide dissolved in 15 mL of water added, and reaction stirred for 40 minutes. The reaction was then diluted with 75 mL of water, pH adjusted to less than 4 with 6 M HCl, and extracted with EtOAc (3×75 mL). The EtOAc extracts were combined, dried over MgSO$_4$, and solvent removed in vacuo. Obtained 865 mg (94% yield). Purity was determined by HPLC and structure by NMR and MS.

Example 5

This example concerns the synthesis of oxopodophyllotoxin from podophyllotoxin.

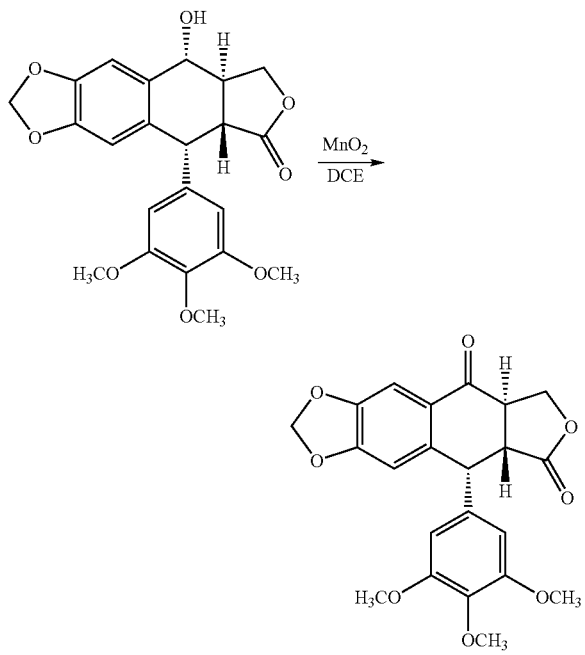

Podophyllotoxin (3.15 g, 7.61 mmol, 1.0 eq) was dissolved in 50 mL of DCE, manganese(IV) oxide (6.6 g, 76 mmol, 10 eq.) added, and the reaction mixture was refluxed for 1 hour. Additional manganese(IV) oxide (6.6 g, 76 mmol, 10 eq.) was added, and refluxing continued for 5 more hours, then reaction stirred at room temperature for 60 hours. The reaction was then filtered through celite to give a red-brown solution, filtrate solvent removed in vacuo, and resulting residue recrystallized from EtOH. Obtained 1.968 g (63% yield). Purity was determined by HPLC and structure by NMR and MS.

Example 6

This example concerns the synthesis of pyrazopodophyllic acid.

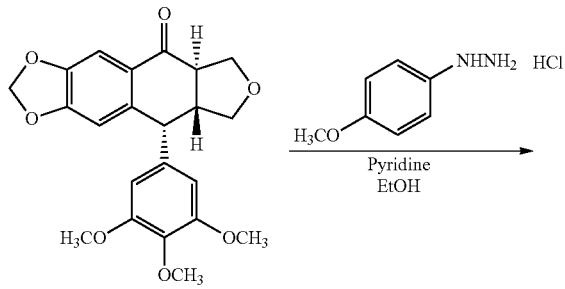

-continued

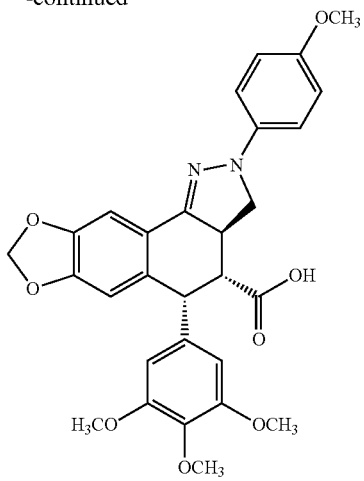

Oxopodophyllotoxin (200 mg, 0.485 mmol, 1.0 eq) was stirred-suspended in 10 mL of EtOH. Methoxyphenyl hydrazine hydrochloride (110 mg, 0.631 mmol, 1.3 eq) was added, pyridine (0.300 mL, 3.71 mmol, 7.6 eq) was added, and the reaction mixture stirred under N$_2$, at 95° C., for 18 hours. The reaction was then allowed to cool, poured into 20 mL of saturated sodium bicarbonate, and extracted with EtOAc (3×20 mL). The EtOAc extracts were combined, dried over MgSO$_4$, solvent removed in vacuo, and resulting residue purified by flash chromatography, eluting with DCM/MeOH (98/2). Obtained 121 mg (47% yield). Purity was determined by HPLC and structure by NMR and MS.

Example 7

This example concerns an exemplary synthesis of hapten carboxylic acid N-hydroxysuccinimidyl esters.

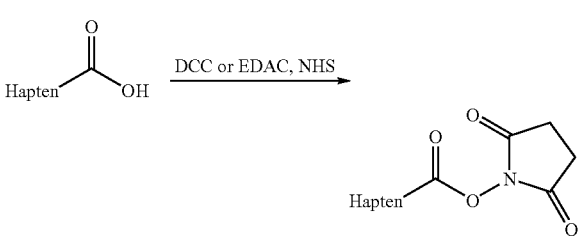

The hapten carboxylic acid (5.0 mmol, 1.0 eq.) was taken up in 10 ml of dry DCM in a 50 ml round bottom flask. The solution was blanketed with dry nitrogen and NHS (5.5 mmol, 1.1 eq.) was added followed by 1.0 M DCC in DCM (6.0 mmol, 1.2 eq.), and triethylamine (6.0 mmol, 1.2 eq.). The reaction was allowed to stir at room temperature under dry nitrogen for 16 hours at which point the solvent was removed under vacuum. The residue was taken up in 2 ml of dry DCM and filtered to remove the urea byproduct. The filter cake was then washed 2 times with 0.5 ml of dry DCM. The combined DCM portions were then dried under vacuum to give the hapten NHS ester which was used without further purification.

Example 8

This example concerns an exemplary synthesis of hapten-dPEG$_8$-carboxylic acids.

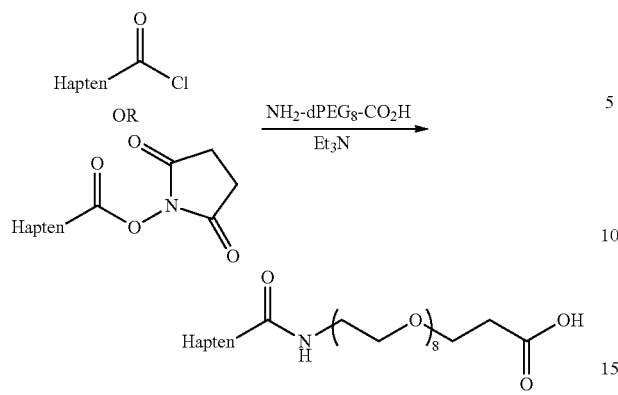

The hapten NHS ester or hapten acyl chloride (5.0 mmol, 1.0 eq.) was taken up in 10 ml of dry DCM in a 50 ml round bottom flask. The solution was blanketed with dry nitrogen and amino-dPEG$_8$-carboxylic acid (5.5 mmol, 1.1 eq.) was added followed by triethylamine (6.0 mmol, 1.2 eq.). The reaction was allowed to stir at room temperature under dry nitrogen for 16 hours at which point the solvent was removed under vacuum. The residue was taken up in minimal methanol and purified by preparative HPLC. The appropriate fractions were then pooled and dried under high vacuum to give the pure hapten-dPEG$_8$-acid.

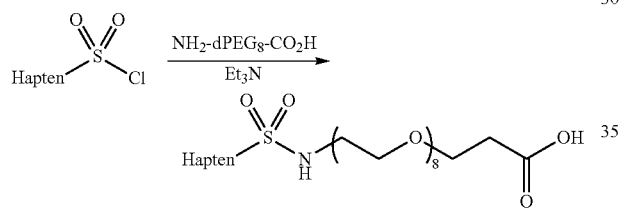

Alternatively, haptens that have a sulfonyl chloride moiety, such as the thiazole-based haptens in Scheme 10 and the azoaryl-based haptens in Scheme 15, could be directly coupled to amino-dPEG$_8$-carboxylic acid under the same stoichiometry and reaction conditions to produce hapten sulfamide-dPEG$_8$-carboxylic acid.

Example 9

This example concerns an exemplary synthesis of hapten-dPEG$_8$-carboxylic acid N-hydroxysuccinimidyl esters.

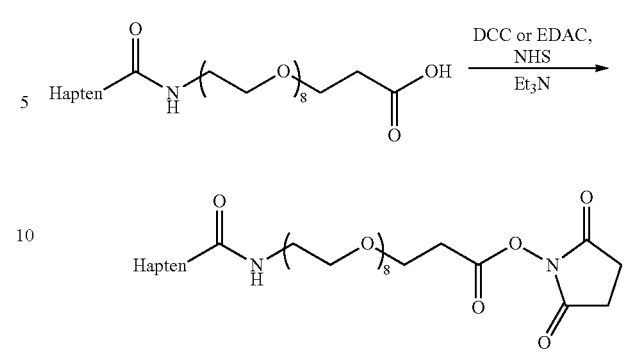

The hapten-dPEG$_8$-carboxylic acid (5.0 mmol, 1.0 eq.) was taken up in 10 ml of dry DCM in a 50 ml round bottom flask. The solution was blanketed with dry nitrogen and NHS (5.5 mmol, 1.1 eq.) was added, followed by 1.0 M DCC in DCM (6.0 mmol, 1.2 eq.), and triethylamine (6.0 mmol, 1.2 eq.). The reaction was allowed to stir at room temperature under dry nitrogen for 16 hours at which point the solvent was removed under vacuum. The residue was taken up in 2 ml of dry DCM and filtered to remove the urea byproduct. The filter cake was then washed 2 times with 0.5 ml of dry DCM. The combined DCM portions were then dried under vacuum to give the hapten-dPEG$_8$-NHS ester which was used without further purification.

Example 10

This example concerns an exemplary synthesis of hapten-dPEG$_8$-hydrazides.

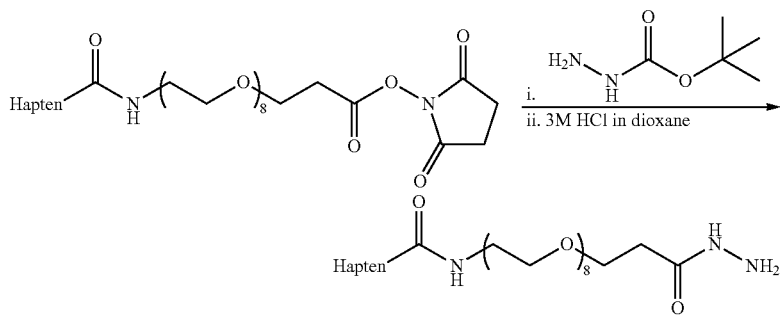

The hapten-dPEG$_8$-NHS ester (1.0 mmol, 1.0 eq.) was taken up in 5 ml of dry DCM in a 25 ml round bottom flask. The solution was blanketed with dry nitrogen and BOC hydrazide (1.2 mmol, 1.2 eq.) was added. The reaction was allowed to stir at room temperature under dry nitrogen for 16 hours at which point the solvent was removed under vacuum. The residue was then taken up in 10 ml of 4N HCl in dioxane and stirred at room temperature for three hours. The solvent was then removed under vacuum and the residue purified by preparative HPLC to give the pure hapten-dPEG$_8$-hydrazide.

Example 11

The following examples concern an exemplary synthesis of hapten-ethylamines by reacting ethylene diamine with a hapten-NHS, -sulfonyl chloride, -acid chloride or 1-fluoro-2,4-dinitrobenzene.

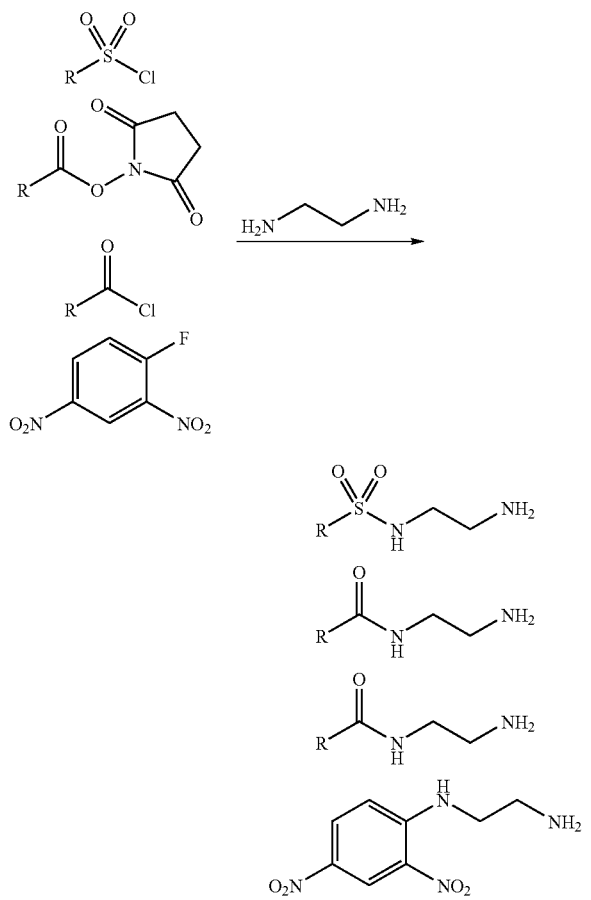

The hapten-NHS ester, hapten-sulfonyl chloride, hapten-acid chloride, or 1-fluoro-2,4-dinitrobenzene (1 mmol, 1.0 eq.) was dissolved in anhydrous methylene chloride (10 mL) and added dropwise to a solution of ethylene diamine (20 mmol, 20 eq.) in anhydrous methylene chloride (10 mL) under nitrogen and ambient conditions. The reaction mixture was stirred for one hour and the solvent removed in vacuo. The residue was taken up in an appropriate solvent and chromatographed on flash silica gel or by preparative HPLC. Typical yields were 30-60%. Purity was determined by HPLC and structure by $^1H/^{13}C$-NMR and MS.

Example 12

This examples concerns reacting N-butoxycarbonyl ethylene diamine with a hapten-NHS ester, -sulfonyl chloride, -acid chloride or 1-fluoro-2,4-dinitrobenzene.

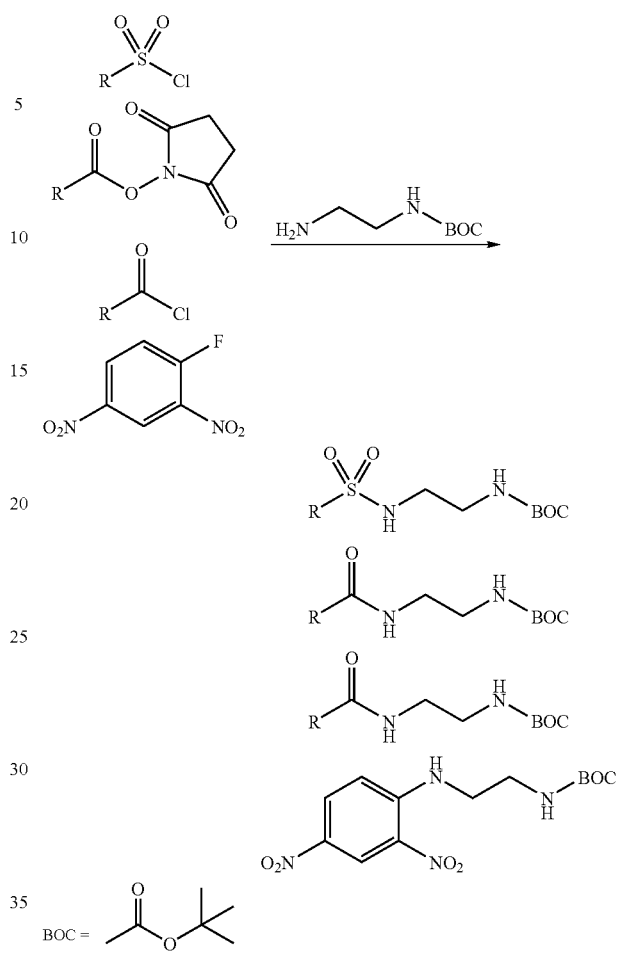

The hapten-NHS ester, hapten-sulfonyl chloride, hapten-acid chloride, or 1-fluoro-2,4-dinitrobenzene (1.0 mmol, 1.0 eq.) was dissolved in anhydrous methylene chloride (10 mL) and added dropwise to a solution of N-butoxycarbonyl ethylene diamine (1.0 mmol, 1.0 eq.) in anhydrous methylene chloride (10 mL) under nitrogen and ambient conditions. The reaction mixture was stirred for two hours and the solvent removed in vacuo. The residue was taken up in an appropriate solvent and chromatographed on flash silica gel or by preparative HPLC. Typical yields were 20-40%. Purity was determined by HPLC and structure by $^1H/^{13}C$-NMR and MS.

Example 13

This example concerns deprotecting hapten-BOC-ethylene diamine compounds.

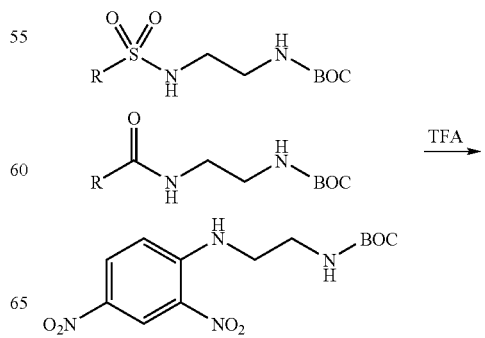

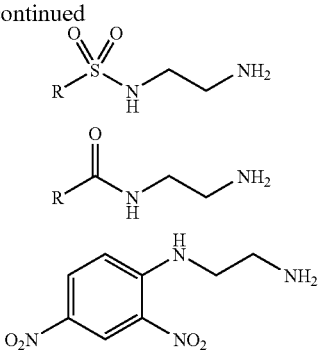

The hapten-BOC-ethylene diamine (1.0 mmol, 1.0 eq.) was dissolved in anhydrous methylene chloride (2.0 mL). Trifluoroacetic acid (2.0 mL) was added under ambient conditions and stirred for 30 minutes. The solvent was removed under vacuum to constant weight and the material used without purification. Typical yields were 90-95%. Purity was determined by HPLC and structure by $^1H/^{13}C$-NMR and MS.

Example 14

This example concerns an exemplary synthesis of hapten-dPEG$_8$-maleimides.

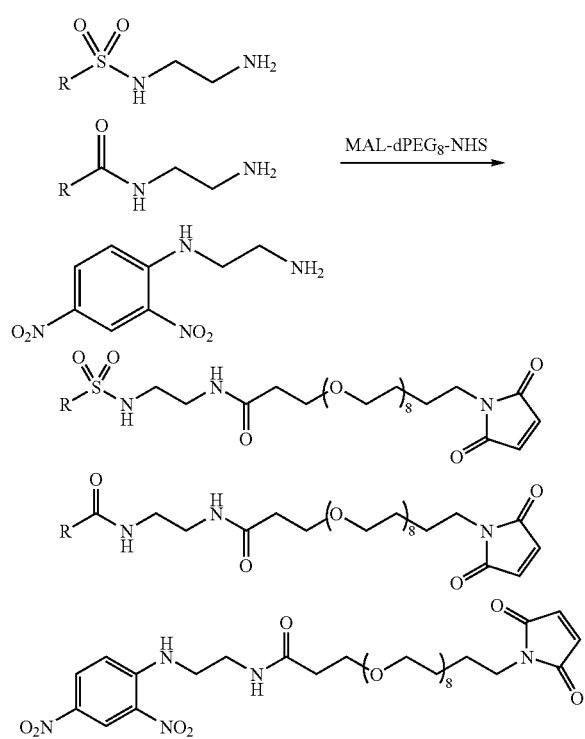

The hapten-ethylene diamine derivative (1.0 mmol, 1.0 eq.) was dissolved in anhydrous dimethyl formamide (5.0 mL) and triethylamine (4.0 mmol, 4.0 eq.) was added and stirred at ambient conditions under nitrogen. MAL-dPEG$_8$-NHS (1.0 mmol, 1.0 eq., Quanta BioDesign) was dissolved in anhydrous dimethyl formamide (5.0 mL) and added to the hapten-ethylene diamine solution. The reaction was stirred at ambient conditions under nitrogen overnight. The solvent was removed under vacuum and purified by preparative HPLC. Typical yields were 70-90%. Purity was determined by HPLC and structure by $^1H/^{13}C$-NMR and MS.

Example 15

This example concerns an exemplary synthesis of hapten-dPEG$_7$-alcohols.

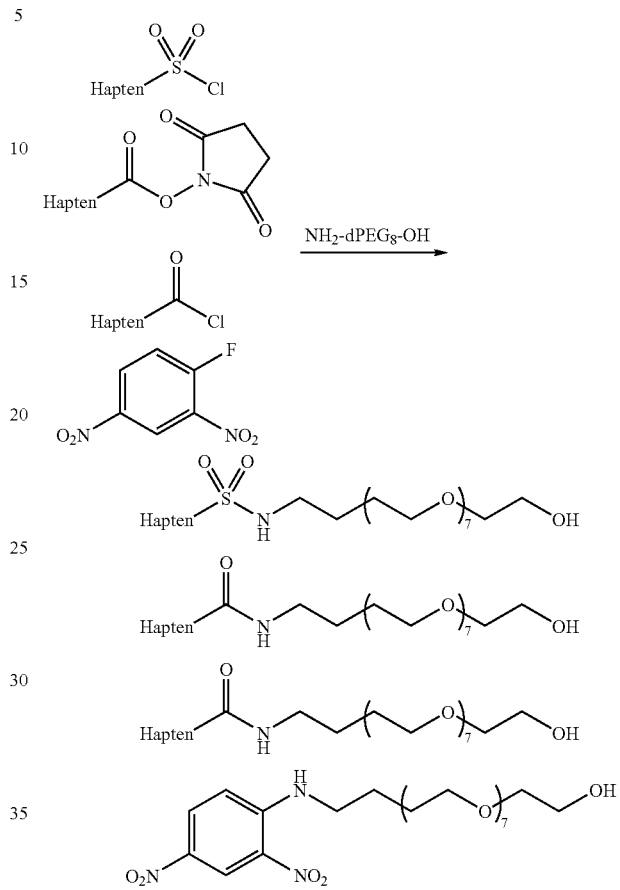

In a 25 ml RB flask, the hapten-NHS ester, hapten-sulfonyl chloride, hapten-acid chloride, or 1-fluoro-2,4-dinitrobenzene (1.0 eq., 2.7 mmol) is reacted with amino-dPEG$_7$-alcohol (1.0 eq., 2.7 mmol, Quanta BioDesign) in 5 ml of dry DMF. The reaction is then blanketed with dry nitrogen and stirred at room temperature for 16 hours. The solvent is removed under vacuum and the target alcohol purified by either silica gel chromatography or preparative HPLC. Product purity and identity was determined by HPLC, MS, and $^1H/^{13}C$-NMR.

Example 16

This example concerns an exemplary procedure of hapten-dPEG$_7$-mesylates.

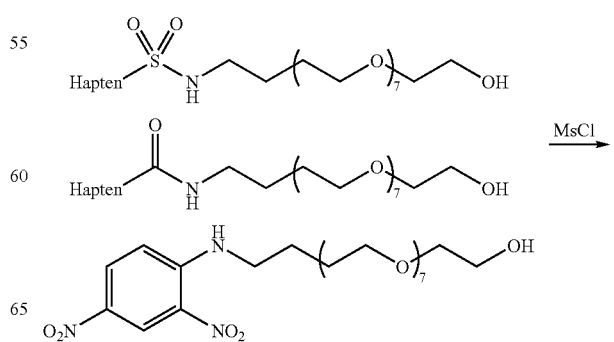

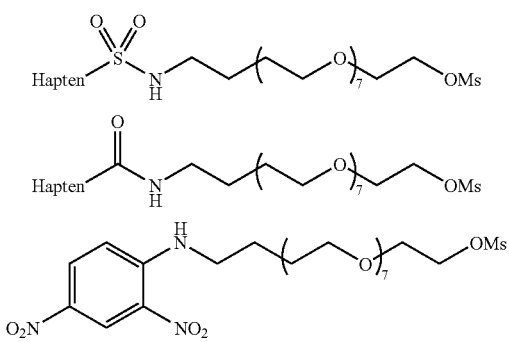

The hapten-dPEG$_7$-alcohol was taken up in anhydrous DMF (7 mL) in a 25 ml RB flask. The flask was purged with dry nitrogen and mesyl chloride (1.1 eq.) was added via syringe. The solution was stirred at room temperature for two minutes before adding anhydrous triethylamine (2.2 eq.) over approximately 20 minutes. The reaction was stirred for 16 hours at room temperature before removing the solvent under vacuum. The residue was taken up in dry DCM and purified via silica gel chromatography to afford the mesylate after removing the solvent under vacuum. Product purity and identity was determined by HPLC, MS, and $^1$H/$^{13}$C-NMR.

Example 17

This example concerns an exemplary procedure of hapten-dPEG$_7$-iodides.

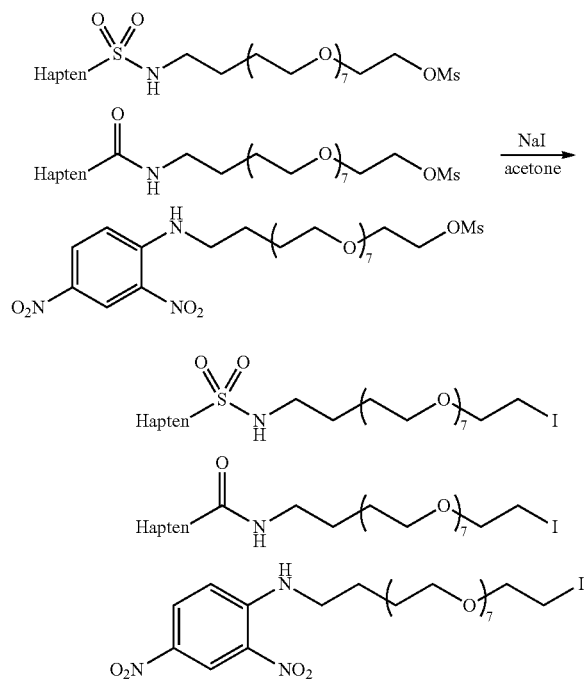

The hapten-dPEG$_7$-mesylate was dissolved in dry acetone (10 mL) and converted to the iodide by refluxing in the presence of sodium iodide (10 eq.) for three hours. The pure iodide was obtained after silica gel chromatography. Product purity and identity was determined by HPLC, MS, and $^1$H/$^{13}$C-NMR.

Example 18

This example concerns an exemplary procedure of hapten-dPEG$_7$-carbodiimides.

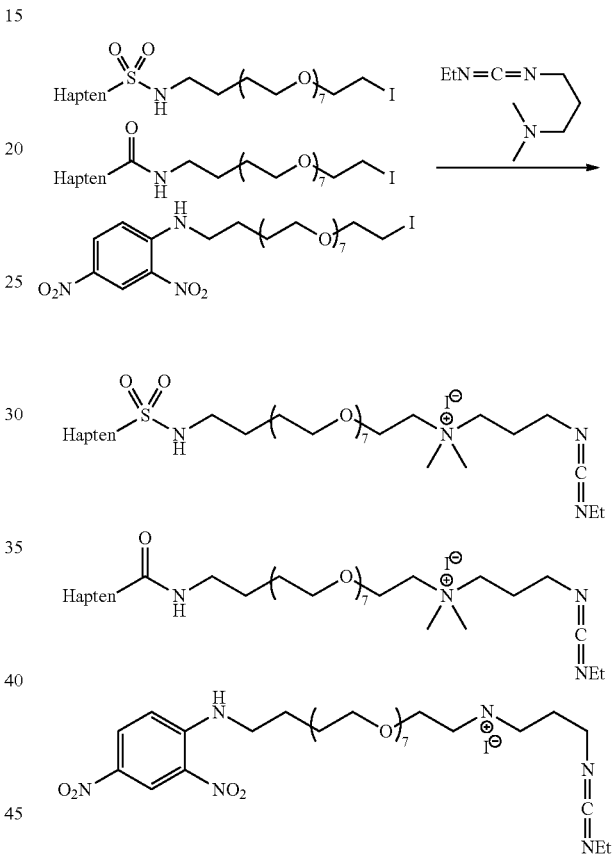

The hapten-dPEG$_7$-iodide was dissolved in dry DMF (10 mL), and treated with ethyl-N,N-dimethyl propyl carbodiimide (10 eq.) under nitrogen. After stirring at room temperature under dry nitrogen for 16 hours, the solvent was removed under vacuum to give a biphasic system composed of the desired carbodiimide and the excess ethyl-N,N-dimethylpropyl carbodiimide. The later was decanted off and the desired product dried under high vacuum. Product purity and identity was determined by HPLC, MS, and $^1$H/$^{13}$C-NMR.

Example 19

This example concerns an exemplary procedure of generating a 4-amino-deoxycytidine triphosphate-dPEG$_8$-hapten.

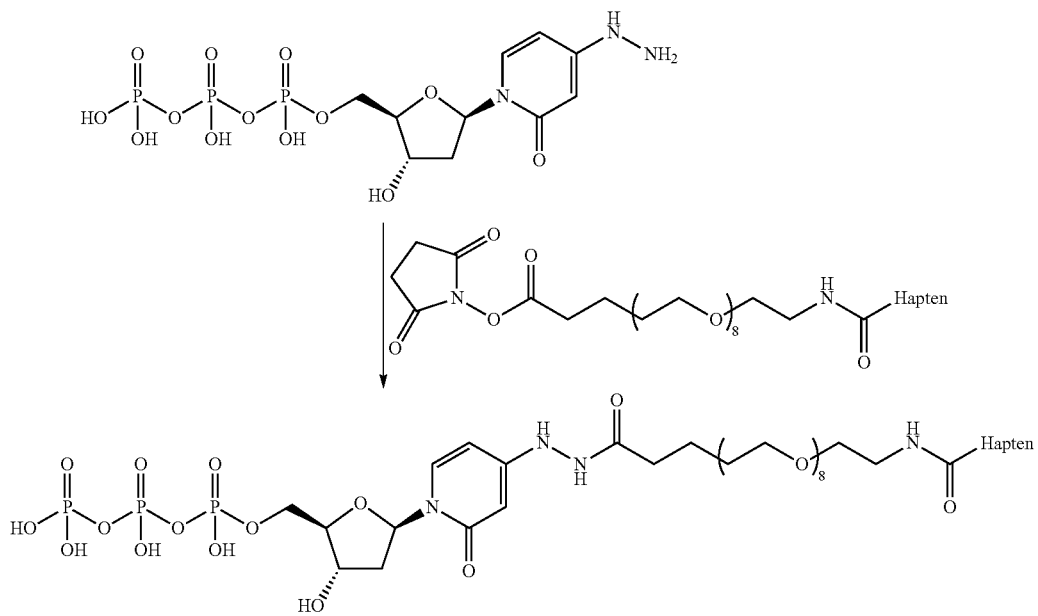

4-Amino-deoxycytidine triphosphate (1.0 eq. as the triethylammonium salt) was dissolved in anhydrous DMSO to produce a 0.01M solution. A solution of the hapten-dPEG$_8$-NHS (1.1 eq) in anhydrous DMSO was added to the 4-amino-deoxycytidine triphosphate and stirred for 16-24 hrs. under nitrogen. The 4-amino-deoxycytidine triphosphate-dPEG$_8$-hapten was purified by preparative HPLC using a Waters Sunfire OBD Preparative column (10 μm, C18, 50×250 mm) and eluting with a gradient of acetonitrile:water:0.8M triethylammonium carbonate (1:83:16 to 25:59:16 over 30 min). The pure fractions were combined, lyophilized, and redissolved in a minimal amount of DI water. The water solution was passed through a sodium ion-exchange column (SP Sephadex C-25, GE Lifesciences). The sodium salt of 4-amino-deoxycytidine triphosphate-dPEG$_8$-hapten was lyophilized to constant weight, and characterized by HPLC, $^1$H/$^{13}$C-NMR and MS.

Example 20

This example concerns an exemplary procedure of generating an immunogen with an immunogenic carrier protein and hapten-dPEG$_8$-NHS. A lyophilized immunogenic carrier protein, such as keyhole limpet hemocyanin (KLH), bovine thyroglobulin (BtG), or bovine serum albumin (BSA), was reconstituted in 1.0 mL PBS, pH 7.2 to give approximately a 10 mg/mL protein solution. The hapten-dPEG$_8$-NHS (300 eq. for KLH, 150 eq. for BtG, or 60 eq. for BSA) was dissolved in 100 μL DMF, added to the protein solution and rotated at room temperature overnight. The reaction was passed through a 0.2 μm GHP syringe filter and purified by SEC chromatography on an AKTA Purifier running at 0.9 mL/min. over a GE Lifesciences Superdex 200 10/300 GL column with PBS, pH 7.2. Fractions were pooled and collected corresponding to the monomeric immunogenic protein. The hapten-labeled protein was characterized by BCA protein assay (Pierce) for protein concentration and fluorescamine lysine assay (Bio-Tek) for hapten loading.

Example 21

This example concerns an exemplary procedure of conjugating a primary antibody with a hapten-dPEG$_8$-NHS. A polyclonal or monoclonal antibody in PBS, pH 7.0-7.5, was treated with a solution of hapten-dPEG$_8$-NHS (20 eq.) in anhydrous DMSO to give a final DMSO concentration not to exceed 10% v/v. The reaction was rotated 18 hours in an amber vial at room temperature and filtered (0.2 μm GHP syringe filter) prior to purification by SEC chromatography on an AKTA Purifier running at 0.9 mL/min. over a GE Lifesciences Superdex 200 10/300 GL column with PBS, pH 7.2. Typical yields were 70-80% with hapten coverage of 4-6 haptens per antibody.

Example 22

This example concerns an exemplary procedure of conjugating to the Fc-region on a primary antibody with a hapten-dPEG$_8$-NHS. A polyclonal or monoclonal antibody in PBS, pH 7.0-7.5, was treated with an unbuffered, aqueous solution of 100 mM sodium periodate to give a final concentration of 20 mM periodate. The solution was rotated at room temperature in an amber vial for two hours. The antibody was desalted and buffer exchanged by passing through a Sephadex G-25 column (PD-10, GE Lifesciences) with ABS (0.1M acetate, 0.15M NaCl, pH 5.5). The oxidized antibody solution was reacted with an unbuffered, aqueous solution of polyacrylamide hydrazide (50 eq) (further detail concerning using polyacrylamide hydrazide is provided by assignee's copending application No. 60/931,546, which was filed on May 23, 2007, and is incorporated herein by reference) and incubated for one hour at ambient temperature. Sodium cyanoborohydride (100 eq.) was added and the reaction was rotated overnight. The PAH-Ab conjugate was purified by SEC chromatography on an AKTA Purifier running at 0.9 mL/min. over a GE Lifesciences Superdex 200 10/300 GL column with ABS, pH 5.5. The hapten-dPEG$_8$-NHS (20 eq.) in anhydrous DMSO was added to give a final DMSO concentration not to exceed 10% v/v. The hapten-dPEG$_8$-PAH-Ab conjugate was purified by SEC chromatography on an AKTA Purifier running at 0.9 mL/min. over a GE Lifesciences Superdex 200 10/300 GL column with PBS, pH 7.2.

Example 23

This example concerns an exemplary procedure of conjugating to the Fc-region on a primary antibody with a hapten-dPEG$_8$-hydrazide. A polyclonal or monoclonal antibody in PBS, pH 7.0-7.5, was treated with an unbuffered, aqueous solution of 100 mM sodium periodate to give a final concentration of 20 mM periodate. The solution was rotated at room temperature in an amber vial for two hours. The antibody was desalted and buffer exchanged by passing through a Sephadex G-25 column (PD-10, GE Lifesciences) with ABS (0.1 M acetate, 0.15 M NaCl, pH 5.5). The oxidized antibody solution was reacted for one hour at room temperature with a solution of the hapten-dPEG-hydrazide (20 eq.) in DMSO, such that the final concentration of DMSO did not exceed 10% v/v. Sodium cyanoborohydride (100 eq.) was added and the reaction was rotated overnight. The hapten-dPEG$_8$-Ab conjugate was purified by SEC chromatography on an AKTA Purifier running at 0.9 mL/min. over a GE Lifesciences Superdex 200 10/300 GL column with PBS, pH 7.2.

Example 24

This example concerns an exemplary procedure of conjugating a primary antibody with a hapten-dPEG$_8$-maleimide. To a solution of polyclonal or monoclonal antibody in 100 mM phosphate, 1 mM EDTA, pH 6.5 buffer was added DTT at a final concentration of 25 mM. This mixture was rotated for precisely 25 minutes before desalting on a Sephadex G25 (PD-10, GE Lifesciences) in 100 mM phosphate, 1 mM EDTA, pH 6.5 buffer. Hapten-dPEG$_8$-maleimide (50 eq.) was added as a DMF solution, such that the final concentration of DMF did not exceed 10% v/v. The reaction mixture was rotated overnight in an amber vial under ambient conditions. The hapten-dPEG$_8$-Ab conjugate was purified by SEC chromatography on an AKTA Purifier running at 0.9 mL/min. over a GE Lifesciences Superdex 200 10/300 GL column with PBS, pH 7.5.

Example 25

This example concerns an exemplary procedure of conjugating single-stranded DNA with a hapten-dPEG$_8$-carbodiimide. DNA (100 µg) was taken up in TE buffer at 1 mg/ml in a tube and heated to 98° C. for one minute. The reaction mixture was frozen in dry ice-ethanol and 100 µL 0.5 M borate buffer, pH 9.5 was added. The reaction mixture was warmed to room temp and the hapten-dPEG$_8$-EDC (100l of 1.0 mM in DMSO) was added. The mixture was incubated at 60° C. for one hour, then added salt and precipitated with isopropanol. The precipitate was washed three times with 80% EtOH.

Figure 17:
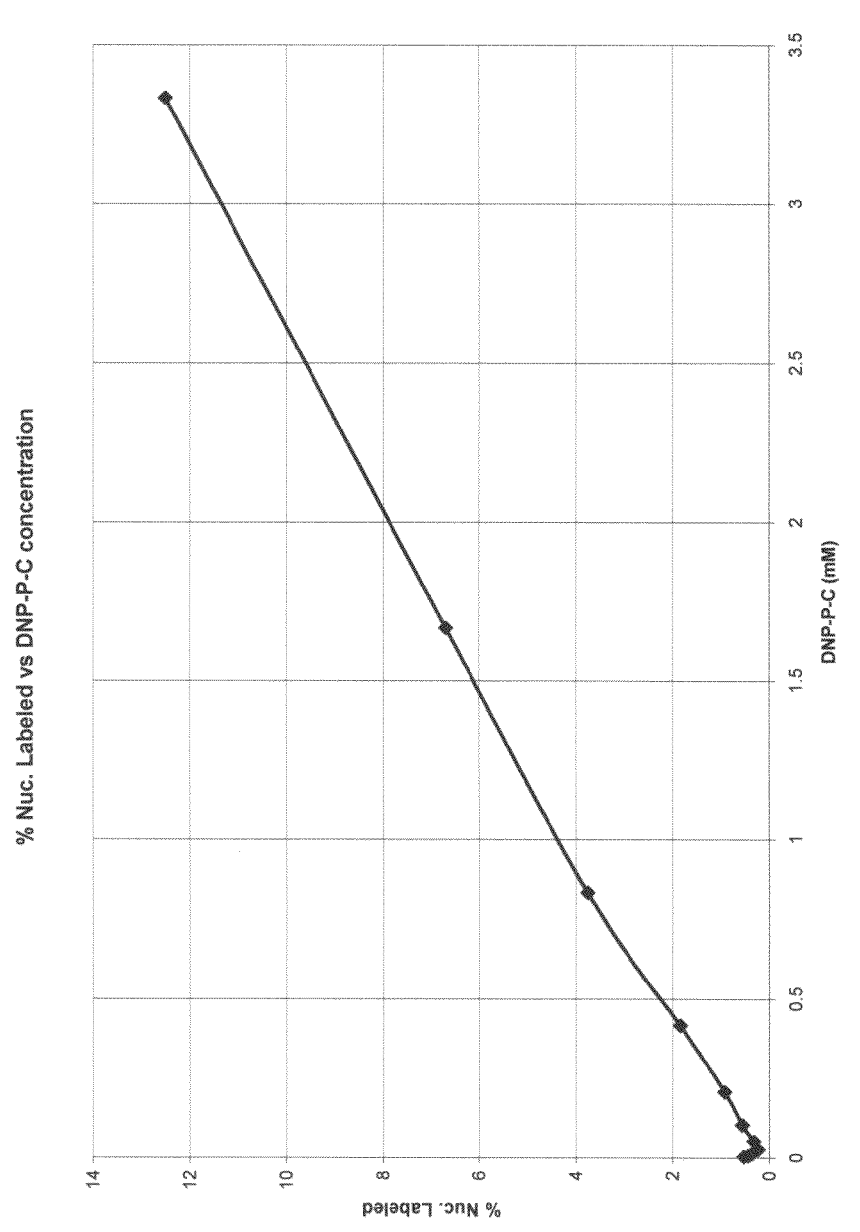
FIG. 17 is a graph of percent nucleotide versus DNP concentration.
Figure 18:
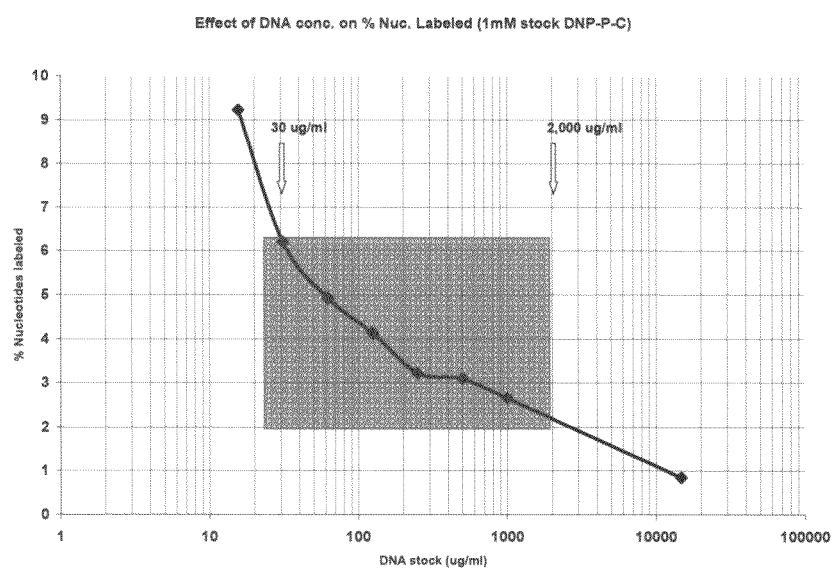
FIG. 18 is a graph of salmon DNA concentration on percent nucleotide labeled.
Figure 19:
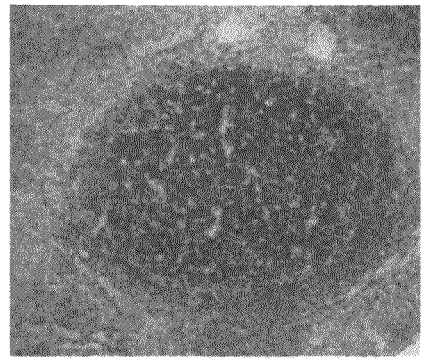
FIG. 19 is a chromogenic IHC staining of CD20-biotin-labeled primary antibodies with anti-biotin HRP conjugates on normal tonsil tissue.
Figure 20:
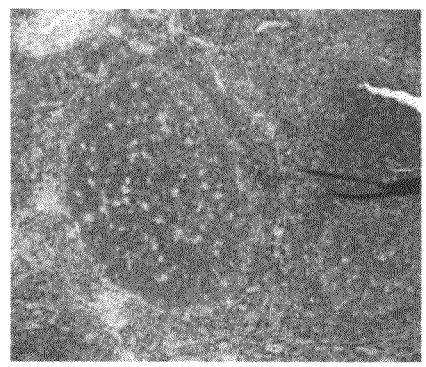
FIG. 20 is a chromogenic IHC staining of a CD45 thiazole sulfonamide-based hapten-labeled primary antibodies with anti-thiazole sulfonamide HRP conjugates on normal tonsil tissue.
Figure 21:
FIG. 21 is a chromogenic IHC staining of a Ki-67 benzofurazan-based hapten-labeled primary antibodies with anti-benzofurazan HRP conjugates on normal tonsil tissue.
Figure 22:
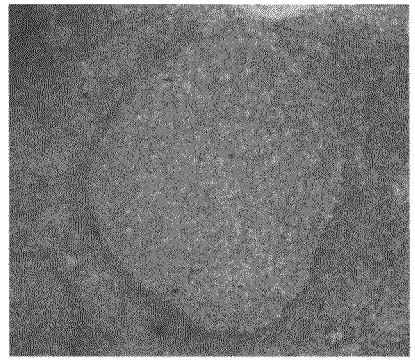
FIG. 22 is a chromogenic IHC staining of a CD34 nitropyrazole-based hapten-labeled primary antibodies with anti-nitropyrazole HRP conjugates on normal tonsil tissue.
Figure 23:
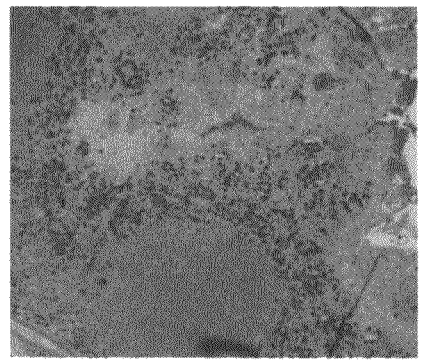
FIG. 23 is a chromogenic IHC staining of a Kappa dinitrophenyl-based hapten-labeled primary antibodies with anti-dinitrophenyl HRP conjugates on normal tonsil tissue.
Figure 24:
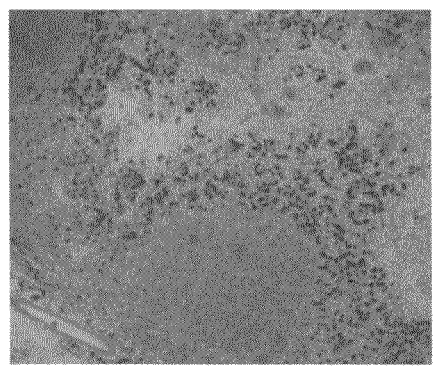
FIG. 24 is a chromogenic IHC staining of Lambda rotenone-based hapten-labeled primary antibodies with anti-rotenone HRP conjugates on normal tonsil tissue.
Figure 25:
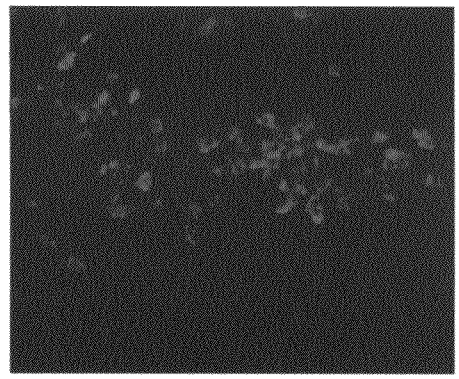
FIG. 25 is a fluorescent IHC staining in normal tonsil using anti-lambda attached to biotin and detected with anti-biotin antibody QDot conjugate.
Figure 26:
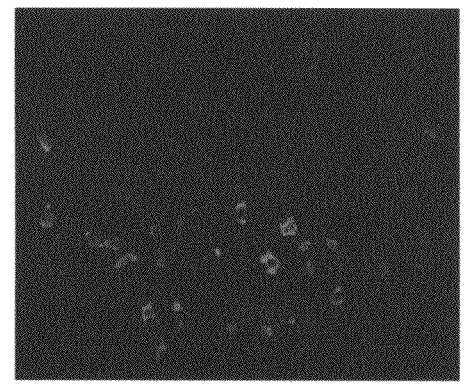
FIG. 26 is a fluorescent IHC staining in normal tonsil using anti-lambda attached to thiazole sulfonamide-based hapten and detected with anti-thiazole sulfonamide antibody QDot conjugate.
Figure 27:
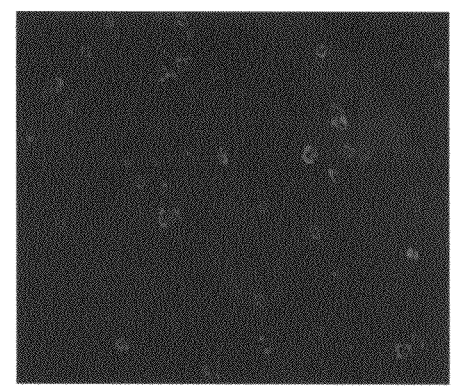
FIG. 27 is a fluorescent IHC staining in normal tonsil using anti-lambda attached to benzofurazan-based hapten and detected with anti-benzofurazan antibody QDot conjugate.
Figure 28:
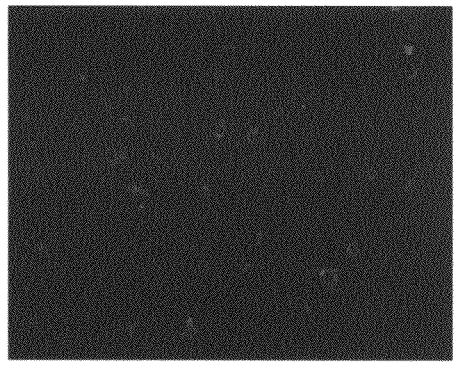
FIG. 28 is a fluorescent IHC staining in normal tonsil using anti-lambda attached to dinitrophenyl-based hapten and detected with anti-dinitrophenyl antibody QDot conjugate.
Figure 29:
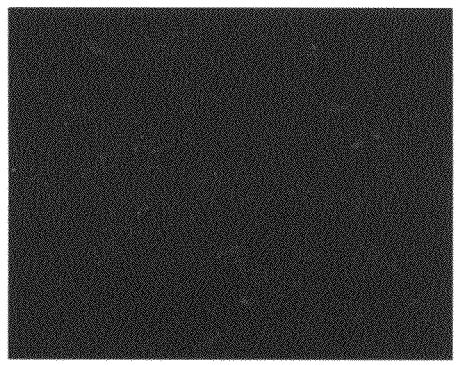
FIG. 29 is a fluorescent IHC staining in normal tonsil using anti-lambda attached to nitropyrazole-based hapten and detected with anti-nitropyrazole antibody QDot conjugate.
Figure 30:
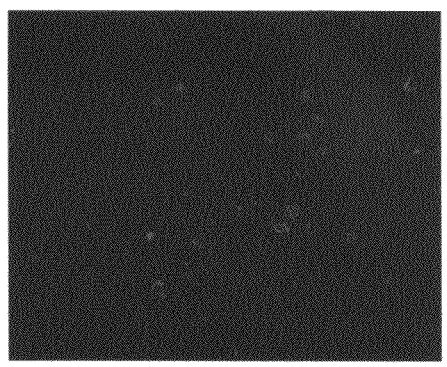
FIG. 30 is a fluorescent IHC staining in normal tonsil using anti-lambda attached to rotenone-based hapten and detected with anti-rotenone antibody QDot conjugate.
Figure 31:
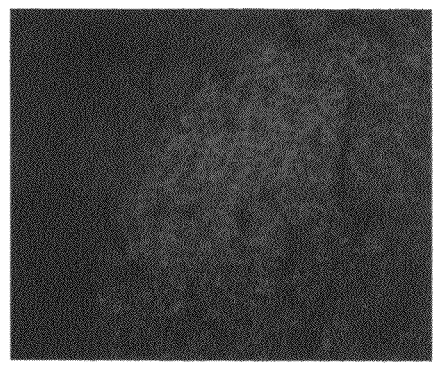
FIG. 31 is a fluorescent IHC staining of biotin labeled CD20 primary antibody and anti-biotin QDot 525 conjugate on normal tonsil tissue.
Figure 32:
FIG. 32 is a fluorescent IHC staining of thiazole sulfonamide-based hapten labeled CD45 primary antibody and anti-thiazole sulfonamide antibody QDot 565 conjugate on normal tonsil tissue.
Figure 33:
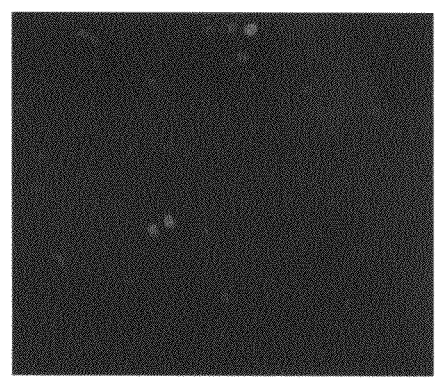
FIG. 33 is a fluorescent IHC staining of benzofurazan-based hapten labeled Ki67 primary antibody and anti-benzofurazan antibody QDot 585 conjugate on normal tonsil tissue.
Figure 34:
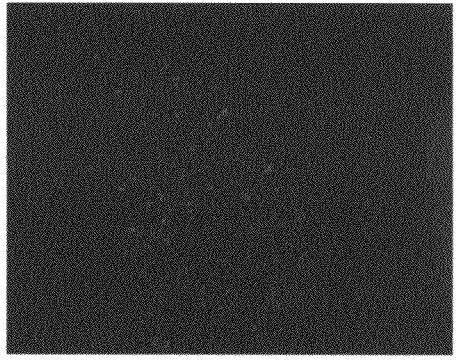
FIG. 34 is a fluorescent IHC staining of dinitrophenyl-based hapten labeled Kappa primary antibody and anti-dinitrophenyl antibody QDot 605 conjugate on normal tonsil tissue.
Figure 35:
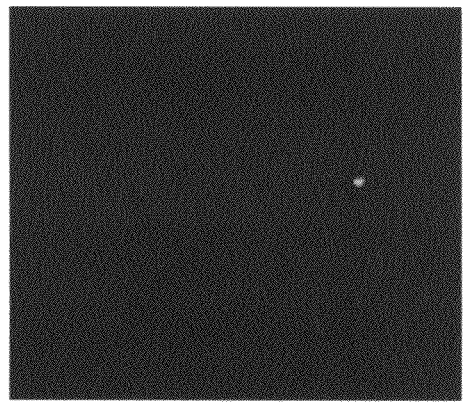
FIG. 35 is a fluorescent IHC staining of nitropyrazole-based hapten labeled CD34 primary antibodies anti-nitropyrazole antibody QDot 655 conjugate on normal tonsil tissue.
Figure 36:
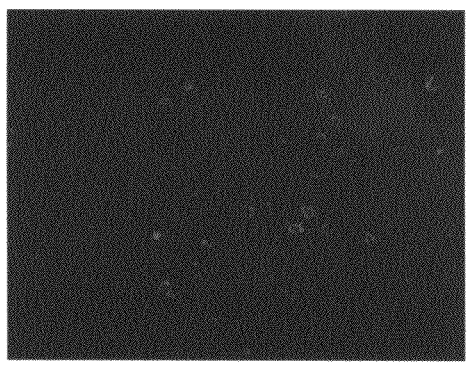
FIG. 36 is a fluorescent IHC staining of rotenone-based hapten labeled Lambda primary antibodies and anti-rotenone antibody QDot 705 conjugate on normal tonsil tissue.

The results of the ssDNA labeling with DNP-dPEG$_8$-EDC are provided in FIGS. 17 and 18. FIG. 17 indicates that the percent of nucleotide labeling increases, substantially linearly, with increased hapten conjugate. FIG. 17 illustrates that the percent nucleotide labeled decreased with increasing DNA stock concentration.

Example 26

This example concerns an exemplary procedure of labeling DNA with a hapten-dPEG$_8$-amino-dCTP. The incorporation of the hapten label onto DNA was accomplished by the nick translation procedure described in Rigby, P W; Dieckmann, M; Rhodes, C. and Berg, P., "Labeling deoxyribonucleic acid to high specific activity in vitro by nick translation with DNA polymerase I", *J. Mol. Biol.*, V113:237-251, 1977. Labeling efficiency was 2-6% based on comparison of the 260 nm absorbance of DNA and $\lambda_{max}$ and $\epsilon$ (extinction coefficient) of the specific hapten.

Example 27

This example concerns an exemplary procedure of screening anti-hapten hybridomas. Benzofurazan-dPEG$_8$-BSA (VMSI-1357-98) was coated onto microplates. The dilution buffer used was 0.15 molar phosphate buffered saline (PBS). The concentration of the Benzofurazan-dPEG$_8$-BSA was 2 µg/ml, and the well concentration was 50 µL. These samples were incubated at 4° C. overnight. 1% Nonfat dry milk (NFDM) (10 mg/mL, 300 µL/well) was used as a blocking reagent, followed by incubation at 37° C. for 120 minutes. Plates were washed, as deemed necessary, using 0.15 M PBS comprising 0.05% Tween 20. Each tested hapten then was used to produce mouse antisera. A total concentration of 80 µL per well mouse antisera diluted with 1% NFDM in 0.15 M PBS was provided using the dilutions and plate design protocol indicated below in Table 6. The plates were then incubated at 37° C. for 150 minutes. A goat antimouse-horseradish peroxidase conjugate (Gt-α-Mu-HRP, Pierce) was used as a secondary antibody at a concentration of 1:10,000 in 0.15 M PBS with 0.05% Tween 20 to provide a total well volume of 50 µL/well. The plates were then incubated for 60 minutes at 37° C. The ELISA set up and results are summarized below in Table 2.

TABLE 2

ELISA Results
Accession: 500421
Customer: Ventana
Sample tested: mouse antisera
Assay parameters:

| Step | Reagent | Serial dilution | Dilution buffer | Concentration | Volume/well | Incubation |
|---|---|---|---|---|---|---|
| Ag coating | VMSI-1357-98 | — | 0.15M PBS | 2 µg/mL | 50 µL | ON @ 4 C. |
| Blocking | 1% NFDM | — | 0.15M PBS | 10 mg/mL | 300 µL | 2 hr. @ 37 C. |
| Sample Dilution | see below | 5 X | 1% NFDM in 0.15M PBS | starting @ 1:50 | 80 µL | 2.5 hr. @ 37 C. |
| Secondary Ab | Gt-α-Mu-HRP | — | .15M PBS w/0.05% Tween20 | 1:10000 | 50 µL | 1 hr. @ 37 C. |

Plate design:
Sample dilution

| | | 1:50 | | 1:250 | | 1:1250 | | 1:6250 | | 1:31250 | | 1:156250 | |
|---|---|---|---|---|---|---|---|---|---|---|---|---|---|
| | | 1 | 2 | 3 | 4 | 5 | 6 | 7 | 8 | 9 | 10 | 11 | 12 |
| Mu #1 | A | 1.89 | 0.01 | 1.81 | 0.00 | 1.82 | 0.00 | 1.60 | 0.00 | 1.06 | 0.00 | 0.56 | 0.00 |
| Mu #2 | B | 1.76 | 0.01 | 1.87 | 0.00 | 1.73 | 0.00 | 1.25 | 0.00 | 0.60 | 0.00 | 0.25 | 0.00 |
| Mu #3 | C | 1.70 | 0.01 | 1.83 | 0.00 | 1.87 | 0.00 | 1.50 | 0.00 | 0.95 | 0.01 | 0.37 | 0.00 |
| Mu #4 | D | 1.75 | 0.01 | 1.73 | 0.02 | 1.83 | 0.00 | 1.49 | 0.01 | 0.98 | 0.00 | 0.42 | 0.00 |
| Mu #5 | E | 1.62 | 0.01 | 1.58 | 0.00 | 1.72 | 0.00 | 1.35 | 0.00 | 0.74 | 0.00 | 0.33 | 0.00 |

TABLE 2-continued

ELISA Results
Accession: 500421
Customer: Ventana
Sample tested: mouse antisera
Assay parameters:

| Prebleed pool | F | 0.06 | 0.01 x | 0.01 | 0.00 x | 0.00 | 0.01 x | 0.00 | 0.00 x | 0.00 | 0.00 x | 0.00 | 0.00 x |
|---|---|---|---|---|---|---|---|---|---|---|---|---|---|

Antigen: VMSI-1357-98 Lot #C05081610
Wash Buffer: 0.15M PBS with 0.05% Tween 20
Secondary Ab: HRP-goat-α-mu IgG Fc specific min. x-react #60312
Substrate: TMB lot #P502807
x = blank (no antigen)
NFDM = non-fat dried milk
Bleed date: Sep. 12, 2005
Assay date: Sep. 13, 2005

The results shown in Table 2 indicate that each of the mice tested is suitable for raising an antibody response, and further that such haptens can be visualized to confirm a response. With respect to the particular hapten tested, mouse number 1 appears to provide the best response over all dilutions tested.

Example 28

This example concerns an exemplary procedure of conjugation of anti-hapten antibodies to horseradish peroxidase (HRP). Images produced using such conjugates are provided by FIGS. 19-24.
Activation of HRP
To a 4 mL amber vial was added 78.8 mg (100 eq.) of MAL-dPEG$_4$™ NHS ester (Quanta Biodesign, Powell, Ohio, F.W.=513.50), followed by 2.46 mL (61.5 mg, 1.53 μM) of HRP (Horseradish Peroxidase, Pierce, Rockford, Ill. Lot FJ925901) as a 25 mg/mL solution in 0.1 M sodium phosphate, pH 7.5. The vial was then placed on an autorotator in the dark at ambient temperature (23-25° C.), and the amide bond forming reaction was allowed to proceed for one hour. A 400 μl aliquot was then removed for purification, and the remainder of the solution was temporarily stored at 4° C. Pure HRP-PEG$_4$-maleimide was then obtained by fractionating the sample on an AKTA Purifier fitted with a Superdex 10/300 column (GE Lifesciences) eluted with 0.1 M sodium phosphate, pH 7.5 at 1.0 mL/min. The HRP containing fractions were pooled to give 2.0 ml of a 4.52 mg/mL solution of HRP-PEG$_4$-maleimide (90% recovery) as measured by UV/VIS spectrophotometry using an extinction coefficient at 280 nm of a 1% solution (pH 6.5) of 6.52.
Introduction of Thiols to Antibodies
To a 8 mL amber vial was added 3.0 mL of a mouse anti-hapten monoclonal antibody as a 2.1 mg/mL solution in 0.1 M sodium phosphate, 1.0 mM EDTA, pH 6.5. To this solution was then added 216 μL of a freshly prepared 500 mM solution of the reducing agent DTT (1,4-Dithiothreitol, Sigma-Aldrich, St. Louis, Mo.). The vial was placed in the dark on an autorotator and the disulfide reduction was allowed to proceed for 25 minutes. The reaction solution was split into four equal volumes (due to the limited capacity of a desalting column used), and excess DTT was removed by passing each of the fractions across a PD-10 desalting column (GE Lifesciences) eluted with 0.1 M sodium phosphate, 1.0 mM EDTA, pH 6.5. The antibody containing fractions were combined to give 8.0 mL of a 0.8 mg/mL solution of reduced mouse anti-hapten antibody (71% recovery) as measured by UV/VIS spectrophotometry using an extinction coefficient at 280 nm of a 1% solution at pH 6.5 of 14.

HRP-Antibody Conjugation
To the reduced antibody (such as mouse anti-nitropyrazole monoclonal antibody), is added a three fold molar excess of HRP-PEG$_4$-maleimide. The reaction is then incubated at ambient temperature (23-25° C.) for 16 hours. After purification across a Superdex 200 10/300 GL SE column a conjugate, typically with an average of 2 or 3 HRPs per antibody, is obtained. The number of HRPs per antibody was determined by measuring the ratio of absorbances at 280 nm/403 nm of the conjugate. The conjugate was then stored in a cold room at 4° C. until use.

Example 29

This example concerns an exemplary procedure of conjugation of anti-hapten antibodies to quantum dots (QD).
Reduction of Inter-Chain Disulfides on Antibodies
To a solution of polyclonal or monoclonal antibody in 100 mM phosphate, 1 mM EDTA, pH 6.5 buffer was added DTT at a final concentration of 25 mM. This mixture was rotated for precisely 25 minutes before desalting on a Sephadex G25 (PD-10, GE Lifesciences) in 100 mM phosphate, 1 mM EDTA, pH 6.5 buffer.
Synthesis of QD-dPEG$_{12}$-MAL
To a solution of quantum dots (8-9 μM in 50 mM borate buffer, pH 8.0) was added NHS-dPEG$_{12}$-MAL (50 eq.) and rotated for two hours. The maleimide-functionalized quantum dots (QD-dPEG$_{12}$-MAL) were purified by desalting on a Sephadex G25 column (PD-10, GE Lifesciences) in 0.1 M phosphate, 0.1 M NaCl, pH 7.0 buffer.
Synthesis of QD-MAL-Antibody Conjugate
The purified QD-maleimide was combined with the purified thiolated antibody in molar ratios of 4:1 antibodies to QD and rotated for a 16 hour period. The QD-Ab conjugate was purified by SEC chromatography on an AKTA Purifier running at 0.9 mL/min. over a GE Lifesciences Superdex 200 10/300 GL column with 50 mM borate buffer, pH 8.0.

Example 30

This example demonstrates the ability of primary antibody-hapten conjugates to be visualized by chromogenic immunohistochemistry (IHC). Stainings representative of this approach are provided by FIGS. 19-24. FIG. 6 also is a staining representative of this approach, where methods for conjugating a primary antibody with a hapten are described in Examples 21-24. FIG. 7 is a control, whereby tissue treated with an antibody other than the appropriate anti-hapten antibody. FIG. 7 establishes the specificity of the method as no visualization occurs unless the appropriate anti-hapten antibody is used.

Tonsil tissue sections were treated with an anti-lambda polyclonal antibody (Dako) conjugated with haptens by the method in Examples 21, 22, 23 or 24. The slides were developed using standard protocols for HRP signal generation (by addition of DAB) on an automated stainer (BenchMark® XT, Ventana Medical Systems, Inc, Tucson, Ariz.). A typical automated protocol includes deparaffinization, several rinse steps, addition of a reaction buffer, addition of the primary antibody (anti-lambda:hapten conjugate), addition of the secondary antibody (anti-hapten:HRP conjugate), addition of DAB and hydrogen peroxide, and addition of a counterstain.

Manual scoring was conducted by Board-certified pathologists. Staining intensities, percentage of reactive cells, and cellular localization were recorded. For qualitative stain intensity, 0 is the most negative and 3+ is the most positive. Slides were reviewed and scored by the pathologist prior to quantitation by optical imaging.

For optical imaging, a digital application (VMSI) with image quantification based on the intensity (expressed as average optical density, or avg. OD) of the stain converted to a numerical score was utilized. A high-resolution image was captured for each sample and the OD value was determined based on specific classifiers for the shape and color range for positively stained cells. At least three different areas per specimen were captured using either a 20× or 40× objective lens. In some cases, a "combined score" or multiplicative index was derived that incorporates both the percentage of positive cells and the staining intensity according to the following formula: Combined score=(% positive)×(optical density score).

Example 31

This example demonstrates the ability of primary antibody-hapten conjugates to be visualized by fluorescent (Quantum Dot) immunohistochemistry (IHC).

Tonsil tissue sections were treated with an anti-Kappa polyclonal antibody (Dako) conjugated with haptens by the method in Examples 21, 22, 23 or 24. The slides were developed using a standard protocol for an automated stainer (BenchMark® XT, Ventana Medical Systems, Inc, Tucson, Ariz.). A typical automated protocol is as follows: the paraffin coated tissue on the slide was heated to 75° C. for 8 minutes and treated twice with EZPrep (VMSI), volume adjusted at 75° C. before application of the Liquid Cover Slip or LCS (VMSI). After two 8 minute incubation times at 75° C., the slide was rinsed and EZPrep volume was adjusted, followed with LCS to deparaffinize the tissue. The slide was cooled to 37° C., incubated for 2 minutes and rinsed once with Reaction Buffer (VMSI). The slide was treated with Cell Conditioner (VMSI) twice, followed by LCS. The slide was heated to 95° C. for 8 minutes, followed by LCS, and was heated to 100° C. for 4 minutes, followed by LCS. Cell Conditioner, incubate for 4 minutes, apply LCS, this incubation process with Cell Conditioner was repeated 9 times at 100° C. The slide was cooled down for 8 minutes, rinsed with Reaction Buffer, volume adjusted, and followed by another dispense of LCS. The slide was heated to 37° C. for 2 minutes and rinsed two times before the addition of anti-Kappa:hapten conjugate (100 μL at 1.0 mg/mL) followed by LCS and incubation at 37° C. for 32 minutes. The slide was rinsed twice with Reaction Buffer followed by the application of liquid cover slip and the addition of QDot:anti-hapten conjugate (100 μL, 20-50 nmol) and incubated at 37° C. for 32 minutes. The slide was rinsed two times with buffer followed by LCS. The slide was removed from the instrument and treated to a detergent wash before manual application of a cover slip. Results were interpreted using a light microscope and aid in the differential diagnosis of pathophysiological processes, which may or may not be associated with a particular antigen.

Example 32

This example demonstrates the ability of hapten-labeled DNA to be visualized by chromogenic in situ hybridization (ISH). Automated silver or diaminobenzidine (DAB) in-situ hybridization protocols for detection of HER2 gene copy number were developed on the Ventana Medical Systems Benchmark XT instrument. Staining is completed on formalin fixed paraffin embedded tissue on glass slides within nine hours. The steps of the procedure are as follows: deparaffination, cell conditioning using VMSI protease 3, addition of the hapten-labeled HER2 DNA probe (from Example 26), tissue and probe denaturation, hybridization of four hours, and detection with chromogenic silver catalyzed by HRP. Specifically, a Nitropyrazole labeled HER2 probe was hybridized in an automated fashion on formalin-fixed breast tissue, followed by detection with anti-Nitropyrazole Ab-HRP conjugate. Detection can be accomplished by use of the UltraView detection kit (Ventana Medical Systems) or through silver deposition using the HER2 SISH (Ventana Medical Systems) automated protocol. Results were interpreted using a light microscope and aid in the differential diagnosis of pathophysiological processes, which may or may not be associated with a particular antigen.

Example 33

This example demonstrates the ability of hapten-labeled DNA to be visualized by fluorescent (Quantum Dot) in situ hybridization (ISH). Automated fluorescent (via Quantum Dots) in-situ hybridization protocols for detection of HER2 gene copy number were developed on the Ventana Medical Systems Benchmark XT instrument. Staining is completed on formalin fixed paraffin embedded tissue on glass slides within nine hours. The steps of the procedure are as follows: deparaffination, cell conditioning using VMSI protease 3, addition of the hapten-labeled HER2 DNA probe (from Example 26), tissue and probe denaturation, hybridization of four hours, and detection with anti-hapten Ab:Quantum Dot conjugates (from Example 29). Specifically, a Benzofurazan labeled HER2 probe was hybridized in an automated fashion, followed by detection with anti-Benzofurazan Ab-Quantum Dot 655 conjugate. Imaging was performed on a Nikon fluorescence scope.

Example 34

This example demonstrates the ability to multiplex primary antibody-hapten conjugates and detect by multiplex fluorescent (Quantum Dot) immunohistochemistry (IHC). This approach is schematically illustrated in FIG. 8. Tonsil tissue sections were treated with a mixture of primary antibody-hapten conjugates: anti-CD20 Ab-biotin, anti-CD34 Ab-nitropyrazole, anti-CD45 Ab-thiazolesulfonamide, anti-Kappa Ab-dinitrophenyl, anti-Lambda Ab-rotenone, and anti-Ki67 Ab-benzofurazan. The anti-CD20-biotin conjugate was made by coupling antibody thiol functional groups to maleimide-dPEG11-biotin used in a 20-fold excess (described in Example 24). The anti-CD34-nitropyrazole conjugate was formed by coupling to the Fc portion of the antibody using polyacrylamide hydrazide and a 20-fold excess of NHS-dPEG8-NP (described in Example 22). This resulted in 12 nitropyrazole haptens per antibody. The anti-CD45-thiazolesulfonamide conjugate was made by reacting antibody lysines with a 20-fold excess of NHS-dPEG8-TS (described in Example 21). This resulted in 10 thiazolesulfonamide haptens per antibody. The Kappa-dinitrophenyl conjugate was formed by coupling to the Fc portion of the antibody using polyacrylamide hydrazide and a 100-fold excess of NHS-dPEG8-DNP (described in Example 22). This resulted in 62 dinitrophenyl haptens per antibody. Both the Lambda rotenone conjugate and the Ki67 benzofurazan conjugate were made by reacting anibody lysines to NHS-dPEG8-ROT and NHS-dPEG8-BF respectively (described in Example 21). This resulted in 0.3 rotenone haptens per antibody, and 2 benzofurazan haptens per antibody. The tonsil sections were then treated with a cocktail of secondary antibodies that were synthesized using the procedure in Example 29: Gt α-biotin polyAb:QD 525 (300 nM); Ms α-NP mAb:QD 655 (50 nM); Ms α-TS mAb:QD 565 (300 nM); Rb α-DNP polyAB:QD 605 (100 nM); Ms α-ROT mAb:QD 705 (200 nM); and Ms aBF mAb:QD 585 (300 nM).

Fluorescence Microscopy

Imaging was performed on a Nikon fluorescence scope. Unmixing of fluorescence spectra was achieved utilizing a CR1 camera. DAPI was used for counterstaining for the multiplexed tonsil sections.

Figure 37:
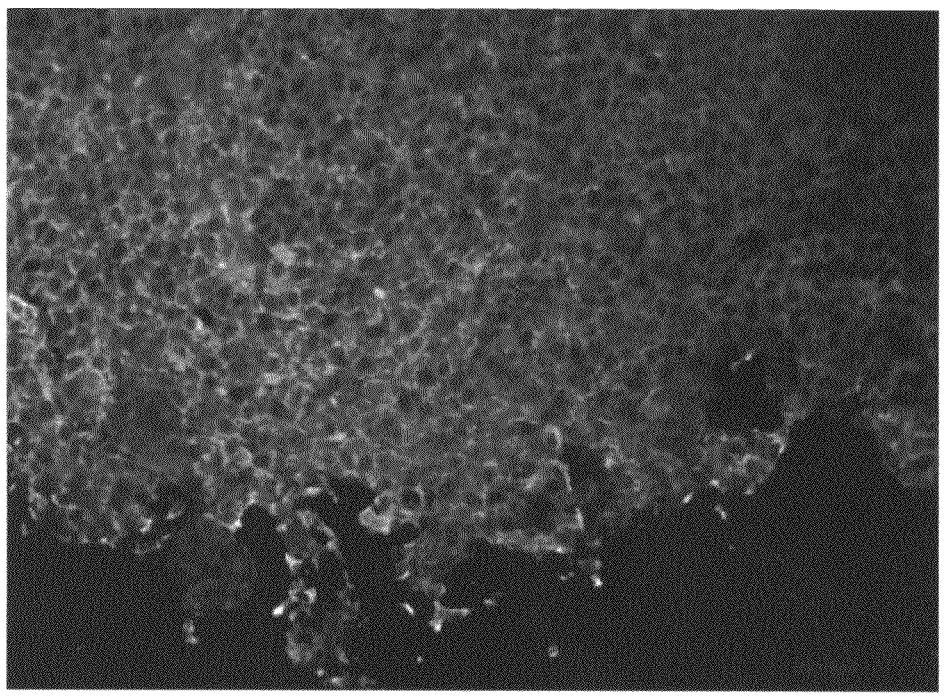
FIG. 37 is multiplexed staining composite using a mixture of the primary antibody-hapten conjugates and sequentially visualized with a mixture of anti-hapten antibody QDot conjugates on normal tonsil tissue as stated in FIGS. 31-36 and in Example 34.
Figure 38:
FIG. 38 is an image extracted from a multiplexed staining composite that represents anti CD45-thiazole sulfonamide-conjugate and hapten primary antibody and anti-thiazole sulfonamide antibody QDot 565 conjugate on normal tonsil tissue.
Figure 39:
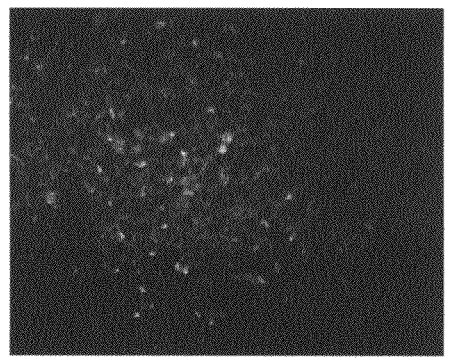
FIG. 39 is an image extracted from a multiplexed staining composite from FIG. 37 that represents the staining from the Ki67 benzofurazan-conjugate and hapten primary antibody and anti-benzofurazan-based antibody QDot 585 conjugate on normal tonsil tissue.
Figure 40:
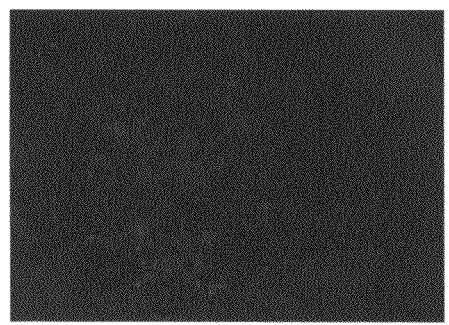
FIG. 40 is an image extracted from a multiplexed staining composite from FIG. 37 that represents anti Kappa-dinitrophenyl-conjugate and hapten primary antibody and anti-dinitrophenyl-based hapten antibody QDot 605 conjugates on normal tonsil tissue.
Figure 41:
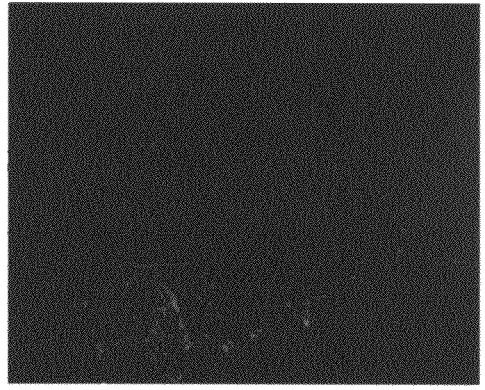
FIG. 41 is an image extracted from a multiplexed staining composite from FIG. 37 with anti CD34 nitropyrazole-conjugate and hapten primary antibody and anti-nitropyrazole-based hapten antibody QDot 655 conjugate on normal tonsil tissue.
Figure 42:
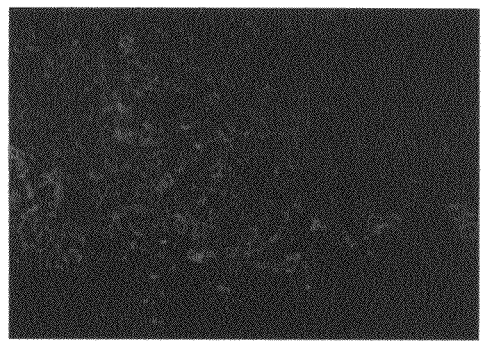
FIG. 42 is an image extracted from a multiplexed staining composite from FIG. 37 with anti CD20 biotin primary antibody QDot 525 conjugate on normal tonsil tissue.
Figure 43:
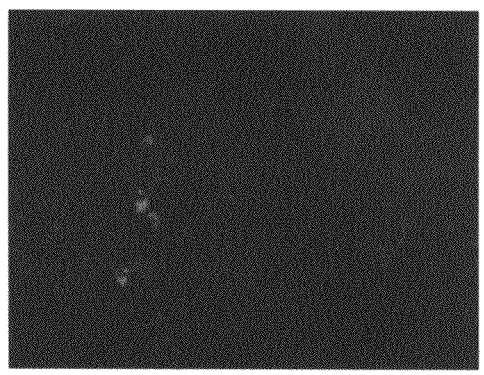
FIG. 43 is an image extracted from a multiplexed staining composite from FIG. 37 with Lambda-rotenone-conjugate and hapten primary antibody and anti-rotenone-based hapten antibody QDot 705 conjugate on normal tonsil tissue.

FIG. 37 is multiplexed staining composite that was produced using a mixture of primary antibody-hapten conjugates and sequentially visualized with a mixture of anti-hapten antibody QDot conjugates as stated in FIGS. 31-36 and in this Example 34.

Figure 44:
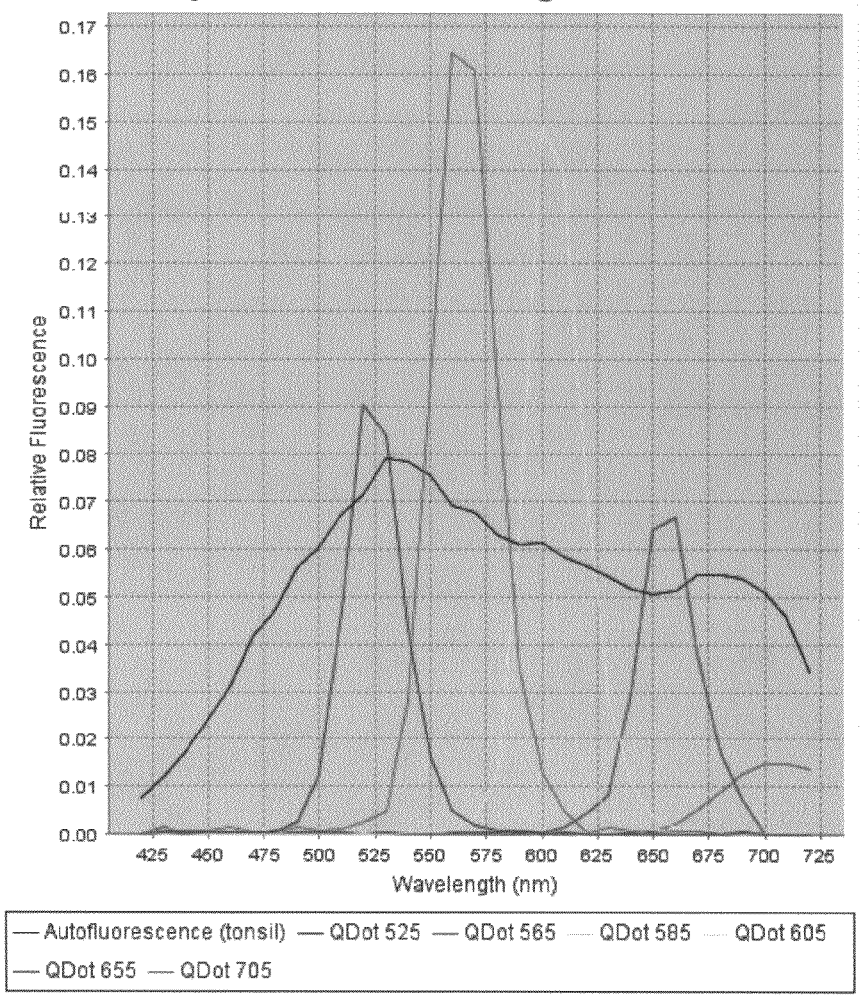
FIG. 44 is a graph of wavelength versus relative fluorescence that represents the wavelengths used to extract individual QDot signals from the multiplexed staining composite of FIG. 37 and shows the signal is above the nominal autofluorescence of the tonsil tissue.

FIGS. 38-43 are images extracted from the multiplexed staining of FIG. 37. FIG. 44 is a graph of wavelength versus relative fluorescence that represents the wavelengths used to extract individual QDot signals from the multiplexed staining composite of FIG. 37. FIG. 44 also establishes that the fluorescent signal is above the nominal autofluorescence of the tonsil tissue.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An anti-hapten antibody that specifically binds to a heterobiaryl hapten conjugate comprising a heterobiaryl hapten, an alkylene oxide linker, and a specific binding moiety, wherein the heterobiaryl hapten has, prior to conjugation with the alkylene oxide linker and the specific binding moiety, a structure

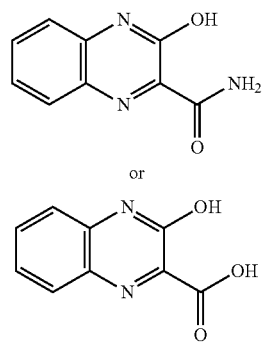

wherein the specific binding moiety in the heterobiaryl hapten conjugate is covalently linked to the carbonyl group of the structure through the alkylene oxide linker.

2. The anti-hapten antibody according to claim 1 coupled to a detectable label.

3. The anti-hapten antibody according to claim 2 where the detectable label is an enzyme, a chromophore, a fluorophore, a quantum dot, or combinations thereof.

4. The anti-hapten antibody according to claim 2 where the detectable label is a quantum dot.

5. A method for making an anti-hapten antibody that specifically binds to a heterobiaryl hapten conjugate comprising a heterobiaryl hapten, an alkylene oxide linker, and an immunogenic carrier, comprising:

administering to a subject the heterobiaryl hapten conjugate wherein the heterobiaryl hapten has, prior to conjugation with the alkylene oxide linker and the specific immunogenic carrier, a structure

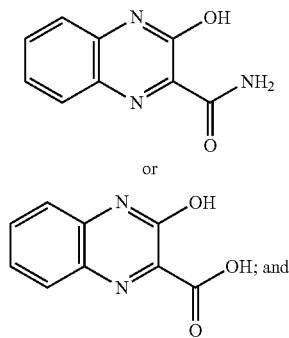

isolating the anti-hapten antibody, wherein the immunogenic carrier in the heterobiaryl hapten conjugate is covalently linked to the carbonyl group of the structure through the alkylene oxide linker.

* * * * *